US010035983B2

(12) United States Patent
Gruber et al.

(10) Patent No.: US 10,035,983 B2
(45) **Date of Patent: *Jul. 31, 2018**

(54) GENE THERAPY VECTORS AND CYTOSINE DEAMINASES

(71) Applicant: Tocagen Inc., San Diego, CA (US)

(72) Inventors: Harry E. Gruber, Rancho Santa Fe, CA (US); Douglas J. Jolly, Encinitas, CA (US); Omar D. Perez, San Diego, CA (US); Christopher R. Logg, South Pasadena, CA (US)

(73) Assignee: Tocagen Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/274,556

(22) Filed: May 9, 2014

(65) Prior Publication Data

US 2014/0242033 A1 Aug. 28, 2014

Related U.S. Application Data

(63) Continuation of application No. 13/072,705, filed on Mar. 26, 2011, now Pat. No. 8,722,867, which is a continuation-in-part of application No. PCT/US2009/058510, filed on Sep. 26, 2009.

(60) Provisional application No. 61/100,666, filed on Sep. 26, 2008, provisional application No. 61/120,618, filed on Dec. 8, 2008, provisional application No. 61/186,823, filed on Jun. 13, 2009, provisional application No. 61/318,728, filed on Mar. 29, 2010.

(51) Int. Cl.

| | |
|---|---|
| ***C12N 7/00*** | (2006.01) |
| ***C07K 14/55*** | (2006.01) |
| ***C07K 14/57*** | (2006.01) |
| ***C07K 16/28*** | (2006.01) |
| ***C12N 9/10*** | (2006.01) |
| ***C12N 9/78*** | (2006.01) |
| ***C12N 15/113*** | (2010.01) |
| ***C12N 15/86*** | (2006.01) |
| *A61K 39/00* | (2006.01) |

(52) U.S. Cl.

CPC ................ *C12N 7/00* (2013.01); *C07K 14/55* (2013.01); *C07K 14/57* (2013.01); *C07K 16/2818* (2013.01); *C12N 9/1077* (2013.01); *C12N 9/78* (2013.01); *C12N 15/113* (2013.01); *C12N 15/86* (2013.01); *C12Y 305/04001* (2013.01); *A61K 2039/505* (2013.01); *C07K 2317/622* (2013.01); *C07K 2319/00* (2013.01); *C12N 2310/141* (2013.01); *C12N 2740/13043* (2013.01); *C12N 2840/102* (2013.01); *C12N 2840/203* (2013.01)

(58) Field of Classification Search

None

See application file for complete search history.

(56) References Cited

U.S. PATENT DOCUMENTS

| | | | | |
|---|---|---|---|---|
| 6,033,905 | A | 3/2000 | Eiden et al. | |
| 6,117,681 | A | 9/2000 | Salmons et al. | |
| 6,303,380 | B1 | 10/2001 | Lin et al. | |
| 6,410,313 | B1 | 6/2002 | Kasahara et al. | |
| 6,448,390 | B1 | 9/2002 | Albritton et al. | |
| 6,451,304 | B1 | 9/2002 | Friedmann et al. | |
| 6,576,463 | B1 | 6/2003 | Kasahara et al. | |
| 6,806,080 | B2 | 10/2004 | Kasahara et al. | |
| 6,899,871 | B2 | 5/2005 | Kasahara et al. | |
| 6,953,688 | B2 | 10/2005 | Ferrick et al. | |
| 7,056,730 | B2 | 6/2006 | Pedersen et al. | |
| 8,722,867 | B2 * | 5/2014 | Gruber et al. | 536/23.2 |
| 8,829,173 | B2 * | 9/2014 | Gruber et al. | 536/23.2 |
| 9,732,326 | B2 * | 8/2017 | Gruber | C12N 7/00 |
| 2002/0068362 | A1 | 6/2002 | Murray et al. | |
| 2002/0137889 | A1 | 9/2002 | Soong et al. | |
| 2003/0003565 | A1 | 1/2003 | Dubensky | |
| 2003/0121068 | A1 | 6/2003 | Orchard et al. | |
| 2003/0157070 | A1 | 8/2003 | Jolly | |
| 2003/0157718 | A1 | 8/2003 | Pedersen et al. | |
| 2003/0165466 | A1 | 9/2003 | Gromeier et al. | |
| 2003/0219410 | A1 | 11/2003 | Calatrava | |
| 2004/0068762 | A1 | 4/2004 | Attar et al. | |
| 2004/0096972 | A1 | 5/2004 | Audit et al. | |
| 2004/0142449 | A1 | 7/2004 | Tonjes et al. | |
| 2004/0146489 | A1 | 7/2004 | Yu et al. | |
| 2004/0197308 | A1 | 10/2004 | Takahashi et al. | |
| 2004/0248827 | A1 | 12/2004 | Zheng et al. | |
| 2005/0002903 | A1 | 1/2005 | Kasahara et al. | |
| 2005/0059004 | A1 | 3/2005 | Atabekov et al. | |
| 2005/0063945 | A1 | 3/2005 | Paul et al. | |
| 2006/0147429 | A1 * | 7/2006 | Diamond | 424/93.7 |
| 2007/0003522 | A1 | 1/2007 | Albritton | |
| 2007/0254357 | A1 | 11/2007 | Gregory et al. | |
| 2008/0008685 | A1 | 1/2008 | Kasahara | |
| 2008/0227736 | A1 | 9/2008 | Chen et al. | |
| 2009/0028842 | A1 * | 1/2009 | Gojkovic et al. | 424/94.6 |
| 2009/0169580 | A1 | 7/2009 | Whelan et al. | |
| 2012/0052554 | A1 | 3/2012 | Kasahara et al. | |

FOREIGN PATENT DOCUMENTS

| | | | |
|---|---|---|---|
| WO | 1999020742 | A2 | 4/1999 |
| WO | 1999036561 | A1 | 7/1999 |

(Continued)

OTHER PUBLICATIONS

Logg et al, Tissue-Specific Transcriptional Targeting of a Replication-Competent Retroviral Vector, Journal of Virology, Dec. 2002, p. 12783-12791.*

(Continued)

*Primary Examiner* — Maria Marvich

(74) *Attorney, Agent, or Firm* — Gabrilovich, Dodd & Lindsey LLP

(57) ABSTRACT

This disclosure provides modified cytosine deaminases (CDs). The disclosure further relates to cells and vector expressing or comprising such modified CDs and methods of using such modified CDs in the treatment of disease and disorders.

6 Claims, 29 Drawing Sheets

(56) References Cited

FOREIGN PATENT DOCUMENTS

| | | | |
|---|---|---|---|
| WO | 0104266 | A1 | 1/2001 |
| WO | 2005/086922 | A2 | 9/2005 |
| WO | 2006/048749 | A1 | 5/2006 |
| WO | 2006127980 | A2 | 11/2006 |
| WO | 2007095201 | A2 | 8/2007 |
| WO | 2007107156 | A2 | 9/2007 |
| WO | 2008151633 | A2 | 12/2008 |
| WO | 2010002937 | A1 | 1/2010 |
| WO | 2010036986 | A2 | 4/2010 |
| WO | 2010045002 | A1 | 4/2010 |
| WO | 2011126864 | A2 | 10/2011 |
| WO | 2012021794 | A1 | 2/2012 |

OTHER PUBLICATIONS

Mechold et al, Codon optimization of the BirA enzyme gene leads to higher expression and an improved efficiency of biotinylation of target proteins in mammalian cells, Journal of Biotechnology 116 (2005) 245-249.*

Lesk et al, Prediction of Protein Function from Protein Sequence and Structure, p. 27 and p. 28, downloaded Sep. 16, 2007.*

Guo et al, Protein tolerance to random amino acid change, PNAS, 2004, vol. 101 (25), pp. 9205-9210.*

Akimoto, M. et al., A new delivery system for 5-fluorouracil using prodrug and converting enzyme; Laboratory Science; Br J Ophthalmol 2002;86:581-586; www.bjophthalmol.com.

Erbs, P., et al., Modified vaccinia virus Ankara as a vector for suicide gene therapy; Cancer Gene Therapy (2008) 15, 18-28; Nature Publishing Group.

Erbs, P., et al., In Vivo Cancer Gene Therapy by Adenovirus-mediated Transfer of a Bifunctional Yeast Cytosine Deaminase/Uracil Phosphoribosyltransferase Fusion Gene; Cancer Res 2000;60:3813-3822; American Association for Cancer Research.

Erbs, P., et al., Characterization of the *Saccharomyces cerevisiae* FCY1 gene encoding cytosine deaminase and its homologue FCA1 of Candida albicans; Curr Genet 31: 1-6; Springer-Verlag 1997.

Fischer, U. et al., Mechanisms of thymidine kinase/ganciclovir and cytosine deaminase/5-fluorocytosine suicide gene therapy-induced cell death in glioma cells; Oncogene (2005) 24,1231-1243; Nature Publishing Group.

Freytag, S. et al., Phase I Study of Replication-competent Adenovirus-mediated Double Suicide Gene Therapy for the Treatment of Locally Recurrent Prostate Cancer; Cancer Res 2002;62:4968-4976; American Association for Cancer Research.

Gene-Bank-AAG33626; cytosine deaminase-uracil phosphoribosylransferase fusion protein [synthetic contruct]; Gene-Bank-AAG33626; pp. 1-2; http://www.ncbi.nlm.nih.gov/protein/AAg33626.

Gene-Bank-Y1SB_A; Chain A, Yeast Cytosine Deaminase Triple Mutant; pp. 1-2; http://www.ncbi.nlm.nih.gov/protein/1ySB_A.

Guffey, M. et al., Engineered herpes simplex virus expressing bacterial cytosine deaminase for experimental therapy of brain tumors; Cancer Gene Therapy (2007) 14, 45-56; 2007 Nature Publishing Group.

Hiraoka, K., et al., Vector-Mediated Suicide Gene Therapy in a MultifocalTherapeutic Efficacy of Replication-Competent Retrovirus Colorectal Cancer Metastasis Model; AACR; Cancer Res 2007;67: (11); 5345-5353.;Published online Jun. 1, 2007; www.aacrjournals.org.

Hirschowitz, E., et al., In Vivo Adenvirus—Mediated Gene Transfer of the *Escherichia coli* Cytosine Deaminase Gene to Human Colon Carcinoma-Derived Tumors Induces Chemosensitivity to 5-Fluorocytosine; Human Gene Therapy 6:1055-1063; Mary Ann Liebert, Inc.; (Aug. 1995).

Huber, B., et al., Metabolism of 5-fluorocytosine to 5-fluorouracil in human colorectal tumor cells transduced with the cytosine deaminase gene: Significant antitumor effects when only a small percentage of tumor cells express cytosine deaminase; Proc. Natl. Acad. Sci. USA 91 (Aug. 1994); Medical Sciences; 8302-8306.

Ireton, G. et al., The Structure of *Escherichia coli* Cytosine Deaminase; J. Mol. Biol. (2002) 315, Academic Press; 687-697.

Ireton, G. et al., The 1.14A° Crystal Structure of Yeast Cytosine Deaminase: Evolution of Nucleotide Salvage Enzymes and Implications for Genetic Chemotherapy; Structure, vol. 11, 961-972, Aug. 2003, Elsevier Science Ltd.

Kaliberov, SA. et al., Mutation of *Escherichia coli* cytosine deaminase significantly enhances molecular chemotherapy of human glioma; Gene Therapy (2007) 14, 1111-1119; Nature Publishing Group; www.nature.com/gt.

Kaliberova, L. et al., Molecular chemotherapy of pancreatic cancer using novel mutant bacterial cytosine deaminase gene; Mol Cancer Ther 2008;7:2845-2854; American Association for Cancer Research; Published online Sep. 11, 2008.

Kawasaki, Y. et al., Replication-competent retrovirus vector-mediated prodrug activator gene therapy in experimental models of human malignant mesothelioma; Cancer Gene Ther.; Aug. 2011; 18(8); National Institutes of Health; 571-578.

Kern, L et al., The FUR1 gene of *Sacckaromyces ceret*, isiae: cloning, structure and expression of wild-type and mutant alleles; Gene, 88 (1990) 149-157; 1990 Elsevier Science Publishers B.V. (Biomedical Division).

Kikuchi, E. et al., Highly Efficient Gene Delivery for Bladder Cancers by Intravesically Administered Replication-Competent Retroviral Vectors; Clin Cancer Res 2007;13:4511-4518; American Association for Cancer Research; Published online Aug. 1, 2007.

Korkegian, A. et al., Computational Thermostabilization of an Enzyme; Science vol. 308; May 6, 2005; 857-860; www.sciencemag.org.

Kurozumi, K. et al., Apoptosis induction with 5-fluorocytosine/cytosine deaminase gene therapy for human malignant glioma cells mediated by adenovirus; Journal of Neuro-Oncology 66: 117-127, 2004; Kluwer Academic Publishers. Printed in the Netherlands.

Liu, Y. et al., Engineering conditionally replication-competent adenoviral vectors carrying the cytosine deaminase gene increases the infectivity and therapeutic effect for breast cancer gene therapy; Cancer Gene Therapy (2006) 13, 346-356; Nature Publishing Group.

Liu, Y. et al., Tumor-specific therapeutic effect induced by an oncolytic adenoviral vector containing heat shock protein 70 and prodrug activation genes; Gene Therapy (2006) 13, 1235-1243; Nature Publishing Group.

Mahan, S. et al., Random mutagenesis and selection of *Escherichia coli* cytosine deaminase for cancer gene therapy; Protein Engineering, Design & Selection vol. 17 No. 8 pp. 625-633, 2004;Published online Sep. 20, 2004.

Mahan, S. et al., Alanine-Scanning Mutagenesis Reveals a Cytosine Deaminase Mutant with Altered Substrate Preference; Biochemistry 2004, 43, 8957-8964; American Chemical Society.

Miller, C. et al., Intratumoral 5-Fluorouracil Produced by Cytosine Experimental Human Glioblastomas Deaminase/5-Fluorocytosine Gene Therapy Is Effective for Experimental Human Glioblastomas; Cancer Research 62, 773-780; Feb. 1, 200; American Association for Cancer Research.

Nyati, M. et al., High and Selective Expression of Yeast Cytosine Deaminase under a Carcinoembryonic Antigen Promoter-Enhancer; Cancer Res 2002;62:2337-2342; American Association for Cancer Research.

Mullen, G. et al., Transfer of the bacterial gene for cytosine deaminase to mammalian cells confers lethal sensitivity to 5-fluorocytosine: A negative selection system; Proc. Natl. Acad. Sci. USA; vol. 89, pp. 33-37, Jan. 1992; Medical Sciences.

Nakamura, H. et al., Multimodality Therapy with a Replication-conditional Herpes Simplex Virus 1 Mutant that Expresses Yeast Cytosine Deaminase for Intratumoral Conversion of 5-Fluorocytosine to 5-Fluorouracil; Cancer Res 2001;61:5447-5452; American Association for Cancer Research.

Negroni, L. et al., Treatment of colon cancer cells using the cytosine deaminase/5-fluorocytosine suicide system induces deaminase/5-

(56) References Cited

OTHER PUBLICATIONS fluorocytosine suicide system induces phosphorylation; Mol Cancer Ther 2007;6:2747-2756; American Association for Cancer Research.
Nishiyama, T. et al., Antineoplastic Effects in Rats of 5-Fluorocytosine in Combination with Cytosine Deaminase Capsules; Cancer Res 1985;45:1753-1761; American Association for Cancer Research.
Fogar, P. et al., Suicide Gene Therapy With the Yeast Fusion Gene Cytosine Deaminase/Uracil Phosphoribosyltransferase Is Not Enough for Pancreatic Cancer; Pancreas & Volume 35, No. 3, Oct. 2007; Lippincott Williams & Wilkins.
Poltoratsky, V., Recombinogenic Phenotype of Human Activation-Induced Cytosine Deaminas; J Immunol 2004; 172:4308-4313; http://www.jimmunol.org/content/172/7/4308; The American Association of Immunologists, Inc.
Shen, H. et al., Targeting of the Activation-Induced Cytosine Deaminase Is Strongly Influenced by the Sequence and Structure of the Targeted DNA; Molecular and Cellular Biology, Dec. 2005, p. 10815-10821 vol. 25, No. 24; doi:10.1128/MCB.25.24.10815-10821.2005; American Society for Microbiology.
Sotos, G. et al., Preclinical and clinical aspects of biomodulation of 5-fluorouracil; Cancer Treatment Reviews (1994) 20, 11-49; W. B. Saunders.
Stolworthy, T., et al., Yeast Cytosine Deaminase Mutants with Increased Thermostability Impart Sensitivity to 5-Fluorocytosine; J Mol Biol. Mar. 28, 2008; 377(3): 854-869; National Institutes of Health.
Tai, C. et al., Single-Shot, Multicycle Suicide Gene Therapy by Replication-Competent Retrovirus Vectors Achieves Long-Term Survival Benefit in Experimental Glioma; Molecular Therapy vol. 12, No. 5, Nov. 2005; The American Society of Gene Therapy, p. 842-851.
Wallace, P. et al., Intratumoral Generation of 5-Fluorouracil Mediated by an Antibody-Cytosine Deaminase Conjugate in Combination with 5-Fluorocytosine; Cancer Res 1994;54:2719-2723; American Association for Cancer Research.
Wang, W. et al., Use of replication-competent retroviral vectors in an immunocompetent intracranial glioma model; Neurosurg. Focus; vol. 20; Apr. 2006; pp. 1-9.
Warmann,S. et al., Adenovirus-Mediated Cytosine Deaminase/5-Fluorocytosine Suicide Gene Therapy of Human Hepatoblastoma In Vitro; Pediatr Blood Cancer 2009;53:145-151; Wiley-Liss, Inc.
Zhang, J., et al., A Novel Oncolytic Adenovirus Expressing *Escherichia coli* Cytosine Deaminase Exhibits Potent Antitumor Effect on Human Solid Tumors; Cancer Biotherapy and Radiopharmaceuticals; vol. 25, No. 4, 2010; pp. 487-495; Mary Ann Liebert, Inc.
Chen et al., "Inhibition of Marek's disease virus replication by retroviral vector-based RNA interference," Virology, 2008, vol. 377, No. 2, 265-272.
Perez et al., "Design and selection of toca 511 for clinical use: modified retroviral replicating vector with improved stability and gene expression", Molecular Therapy, 2012, vol. 20, No. 9, May 1, 2012, 1689-1698.
Stewart et al., "Lentivirus-delivered gene stable gene silencing by RNAi in primary cells", RNA, 2003, vol. 9, No. 4, 493-501.
Chang et al., "A Replication-Competent Feline Leukemia Virus, Subgroup A (FeLV-A), Tagged with Green Fluorescent Protein Reporter Exhibits In Vitro Biological Properties Similar to Those of the Parental FeLV-A," J. of Virol., 75(18):8837-8841, Sep. 2001.
Kubo et al., "Highly efficient tumor transduction and antitumor efficacy in experimental human malignant mesothelioma using replicating gibbon ape leukemia virus," Canc. Gene Ther., 20:671-677, 2013.
Yin et al., "Insertion of sequences into the 3' untranslated region of a replication-competent spleen necrosis virus vector disrupts env gene expression," Arch Virol (1999) 144:73-87.
Akbulut, et al., "Cytotoxic effect of replication-competent adenoviral vectors carrying L-plastin promoter regulated E1A and cytosine deaminase genes in cancers of the breast, ovary, and colon," Cancer Gene Therapy 10:388-395 (2003).
Akbulut et al., "Vector targeting makes 5-fluorouracil chemotherapy less toxic and more effective in animal models of epithelial neoplasms," 10(22):7738-46 (2004).
Beijer, Gijsbertus. International Preliminary Report on Patentability. International Application No. PCT/US2009/058512. dated Apr. 7, 2011.
Blackburn et al., "Adenovrial transduction of a cytosine deaminase/thymidine kinase fusion gene into prostate carcinoma cells enhances prodrug and radiation sensitivity," International Journal of Cancer 82(2):293-297 (1999).
Bourbeau et al., "Suicide gene therapy with an adenovirus expressing the fusion gene CD::UPRT in human glioblastomas: different sensitivities correlate with p53 status," The Journal of Gene Medicine 6:1320-1332 (2004).
Bourbeau et al., "Improvement of antitumor activity by gene amplification with a replicating but nondisseminating adenovirus," 67(7):3387-95 (2007).
Chang et al., "A Replication-Competent Feline Leukemia Virus, Subgroup A (FELV-A), Tagged with Green Fluorescent Protein Reporter Exhibits In Vitro Biological Properties Similar to Those of the Parental FelV-A," Journal of Virology 75(18):8837-8841 (2001).
Dias et al., "Targeted chemotherapy for head and neck cancer with a chimeric oncolytic adenovirus coding for bifunctional suicide protein FCU1," Clin. Cancer Res. 16(9):2540-9; Epub Apr. 13, 2010.
Foloppe et al., "Targeted delivery of a suicide gene to human colorectal tumors by a conditionally replicating vaccinia virus," Gene Ther. 15(20):1361-71 (2008); Epub May 15, 2008.
Svarovskaia et al., Retroviral mutation rates and reverse transcriptase fidelity, Front. Biosci. 8:d117—d134 (2003).
Swanstrom et al., "Synthesis, assembly, and processing of viral proteins," In Retroviruses (Coffin, J. M., Hughes, S. H. & Varmus, H., eds), pp. 263-334, (1997). Cold Spring Harbor Laboratory Press, Plainview, NY.
Tai et al., "Antibody-Mediated Targeting of Replication-Competent Retroviral Vectors," Human Gene Therapy 14:789-802 (2003).
Tai et al., "Replication-competent retrovirus vectors for cancer gene therapy," Frontiers in Bioscience 13:3083-95 (2008).
Trubetskoy et al., "R region sequences in the long terminal repeat of a murine retrovirus specifically increase expression of unspliced RNAs," J. Virol. 73:3477-3483 (1999).
Valsamakis et al., The human immunodeficiency virus type 1 polyadenylylation signal: a 3' long terminal repeat element upstream of the AAUAAA necessary for efficient polyadenylylation, Proc. Natl. Acad. Sci. USA 88:2108-2112 (1991).
Van Santen et al., "mRNA precursor splicing in vivo: sequence requirements determined by deletion analysis of an intervening sequence," Proc. Natl Acad. Sci. USA 82:2885-2889 (1985).
Wang et al., "Highly Efficient and Tumor-Restricted Gene Transfer to Malignant Gliomas by Replication-Competent Retroviral Vectors," Human Gene Therapy 14:117-127 (2003).
Xie et al., "Adenovirus-mediated tissue-targeted expression of a caspase-9-based artificial death switch for the treatment of prostate cancer," Cancer Res. 61:6795-6804 (2001).
Xie et al., "Enhanced Retinal Ganglion Cell Differentiation by ath5 and NSCL1 Coexpression," IOVS 45(9):2922-2928 (2004).
Yamashita et al., "The cell cycle independence of HIV infections is not determined by known karyophilic viral elements," PLoS Pathog. 1:e18 (2005).
Yap et al., "Trim5alpha protein restricts both HIV-1 and murine leukemia virus," Proc. Natl. Acad. Sci. USA 101:10786-10791 (2004).
Yi, et al., "Retroviral gene therapy: safety issues and possible solutions," Curr. Gene Ther. 5:25-35 (2005).
Young et al., "Chimeric Retroviral Helper Virus and Picomavirus IRES Sequence to Eliminate DNA Methylation for Improved Retroviral Packaging Cells," J. Viral. 74(11):5242-5249 (2000).
Aagaard et al., "Fv1-like restriction of N-tropic replication-competent murine leukaemia viruses in mCAT-1-expressing human cells," Journal of General Virology 83:439-442 (2002).

(56) References Cited

OTHER PUBLICATIONS

Addison et al., "Comparison of the human versus murine cytomegalovirus immediate early gene promoters for transgene expression by adenoviral vectors," J. Gen. Viral. 78:1653-1661 (1997).
Ambrose et al., "In vitro characterization of a simian immunodeficiency virus human immunodeficiency virus (HIV) chimera expressing HIV type 1 reverse transcriptase to study antiviral resistance in pigtail macaques," J. Virol. 78:13553-13561 (2004).
Anello et al., "Adenovirus Mediated Cytosine Deaminase Gene Transduction and 5-fluorocytosine Therapy Sensitizes Mouse Prostate Cancer to Irradiation," The Journal of Urology 164(6):2173-2177 (2005).
Arrigo et al., "Regulation of Rous sarcoma virus RNA splicing and stability," Mol. Cell Biol. 8:4858-4867 (1988).
Attar et al., Score Result downloaded Jan. 13, 2013.
Bachrach et al., "Efficient Gene Transfer into Spleen Cells of Newborn Mice by a Replication-Competent Retroviral Vector," 293(2):328-334 (2002).
Bachrach et al., "In Vivo Infection of Mice by Replication-Competent MLV-Based Retrovirus Vectors," Methods in Molecular Medicine 76:343-352 (2003).
Baranick, Brian Thomas, "Characterization and utilization of simple replication -competent retroviral vectors", 2007, 168 pages.
Baranick et al., "Splicing mediates the activity of four putative cellular internal ribosome entry sites," PNAS 105 (12):4733-4738 (2008).
Barsov et al., "Adaptation of chimeric retroviruses in vitro and in vivo: isolation of avian retroviral vectors with extended host range," J. Virol. 75.4973-4983 (2001).
Bunnell et al., "Transplantation of transduced nonhuman primate CD34+ cells using a gibbon ape leukemia virus vector: restricted expression of the gibbon ape leukemia virus receptor to a subset of CD34+ cells," Gene Ther. 6:48-56 (1999).
Cherry et al., "Retroviral Expression in Embryonic Stem Cells and Hematopoietic Stem Cells," Molecular and Cellular Biology 20(20):7419-7426 (2000).
Coulombe et al., "A replication-competent promoter-trap retrovirus," J. Virol. 70:6810-6815 (1996).
Cupelli et al., "Transcriptional initiation and postinitiation effects of murine leukemia virus long terminal repeat R-egion sequences," J. Virol. 65:6961-6968 (1991).
Cupelli et al., "The secondary structure of the R region of a murine leukemia virus is important for stimulation of long terminal repeat-driven gene expression," J. Virol. 72:7807-7814 (1998).
Delassus et al., "Genetic organization of gibbon ape leukemia virus," Virology 173:205-213 (1989).
Delviks, Krista Anda., "Development of murine leukemia virus-based vectors for more effective gene therapy: genetic analysis of direct repeat deletions," Dissertation, West Virginia (1999).
Diaz et al., "Exchange of viral promoter/enhancer elements with heterologous regulatory sequences generates targeted hybrid long terminal repeat vectors for gene therapy of melanoma," J. Virol. 72:789-795 (1998).
Dillon et al., "Construction of a replication competent murine retrovirus vector expressing the human immunodeficiency virus type 1 Tat transactivator protein," J. Virol. 65:4490-4493 (1991).
Donahue et al., "Helper virus induced T cell lymphoma in nonhuman primates after retroviral mediated gene transfer," J. Expt. Med. 176:1125-1135 (1992).
Duch et al., "Transgene stability for three replication-competent murine leukemia virus vectors," Gene 329:61-69 (2004).
Edelstein et al., "Gene therapy clinical trials worldwide 1989-2004—an overview," J. Gene Med. 6:597-602 (2004).
Erlwein et al., "The proline-rich region of the ecotropic Moloney murine leukaemia virus envelope protein tolerates the insertion of the green fluorescent protein and allows the generation of replication-competent virus," J. Gen. Virol. 84:369-373 (2003).
Ernst et al., "A structured retroviral RNA element that mediates nucleocytoplasmic export of intron containing RNA," Mol. Cell Biol. 17:135-144. (1997).
Evans et al., "A neutralizable epitope common to the envelope glycoproteins of ecotropic, polytropic, xenotropic, and amphotropic murine leukemia viruses," J. Virol. 64: 6176-6183 (1990).
Ferrick et al., Scorre Result p. 1, downloaded Jan. 14, 2013.
Finger et al., "Replicating retroviral vectors mediating continuous production and secretion of therapeutic gene products from cancer cells," Cancer Gene Ther. 12:464-474 (2005).
Friedmann et al., Score Result pp. 1-3, downloaded Jan. 14, 2017.
Garton et al., "Efficient Expression of Exogenous Genes in Primary Vascular Cells Using IRES-Based Retroviral Vectors," Biotechniques 32:830-843 (2002).
Hacein-Bey-Abina et al., "LMO2-associated clonal T cell proliferation intwo patients after gene therapy for SCID-X1," Science 302:415-419 (2003).
Hiavaty et al., "Effects of sequences of prokaryotic origin on titer and transgene expression in retroviral vectors," Virology 330:351-360 (2004).
Hiraoka et al., "Tumor-Selective Gene Expression in a Hepatic Metastasis Model after Locoregional Delivery of a Replication-Competent Retrovirus Vector," Clin. Cancer Res. 12(23):7108-7116 (2006).
Horn et al., "Highly efficient gene transfer into baboon marrow repopulating cells using GALV-pseudotype oncoretroviral vectors produced by human packaging cells," Blood 100:3960-3967 (2002).
Hughes, Stephen H., "The RCAS Vector System," Folia Biologics (Praha) 50(3-4):107019 (2004).
Jespersen et al., "Epression of hterologous genes from an IRES translational cassette in replication competent murine leukemia virus vectors," Gene 239(2):227-235 (1999).
Johann et al., "Definition of a domain of GLVR1 which is necessary for infection by gibbon ape leukemia virus and which is highly polymorphic between species," J. Virol. 67:6733-6736 (1993).
Kasahara et al., Three different Score results, 2008 pp. 1-10, downloaded Jan. 14, 2017.
Klein et al., "Rapid identification of viable retrovirus-transduced cells using the green fluorescent protein as a marker," Gene Ther. 4:1256-1260 (1997).
Kornblihtt et al., "Multiple links between transcription and splicing," RNA 10:1489-1498 (2004).
Kurozumi et al., "Apotosis Induction With 5-Fluorocytosine/Cytosine Deaminase gene therapy for Human Malignant Glioma Cells Mediated by Adenovirus," Journal of Neuro-Oncology 66(1-2):117-127 (2004).
Lazo et al., "Splice acceptor site for the env message of Moloney murine leukemia virus," J. Virol. 61:2038-2041 (1987).
Lipinski et al., "Optimization of a synthetic beta-catenin-dependent promoter for tumor-specific cancer gene therapy," Mol. Ther. 10:150-161 (2004).
Liu et al., "The receptors for gibbon ape leukemia virus and amphotropic murine leukemia virus are not downregulated in productively infected cells," Retrovirology 8:53 (2011).
Logg et al "A Uniquely Stable Replication-Competent Retrovirus Vector Achieves Efficient Gene Delivery in Vitro and Solid Tumors," Human Gene Therapy 12:921-932 (2001).
Logg et al., "Genomic Stability of Murine Leukemia Viruses Containing Insertions at the Env-3' Untranslated Region Boundary,"Journal of Virology 75(15):6989-6998 (2001).
Logg et al., "Retrovirus-Mediated Gene Transfer to Tumors," Methods in Molecular Biology 246:499-525 (2004).
Lu et al., "Highly efficient gene transfer to solid tumors in vivo by tumor-selective replicating retrovirus vectors," Int. J. Mol. Med. 25(5):769-75 (2010).
Malim et al., "The HIV-1 rev trans-activator acts through a structured target sequence to activate nuclear export of unspliced viral mRNA," Nature 338:254-257 (1989).
Marzio et al., "In vitro evolution of a highly replicating, doxycycline-dependent HIV for applications in vaccine studies," Proc. Natl Acad. Sci. USA 98:6342-6347 (2001).

(56) References Cited

OTHER PUBLICATIONS

Metzl et al., "Tissue- and Tumor-Specific Targeting of Murine Leukemia Virus-Based Replication-Competent Retroviral Vectors," Journal of Virology 80(14):7070-7078 (2006).
Mild et al., "Frequent intrapatient recombination between human immunodeficiency virus type 1 R5 and X4 envelopes: implications for coreceptor switch," J. Virol. 81:3369-3376 (2007).
Miller et al., "Gene transfer by retrovirus vectors occurs only in cells that are actively replicating at the time of infection," Mol. Cell. Biol. 10:4239-4242 (1990).
Miller et al., "Construction and properties of retrovirus packaging cells based on gibbon ape leukemia virus," J. Virol. 65:2220-2224 (1991).
Morgan et al., "Retroviral vectors containing putative internal ribosome entry sites: development of a polycistronic gene transfer system and applications to human gene therapy," Nucleic Acids Research 20(6):1293-1299 (1992).
Mukesh et al., "High and Selective Expression of Yeast Cytosine Deaminase Under a Carcinoembryonic Antigen Promoter-Enhancer," Cancer Res. 62:2337-2342 (2002).
Murakami et al., "High-level expression of exogenous genes by replication-competent retrovirus vectors with an internal ribosomal entry site," Gene 202:23-29 (1997).
Nack et al., "Replacement of the murine leukemia virus (MLV) envelope gene with a truncated HIV envelope gene in MLV generates a virus with impaired replication capacity," Virology 315:209-216 (2003).
Naldini et al., "Efficient transfer, integration, and sustained long-term expression of the transgene in adult rat brains injected with a lentiviral vector," Proc. Natl. Acad. Sci. USA 93:11382-11388 (1996).
Nogues et al., "Transcriptional activators differ in their abilities to control alternative splicing," J. Biol. Chem. 277:43110-43114 (2002).
O'Reilly et al., "Second-site changes affect viability of amphotropic/ecotropic chimeric enveloped murine leukemia viruses," J. Virol. 74:899-913 (2000).
Overbaugh et al., "Receptors and entry cofactors for retroviruses include single and multiple transmembrane-spanning proteins as well as newly described glycophosphatidylinositol-anchored and secreted proteins," Microbiol. Mol. Biol. Rev. 65:371-389 (2001).
Owens et al., "Human and simian immunodeficiency virus capsid proteins are major viral determinants of early, Postentry replication blocks in simian cells," J. Virol. 77:726-731 (2003).
Paar et al., "Effects of Viral Strain, Transgene Position, and Target Cell Type on Replication Kinetics, Genomic Stability and Transgene Expression of Replication-Competent Murine Leukemia Virus-Based Vectors," Journal of Virology 81(13):6973-6983 (2007).
Paar et al., "Influence of vector design and host cell on the mechanism of recombination and emergence of mutant subpopulations of replicating retroviral vectors," BMC Molecular Biology 10(8) (2009).
Pao et al., "Use of avian retroviral vectors to introduce transcriptional regulators into mammalian cells for analyses of tumor maintenance," PNAS 100(15):8764-8769 2003.
Poon et al. "Nucleocapsid and matrix protein contributions to selective human immunodeficiency virus type 1 Jenomic RNA packaging," J. Virol. 72:1983-1993 (1998).
Qiao et al. "VSV-G pseudotyped, MuLV-based, semi-replication-competent retrovirus for cancer treatment. Gene Ther," 13:1457-1470 (2006).
Rainov et al., "Clinical trials with retrovirus mediated gene therapy—what have we learned?," J. Neurooncol. 65:227-236 (2003).
Reik et al., Replication-competent Moloney murine leukemia virus carrying a bacterial suppressor tRNA gene: selective cloning of proviral and flanking host sequences. Proc. Natl. Acad. Sci. USA 82:1141-1145 (1985).
Robson et al., "Selection of optimal polypurine tract region sequences during Moloney murine leukemia virus replication," J. Virol. 74:10293-10303 (2000).
Roscigno et al., "A mutational analysis of the polypyrimidine tract of introns. Effects of sequence differences in pyrimidine tracts on splicing," J. Biol. Chem. 268:11222-11229 (1993).
Saavedra et al., "The simian retrovirus-1 constitutive transport element, unlike the HIV-1 RRE, uses factors required for cellular mRNA export," Curr. Biol. 7:619-628 (1997).
Sanders, D. A "No false start for novel pseudotyped vectors," Curr. Opin. Biotechnol. 13,437-442 (2002).
Segall et al., "Characterization and Detection of Artificial Replication-Competent Lentivirus of Altered Host Range," Molecular Therapy 8:118-129 (2003).
Shikova-Lekova et al. "Replication-competent hybrids between murine leukemia virus and foamy virus," J. Virol. 77, 7677-7681 (2003).
Shin et al., "Replication of lengthened Moloney murine leukemia virus genomes is impaired at multiple stages," J. Virol. 74:2694-2702 (2000).
Short et al., "Correlation of leukemogenic potential of murine retroviruses with transcriptional tissue preference of the viral long terminal repeats," J. Virol. 61:1067-1072 (1987).
Sliva et al., "Stable integration of a functional shRNA expression cassette into the murine leukemia virus genome," Virology 351(1):218-225 (2006).
Sodroski et al., "Repetitive structure in the long-terminal-repeat element of a type II human T-cell leukemia virus," Proc. Natl. Acad. Sci. USA 81:4617-4621. 1984.
Soifer et al., "A Novel, Helper-Dependent, Adenovirus-Retrovirus Hybrid Vector: Stable Transduction by a Two-Stage Mechanism," Molecular Therapy 5(5):599-608 (2002).
Solly et al., "Replicative retroviral vectors for cancer gene therapy," Cancer Gene Ther. 10:30-39 (2003).
Staffa et al., Identification of positive and negative splicing regulatory elements within the terminal tat-rev exon of human immunodeficiency virus type 1. Mol. Cell Biol. 15:4597-4605 (1995).
Stuhlmann et al., "Construction and properties of replication-competent murine retroviral vectors encoding methotrexate resistance," Mol. Cell. Biol. 9:100-108 (1989).
Subramanian et al., "Temperature-sensitive replication-competent adenovirus shRNA vectors to study cellular genes in virus-induced apoptosis," Methods in Molecular Medicine 130:125-134 (2007).
Sun et al., "Chronic gene delivery of interferon-inducible protein 10 through replication competent retrovirus vectors suppresses tumor growth," Cancer Gene Ther. 12:900-912 (2005).
Paola et al., "Suicide Gene Therapy With the Yeast Fusion Gene Cytosine Deaminase/Uracil Phosphoribosyltransferase is Not Enough for Pancreatic Cancer," Pancreas 35(3):224-231 (2007).
Takeuchi et al., "Type C retrovirus inactivation by human complement is determined by both the viral genome and the producer cell," J. Virol. 68: 8001-8007 (1994).

* cited by examiner

TAGTTATTAATAGTAATCAATTACGGGGTCATTAGTTCATAGCCCATATATGGAGTTCCGCGTTACATAACTTACGGTAAAT
GGCCCGCCTGGCTGACCGCCCAACGACCCCCGCCCATTGACGTCAATAATGACGTATGTTCCCATAGTAACGCCAATAGGGA
CTTTCCATTGACGTCAATGGGTGGAGTATTTACGGTAAACTGCCCACTTGGCAGTACATCAAGTGTATCATATGCCAAGTAC
GCCCCCTATTGACGTCAATGACGGTAAATGGCCCGCCTGGCATTATGCCCAGTACATGACCTTATGGGACTTTCCTACTTGG CMV promoter
CAGTACATCTACGTATTAGTCATCGCTATTACCATGGTGATGCGGTTTTGGCAGTACATCAATGGGCGTGGATAGCGGTTTG
ACTCACGGGGATTTCCAAGTCTCCACCCCATTGACGTCAATGGGAGTTTGTTTTGGCACCAAAATCAACGGGACTTTCCAAA
ATGTCGTAACAACTCCGCCCCATTGACGCAAATGGGCGGTAGGCGTGTACGGTGGGAGGTCTATATAAGCAGAGCTGGTTTA
GTGAACCGCGCCAGTCCTCCGATTGACTGAGTCGCCCGGGTACCCGTGTATCCAATAAACCCTCTTGCAGTTGCATCCGAC R
TTGTGGTCTCGCTGTTCCTTGGGAGGGTCTCCTCTGAGTGATTGACTACCCGTCAGCGGGGGTCTTTCATTTGGGGGCTCGT U5
CCGGGATCGGGAGACCCCTGCCCAGGGACCACCGACCCACCACCGGGAGGTAAGCTGGCCAGCAACTTATCTGTGTCTGTCC GT = 5'ss
GATTGTCTAGTGTCTATGACTGATTTTATGCGCCTGCGTCGGTACTAGTTAGCTAACTAGCTCTGTATCTGGCGGACCCGTG
GTGGAACTGACGAGTTCGGAACACCCGGCCGCAACCCTGGGAGACGTCCCAGGGACTTCGGGGGCCGTTTTTGTGGCCCGAC
CTGAGTCCAAAAATCCCGATCGTTTTGGACTCTTTGGTGCACCCCCCTTAGAGGAGGGATATGTGGTTCTGGTAGGAGACGA
GAACCTAAAACAGTTCCCGCCTCCGTCTGAATTTTTGCTTTCGGTTTGGGACCGAAGCCGCGCCGCGCGTCTTGTCTGCTGC
AGCATCGTTCTGTGTTGTCTCTGTCTGACTGTGTTTCTGTATTTGTCTGAGAATATGGGCCAGACTGTTACCACTCCCTTAA
GTTTGACCTTAGGTCACTGGAAAGATGTCGAGCGGATCGCTCACAACCAGTCGGTAGATGTCAAGAAGAGACGTTGGGTTAC
CTTCTGCTCTGCAGAATGGCCAACCTTTAACGTCGGATGGCCGCGAGACGGCACCTTTAACCGAGACCTCATCACCCAGGTT
AAGATCAAGGTCTTTTCACCTGGCCCGCATGGACACCCAGACCAGGTCCCCTACATCGTGACCTGGGAAGCCTTGGCTTTTG
ACCCCCCTCCCTGGGTCAAGCCCTTTGTACACCCTAAGCCTCCGCCTCCTCTTCCTCCATCCGCCCCGTCTCTCCCCCTTGA
ACCTCCTCGTTCGACCCCGCCTCGATCCTCCCTTTATCCAGCCCTCACTCCTTCTCTAGGCGCCAAACCTAAACCTCAAGTT
CTTTCTGACAGTGGGGGGCCGCTCATCGACCTACTTACAGAAGACCCCCCGCCTTATAGGGACCCAAGACCACCCCCTTCCG
ACAGGGACGGAAATGGTGGAGAAGCGACCCCTGCGGGAGAGGCACCGGACCCCTCCCCAATGGCATCTCGCCTACGTGGGAG
ACGGGAGCCCCCTGTGGCCGACTCCACTACCTCGCAGGCATTCCCCCTCCGCGCAGGAGGAAACGGACAGCTTCAATACTGG gag
CCGTTCTCCTCTTCTGACCTTTACAACTGGAAAAATAATAACCCTTCTTTTTCTGAAGATCCAGGTAAACTGACAGCTCTGA
TCGAGTCTGTTCTCATCACCCATCAGCCCACCTGGGACGACTGTCAGCAGCTGTTGGGGACTCTGCTGACCGGAGAAGAAAA
ACAACGGGTGCTCTTAGAGGCTAGAAAGGCGGTGCGGGGCGATGATGGGCGCCCCACTCAACTGCCCAATGAAGTCGATGCC
GCTTTTCCCCTCGAGCGCCCAGACTGGGATTACACCACCCAGGCAGGTAGGAACCACCTAGTCCACTATCGCCAGTTGCTCC
TAGCGGGTCTCCAAAACGCGGGCAGAAGCCCCACCAATTTGGCCAAGGTAAAAGGAATAACACAAGGGCCCAATGAGTCTCC
CTCGGCCTTCCTAGAGAGACTTAAGGAAGCCTATCGCAGGTACACTCCTTATGACCCTGAGGACCCAGGGCAAGAAACTAAT
GTGTCTATGTCTTTCATTTGGCAGTCTGCCCCAGACATTGGGAGAAAGTTAGAGAGGTTAGAAGATTTAAAAAACAAGACGC
TTGGAGATTTGGTTAGAGAGGCAGAAAAGATCTTTAATAAACGAGAAACCCCGGAAGAAAGAGAGGAACGTATCAGGAGAGA
AACAGAGGAAAAAGAGGAACGCCGTAGGACAGAGGATGAGCAGAAAGAGAAAGAAAGAGATCGTAGGAGACATAGAGAGATG
AGCAAGCTATTGGCCACTGTCGTTAGTGGACAGAAACAGGATAGACAGGGAGGAGAACGAAGGAGGTCCCAACTCGATCGCG
ACCAGTGTGCCTACTGCAAAGAAAAGGGGCACTGGGCTAAAGATTGTCCCAAGAAACCACGAGGACCTCGGGGACCAAGACC

FIGURE 1D-1

CCAGACCTCCCTCCTGACCCTAGATGACTAGGGAGGTCAGGGTCAGGAGCCCCCCCCTGAACCCAGGATAACCCTCAAAGTC
GGGGGGCAACCCGTCACCTTCCTGGTAGATACTGGGGCCCAACACTCCGTGCTGACCCAAAATCCTGGACCCCTAAGTGATA
AGTCTGCCTGGGTCCAAGGGGCTACTGGAGGAAAGCGGTATCGCTGGACCACGGATCCCAAAGTACATCTAGCTACCGGTAA
GGTCACCCACTCTTTCCTCCATGTACCAGACTGTCCCTATCCTCTGTTAGGAAGAGATTTGCTGACTAAACTAAAAGCCCAA
ATCCACTTTGAGGGATCAGGAGCCCAGGTTATGGGACCAATGGGGCAGCCCCTGCAAGTGTTGACCCTAAATATAGAAGATG
AGCATCGGCTACATGAGACCTCAAAAGAGCCAGATGTTTCTCTAGGGTCCACATGGCTGTCTGATTTTCCTCAGGCCTGGGC
GGAAACCGGGGGCATGGGACTGGCAGTTCGCCAAGCTCCTCTGATCATACCTCTGAAAGCAACCTCTACCCCCGTGTCCATA
AAACAATACCCCATGTCACAAGAAGCCAGACTGGGGATCAAGCCCCACATACAGAGACTGTTGCACCAGGGAATACTGGTAC
CCTGCCAGTCCCCCTGGAACACGCCCCTGCTACCCGTTAAGAAACCAGGGACTAATGATTATAGGCCTGTCCAGGATCTGAG
AGAAGTCAACAAGCGGGTGGAAGACATCCACCCCACCGTGCCCAACCCTTACAACCTCTTGAGCGGGCTCCCACCGTCCCAC
CAGTGGTACACTGTGCTTGATTTAAAGGATGCCTTTTTCTGCCTGAGACTCCACCCCACCAGTCAGCCTCTCTTCGCCTTTG
AGTGGAGAGATCCAGAGATGGGAATCTCAGGACAATTGACCTGGACCAGACTCCCACAGGGTTTCAAAAACAGTCCCACCCT
GTTTGATGAGGCACTGCACAGAGACCTAGCAGACTTCCGGATCCAGCACCCAGACTTGATCCTGCTACAGTACGTGGATGAC
TTACTGCTGGCCGCCACTTCTGAGCTAGACTGCCAACAAGGTACTCGGGCCCTGTTACAAACCCTAGGGAACCTCGGGTATC
GGGCCTCGGCCAAGAAAGCCCAAATTTGCCAGAAACAGGTCAAGTATCTGGGGTATCTTCTAAAAGAGGGTCAGAGATGGCT
GACTGAGGCCAGAAAAGAGACTGTGATGGGGCAGCCTACTCCGAAGACCCCTCGACAACTAAGGGAGTTCCTAGGGACGGCA
GGCTTCTGTCGCCTCTGGATCCCTGGGTTTGCAGAAATGGCAGCCCCCTTGTACCCTCTCACCAAAACGGGGACTCTGTTTA
ATTGGGGCCCAGACCAACAAAAGGCCTATCAAGAAATCAAGCAAGCTCTTCTAACTGCCCCAGCCCTGGGGTTGCCAGATTT
GACTAAGCCCTTTGAACTCTTTGTCGACGAGAAGCAGGGCTACGCCAAAGGTGTCCTAACGCAAAAACTGGGACCTTGGCGT pol
CGGCCGGTGGCCTACCTGTCCAAAAAGCTAGACCCAGTAGCAGCTGGGTGGCCCCCTTGCCTACGGATGGTAGCAGCCATTG
CCGTACTGACAAAGGATGCAGGCAAGCTAACCATGGGACAGCCACTAGTCATTCTGGCCCCCCATGCAGTAGAGGCACTAGT
CAAACAACCCCCCGACCGCTGGCTTTCCAACGCCCGGATGACTCACTATCAGGCCTTGCTTTTGGACACGGACCGGGTCCAG
TTCGGACCGGTGGTAGCCCTGAACCCGGCTACGCTGCTCCCACTGCCTGAGGAAGGGCTGCAACACAACTGCCTTGATATCC
TGGCCGAAGCCCACGGAACCCGACCCGACCTAACGGACCAGCCGCTCCCAGACGCCGACCACACCTGGTACACGGATGGAAG
CAGTCTCTTACAAGAGGGACAGCGTAAGGCGGGAGCTGCGGTGACCACCGAGACCGAGGTAATCTGGGCTAAAGCCCTGCCA
GCCGGGACATCCGCTCAGCGGGCTGAACTGATAGCACTCACCCAGGCCCTAAAGATGGCAGAAGGTAAGAAGCTAAATGTTT
ATACTGATAGCCGTTATGCTTTTGCTACTGCCCATATCCATGGAGAAATATACAGAAGGCGTGGGTTGCTCACATCAGAAGG
CAAAGAGATCAAAAATAAAGACGAGATCTTGGCCCTACTAAAAGCCCTCTTTCTGCCCAAAAGACTTAGCATAATCCATTGT
CCAGGACATCAAAAGGGACACAGCGCCGAGGCTAGAGGCAACCGGATGGCTGACCAAGCGGCCCGAAAGGCAGCCATCACAG
AGACTCCAGACACCTCTACCCTCCTCATAGAAAATTCATCACCCTACACCTCAGAACATTTTCATTACACAGTGACTGATAT

FIGURE 1D-2

AAAGGACCTAACCAAGTTGGGGCCCATTTATGATAAAACAAAGAAGTATTGGGTCTACCAAGGAAAACCTGTGATGCCTGAC
CAGTTTACTTTTGAATTATTAGACTTTCTTCATCAGCTGACTCACCTCAGCTTCTCAAAAATGAAGGCTCTCCTAGAGAGAA
GCCACAGTCCCTACTACATGCTGAACCGGATCGAACACTCAAAAATATCACTGAGACCTGCAAAGCTTGTGCACAAGTCAA
CGCCAGCAAGTCTGCCGTTAAACAGGGAACTAGGGTCCGCGGGCATCGGCCCGGCACTCATTGGGAGATCGATTTCACCGAG
ATAAAGCCCGGATTGTATGGCTATAAATATCTTCTAGTTTTTATAGATACCTTTTCTGGCTGGATAGAAGCCTTCCCAACCA
AGAAAGAAACCGCCAAGGTCGTAACCAAGAAGCTACTAGAGGAGATCTTCCCCAGGTTCGGCATGCCTCAGGTATTGGGAAC
TGACAATGGGCCTGCCTTCGTCTCCAAGGTGAGTCAGACAGTGGCCGATCTGTTGGGGATTGATTGGAAATTACATTGTGCA
TACAGACCCCAAAGCTCAGGCCAGGTAGAAAGAATGAATAGAACCATCAAGGAGACTTTAACTAAATTAACGCTTGCAACTG
GCTCTAGAGACTGGGTGCTCCTACTCCCCTTAGCCCTGTACCGAGCCCGCAACACGCCGGGCCCCCATGGCCTCACCCCATA
TGAGATCTTATATGGGGCACCCCCGCCCCTTGTAAACTTCCCTGACCCTGACATGACAAGAGTTACTAACAGCCCCTCTCTC AG = 3'ss
CAAGCTCACTTACAGGCTCTCTACTTAGTCCAGCACGAAGTCTGGAGACCTCTGGCGGCAGCCTACCAAGAACAACTGGACC
GACCGGTGGTACCTCACCCTTACCGAGTCGGCGACACAGTGTGGGTCCGCCGACACCAGACTAAGAACCTAGAACCTCGCTG
GAAAGGACCTTACACAGTCCTGCTGACCACCCCCACCGCCCTCAAAGTAGACGGCATCGCAGCTTGGATACACGCCGCCCAC
GTGAAGGCTGCCGACCCCGGGGGTGGACCATCCTCTAGACTGACATGGCGCGTTCAACGCTCTCAAAACCCCCTCAAGATAA
GATTAACCCGTGGAAGCCCTTAATAGTCATGGGAGTCCTGTTAGGAGTAGGGATGGCAGAGAGCCCCCATCAGGTCTTTAAT
GTAACCTGGAGAGTCACCAACCTGATGACTGGGCGTACCGCCAATGCCACCTCCCTCCTGGGAACTGTACAAGATGCCTTCC
CAAAATTATATTTTGATCTATGTGATCTGGTCGGAGAGGAGTGGGACCCTTCAGACCAGGAACCGTATGTCGGGTATGGCTG
CAAGTACCCCGCAGGGAGACAGCGGACCCGGACTTTTGACTTTTACGTGTGCCCTGGGCATACCGTAAAGTCGGGGTGTGGG
GGACCAGGAGAGGGCTACTGTGGTAAATGGGGGTGTGAAACCACCGGACAGGCTTACTGGAAGCCCACATCATCGTGGGACC
TAATCTCCCTTAAGCGCGGTAACACCCCCTGGGACACGGGATGCTCTAAAGTTGCCTGTGGCCCCTGCTACGACCTCTCCAA
AGTATCCAATTCCTTCCAAGGGGCTACTCGAGGGGGCAGATGCAACCCTCTAGTCCTAGAATTCACTGATGCAGGAAAAAAG
GCTAACTGGGACGGGCCCAAATCGTGGGGACTGAGACTGTACCGGACAGGAACAGATCCTATTACCATGTTCTCCCTGACCC
GGCAGGTCCTTAATGTGGGACCCCGAGTCCCCATAGGGCCCAACCCAGTATTACCCGACCAAAGACTCCCTTCCTCACCAAT
AGAGATTGTACCGGCTCCACAGCCACCTAGCCCCCTCAATACCAGTTACCCCCCTTCCACTACCAGTACACCCTCAACCTCC 4070A env
CCTACAAGTCCAAGTGTCCCACAGCCACCCCCAGGAACTGGAGATAGACTACTAGCTCTAGTCAAAGGAGCCTATCAGGCGC
TTAACCTCACCAATCCCGACAAGACCCAAGAATGTTGGCTGTGCTTAGTGTCGGGACCTCCTTATTACGAAGGAGTAGCGGT
CGTGGGCACTTATACCAATCATTCCACCGCTCCGGCCAACTGTACGGCCACTTCCCAACATAAGCTTACCCTATCTGAAGTG
ACAGGACAGGGCCTATGCATGGGGGCAGTACCTAAAACTCACCAGGCCTTATGTAACACCACCCAAAGCGCCGGCTCAGGAT
CCTACTACCTTGCAGCACCCGCCGGAACAATGTGGGCTTGCAGCACTGGATTGACTCCCTGCTTGTCCACCACGGTGCTCAA
TCTAACCACAGATTATTGTGTATTAGTTGAACTCTGGCCCAGAGTAATTTACCACTCCCCCGATTATATGTATGGTCAGCTT
GAACAGCGTACCAAATATAAAAGAGAGCCAGTATCATTGACCCTGGCCCTTCTACTAGGAGGATTAACCATGGGAGGGATTG
CAGCTGGAATAGGGACGGGGACCACTGCCTTAATTAAAACCCAGCAGTTTGAGCAGCTTCATGCCGCTATCCAGACAGACCT
CAACGAAGTCGAAAAGTCAATTACCAACCTAGAAAAGTCACTGACCTCGTTGTCTGAAGTAGTCCTACAGAACCGCAGAGGC
CTAGATTTGCTATTCCTAAAGGAGGGAGGTCTCTGCGCAGCCCTAAAAGAAGAATGTTGTTTTTATGCAGACCACACGGGGC
TAGTGAGAGACAGCATGGCCAAATTAAGAGAAAGGCTTAATCAGAGACAAAAACTATTTGAGACAGGCCAAGGATGGTTCGA
AGGGCTGTTTAATAGATCCCCCTGGTTTACCACCTTAATCTCCACCATCATGGGACCTCTAATAGTACTCTTACTGATCTTA
CTCTTTGGACCCTGCATTCTCAATCGATTGGTCCAATTTGTTAAAGACAGGATCTCAGTGGTCCAGGCTCTGGTTTTGACTC
AGCAATATCACCAGCTAAAACCCATAGAGTACGAGCCATGAACGCGTTACTGGCCGAAGCCGCTTGGAATAAGGCCGGTGTG MluI
CGTTTGTCTATATGTTATTTTCCACCATATTGCCGTCTTTTGGCAATGTGAGGGCCCGGAAACCTGGCCCTGTCTTCTTGAC
GAGCATTCCTAGGGGTCTTTCCCCTCTCGCCAAAGGAATGCAAGGTCTGTTGAATGTCGTGAAGGAAGCAGTTCCTCTGGAA
GCTTCTTGAAGACAAACAACGTCTGTAGCGACCCTTTGCAGGCAGCGGAACCCCCCACCTGGCGACAGGTGCCTCTGCGGCC EMCV IRES
AAAAGCCACGTGTATAAGATACACCTGCAAAGGCGGCACAACCCCAGTGCCACGTTGTGAGTTGGATAGTTGTGGAAAGAGT
CAAATGGCTCTCCTCAAGCGTATTCAACAAGGGGCTGAAGGATGCCCAGAAGGTACCCCATTGTATGGGATCTGATCTGGGG
CCTCGGTGCACATGCTTTACATGTGTTTAGTCGAGGTTAAAAAAACGTCTAGGCCCCCCGAACCACGGGGACGTGGTTTTCC
TTTGAAAAACACGATTATAAATGGTGACCGGCGGGATGGGCTCCAAGTGGGATCAAAAGGGCATGGATATCGCTTACGAGGA PsiI
GGCCCTGCTGGGCTACAAGGAGGGCGGCGTGCCTATCGGCGGCTGTCTGATCAACAACAAGGACGGCAGTGTGCTGGGCAGG
GGCCACAACATGAGGTTCCAGAAGGGCTCCGCCACCCTGCACGGCGAGATCTCCACCCTGGAGAACTGTGGCAGGCTGGAGG
GCAAGGTGTACAAGGACACCACCCTGTACACCACCCTGTCCCCTTGTGACATGTGTACCGGCGCTATCATCATGTACGGCAT yCD2
CCCTAGGTGTGTGATCGGCGAGAACGTGAACTTCAAGTCCAAGGGCGAGAAGTACCTGCAAACCAGGGGCCACGAGGTGGTG
GTTGTTGACGATGAGAGGTGTAAGAAGCTGATGAAGCAGTTCATCGACGAGAGGCCTCAGGACTGGTTCGAGGATATCGGCG

FIGURE 1D-3

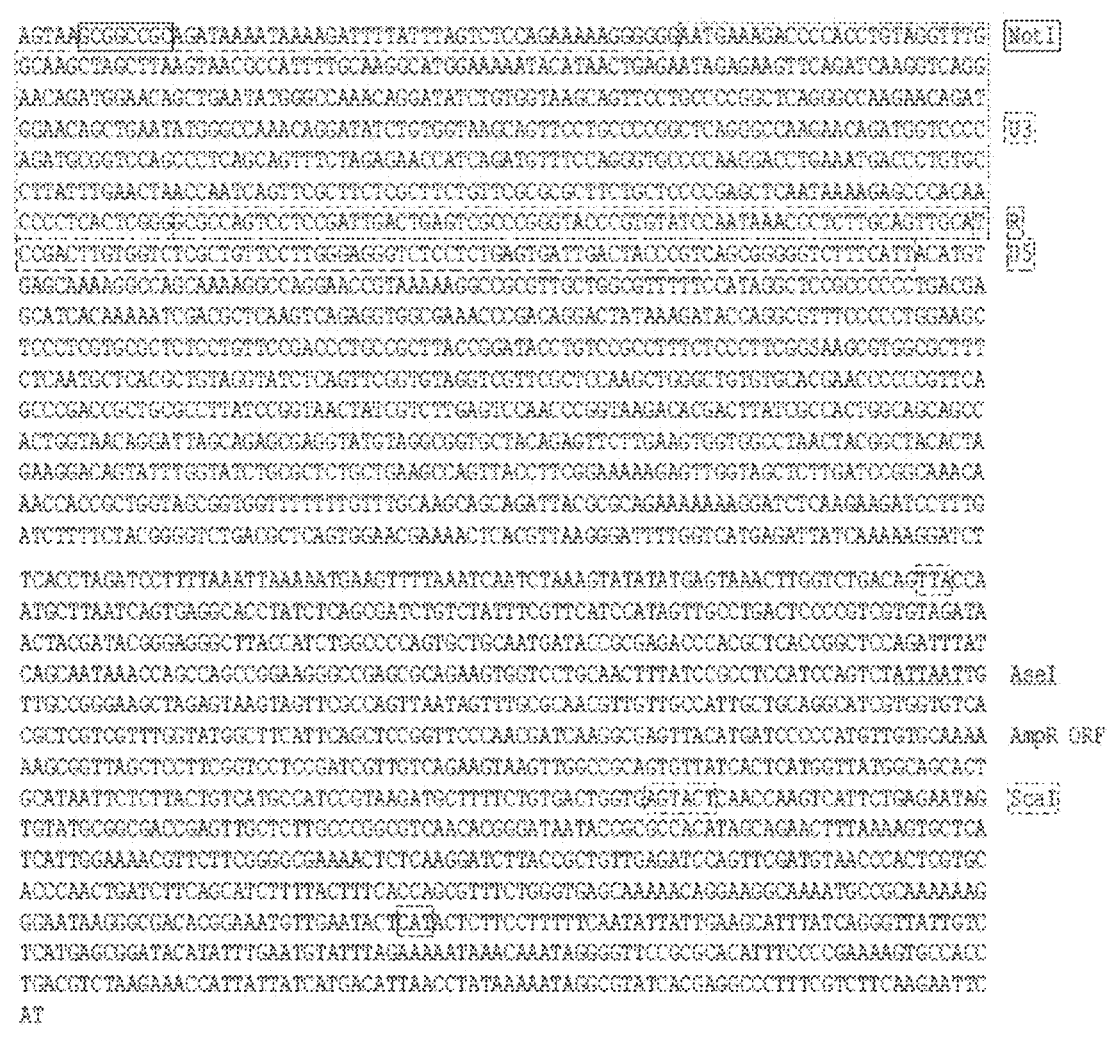

```
AGTAAGCGGCCGCAGATAAAATAAAAGATTTTATTTAGTCTCCAGAAAAAGGGGGGAATGAAAGACCCCACCTGTAGGTTTG  NotI
GCAAGCTAGCTTAAGTAACGCCATTTTGCAAGGCATGGAAAAATACATAACTGAGAATAGAGAAGTTCAGATCAAGGTCAGG
AACAGATGGAACAGCTGAATATGGGCCAAACAGGATATCTGTGGTAAGCAGTTCCTGCCCCGGCTCAGGGCCAAGAACAGAT
GGAACAGCTGAATATGGGCCAAACAGGATATCTGTGGTAAGCAGTTCCTGCCCCGGCTCAGGGCCAAGAACAGATGGTCCCC  U3
AGATGCGGTCCAGCCCTCAGCAGTTTCTAGAGAACCATCAGATGTTTCCAGGGTGCCCCAAGGACCTGAAATGACCCTGTGC
CTTATTTGAACTAACCAATCAGTTCGCTTCTCGCTTCTGTTCGCGCGCTTCTGCTCCCCGAGCTCAATAAAAGAGCCCACAA
CCCCTCACTCGGGGCGCCAGTCCTCCGATTGACTGAGTCGCCCGGGTACCCGTGTATCCAATAAACCCTCTTGCAGTTGCAT  R
CCGACTTGTGGTCTCGCTGTTCCTTGGGAGGGTCTCCTCTGAGTGATTGACTACCCGTCAGCGGGGGTCTTTCATTACATGT  U5
GAGCAAAAGGCCAGCAAAAGGCCAGGAACCGTAAAAAGGCCGCGTTGCTGGCGTTTTTCCATAGGCTCCGCCCCCCTGACGA
GCATCACAAAAATCGACGCTCAAGTCAGAGGTGGCGAAACCCGACAGGACTATAAAGATACCAGGCGTTTCCCCCTGGAAGC
TCCCTCGTGCGCTCTCCTGTTCCGACCCTGCCGCTTACCGGATACCTGTCCGCCTTTCTCCCTTCGGGAAGCGTGGCGCTTT
CTCAATGCTCACGCTGTAGGTATCTCAGTTCGGTGTAGGTCGTTCGCTCCAAGCTGGGCTGTGTGCACGAACCCCCCGTTCA
GCCCGACCGCTGCGCCTTATCCGGTAACTATCGTCTTGAGTCCAACCCGGTAAGACACGACTTATCGCCACTGGCAGCAGCC
ACTGGTAACAGGATTAGCAGAGCGAGGTATGTAGGCGGTGCTACAGAGTTCTTGAAGTGGTGGCCTAACTACGGCTACACTA
GAAGGACAGTATTTGGTATCTGCGCTCTGCTGAAGCCAGTTACCTTCGGAAAAAGAGTTGGTAGCTCTTGATCCGGCAAACA
AACCACCGCTGGTAGCGGTGGTTTTTTTGTTTGCAAGCAGCAGATTACGCGCAGAAAAAAAGGATCTCAAGAAGATCCTTTG
ATCTTTTCTACGGGGTCTGACGCTCAGTGGAACGAAAACTCACGTTAAGGGATTTTGGTCATGAGATTATCAAAAAGGATCT

TCACCTAGATCCTTTTAAATTAAAAATGAAGTTTTAAATCAATCTAAAGTATATATGAGTAAACTTGGTCTGACAGTTACCA
ATGCTTAATCAGTGAGGCACCTATCTCAGCGATCTGTCTATTTCGTTCATCCATAGTTGCCTGACTCCCCGTCGTGTAGATA
ACTACGATACGGGAGGGCTTACCATCTGGCCCCAGTGCTGCAATGATACCGCGAGACCCACGCTCACCGGCTCCAGATTTAT
CAGCAATAAACCAGCCAGCCGGAAGGGCCGAGCGCAGAAGTGGTCCTGCAACTTTATCCGCCTCCATCCAGTCTATTAATTG  AseI
TTGCCGGGAAGCTAGAGTAAGTAGTTCGCCAGTTAATAGTTTGCGCAACGTTGTTGCCATTGCTGCAGGCATCGTGGTGTCA
CGCTCGTCGTTTGGTATGGCTTCATTCAGCTCCGGTTCCCAACGATCAAGGCGAGTTACATGATCCCCCATGTTGTGCAAAA  AmpR ORF
AAGCGGTTAGCTCCTTCGGTCCTCCGATCGTTGTCAGAAGTAAGTTGGCCGCAGTGTTATCACTCATGGTTATGGCAGCACT
GCATAATTCTCTTACTGTCATGCCATCCGTAAGATGCTTTTCTGTGACTGGTGAGTACTCAACCAAGTCATTCTGAGAATAG  ScaI
TGTATGCGGCGACCGAGTTGCTCTTGCCCGGCGTCAACACGGGATAATACCGCGCCACATAGCAGAACTTTAAAAGTGCTCA
TCATTGGAAAACGTTCTTCGGGGCGAAAACTCTCAAGGATCTTACCGCTGTTGAGATCCAGTTCGATGTAACCCACTCGTGC
ACCCAACTGATCTTCAGCATCTTTTACTTTCACCAGCGTTTCTGGGTGAGCAAAAACAGGAAGGCAAAATGCCGCAAAAAAG
GGAATAAGGGCGACACGGAAATGTTGAATACTCATACTCTTCCTTTTTCAATATTATTGAAGCATTTATCAGGGTTATTGTC
TCATGAGCGGATACATATTTGAATGTATTTAGAAAAATAAACAAATAGGGGTTCCGCGCACATTTCCCCGAAAAGTGCCACC
TGACGTCTAAGAAACCATTATTATCATGACATTAACCTATAAAAATAGGCGTATCACGAGGCCCTTTCGTCTTCAAGAATTC
AT
```

FIGURE 1D-4

```
     CMV Promotor (1-582)>>>
     |
1    TAGTTATTAATAGTAATCAATTACGGGGTCATTAGTTCATAGCCCATATATGGAGTTCCG 60
     ATCAATAATTATCATTAGTTAATGCCCCAGTAATCAAGTATCGGGTATATACCTCAAGGC

61   CGTTACATAACTTACGGTAAATGGCCCGCCTGGCTGACCGCCCAACGACCCCCGCCCATT 120
     GCAATGTATTGAATGCCATTTACCGGGCGGACCGACTGGCGGGTTGCTGGGGGCGGGTAA

121  GACGTCAATAATGACGTATGTTCCCATAGTAACGCCAATAGGGACTTTCCATTGACGTCA 180
     CTGCAGTTATTACTGCATACAAGGGTATCATTGCGGTTATCCCTGAAAGGTAACTGCAGT

181  ATGGGTGGAGTATTTACGGTAAACTGCCCACTTGGCAGTACATCAAGTGTATCATATGCC 240
     TACCCACCTCATAAATGCCATTTGACGGGTGAACCGTCATGTAGTTCACATAGTATACGG

241  AAGTACGCCCCCTATTGACGTCAATGACGGTAAATGGCCCGCCTGGCATTATGCCCAGTA 300
     TTCATGCGGGGGATAACTGCAGTTACTGCCATTTACCGGGCGGACCGTAATACGGGTCAT

                                             Eco105I
                                             |
                                             SnaBI
                                             |
                                             BstSNI
                                             |
301  CATGACCTTATGGGACTTTCCTACTTGGCAGTACATCTACGTATTAGTCATCGCTATTAC 360
     GTACTGGAATACCCTGAAAGGATGAACCGTCATGTAGATGCATAATCAGTAGCGATAATG

361  CATGGTGATGCGGTTTTGGCAGTACATCAATGGGCGTGGATAGCGGTTTGACTCACGGGG 420
     GTACCACTACGCCAAAACCGTCATGTAGTTACCCGCACCTATCGCCAAACTGAGTGCCCC

421  ATTTCCAAGTCTCCACCCCATTGACGTCAATGGGAGTTTGTTTTGGCACCAAAATCAACG 480
     TAAAGGTTCAGAGGTGGGGTAACTGCAGTTACCCTCAAACAAAACCGTGGTTTTAGTTGC

481  GGACTTTCCAAAATGTCGTAACAACTCCGCCCCATTGACGCAAATGGGCGGTAGGCGTGT 540
     CCTGAAAGGTTTTACAGCATTGTTGAGGCGGGGTAACTGCGTTTACCCGCCATCCGCACA

                                              R region (583-650)>>>
                                              |
541  ACGGTGGGAGGTCTATATAAGCAGAGCTGGTTTAGTGAACCGGCGCCAGTCCTCCGATTG 600
     TGCCACCCTCCAGATATATTCGTCTCGACCAAATCACTTGGCCGCGGTCAGGAGGCTAAC
```

FIGURE 1D-5

```
                                                       U5 region (651-1202)>>>
                                                        |
601   ACTGAGTCGCCCGGGTACCCGTGTATCCAATAAACCCTCTTGCAGTTGCATCCGACTTGT 660
      TGACTCAGCGGGCCCATGGGCACATAGGTTATTTGGGAGAACGTCAACGTAGGCTGAACA

661   GGTCTCGCTGTTCCTTGGGAGGGTCTCCTCTGAGTGATTGACTACCCGTCAGCGGGGGTC 720
      CCAGAGCGACAAGGAACCCTCCCAGAGGAGACTCACTAACTGATGGGCAGTCGCCCCCAG

721   TTTCATTTGGGGGCTCGTCCGGGATCGGGAGACCCCTGCCCAGGGACCACCGACCCACCA 780
      AAAGTAAACCCCCGAGCAGGCCCTAGCCCTCTGGGGACGGGTCCCTGGTGGCTGGGTGGT

           5'SS (788)
           |
781   CCGGGAGGTAAGCTGGCCAGCAACTTATCTGTGTCTGTCCGATTGTCTAGTGTCTATGAC 840
      GGCCCTCCATTCGACCGGTCGTTGAATAGACACAGACAGGCTAACAGATCACAGATACTG

841   TGATTTTATGCGCCTGCGTCGGTACTAGTTAGCTAACTAGCTCTGTATCTGGCGGACCCG 900
```

FIGURE 1D-6

```
     ACTAAAATACGCGGACGCAGCCATGATCAATCGATTGATCGAGACATAGACCGCCTGGGC

901  TGGTGGAACTGACGAGTTCGGAACACCCGGCCGCAACCCTGGGAGACGTCCCAGGGACTT 960
     ACCACCTTGACTGCTCAAGCCTTGTGGGCCGGCGTTGGGACCCTCTGCAGGGTCCCTGAA

961  CGGGGGCCGTTTTTGTGGCCCGACCTGAGTCCAAAAATCCCGATCGTTTTGGACTCTTTG 1020
     GCCCCCGGCAAAAACACCGGGCTGGACTCAGGTTTTTAGGGCTAGCAAAACCTGAGAAAC

1021 GTGCACCCCCCTTAGAGGAGGGATATGTGGTTCTGGTAGGAGACGAGAACCTAAAACAGT 1080
     CACGTGGGGGGAATCTCCTCCCTATACACCAAGACCATCCTCTGCTCTTGGATTTTGTCA

1081 TCCCGCCTCCGTCTGAATTTTTGCTTTCGGTTTGGGACCGAAGCCGCGCCGCGCGTCTTG 1140
     AGGGCGGAGGCAGACTTAAAAACGAAAGCCAAACCCTGGCTTCGGCGCGGCGCGCAGAAC

1141 TCTGCTGCAGCATCGTTCTGTGTTGTCTCTGTCTGACTGTGTTTCTGTATTTGTCTGAGA 1200
     AGACGACGTCGTAGCAAGACACAACAGAGACAGACTGACACAAAGACATAAACAGACTCT

       gag(1203,2819)>>>
       |
1201 ATATGGGCCAGACTGTTACCACTCCCTTAAGTTTGACCTTAGGTCACTGGAAAGATGTCG 1260
     TATACCCGGTCTGACAATGGTGAGGGAATTCAAACTGGAATCCAGTGACCTTTCTACAGC

1261 AGCGGATCGCTCACAACCAGTCGGTAGATGTCAAGAAGAGACGTTGGGTTACCTTCTGCT 1320
     TCGCCTAGCGAGTGTTGGTCAGCCATCTACAGTTCTTCTCTGCAACCCAATGGAAGACGA

1321 CTGCAGAATGGCCAACCTTTAACGTCGGATGGCCGCGAGACGGCACCTTTAACCGAGACC 1380
     GACGTCTTACCGGTTGGAAATTGCAGCCTACCGGCGCTCTGCCGTGGAAATTGGCTCTGG

1381 TCATCACCCAGGTTAAGATCAAGGTCTTTTCACCTGGCCCGCATGGACACCCAGACCAGG 1440
     AGTAGTGGGTCCAATTCTAGTTCCAGAAAAGTGGACCGGGCGTACCTGTGGGTCTGGTCC

1441 TCCCCTACATCGTGACCTGGGAAGCCTTGGCTTTTGACCCCCCTCCCTGGGTCAAGCCCT 1500
     AGGGGATGTAGCACTGGACCCTTCGGAACCGAAAACTGGGGGGAGGGACCCAGTTCGGGA

1501 TTGTACACCCTAAGCCTCCGCCTCCTCTTCCTCCATCCGCCCCGTCTCTCCCCCTTGAAC 1560
     AACATGTGGGATTCGGAGGCGGAGGAGAAGGAGGTAGGCGGGGCAGAGAGGGGGAACTTG

1561 CTCCTCGTTCGACCCCGCCTCGATCCTCCCTTTATCCAGCCCTCACTCCTTCTCTAGGCG 1620
     GAGGAGCAAGCTGGGGCGGAGCTAGGAGGGAAATAGGTCGGGAGTGAGGAAGAGATCCGC

1621 CCAAACCTAAACCTCAAGTTCTTTCTGACAGTGGGGGGCCGCTCATCGACCTACTTACAG 1680
     GGTTTGGATTTGGAGTTCAAGAAAGACTGTCACCCCCCGGCGAGTAGCTGGATGAATGTC

1681 AAGACCCCCCGCCTTATAGGGACCCAAGACCACCCCCTTCCGACAGGGACGGAAATGGTG 1740
     TTCTGGGGGGCGGAATATCCCTGGGTTCTGGTGGGGGAAGGCTGTCCCTGCCTTTACCAC
```

FIGURE 1D-7

```
1741  GAGAAGCGACCCCTGCGGGAGAGGCACCGGACCCCTCCCCAATGGCATCTCGCCTACGTG 1800
      CTCTTCGCTGGGGACGCCCTCTCCGTGGCCTGGGGAGGGGTTACCGTAGAGCGGATGCAC

1801  GGAGACGGGAGCCCCCTGTGGCCGACTCCACTACCTCGCAGGCATTCCCCCTCCGCGCAG 1860
      CCTCTGCCCTCGGGGGACACCGGCTGAGGTGATGGAGCGTCCGTAAGGGGGAGGCGCGTC

1861  GAGGAAACGGACAGCTTCAATACTGGCCGTTCTCCTCTTCTGACCTTTACAACTGGAAAA 1920
      CTCCTTTGCCTGTCGAAGTTATGACCGGCAAGAGGAGAAGACTGGAAATGTTGACCTTTT

1921  ATAATAACCCTTCTTTTTCTGAAGATCCAGGTAAACTGACAGCTCTGATCGAGTCTGTTC 1980
      TATTATTGGGAAGAAAAAGACTTCTAGGTCCATTTGACTGTCGAGACTAGCTCAGACAAG

1981  TCATCACCCATCAGCCCACCTGGGACGACTGTCAGCAGCTGTTGGGGACTCTGCTGACCG 2040
      AGTAGTGGGTAGTCGGGTGGACCCTGCTGACAGTCGTCGACAACCCCTGAGACGACTGGC

3121  ACTTTGAGGGATCAGGAGCCCAGGTTATGGGACCAATGGGGCAGCCCCTGCAAGTGTTGA 3180
      TGAAACTCCCTAGTCCTCGGGTCCAATACCCTGGTTACCCCGTCGGGGACGTTCACAACT

3181  CCCTAAATATAGAAGATGAGCATCGGCTACATGAGACCTCAAAAGAGCCAGATGTTTCTC 3240
      GGGATTTATATCTTCTACTCGTAGCCGATGTACTCTGGAGTTTTCTCGGTCTACAAAGAG

3241  TAGGGTCCACATGGCTGTCTGATTTTCCTCAGGCCTGGGCGGAAACCGGGGGCATGGGAC 3300
      ATCCCAGGTGTACCGACAGACTAAAAGGAGTCCGGACCCGCCTTTGGCCCCCGTACCCTG

                     3'SS (3314)
                      |
3301  TGGCAGTTCGCCAAGCTCCTCTGATCATACCTCTGAAAGCAACCTCTACCCCCGTGTCCA 3360
      ACCGTCAAGCGGTTCGAGGAGACTAGTATGGAGACTTTCGTTGGAGATGGGGGCACAGGT

3361  TAAAACAATACCCCATGTCACAAGAAGCCAGACTGGGGATCAAGCCCCACATACAGAGAC 3420
      ATTTTGTTATGGGGTACAGTGTTCTTCGGTCTGACCCCTAGTTCGGGGTGTATGTCTCTG

3421  TGTTGGACCAGGGAATACTGGTACCCTGCCAGTCCCCCTGGAACACGCCCCTGCTACCCG 3480
      ACAACCTGGTCCCTTATGACCATGGGACGGTCAGGGGGACCTTGTGCGGGGACGATGGGC

3481  TTAAGAAACCAGGGACTAATGATTATAGGCCTGTCCAGGATCTGAGAGAAGTCAACAAGC 3540
      AATTCTTTGGTCCCTGATTACTAATATCCGGACAGGTCCTAGACTCTCTTCAGTTGTTCG

3541  GGGTGGAAGACATCCACCCCACCGTGCCCAACCCTTACAACCTCTTGAGCGGGCTCCCAC 3600
      CCCACCTTCTGTAGGTGGGGTGGCACGGGTTGGGAATGTTGGAGAACTCGCCCGAGGGTG

3601  CGTCCCACCAGTGGTACACTGTGCTTGATTTAAAGGATGCCTTTTTCTGCCTGAGACTCC 3660
      GCAGGGTGGTCACCATGTGACACGAACTAAATTTCCTACGGAAAAAGACGGACTCTGAGG

                                                            PfeI
                                                             |
                                                            TfiI
                                                             |
3661  ACCCCACCAGTCAGCCTCTCTTCGCCTTTGAGTGGAGAGATCCAGAGATGGGAATCTCAG 3720
      TGGGGTGGTCAGTCGGAGAGAAGCGGAAACTCACCTCTCTAGGTCTCTACCCTTAGAGTC
```

FIGURE 1D-8

```
          MfeI
          |
          MunI
          |
3721  GACAATTGACCTGGACCAGACTCCCACAGGGTTTCAAAAACAGTCCCACCCTGTTTGATG 3780
      CTGTTAACTGGACCTGGTCTGAGGGTGTCCCAAAGTTTTTGTCAGGGTGGGACAAACTAC

                                  MroI
                                  |
                                  BseAI
                                  |
                                  Bsp13I
                                  |
                                  BspEI
                                  |
                                  Kpn2I
                                  |
                                  AccIII
                                  |
3781  AGGCACTGCACAGAGACCTAGCAGACTTCCGGATCCAGCACCCAGACTTGATCCTGCTAC 3840
      TCCGTGACGTGTCTCTGGATCGTCTGAAGGCCTAGGTCGTGGGTCTGAACTAGGACGATG

3841  AGTACGTGGATGACTTACTGCTGGCCGCCACTTCTGAGCTAGACTGCCAACAAGGTACTC 3900
      TCATGCACCTACTGAATGACGACCGGCGGTGAAGACTCGATCTGACGGTTGTTCCATGAG

3121  ACTTTGAGGGATCAGGAGCCCAGGTTATGGACCAATGGGGCAGCCCCTGCAAGTGTTGA 3180
      TGAAACTCCCTAGTCCTCGGGTCCAATACCTGGTTACCCCGTCGGGGACGTTCACAACT

3181  CCCTAAATATAGAAGATGAGCATCGGCTACATGAGACCTCAAAAGAGCCAGATGTTTCTC 3240
      GGGATTTATATCTTCTACTCGTAGCCGATGTACTCTGGAGTTTTCTCGGTCTACAAAGAG

3241  TAGGGTCCACATGGCTGTCTGATTTTCCTCAGGCCTGGGCGGAAACCGGGGGCATGGGAC 3300
      ATCCCAGGTGTACCGACAGACTAAAAGGAGTCCGGACCCGCCTTTGGCCCCCGTACCCTG

                  3'SS (3314)
                  |
3301  TGGCAGTTCGCCAAGCTCCTCTGATCATACCTCTGAAAGCAACCTCTACCCCCGTGTCCA 3360
      ACCGTCAAGCGGTTCGAGGAGACTAGTATGGAGACTTTCGTTGGAGATGGGGGCACAGGT

3361  TAAAACAATACCCCATGTCACAAGAAGCCAGACTGGGGATCAAGCCCCACATACAGAGAC 3420
      ATTTTGTTATGGGGTACAGTGTTCTTCGGTCTGACCCCTAGTTCGGGGTGTATGTCTCTG

3421  TGTTGGACCAGGGAATACTGGTACCCTGCCAGTCCCCCTGGAACACGCCCCTGCTACCCG 3480
      ACAACCTGGTCCCTTATGACCATGGGACGGTCAGGGGGACCTTGTGCGGGGACGATGGGC

3481  TTAAGAAACCAGGGACTAATGATTATAGGCCTGTCCAGGATCTGAGAGAAGTCAACAAGC 3540
      AATTCTTTGGTCCCTGATTACTAATATCCGGACAGGTCCTAGACTCTCTTCAGTTGTTCG
```

FIGURE 1D-9

```
3541  GGGTGGAAGACATCCACCCCACCGTGCCCAACCCTTACAACCTCTTGAGCGGGCTCCCAC 3600
      CCCACCTTCTGTAGGTGGGGTGGCACGGGTTGGGAATGTTGGAGAACTCGCCCGAGGGTG

3601  CGTCCCACCAGTGGTACACTGTGCTTGATTTAAAGGATGCCTTTTTCTGCCTGAGACTCC 3660
      GCAGGGTGGTCACCATGTGACACGAACTAAATTTCCTACGGAAAAAGACGGACTCTGAGG

                                                             PfeI
                                                             |
                                                             TfiI
                                                             |
3661  ACCCCACCAGTCAGCCTCTCTTCGCCTTTGAGTGGAGAGATCCAGAGATGGGAATCTCAG 3720
      TGGGGTGGTCAGTCGGAGAGAAGCGGAAACTCACCTCTCTAGGTCTCTACCCTTAGAGTC

         MfeI
         |
         MunI
         |
3721  GACAATTGACCTGGACCAGACTCCCACAGGGTTTCAAAAACAGTCCCACCCTGTTTGATG 3780
      CTGTTAACTGGACCTGGTCTGAGGGTGTCCCAAAGTTTTTGTCAGGGTGGGACAAACTAC

                                MroI
                                |
                                BseAI
                                |
                                Bsp13I
                                |
                                BspEI
                                |
                                Kpn2I
                                |
                                AccIII
                                |
3781  AGGCACTGCACAGAGACCTAGCAGACTTCCGGATCCAGCACCCAGACTTGATCCTGCTAC 3840
      TCCGTGACGTGTCTCTGGATCGTCTGAAGGCCTAGGTCGTGGGTCTGAACTAGGACGATG

3841  AGTACGTGGATGACTTACTGCTGGCCGCCACTTCTGAGCTAGACTGCCAACAAGGTACTC 3900
      TCATGCACCTACTGAATGACGACCGGCGGTGAAGACTCGATCTGACGGTTGTTCCATGAG
```

FIGURE 1D-10

```
3901 GGGCCCTGTTACAAACCCTAGGGAACCTCGGGTATCGGGCCTCGGCCAAGAAAGCCCAAA 3960
     CCCGGGACAATGTTTGGGATCCCTTGGAGCCCATAGCCCGGAGCCGGTTCTTTCGGGTTT

3961 TTTGCCAGAAACAGGTCAAGTATCTGGGGTATCTTCTAAAAGAGGGTCAGAGATGGCTGA 4020
     AAACGGTCTTTGTCCAGTTCATAGACCCCATAGAAGATTTTCTCCCAGTCTCTACCGACT

4021 CTGAGGCCAGAAAAGAGACTGTGATGGGGCAGCCTACTCCGAAGACCCCTCGACAACTAA 4080
     GACTCCGGTCTTTTCTCTGACACTACCCCGTCGGATGAGGCTTCTGGGGAGCTGTTGATT

4081 GGGAGTTCCTAGGGACGGCAGGCTTCTGTCGCCTCTGGATCCCTGGGTTTGCAGAAATGG 4140
     CCCTCAAGGATCCCTGCCGTCCGAAGACAGCGGAGACCTAGGGACCCAAACGTCTTTACC

4141 CAGCCCCCTTGTACCCTCTCACCAAAACGGGGACTCTGTTTAATTGGGGCCCAGACCAAC 4200
     GTCGGGGGAACATGGGAGAGTGGTTTTGCCCCTGAGACAAATTAACCCCGGGTCTGGTTG

4201 AAAAGGCCTATCAAGAAATCAAGCAAGCTCTTCTAACTGCCCCAGCCCTGGGGTTGCCAG 4260
     TTTTCCGGATAGTTCTTTAGTTCGTTCGAGAAGATTGACGGGGTCGGGACCCCAACGGTC

                                           SalI
                                           |
4261 ATTTGACTAAGCCCTTTGAACTCTTTGTCGACGAGAAGCAGGGCTACGCCAAAGGTGTCC 4320
     TAAACTGATTCGGGAAACTTGAGAAACAGCTGCTCTTCGTCCCGATGCGGTTTCCACAGG

4321 TAACGCAAAAACTGGGACCTTGGCGTCGGCCGGTGGCCTACCTGTCCAAAAAGCTAGACC 4380
     ATTGCGTTTTTGACCCTGGAACCGCAGCCGGCCACCGGATGGACAGGTTTTTCGATCTGG

4381 CAGTAGCAGCTGGGTGGCCCCCTTGCCTACGGATGGTAGCAGCCATTGCCGTACTGACAA 4440
     GTCATCGTCGACCCACCGGGGGAACGGATGCCTACCATCGTCGGTAACGGCATGACTGTT

4441 AGGATGCAGGCAAGCTAACCATGGGACAGCCACTAGTCATTCTGGCCCCCCATGCAGTAG 4500
     TCCTACGTCCGTTCGATTGGTACCCTGTCGGTGATCAGTAAGACCGGGGGGTACGTCATC

4501 AGGCACTAGTCAAACAACCCCCCGACCGCTGGCTTTCCAACGCCCGGATGACTCACTATC 4560
     TCCGTGATCAGTTTGTTGGGGGGCTGGCGACCGAAAGGTTGCGGGCCTACTGAGTGATAG

4561 AGGCCTTGCTTTTGGACACGGACCGGGTCCAGTTCGGACCGGTGGTAGCCCTGAACCCGG 4620
     TCCGGAACGAAAACCTGTGCCTGGCCCAGGTCAAGCCTGGCCACCATCGGGACTTGGGCC

4621 CTACGCTGCTCCCACTGCCTGAGGAAGGGCTGCAACACAACTGCCTTGATATCCTGGCCG 4680
     GATGCGACGAGGGTGACGGACTCCTTCCCGACGTTGTGTTGACGGAACTATAGGACCGGC

4681 AAGCCCACGGAACCCGACCCGACCTAACGGACCAGCCGCTCCCAGACGCCGACCACACCT 4740
     TTCGGGTGCCTTGGGCTGGGCTGGATTGCCTGGTCGGCGAGGGTCTGCGGCTGGTGTGGA

4741 GGTACACGGATGGAAGCAGTCTCTTACAAGAGGGACAGCGTAAGGCGGGAGCTGCGGTGA 4800
     CCATGTGCCTACCTTCGTCAGAGAATGTTCTCCCTGTCGCATTCCGCCCTCGACGCCACT
```

FIGURE 1D-11

```
                                                          BlpI
                                                          |
                                                          CelII
                                                          |
                                                          Bpu1102I
                                                          |
                                                          Bsp1720I
                                                          |
4801  CCACCGAGACCGAGGTAATCTGGGCTAAAGCCCTGCCAGCCGGGACATCCGCTCAGCGGG 4860
      GGTGGCTCTGGCTCCATTAGACCCGATTTCGGGACGGTCGGCCCTGTAGGCGAGTCGCCC

4861  CTGAACTGATAGCACTCACCCAGGCCCTAAAGATGGCAGAAGGTAAGAAGCTAAATGTTT 4920
      GACTTGACTATCGTGAGTGGGTCCGGGATTTCTACCGTCTTCCATTCTTCGATTTACAAA

4921  ATACTGATAGCCGTTATGCTTTTGCTACTGCCCATATCCATGGAGAAATATACAGAAGGC 4980
      TATGACTATCGGCAATACGAAAACGATGACGGGTATAGGTACCTCTTTATATGTCTTCCG

4981  GTGGGTTGCTCACATCAGAAGGCAAAGAGATCAAAAATAAAGACGAGATCTTGGCCCTAC 5040
      CACCCAACGAGTGTAGTCTTCCGTTTCTCTAGTTTTTATTTCTGCTCTAGAACCGGGATG

5041  TAAAAGCCCTCTTTCTGCCCAAAAGACTTAGCATAATCCATTGTCCAGGACATCAAAAGG 5100
      ATTTTCGGGAGAAAGACGGGTTTTCTGAATCGTATTAGGTAACAGGTCCTGTAGTTTTCC

5101  GACACAGCGCCGAGGCTAGAGGCAACCGGATGGCTGACCAAGCGGCCCGAAAGGCAGCCA 5160
      CTGTGTCGCGGCTCCGATCTCCGTTGGCCTACCGACTGGTTCGCCGGGCTTTCCGTCGGT

5161  TCACAGAGACTCCAGACACCTCTACCCTCCTCATAGAAAATTCATCACCCTACACCTCAG 5220
      AGTGTCTCTGAGGTCTGTGGAGATGGGAGGAGTATCTTTTAAGTAGTGGGATGTGGAGTC

5221  AACATTTTCATTACACAGTGACTGATATAAAGGACCTAACCAAGTTGGGGGCCATTTATG 5280
      TTGTAAAAGTAATGTGTCACTGACTATATTTCCTGGATTGGTTCAACCCCCGGTAAATAC

5281  ATAAAACAAAGAAGTATTGGGTCTACCAAGGAAAACCTGTGATGCCTGACCAGTTTACTT 5340
      TATTTTGTTTCTTCATAACCCAGATGGTTCCTTTTGGACACTACGGACTGGTCAAATGAA

5341  TTGAATTATTAGACTTTCTTCATCAGCTGACTCACCTCAGCTTCTCAAAAATGAAGGCTC 5400
      AACTTAATAATCTGAAAGAAGTAGTCGACTGAGTGGAGTCGAAGAGTTTTTACTTCCGAG

5401  TCCTAGAGAGAAGCCACAGTCCCTACTACATGCTGAACCGGGATCGAACACTCAAAAATA 5460
      AGGATCTCTCTTCGGTGTCAGGGATGATGTACGACTTGGCCCTAGCTTGTGAGTTTTTAT
```

FIGURE 1D-12

```
5461  TCACTGAGACCTGCAAAGCTTGTGCACAAGTCAACGCCAGCAAGTCTGCCGTTAAACAGG 5520
      AGTGACTCTGGACGTTTCGAACACGTGTTCAGTTGCGGTCGTTCAGACGGCAATTTGTCC

                         SacII
                         |
                         SgrBI
                         |
                         Cfr42I
                         |
                         Sfr303I
                         |
                         KspI
                         |
5521  GAACTAGGGTCCGCGGGCATCGGCCCGGCACTCATTGGGAGATCGATTTCACCGAGATAA 5580
      CTTGATCCCAGGCGCCCGTAGCCGGGCCGTGAGTAACCCTCTAGCTAAAGTGGCTCTATT

5581  AGCCCGGATTGTATGGCTATAAATATCTTCTAGTTTTTATAGATACCTTTTCTGGCTGGA 5640
      TCGGGCCTAACATACCGATATTTATAGAAGATCAAAAATATCTATGGAAAAGACCGACCT

5641  TAGAAGCCTTCCCAACCAAGAAAGAAACCGCCAAGGTCGTAACCAAGAAGCTACTAGAGG 5700
      ATCTTCGGAAGGGTTGGTTCTTTCTTTGGCGGTTCCAGCATTGGTTCTTCGATGATCTCC

                              PaeI
                              |
                              BbuI
                              |
                              SpaHI
                              |
                              SphI
                              |
5701  AGATCTTCCCCAGGTTCGGCATGCCTCAGGTATTGGGAACTGACAATGGGCCTGCCTTCG 5760
      TCTAGAAGGGGTCCAAGCCGTACGGAGTCCATAACCCTTGACTGTTACCCGGACGGAAGC

6901  CTTCCAAGGGGCTACTCGAGGGGGCAGATGCAACCCTCTAGTCCTAGAATTCACTGATGC 6960
      GAAGGTTCCCCGATGAGCTCCCCCGTCTACGTTGGGAGATCAGGATCTTAAGTGACTACG

6961  AGGAAAAAAGGCTAACTGGGACGGGCCCAAATCGTGGGGACTGAGACTGTACCGGACAGG 7020
      TCCTTTTTTCCGATTGACCCTGCCCGGGTTTAGCACCCCTGACTCTGACATGGCCTGTCC

7021  AACAGATCCTATTACCATGTTCTCCCTGACCCGGCAGGTCCTTAATGTGGGACCCCGAGT 7080
      TTGTCTAGGATAATGGTACAAGAGGGACTGGGCCGTCCAGGAATTACACCCTGGGGCTCA

7081  CCCCATAGGGCCCAACCCAGTATTACCCGACCAAAGACTCCCTTCCTCACCAATAGAGAT 7140
      GGGGTATCCCGGGTTGGGTCATAATGGGCTGGTTTCTGAGGGAAGGAGTGGTTATCTCTA

7141  TGTACCGGCTCCACAGCCACCTAGCCCCCTCAATACCAGTTACCCCCCTTCCACTACCAG 7200
      ACATGGCCGAGGTGTCGGTGGATCGGGGGAGTTATGGTCAATGGGGGGAAGGTGATGGTC

7201  TACACCCTCAACCTCCCCTACAAGTCCAAGTGTCCCACAGCCACCCCCAGGAACTGGAGA 7260
      ATGTGGGAGTTGGAGGGGATGTTCAGGTTCACAGGGTGTCGGTGGGGGTCCTTGACCTCT

7261  TAGACTACTAGCTCTAGTCAAAGGAGCCTATCAGGCGCTTAACCTCACCAATCCCGACAA 7320
      ATCTGATGATCGAGATCAGTTTCCTCGGATAGTCCGCGAATTGGAGTGGTTAGGGCTGTT
```

FIGURE 1D-13

```
7321  GACCCAAGAATGTTGGCTGTGCTTAGTGTCGGGACCTCCTTATTACGAAGGAGTAGCGGT 7380
      CTGGGTTCTTACAACCGACACGAATCACAGCCCTGGAGGAATAATGCTTCCTCATCGCCA

7381  CGTGGGCACTTATACCAATCATTCCACCGCTCCGGCCAACTGTACGGCCACTTCCCAACA 7440
      GCACCCGTGAATATGGTTAGTAAGGTGGCGAGGCCGGTTGACATGCCGGTGAAGGGTTGT

                                                    EcoT22I
                                                    |
                                                    NsiI
                                                    |
                                                    Mph1103I
                                                    |
                                                    Zsp2I
                                                    |
                                                  BfrBI
                                                  | |
7441  TAAGCTTACCCTATCTGAAGTGACAGGACAGGGCCTATGCATGGGGGCAGTACCTAAAAC 7500
      ATTCGAATGGGATAGACTTCACTGTCCTGTCCCGGATACGTACCCCCGTCATGGATTTTG

                                          NaeI
                                          |
                                          PdiI
                                          |
                                        MroNI
                                        | |
                                        NgoMIV
                                        | |
7501  TCACCAGGCCTTATGTAACACCACCCAAAGCGCCGGCTCAGGATCCTACTACCTTGCAGC 7560
      AGTGGTCCGGAATACATTGTGGTGGGTTTCGCGGCCGAGTCCTAGGATGATGGAACGTCG

                                                           AleI
                                                           |
                                                           OliI
                                                           |
7561  ACCCGCCGGAACAATGTGGGCTTGCAGCACTGGATTGACTCCCTGCTTGTCCACCACGGT 7620
      TGGGCGGCCTTGTTACACCCGAACGTCGTGACCTAACTGAGGGACGAACAGGTGGTGCCA

7621  GCTCAATCTAACCACAGATTATTGTGTATTAGTTGAACTCTGGCCCAGAGTAATTTACCA 7680
      CGAGTTAGATTGGTGTCTAATAACACATAATCAACTTGAGACCGGGTCTCATTAAATGGT
```

FIGURE 1D-14

```
6901  CTTCCAAGGGGCTACTCGAGGGGGCAGATGCAACCCTCTAGTCCTAGAATTCACTGATGC 6960
      GAAGGTTCCCCGATGAGCTCCCCCGTCTACGTTGGGAGATCAGGATCTTAAGTGACTACG

6961  AGGAAAAAAGGCTAACTGGGACGGGCCCAAATCGTGGGGACTGAGACTGTACCGGACAGG 7020
      TCCTTTTTTCCGATTGACCCTGCCCGGGTTTAGCACCCCTGACTCTGACATGGCCTGTCC

7021  AACAGATCCTATTACCATGTTCTCCCTGACCCGGCAGGTCCTTAATGTGGGACCCCGAGT 7080
      TTGTCTAGGATAATGGTACAAGAGGGACTGGGCCGTCCAGGAATTACACCCTGGGGCTCA

7081  CCCCATAGGGCCCAACCCAGTATTACCCGACCAAAGACTCCCTTCCTCACCAATAGAGAT 7140
      GGGGTATCCCGGGTTGGGTCATAATGGGCTGGTTTCTGAGGGAAGGAGTGGTTATCTCTA

7141  TGTACCGGCTCCACAGCCACCTAGCCCCCTCAATACCAGTTACCCCCCTTCCACTACCAG 7200
      ACATGGCCGAGGTGTCGGTGGATCGGGGGAGTTATGGTCAATGGGGGGAAGGTGATGGTC

7201  TACACCCTCAACCTCCCCTACAAGTCCAAGTGTCCCACAGCCACCCCCAGGAACTGGAGA 7260
      ATGTGGGAGTTGGAGGGGATGTTCAGGTTCACAGGGTGTCGGTGGGGGTCCTTGACCTCT

7261  TAGACTACTAGCTCTAGTCAAAGGAGCCTATCAGGCGCTTAACCTCACCAATCCCGACAA 7320
      ATCTGATGATCGAGATCAGTTTCCTCGGATAGTCCGCGAATTGGAGTGGTTAGGGCTGTT

7321  GACCCAAGAATGTTGGCTGTGCTTAGTGTCGGGACCTCCTTATTACGAAGGAGTAGCGGT 7380
      CTGGGTTCTTACAACCGACACGAATCACAGCCCTGGAGGAATAATGCTTCCTCATCGCCA

7381  CGTGGGCACTTATACCAATCATTCCACCGCTCCGGCCAACTGTACGGCCACTTCCCAACA 7440
      GCACCCGTGAATATGGTTAGTAAGGTGGCGAGGCCGGTTGACATGCCGGTGAAGGGTTGT

                                                 EcoT22I
                                                 |
                                                 NsiI
                                                 |
                                                 Mph1103I
                                                 |
                                                 Zsp2I
                                                 |
                                              BfrBI
                                              |  |
7441  TAAGCTTACCCTATCTGAAGTGACAGGACAGGGCCTATGCATGGGGGCAGTACCTAAAAC 7500
      ATTCGAATGGGATAGACTTCACTGTCCTGTCCCGGATACGTACCCCCGTCATGGATTTTG

                                         NaeI
                                         |
                                         PdiI
                                         |
                                      MroNI
                                      |  |
                                      NgoMIV
                                      |  |
7501  TCACCAGGCCTTATGTAACACCACCCAAAGCGCCGGCTCAGGATCCTACTACCTTGCAGC 7560
      AGTGGTCCGGAATACATTGTGGTGGGTTTCGCGGCCGAGTCCTAGGATGATGGAACGTCG
```

FIGURE 1D-15

```
                                                               AleI
                                                               |
                                                               OliI
                                                               |
7561 ACCCGCCGGAACAATGTGGGCTTGCAGCACTGGATTGACTCCCTGCTTGTCCACCACGGT 7620
     TGGGCGGCCTTGTTACACCCGAACGTCGTGACCTAACTGAGGGACGAACAGGTGGTGCCA

7621 GCTCAATCTAACCACAGATTATTGTGTATTAGTTGAACTCTGGCCCAGAGTAATTTACCA 7680
     CGAGTTAGATTGGTGTCTAATAACACATAATCAACTTGAGACCGGGTCTCATTAAATGGT
7681 CTCCCCCGATTATATGTATGGTCAGCTTGAACAGCGTACCAAATATAAAGAGAGCCAGT 7740
     GAGGGGGCTAATATACATACCAGTCGAACTTGTCGCATGGTTTATATTTCTCTCGGTCA

7741 ATCATTGACCCTGGCCCTTCTACTAGGAGGATTAACCATGGGAGGGATTGCAGCTGGAAT 7800
     TAGTAACTGGGACCGGGAAGATGATCCTCCTAATTGGTACCCTCCCTAACGTCGACCTTA

7801 AGGGACGGGGACCACTGCCTTAATTAAAACCCAGCAGTTTGAGCAGCTTCATGCCGCTAT 7860
     TCCCTGCCCCTGGTGACGGAATTAATTTTGGGTCGTCAAACTCGTCGAAGTACGGCGATA

7861 CCAGACAGACCTCAACGAAGTCGAAAAGTCAATTACCAACCTAGAAAAGTCACTGACCTC 7920
     GGTCTGTCTGGAGTTGCTTCAGCTTTTCAGTTAATGGTTGGATCTTTTCAGTGACTGGAG

7921 GTTGTCTGAAGTAGTCCTACAGAACCGCAGAGGCCTAGATTTGCTATTCCTAAAGGAGGG 7980
     CAACAGACTTCATCAGGATGTCTTGGCGTCTCCGGATCTAAACGATAAGGATTTCCTCCC

7981 AGGTCTCTGCGCAGCCCTAAAAGAAGAATGTTGTTTTTATGCAGACCACACGGGGCTAGT 8040
     TCCAGAGACGCGTCGGGATTTTCTTCTTACAACAAAAATACGTCTGGTGTGCCCCGATCA

8041 GAGAGACAGCATGGCCAAATTAAGAGAAAGGCTTAATCAGAGACAAAAACTATTTGAGAC 8100
     CTCTCTGTCGTACCGGTTTAATTCTCTTTCCGAATTAGTCTCTGTTTTTGATAAACTCTG

                    NspV
                    |
                    BstBI
                    |
                    Bsp119I
                    |
                    AsuII
                    |
                    Csp45I
                    |
                    SfuI
                    |
                    Bpu14I
                    |
                    BspT104I
                    |
8101 AGGCCAAGGATGGTTCGAAGGGCTGTTTAATAGATCCCCCTGGTTTACCACCTTAATCTC 8160
     TCCGGTTCCTACCAAGCTTCCCGACAAATTATCTAGGGGGACCAAATGGTGGAATTAGAG
```

FIGURE 1D-16

```
8161  CACCATCATGGGACCTCTAATAGTACTCTTACTGATCTTACTCTTTGGACCTTGCATTCT 8220
      GTGGTAGTACCCTGGAGATTATCATGAGAATGACTAGAATGAGAAACCTGGAACGTAAGA

8221  CAATCGATTGGTCCAATTTGTTAAAGACAGGATCTCAGTGGTCCAGGCTCTGGTTTTGAC 8280
      GTTAGCTAACCAGGTTAAACAATTTCTGTCCTAGAGTCACCAGGTCCGAGACCAAAACTG
                                                      IRES reg(8327,8876)>>>
                                                        |
                                                    MluI(8325)
                                                    |   |
8281  TCAGCAATATCACCAGCTAAAACCCATAGAGTACGAGCCATGAACGCGTTACTGGCCGAA 8340
      AGTCGTTATAGTGGTCGATTTTGGGTATCTCATGCTCGGTACTTGCGCAATGACCGGCTT

                                          ires_emcv reg(8378,8876)>>>
                                          |
8341  GCCGCTTGGAATAAGGCCGGTGTGCGTTTGTCTATATGTTATTTTCCACCATATTGCCGT 8400
      CGGCGAACCTTATTCCGGCCACACGCAAACAGATATACAATAAAAGGTGGTATAACGGCA

8401  CTTTTGGCAATGTGAGGGCCCGGAAACCTGGCCCTGTCTTCTTGACGAGCATTCCTAGGG 8460
      GAAAACCGTTACACTCCCGGGCCTTTGGACCGGGACAGAAGAACTGCTCGTAAGGATCCC
8461  GTCTTTCCCCTCTCGCCAAAGGAATGCAAGGTCTGTTGAATGTCGTGAAGGAAGCAGTTC 8520
      CAGAAAGGGGAGAGCGGTTTCCTTACGTTCCAGACAACTTACAGCACTTCCTTCGTCAAG

8521  CTCTGGAAGCTTCTTGAAGACAAACAACGTCTGTAGCGACCCTTTGCAGGCAGCGGAACC 8580
      GAGACCTTCGAAGAACTTCTGTTTGTTGCAGACATCGCTGGGAAACGTCCGTCGCCTTGG

8581  CCCCACCTGGCGACAGGTGCCTCTGCGGCCAAAAGCCACGTGTATAAGATACACCTGCAA 8640
      GGGGTGGACCGCTGTCCACGGAGACGCCGGTTTTCGGTGCACATATTCTATGTGGACGTT

8641  AGGCGGCACAACCCCAGTGCCACGTTGTGAGTTGGATAGTTGTGGAAAGAGTCAAATGGC 8700
      TCCGCCGTGTTGGGGTCACGGTGCAACACTCAACCTATCAACACCTTTCTCAGTTTACCG

8701  TCTCCTCAAGCGTATTCAACAAGGGGCTGAAGGATGCCCAGAAGGTACCCCATTGTATGG 8760
      AGAGGAGTTCGCATAAGTTGTTCCCCGACTTCCTACGGGTCTTCCATGGGGTAACATACC

8761  GATCTGATCTGGGGCCTCGGTGCACATGCTTTACATGTGTTTAGTCGAGGTTAAAAAAAC 8820
      CTAGACTAGACCCCGGAGCCACGTGTACGAAATGTACACAAATCAGCTCCAATTTTTTTG
```

FIGURE 1D-17

```
                                                 yCD2 (8877,9353)>>>
                                                               |
                                                       PsiI(8874)
                                                         |    |
8821 GTCTAGGCCCCCCGAACCACGGGGACGTGGTTTTCCTTTGAAAAACACGATTATAAATGG 8880
     CAGATCCGGGGGGCTTGGTGCCCCTGCACCAAAAGGAAACTTTTTGTGCTAATATTTACC

8881 TGACCGGCGGCATGGCCTCCAAGTGGGATCAAAAGGGCATGGATATCGCTTACGAGGAGG 8940
     ACTGGCCGCCGTACCGGAGGTTCACCCTAGTTTTCCCGTACCTATAGCGAATGCTCCTCC

8941 CCCTGCTGGGCTACAAGGAGGGCGGCGTGCCTATCGGCGGCTGTCTGATCAACAACAAGG 9000
     GGGACGACCCGATGTTCCTCCCGCCGCACGGATAGCCGCCGACAGACTAGTTGTTGTTCC

9001 ACGGCAGTGTGCTGGGCAGGGGCCACAACATGAGGTTCCAGAAGGGCTCCGCCACCCTGC 9060
     TGCCGTCACACGACCCGTCCCCGGTGTTGTACTCCAAGGTCTTCCCGAGGCGGTGGGACG

9061 ACGGCGAGATCTCCACCCTGGAGAACTGTGGCAGGCTGGAGGGCAAGGTGTACAAGGACA 9120
     TGCCGCTCTAGAGGTGGGACCTCTTGACACCGTCCGACCTCCCGTTCCACATGTTCCTGT

9121 CCACCCTGTACACCACCCTGTCCCCTTGTGACATGTGTACCGGCGCTATCATCATGTACG 9180
     GGTGGGACATGTGGTGGGACAGGGGAACACTGTACACATGGCCGCGATAGTAGTACATGC
9181 GCATCCCTAGGTGTGTGATCGGCGAGAACGTGAACTTCAAGTCCAAGGGCGAGAAGTACC 9240
     CGTAGGGATCCACACACTAGCCGCTCTTGCACTTGAAGTTCAGGTTCCCGCTCTTCATGG

9241 TGCAAACCAGGGGCCACGAGGTGGTGGTTGTTGACGATGAGAGGTGTAAGAAGCTGATGA 9300
     ACGTTTGGTCCCCGGTGCTCCACCACCAACAACTGCTACTCTCCACATTCTTCGACTACT

                                                       NotI(9356)
                                                       |
                                                       CciNI
                                                       |
9301 AGCAGTTCATCGACGAGAGGCCTCAGGACTGGTTCGAGGATATCGGCGAGTAAGCGGCCG 9360
     TCGTCAAGTAGCTGCTCTCCGGAGTCCTGACCAAGCTCCTATAGCCGCTCATTCGCCGGC

                                           U3 Region(9405,9854)>>>
                                           |
9361 CAGATAAAATAAAAGATTTTATTTAGTCTCCAGAAAAAGGGGGGAATGAAAGACCCCACC 9420
     GTCTATTTTATTTTCTAAAATAAATCAGAGGTCTTTTTCCCCCCTTACTTTCTGGGGTGG
```

FIGURE 1D-18

```
                     BmtI
                     |
                 NheI
                 |   |
                 AsuNHI      5_LTR2 other(9447,9998)>>>>
                 |   |       |
9421  TGTAGGTTTGGCAAGCTAGCTTAAGTAACGCCATTTTGCAAGGCATGGAAAAATACATAA 9480
      ACATCCAAACCGTTCGATCGAATTCATTGCGGTAAAACGTTCCGTACCTTTTTATGTATT

9481  CTGAGAATAGAGAAGTTCAGATCAAGGTCAGGAACAGATGGAACAGCTGAATATGGGCCA 9540
      GACTCTTATCTCTTCAAGTCTAGTTCCAGTCCTTGTCTACCTTGTCGACTTATACCCGGT

9541  AACAGGATATCTGTGGTAAGCAGTTCCTGCCCCGGCTCAGGGCCAAGAACAGATGGAACA 9600
      TTGTCCTATAGACACCATTCGTCAAGGACGGGGCCGAGTCCCGGTTCTTGTCTACCTTGT

9601  GCTGAATATGGGCCAAACAGGATATCTGTGGTAAGCAGTTCCTGCCCCGGCTCAGGGCCA 9660
      CGACTTATACCCGGTTTGTCCTATAGACACCATTCGTCAAGGACGGGGCCGAGTCCCGGT

9661  AGAACAGATGGTCCCCAGATGCGGTCCAGCCCTCAGCAGTTTCTAGAGAACCATCAGATG 9720
      TCTTGTCTACCAGGGGTCTACGCCAGGTCGGGAGTCGTCAAAGATCTCTTGGTAGTCTAC

9721  TTTCCAGGGTGCCCCAAGGACCTGAAATGACCCTGTGCCTTATTTGAACTAACCAATCAG 9780
      AAAGGTCCCACGGGGTTCCTGGACTTTACTGGGACACGGAATAAACTTGATTGGTTAGTC

                                                   SacI
                                                   |
                                                   SstI
                                                   |
                        PauI                       Psp124BI
                        |                          |
                        BsePI                    EcoICRI
                        |                        | |
                        BssHII                   Ecl136II
                        |                        | |
9781  TTCGCTTCTCGCTTCTGTTCGCGCGCTTCTGCTCCCCGAGCTCAATAAAAGAGCCCACAA 9840
      AAGCGAAGAGCGAAGACAAGCGCGCGAAGACGAGGGGCTCGAGTTATTTTCTCGGGTGTT

                 R Region(9855,9921)>>>>
                 |
9841  CCCCTCACTCGGGGCGCCAGTCCTCCGATTGACTGAGTCGCCCGGGTACCCGTGTATCCA 9900
      GGGGAGTGAGCCCCGCGGTCAGGAGGCTAACTGACTCAGCGGGCCCATGGGCACATAGGT

                        U5 Region(9922,9998)>>>>
                        |
9901  ATAAACCCTCTTGCAGTTGCATCCGACTTGTGGTCTCGCTGTTCCTTGGGAGGGTCTCCT 9960
      TATTTGGGAGAACGTCAACGTAGGCTGAACACCAGAGCGACAAGGAACCCTCCCAGAGGA

9961  CTGAGTGATTGACTACCCGTCAGCGGGGGTCTTTCATTACATGTGAGCAAAAGGCCAGCA 10020
      GACTCACTAACTGATGGGCAGTCGCCCCCAGAAAGTAATGTACACTCGTTTTCCGGTCGT
```

FIGURE 1D-19 pBR322 origin(10045,10664)<<<
|

10021 AAAGGCCAGGAACCGTAAAAAGGCCGCGTTGCTGGCGTTTTTCCATAGGCTCCGCCCCC 10080
TTTCCGGTCCTTGGCATTTTTCCGGCGCAACGACCGCAAAAAGGTATCCGAGGCGGGGG

10081 TGACGAGCATCACAAAAATCGACGCTCAAGTCAGAGGTGGCGAAACCCGACAGGACTATA 10140
ACTGCTCGTAGTGTTTTTAGCTGCGAGTTCAGTCTCCACCGCTTTGGGCTGTCCTGATAT

10141 AAGATACCAGGCGTTTCCCCCTGGAAGCTCCCTCGTGCGCTCTCCTGTTCCGACCCTGCC 10200
TTCTATGGTCCGCAAAGGGGGACCTTCGAGGGAGCACGCGAGAGGACAAGGCTGGGACGG

10201 GCTTACCGGATACCTGTCCGCCTTTCTCCCTTCGGGAAGCGTGGCGCTTTCTCAATGCTC 10260
CGAATGGCCTATGGACAGGCGGAAAGAGGGAAGCCCTTCGCACCGCGAAAGAGTTACGAG

10261 ACGCTGTAGGTATCTCAGTTCGGTGTAGGTCGTTCGCTCCAAGCTGGGCTGTGTGCACGA 10320
TGCGACATCCATAGAGTCAAGCCACATCCAGCAAGCGAGGTTCGACCCGACACACGTGCT

10321 ACCCCCCGTTCAGCCCGACCGCTGCGCCTTATCCGGTAACTATCGTCTTGAGTCCAACCC 10380
TGGGGGGCAAGTCGGGCTGGCGACGCGGAATAGGCCATTGATAGCAGAACTCAGGTTGGG

10381 GGTAAGACACGACTTATCGCCACTGGCAGCAGCCACTGGTAACAGGATTAGCAGAGCGAG 10440
CCATTCTGTGCTGAATAGCGGTGACCGTCGTCGGTGACCATTGTCCTAATCGTCTCGCTC

10441 GTATGTAGGCGGTGCTACAGAGTTCTTGAAGTGGTGGCCTAACTACGGCTACACTAGAAG 10500
CATACATCCGCCACGATGTCTCAAGAACTTCACCACCGGATTGATGCCGATGTGATCTTC

10501 GACAGTATTTGGTATCTGCGCTCTGCTGAAGCCAGTTACCTTCGGAAAAAGAGTTGGTAG 10560
CTGTCATAAACCATAGACGCGAGACGACTTCGGTCAATGGAAGCCTTTTTCTCAACCATC

10561 CTCTTGATCCGGCAAACAAACCACCGCTGGTAGCGGTGGTTTTTTTGTTTGCAAGCAGCA 10620
GAGAACTAGGCCGTTTGTTTGGTGGCGACCATCGCCACCAAAAAAACAAACGTTCGTCGT

10621 GATTACGCGCAGAAAAAAAGGATCTCAAGAAGATCCTTTGATCTTTTCTACGGGGTCTGA 10680
CTAATGCGCGTCTTTTTTTCCTAGAGTTCTTCTAGGAAACTAGAAAAGATGCCCCAGACT

10681 CGCTCAGTGGAACGAAAACTCACGTTAAGGGATTTTGGTCATGAGATTATCAAAAAGGAT 10740
GCGAGTCACCTTGCTTTTGAGTGCAATTCCCTAAAACCAGTACTCTAATAGTTTTTCCTA

10741 CTTCACCTAGATCCTTTTAAATTAAAAATGAAGTTTTAAATCAATCTAAAGTATATATGA 10800
GAAGTGGATCTAGGAAAATTTAATTTTTACTTCAAAATTTAGTTAGATTTCATATATACT

FIGURE 1D-20

```
                          amp marker(10819,11679)<<<
                          |
10801 GTAAACTTGGTCTGACAGTTACCAATGCTTAATCAGTGAGGCACCTATCTCAGCGATCTG 10860
      CATTTGAACCAGACTGTCAATGGTTACGAATTAGTCACTCCGTGGATAGAGTCGCTAGAC

10861 TCTATTTCGTTCATCCATAGTTGCCTGACTCCCCGTCGTGTAGATAACTACGATACGGGA 10920
      AGATAAAGCAAGTAGGTATCAACGGACTGAGGGGCAGCACATCTATTGATGCTATGCCCT

10921 GGGCTTACCATCTGGCCCCAGTGCTGCAATGATACCGCGAGACCCACGCTCACCGGCTCC 10980
      CCCGAATGGTAGACCGGGGTCACGACGTTACTATGGCGCTCTGGGTGCGAGTGGCCGAGG

10981 AGATTTATCAGCAATAAACCAGCCAGCCGGAAGGGCCGAGCGCAGAAGTGGTCCTGCAAC 11040
      TCTAAATAGTCGTTATTTGGTCGGTCGGCCTTCCCGGCTCGCGTCTTCACCAGGACGTTG


11041 TTTATCCGCCTCCATCCAGTCTATTAATTGTTGCCGGGAAGCTAGAGTAAGTAGTTCGCC 11100
      AAATAGGCGGAGGTAGGTCAGATAATTAACAACGGCCCTTCGATCTCATTCATCAAGCGG

11101 AGTTAATAGTTTGCGCAACGTTGTTGCCATTGCTGCAGGCATCGTGGTGTCACGCTCGTC 11160
      TCAATTATCAAACGCGTTGCAACAACGGTAACGACGTCCGTAGCACCACAGTGCGAGCAG

11161 GTTTGGTATGGCTTCATTCAGCTCCGGTTCCCAACGATCAAGGCGAGTTACATGATCCCC 11220
      CAAACCATACCGAAGTAAGTCGAGGCCAAGGGTTGCTAGTTCCGCTCAATGTACTAGGGG

11221 CATGTTGTGCAAAAAAGCGGTTAGCTCCTTCGGTCCTCCGATCGTTGTCAGAAGTAAGTT 11280
      GTACAACACGTTTTTTCGCCAATCGAGGAAGCCAGGAGGCTAGCAACAGTCTTCATTCAA

11281 GGCCGCAGTGTTATCACTCATGGTTATGGCAGCACTGCATAATTCTCTTACTGTCATGCC 11340
      CCGGCGTCACAATAGTGAGTACCAATACCGTCGTGACGTATTAAGAGAATGACAGTACGG

11341 ATCCGTAAGATGCTTTTCTGTGACTGGTGAGTACTCAACCAAGTCATTCTGAGAATAGTG 11400
      TAGGCATTCTACGAAAAGACACTGACCACTCATGAGTTGGTTCAGTAAGACTCTTATCAC


11401 TATGCGGCGACCGAGTTGCTCTTGCCCGGCGTCAACACGGGATAATACCGCGCCACATAG 11460
      ATACGCCGCTGGCTCAACGAGAACGGGCCGCAGTTGTGCCCTATTATGGCGCGGTGTATC

11461 CAGAACTTTAAAAGTGCTCATCATTGGAAAACGTTCTTCGGGGCGAAAACTCTCAAGGAT 11520
      GTCTTGAAATTTTCACGAGTAGTAACCTTTTGCAAGAAGCCCCGCTTTTGAGAGTTCCTA

11521 CTTACCGCTGTTGAGATCCAGTTCGATGTAACCCACTCGTGCACCCAACTGATCTTCAGC 11580
      GAATGGCGACAACTCTAGGTCAAGCTACATTGGGTGAGCACGTGGGTTGACTAGAAGTCG

11581 ATCTTTTACTTTCACCAGCGTTTCTGGGTGAGCAAAAACAGGAAGGCAAAATGCCGCAAA 11640
      TAGAAAATGAAAGTGGTCGCAAAGACCCACTCGTTTTTGTCCTTCCGTTTTACGGCGTTT

11641 AAAGGGAATAAGGGCGACACGGAAATGTTGAATACTCATACTCTTCCTTTTTCAATATTA 11700
      TTTCCCTTATTCCCGCTGTGCCTTTACAACTTATGAGTATGAGAAGGAAAAAGTTATAAT
```

FIGURE 1D-21

```
                          amp prom(11721,11749)<<<
                          |
11701 TTGAAGCATTTATCAGGGTTATTGTCTCATGAGCGGATACATATTTGAATGTATTTAGAA 11760
      AACTTCGTAAATAGTCCCAATAACAGAGTACTCGCCTATGTATAAACTTACATAAATCTT

11761 AAATAAACAAATAGGGGTTCCGCGCACATTTCCCCGAAAAGTGCCACCTGACGTCTAAGA 11820
      TTTATTTGTTTATCCCCAAGGCGCGTGTAAAGGGGCTTTTCACGGTGGACTGCAGATTCT

11821 AACCATTATTATCATGACATTAACCTATAAAAATAGGCGTATCACGAGGCCCTTTCGTCT 11880
      TTGGTAATAATAGTACTGTAATTGGATATTTTTATCCGCATAGTGCTCCGGGAAAGCAGA

11881 TCAAGAATTCAT 11892
      AGTTCTTAAGTA
```

FIGURE 1D-22

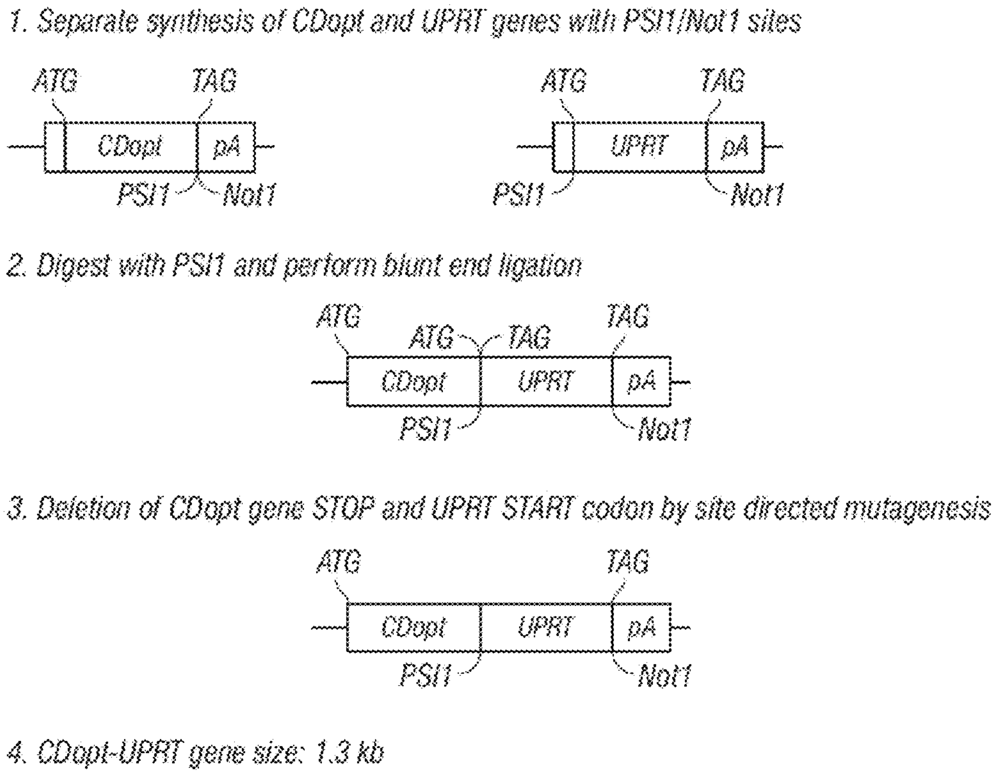

FIGURE 2A

1. *Synthesis of CDopt-LINKER-UPRT: Site directed mutagenesis insertion of linker*

2. *CDopt-Linker-UPRT gene size: 1.36 kb*

1. *Separate synthesis of CDopt gene and OPRT domain with PSI1/Not1 sites*

2. *Digest with PSI1 and perform blunt end ligation*

3. *Deletion of CDopt gene STOP and OPRT START codon by site directed mutagenesis*

4. *CDopt-OPRT gene size: 1.3 kb*

SEQUENCE LISTING

<160> NUMBER OF SEQ ID NOS: 54

<210> SEQ ID NO 1
<211> LENGTH: 477
<212> TYPE: DNA
<213> ORGANISM: Saccharomyces cerevisiae
<220> FEATURE:
<221> NAME/KEY: CDS
<222> LOCATION: (1)..(477)

<400> SEQUENCE: 1

```
atg gtg aca ggg gga atg gca agc aag tgg gat cag aag ggt atg gac       48
Met Val Thr Gly Gly Met Ala Ser Lys Trp Asp Gln Lys Gly Met Asp
1               5                   10                  15

att gcc tat gag gag gcg gcc tta ggt tac aaa gag ggt ggt gtt cct       96
Ile Ala Tyr Glu Glu Ala Ala Leu Gly Tyr Lys Glu Gly Gly Val Pro
            20                  25                  30

att ggc gga tgt ctt atc aat aac aaa gac gga agt gtt ctc ggt cgt      144
Ile Gly Gly Cys Leu Ile Asn Asn Lys Asp Gly Ser Val Leu Gly Arg
        35                  40                  45

ggt cac aac atg aga ttt caa aag gga tcc gcc aca cta cat ggt gag      192
Gly His Asn Met Arg Phe Gln Lys Gly Ser Ala Thr Leu His Gly Glu
    50                  55                  60

atc tcc act ttg gaa aac tgt ggg aga tta gag ggc aaa gtg tac aaa      240
Ile Ser Thr Leu Glu Asn Cys Gly Arg Leu Glu Gly Lys Val Tyr Lys
65                  70                  75                  80

gat acc act ttg tat acg acg ctg tct cca tgc gac atg tgt aca ggt      288
Asp Thr Thr Leu Tyr Thr Thr Leu Ser Pro Cys Asp Met Cys Thr Gly
                85                  90                  95

gcc atc atc atg tat ggt att cca cgc tgt gtt gtc ggt gag aac gtt      336
Ala Ile Ile Met Tyr Gly Ile Pro Arg Cys Val Val Gly Glu Asn Val
            100                 105                 110

aat ttc aaa agt aag ggc gag aaa tat tta caa act aga ggt cac gag      384
Asn Phe Lys Ser Lys Gly Glu Lys Tyr Leu Gln Thr Arg Gly His Glu
        115                 120                 125

gtt gtt gtt gtt gac gat gag agg tgt aaa aag atc atg aaa caa ttt      432
Val Val Val Val Asp Asp Glu Arg Cys Lys Lys Ile Met Lys Gln Phe
    130                 135                 140

atc gat gaa aga cct cag gat tgg ttt gaa gat att ggt gag tag          477
Ile Asp Glu Arg Pro Gln Asp Trp Phe Glu Asp Ile Gly Glu
145                 150                 155
```

<210> SEQ ID NO 2
<211> LENGTH: 158
<212> TYPE: PRT
<213> ORGANISM: Saccharomyces cerevisiae

<400> SEQUENCE: 2

```
Met Val Thr Gly Gly Met Ala Ser Lys Trp Asp Gln Lys Gly Met Asp
1               5                   10                  15

Ile Ala Tyr Glu Glu Ala Ala Leu Gly Tyr Lys Glu Gly Gly Val Pro
            20                  25                  30

Ile Gly Gly Cys Leu Ile Asn Asn Lys Asp Gly Ser Val Leu Gly Arg
        35                  40                  45

Gly His Asn Met Arg Phe Gln Lys Gly Ser Ala Thr Leu His Gly Glu
    50                  55                  60

Ile Ser Thr Leu Glu Asn Cys Gly Arg Leu Glu Gly Lys Val Tyr Lys
65                  70                  75                  80

Asp Thr Thr Leu Tyr Thr Thr Leu Ser Pro Cys Asp Met Cys Thr Gly
                85                  90                  95
```

```
Ala Ile Ile Met Tyr Gly Ile Pro Arg Cys Val Val Gly Glu Asn Val
            100                 105                 110

Asn Phe Lys Ser Lys Gly Glu Lys Tyr Leu Gln Thr Arg Gly His Glu
        115                 120                 125

Val Val Val Val Asp Asp Glu Arg Cys Lys Lys Ile Met Lys Gln Phe
    130                 135                 140

Ile Asp Glu Arg Pro Gln Asp Trp Phe Glu Asp Ile Gly Glu
145                 150                 155


<210> SEQ ID NO 3
<211> LENGTH: 477
<212> TYPE: DNA
<213> ORGANISM: Artificial Sequence
<220> FEATURE:
<223> OTHER INFORMATION: Engineered cytosine deaminase
<220> FEATURE:
<221> NAME/KEY: CDS
<222> LOCATION: (1)..(477)

<400> SEQUENCE: 3

atg gtg aca ggg gga atg gca agc aag tgg gat cag aag ggt atg gac       48
Met Val Thr Gly Gly Met Ala Ser Lys Trp Asp Gln Lys Gly Met Asp
1               5                   10                  15

att gcc tat gag gag gcg tta tta ggt tac aaa gag ggt ggt gtt cct       96
Ile Ala Tyr Glu Glu Ala Leu Leu Gly Tyr Lys Glu Gly Gly Val Pro
            20                  25                  30

att ggc gga tgt ctt atc aat aac aaa gac gga agt gtt ctc ggt cgt      144
Ile Gly Gly Cys Leu Ile Asn Asn Lys Asp Gly Ser Val Leu Gly Arg
        35                  40                  45

ggt cac aac atg aga ttt caa aag gga tcc gcc aca cta cat ggt gag      192
Gly His Asn Met Arg Phe Gln Lys Gly Ser Ala Thr Leu His Gly Glu
    50                  55                  60

atc tcc act ttg gaa aac tgt ggg aga tta gag ggc aaa gtg tac aaa      240
Ile Ser Thr Leu Glu Asn Cys Gly Arg Leu Glu Gly Lys Val Tyr Lys
65                  70                  75                  80

gat acc act ttg tat acg acg ctg tct cca tgc gac atg tgt aca ggt      288
Asp Thr Thr Leu Tyr Thr Thr Leu Ser Pro Cys Asp Met Cys Thr Gly
                85                  90                  95

gcc atc atc atg tat ggt att cca cgc tgt gtc atc ggt gag aac gtt      336
Ala Ile Ile Met Tyr Gly Ile Pro Arg Cys Val Ile Gly Glu Asn Val
            100                 105                 110

aat ttc aaa agt aag ggc gag aaa tat tta caa act aga ggt cac gag      384
Asn Phe Lys Ser Lys Gly Glu Lys Tyr Leu Gln Thr Arg Gly His Glu
        115                 120                 125

gtt gtt gtt gtt gac gat gag agg tgt aaa aag tta atg aaa caa ttt      432
Val Val Val Val Asp Asp Glu Arg Cys Lys Lys Leu Met Lys Gln Phe
    130                 135                 140

atc gat gaa aga cct cag gat tgg ttt gaa gat att ggt gag tag          477
Ile Asp Glu Arg Pro Gln Asp Trp Phe Glu Asp Ile Gly Glu
145                 150                 155


<210> SEQ ID NO 4
<211> LENGTH: 158
<212> TYPE: PRT
<213> ORGANISM: Artificial Sequence
<220> FEATURE:
<223> OTHER INFORMATION: Synthetic Construct

<400> SEQUENCE: 4

Met Val Thr Gly Gly Met Ala Ser Lys Trp Asp Gln Lys Gly Met Asp
1               5                   10                  15

Ile Ala Tyr Glu Glu Ala Leu Leu Gly Tyr Lys Glu Gly Gly Val Pro
```

-continued

```
            20                  25                  30

Ile Gly Gly Cys Leu Ile Asn Asn Lys Asp Gly Ser Val Leu Gly Arg
        35                  40                  45

Gly His Asn Met Arg Phe Gln Lys Gly Ser Ala Thr Leu His Gly Glu
    50                  55                  60

Ile Ser Thr Leu Glu Asn Cys Gly Arg Leu Glu Gly Lys Val Tyr Lys
65                  70                  75                  80

Asp Thr Thr Leu Tyr Thr Thr Leu Ser Pro Cys Asp Met Cys Thr Gly
                85                  90                  95

Ala Ile Ile Met Tyr Gly Ile Pro Arg Cys Val Ile Gly Glu Asn Val
            100                 105                 110

Asn Phe Lys Ser Lys Gly Glu Lys Tyr Leu Gln Thr Arg Gly His Glu
        115                 120                 125

Val Val Val Val Asp Asp Glu Arg Cys Lys Lys Leu Met Lys Gln Phe
    130                 135                 140

Ile Asp Glu Arg Pro Gln Asp Trp Phe Glu Asp Ile Gly Glu
145                 150                 155


<210> SEQ ID NO 5
<211> LENGTH: 480
<212> TYPE: DNA
<213> ORGANISM: Artificial Sequence
<220> FEATURE:
<223> OTHER INFORMATION: Human codon optimized cytosine deaminase
<220> FEATURE:
<221> NAME/KEY: CDS
<222> LOCATION: (1)..(480)

<400> SEQUENCE: 5

atg gtg acc ggc ggc atg gcc tcc aag tgg gat caa aag ggc atg gat       48
Met Val Thr Gly Gly Met Ala Ser Lys Trp Asp Gln Lys Gly Met Asp
1               5                   10                  15

atc gct tac gag gag gcc gca ctg ggc tac aag gag ggc ggc gtg cct       96
Ile Ala Tyr Glu Glu Ala Ala Leu Gly Tyr Lys Glu Gly Gly Val Pro
            20                  25                  30

atc ggc ggc tgt ctg atc aac aac aag gac ggc agt gtg ctg ggc agg      144
Ile Gly Gly Cys Leu Ile Asn Asn Lys Asp Gly Ser Val Leu Gly Arg
        35                  40                  45

ggc cac aac atg agg ttc cag aag ggc tcc gcc acc ctg cac ggc gag      192
Gly His Asn Met Arg Phe Gln Lys Gly Ser Ala Thr Leu His Gly Glu
    50                  55                  60

atc tcc acc ctg gag aac tgt ggc agg ctg gag ggc aag gtg tac aag      240
Ile Ser Thr Leu Glu Asn Cys Gly Arg Leu Glu Gly Lys Val Tyr Lys
65                  70                  75                  80

gac acc acc ctg tac acc acc ctg tcc cct tgt gac atg tgt acc ggc      288
Asp Thr Thr Leu Tyr Thr Thr Leu Ser Pro Cys Asp Met Cys Thr Gly
                85                  90                  95

gct atc atc atg tac ggc atc cct agg tgt gtg gtc ggc gag aac gtg      336
Ala Ile Ile Met Tyr Gly Ile Pro Arg Cys Val Val Gly Glu Asn Val
            100                 105                 110

aac ttc aag tcc aag ggc gag aag tac ctg caa acc agg ggc cac gag      384
Asn Phe Lys Ser Lys Gly Glu Lys Tyr Leu Gln Thr Arg Gly His Glu
        115                 120                 125

gtg gtg gtt gtt gac gat gag agg tgt aag aag atc atg aag cag ttc      432
Val Val Val Val Asp Asp Glu Arg Cys Lys Lys Ile Met Lys Gln Phe
    130                 135                 140

atc gac gag agg cct cag gac tgg ttc gag gat atc ggc gag tga taa      480
Ile Asp Glu Arg Pro Gln Asp Trp Phe Glu Asp Ile Gly Glu
145                 150                 155
```

<210> SEQ ID NO 6
<211> LENGTH: 158
<212> TYPE: PRT
<213> ORGANISM: Artificial Sequence
<220> FEATURE:
<223> OTHER INFORMATION: Synthetic Construct

<400> SEQUENCE: 6

```
Met Val Thr Gly Gly Met Ala Ser Lys Trp Asp Gln Lys Gly Met Asp
1               5                   10                  15

Ile Ala Tyr Glu Glu Ala Ala Leu Gly Tyr Lys Glu Gly Gly Val Pro
            20                  25                  30

Ile Gly Gly Cys Leu Ile Asn Asn Lys Asp Gly Ser Val Leu Gly Arg
        35                  40                  45

Gly His Asn Met Arg Phe Gln Lys Gly Ser Ala Thr Leu His Gly Glu
    50                  55                  60

Ile Ser Thr Leu Glu Asn Cys Gly Arg Leu Glu Gly Lys Val Tyr Lys
65                  70                  75                  80

Asp Thr Thr Leu Tyr Thr Thr Leu Ser Pro Cys Asp Met Cys Thr Gly
                85                  90                  95

Ala Ile Ile Met Tyr Gly Ile Pro Arg Cys Val Val Gly Glu Asn Val
            100                 105                 110

Asn Phe Lys Ser Lys Gly Glu Lys Tyr Leu Gln Thr Arg Gly His Glu
        115                 120                 125

Val Val Val Val Asp Asp Glu Arg Cys Lys Lys Ile Met Lys Gln Phe
    130                 135                 140

Ile Asp Glu Arg Pro Gln Asp Trp Phe Glu Asp Ile Gly Glu
145                 150                 155
```

<210> SEQ ID NO 7
<211> LENGTH: 756
<212> TYPE: DNA
<213> ORGANISM: Saccharomyces cerevisiae
<220> FEATURE:
<221> NAME/KEY: CDS
<222> LOCATION: (1)..(756)

<400> SEQUENCE: 7

```
atg aac ccg tta ttc ttt ttg gct tct cca ttc ttg tac ctt aca tat       48
Met Asn Pro Leu Phe Phe Leu Ala Ser Pro Phe Leu Tyr Leu Thr Tyr
1               5                   10                  15

ctt ata tat tat cca aac aaa ggg tct ttc gtt agc aaa cct aga aat       96
Leu Ile Tyr Tyr Pro Asn Lys Gly Ser Phe Val Ser Lys Pro Arg Asn
            20                  25                  30

ctg caa aaa atg tct tcg gaa cca ttt aag aac gtc tac ttg cta cct      144
Leu Gln Lys Met Ser Ser Glu Pro Phe Lys Asn Val Tyr Leu Leu Pro
        35                  40                  45

caa aca aac caa ttg ctg ggt ttg tac acc atc atc aga aat aag aat      192
Gln Thr Asn Gln Leu Leu Gly Leu Tyr Thr Ile Ile Arg Asn Lys Asn
    50                  55                  60

aca act aga cct gat ttc att ttc tac tcc gat aga atc atc aga ttg      240
Thr Thr Arg Pro Asp Phe Ile Phe Tyr Ser Asp Arg Ile Ile Arg Leu
65                  70                  75                  80

ttg gtt gaa gaa ggt ttg aac cat cta cct gtg caa aag caa att gtg      288
Leu Val Glu Glu Gly Leu Asn His Leu Pro Val Gln Lys Gln Ile Val
                85                  90                  95

gaa act gac acc aac gaa aac ttc gaa ggt gtc tca ttc atg ggt aaa      336
Glu Thr Asp Thr Asn Glu Asn Phe Glu Gly Val Ser Phe Met Gly Lys
            100                 105                 110
```

```
atc tgt ggt gtt tcc att gtc aga gct ggt gaa tcg atg gag caa gga      384
Ile Cys Gly Val Ser Ile Val Arg Ala Gly Glu Ser Met Glu Gln Gly
        115                 120                 125

tta aga gac tgt tgt agg tct gtg cgt atc ggt aaa att tta att caa      432
Leu Arg Asp Cys Cys Arg Ser Val Arg Ile Gly Lys Ile Leu Ile Gln
    130                 135                 140

agg gac gag gag act gct tta cca aag tta ttc tac gaa aaa tta cca      480
Arg Asp Glu Glu Thr Ala Leu Pro Lys Leu Phe Tyr Glu Lys Leu Pro
145                 150                 155                 160

gag gat ata tct gaa agg tat gtc ttc cta tta gac cca atg ctg gcc      528
Glu Asp Ile Ser Glu Arg Tyr Val Phe Leu Leu Asp Pro Met Leu Ala
                165                 170                 175

acc ggt ggt agt gct atc atg gct aca gaa gtc ttg att aag aga ggt      576
Thr Gly Gly Ser Ala Ile Met Ala Thr Glu Val Leu Ile Lys Arg Gly
            180                 185                 190

gtt aag cca gag aga att tac ttc tta aac cta atc tgt agt aag gaa      624
Val Lys Pro Glu Arg Ile Tyr Phe Leu Asn Leu Ile Cys Ser Lys Glu
        195                 200                 205

ggg att gaa aaa tac cat gcc gcc ttc cca gag gtc aga att gtt act      672
Gly Ile Glu Lys Tyr His Ala Ala Phe Pro Glu Val Arg Ile Val Thr
    210                 215                 220

ggt gcc ctc gac aga ggt cta gat gaa aac aag tat cta gtt cca ggg      720
Gly Ala Leu Asp Arg Gly Leu Asp Glu Asn Lys Tyr Leu Val Pro Gly
225                 230                 235                 240

ttg ggt gac ttt ggt gac aga tac tac tgt gtt taa                      756
Leu Gly Asp Phe Gly Asp Arg Tyr Tyr Cys Val
                245                 250
```

```
<210> SEQ ID NO 8
<211> LENGTH: 251
<212> TYPE: PRT
<213> ORGANISM: Saccharomyces cerevisiae

<400> SEQUENCE: 8

Met Asn Pro Leu Phe Phe Leu Ala Ser Pro Phe Leu Tyr Leu Thr Tyr
1               5                   10                  15

Leu Ile Tyr Tyr Pro Asn Lys Gly Ser Phe Val Ser Lys Pro Arg Asn
            20                  25                  30

Leu Gln Lys Met Ser Ser Glu Pro Phe Lys Asn Val Tyr Leu Leu Pro
        35                  40                  45

Gln Thr Asn Gln Leu Leu Gly Leu Tyr Thr Ile Ile Arg Asn Lys Asn
    50                  55                  60

Thr Thr Arg Pro Asp Phe Ile Phe Tyr Ser Asp Arg Ile Ile Arg Leu
65                  70                  75                  80

Leu Val Glu Glu Gly Leu Asn His Leu Pro Val Gln Lys Gln Ile Val
                85                  90                  95

Glu Thr Asp Thr Asn Glu Asn Phe Glu Gly Val Ser Phe Met Gly Lys
            100                 105                 110

Ile Cys Gly Val Ser Ile Val Arg Ala Gly Glu Ser Met Glu Gln Gly
        115                 120                 125

Leu Arg Asp Cys Cys Arg Ser Val Arg Ile Gly Lys Ile Leu Ile Gln
    130                 135                 140

Arg Asp Glu Glu Thr Ala Leu Pro Lys Leu Phe Tyr Glu Lys Leu Pro
145                 150                 155                 160

Glu Asp Ile Ser Glu Arg Tyr Val Phe Leu Leu Asp Pro Met Leu Ala
                165                 170                 175

Thr Gly Gly Ser Ala Ile Met Ala Thr Glu Val Leu Ile Lys Arg Gly
            180                 185                 190
```

```
Val Lys Pro Glu Arg Ile Tyr Phe Leu Asn Leu Ile Cys Ser Lys Glu
        195                 200                 205

Gly Ile Glu Lys Tyr His Ala Ala Phe Pro Glu Val Arg Ile Val Thr
    210                 215                 220

Gly Ala Leu Asp Arg Gly Leu Asp Glu Asn Lys Tyr Leu Val Pro Gly
225                 230                 235                 240

Leu Gly Asp Phe Gly Asp Arg Tyr Tyr Cys Val
                245                 250


<210> SEQ ID NO 9
<211> LENGTH: 1443
<212> TYPE: DNA
<213> ORGANISM: homo sapiens
<220> FEATURE:
<221> NAME/KEY: CDS
<222> LOCATION: (1)..(1443)

<400> SEQUENCE: 9

atg gct gtt gct cgt gct gct ctt ggt cct ctt gtt act ggt ctt tat       48
Met Ala Val Ala Arg Ala Ala Leu Gly Pro Leu Val Thr Gly Leu Tyr
1               5                   10                  15

gat gtt caa gct ttt aaa ttt ggt gat ttt gtt ctt aaa tct ggt ctt       96
Asp Val Gln Ala Phe Lys Phe Gly Asp Phe Val Leu Lys Ser Gly Leu
            20                  25                  30

tct tct cct att tat att gat ctt cgt ggt att gtt tct cgt cct cgt      144
Ser Ser Pro Ile Tyr Ile Asp Leu Arg Gly Ile Val Ser Arg Pro Arg
        35                  40                  45

ctt ctt tct caa gtt gct gat att ctt ttt caa act gct caa aat gct      192
Leu Leu Ser Gln Val Ala Asp Ile Leu Phe Gln Thr Ala Gln Asn Ala
    50                  55                  60

ggt att tct ttt gat act gtt tgt ggt gtt cct tat act gct ctt cct      240
Gly Ile Ser Phe Asp Thr Val Cys Gly Val Pro Tyr Thr Ala Leu Pro
65                  70                  75                  80

ctt gct act gtt att tgt tct act aat caa att cct atg ctt att cgt      288
Leu Ala Thr Val Ile Cys Ser Thr Asn Gln Ile Pro Met Leu Ile Arg
                85                  90                  95

cgt aaa gaa act aaa gat tat ggt act aaa cgt ctt gtt gaa ggt act      336
Arg Lys Glu Thr Lys Asp Tyr Gly Thr Lys Arg Leu Val Glu Gly Thr
            100                 105                 110

att aat cct ggt gaa act tgt ctt att att gaa gat gtt gtt act tct      384
Ile Asn Pro Gly Glu Thr Cys Leu Ile Ile Glu Asp Val Val Thr Ser
        115                 120                 125

ggt tct tct gtt ctt gaa act gtt gaa gtt ctt caa aaa gaa ggt ctt      432
Gly Ser Ser Val Leu Glu Thr Val Glu Val Leu Gln Lys Glu Gly Leu
    130                 135                 140

aaa gtt act gat gct att gtt ctt ctt gat cgt gaa caa ggt ggt aaa      480
Lys Val Thr Asp Ala Ile Val Leu Leu Asp Arg Glu Gln Gly Gly Lys
145                 150                 155                 160

gat aaa ctt caa gct cat ggt att cgt ctt cat tct gtt tgt act ctt      528
Asp Lys Leu Gln Ala His Gly Ile Arg Leu His Ser Val Cys Thr Leu
                165                 170                 175

tct aaa atg ctt gaa att ctt gaa caa caa aaa aaa gtt gat gct gaa      576
Ser Lys Met Leu Glu Ile Leu Glu Gln Gln Lys Lys Val Asp Ala Glu
            180                 185                 190

act gtt ggt cgt gtt aaa cgt ttt att caa gaa aat gtt ttt gtt gct      624
Thr Val Gly Arg Val Lys Arg Phe Ile Gln Glu Asn Val Phe Val Ala
        195                 200                 205

gct aat cat aat ggt tct cct ctt tct att aaa gaa gct cct aaa gaa      672
Ala Asn His Asn Gly Ser Pro Leu Ser Ile Lys Glu Ala Pro Lys Glu
    210                 215                 220
```

```
ctt tct ttt ggt gct cgt gct gaa ctt cct cgt att cat cct gtt gct      720
Leu Ser Phe Gly Ala Arg Ala Glu Leu Pro Arg Ile His Pro Val Ala
225                 230                 235                 240

tct aaa ctt ctt cgt ctt atg caa aaa aaa gaa act aat ctt tgt ctt      768
Ser Lys Leu Leu Arg Leu Met Gln Lys Lys Glu Thr Asn Leu Cys Leu
                245                 250                 255

tct gct gat gtt tct ctt gct cgt gaa ctt ctt caa ctt gct gat gct      816
Ser Ala Asp Val Ser Leu Ala Arg Glu Leu Leu Gln Leu Ala Asp Ala
            260                 265                 270

ctt ggt cct tct att tgt atg ctt aaa act cat gtt gat att ctt aat      864
Leu Gly Pro Ser Ile Cys Met Leu Lys Thr His Val Asp Ile Leu Asn
        275                 280                 285

gat ttt act ctt gat gtt atg aaa gaa ctt att act ctt gct aaa tgt      912
Asp Phe Thr Leu Asp Val Met Lys Glu Leu Ile Thr Leu Ala Lys Cys
    290                 295                 300

cat gaa ttt ctt att ttt gaa gat cgt aaa ttt gct gat att ggt aat      960
His Glu Phe Leu Ile Phe Glu Asp Arg Lys Phe Ala Asp Ile Gly Asn
305                 310                 315                 320

act gtt aaa aaa caa tat gaa ggt ggt att ttt aaa att gct tct tgg     1008
Thr Val Lys Lys Gln Tyr Glu Gly Gly Ile Phe Lys Ile Ala Ser Trp
                325                 330                 335

gct gat ctt gtt aat gct cat gtt gtt cct ggt tct ggt gtt gtt aaa     1056
Ala Asp Leu Val Asn Ala His Val Val Pro Gly Ser Gly Val Val Lys
            340                 345                 350

ggt ctt caa gaa gtt ggt ctt cct ctt cat cgt ggt tgt ctt ctt att     1104
Gly Leu Gln Glu Val Gly Leu Pro Leu His Arg Gly Cys Leu Leu Ile
        355                 360                 365

gct gaa atg tct tct act ggt tct ctt gct act ggt gat tat act cgt     1152
Ala Glu Met Ser Ser Thr Gly Ser Leu Ala Thr Gly Asp Tyr Thr Arg
    370                 375                 380

gct gct gtt cgt atg gct gaa gaa cat tct gaa ttt gtt gtt ggt ttt     1200
Ala Ala Val Arg Met Ala Glu Glu His Ser Glu Phe Val Val Gly Phe
385                 390                 395                 400

att tct ggt tct cgt gtt tct atg aaa cct gaa ttt ctt cat ctt act     1248
Ile Ser Gly Ser Arg Val Ser Met Lys Pro Glu Phe Leu His Leu Thr
                405                 410                 415

cct ggt gtt caa ctt gaa gct ggt ggt gat aat ctt ggt caa caa tat     1296
Pro Gly Val Gln Leu Glu Ala Gly Gly Asp Asn Leu Gly Gln Gln Tyr
            420                 425                 430

aat tct cct caa gaa gtt att ggt aaa cgt ggt tct gat att att att     1344
Asn Ser Pro Gln Glu Val Ile Gly Lys Arg Gly Ser Asp Ile Ile Ile
        435                 440                 445

gtt ggt cgt ggt att att tct gct gct gat cgt ctt gaa gct gct gaa     1392
Val Gly Arg Gly Ile Ile Ser Ala Ala Asp Arg Leu Glu Ala Ala Glu
    450                 455                 460

atg tat cgt aaa gct gct tgg gaa gct tat ctt tct cgt ctt ggt gtt     1440
Met Tyr Arg Lys Ala Ala Trp Glu Ala Tyr Leu Ser Arg Leu Gly Val
465                 470                 475                 480

taa                                                                 1443


<210> SEQ ID NO 10
<211> LENGTH: 480
<212> TYPE: PRT
<213> ORGANISM: homo sapiens

<400> SEQUENCE: 10

Met Ala Val Ala Arg Ala Ala Leu Gly Pro Leu Val Thr Gly Leu Tyr
1               5                   10                  15

Asp Val Gln Ala Phe Lys Phe Gly Asp Phe Val Leu Lys Ser Gly Leu
```

-continued

```
            20                  25                  30

Ser Ser Pro Ile Tyr Ile Asp Leu Arg Gly Ile Val Ser Arg Pro Arg
        35                  40                  45

Leu Leu Ser Gln Val Ala Asp Ile Leu Phe Gln Thr Ala Gln Asn Ala
    50                  55                  60

Gly Ile Ser Phe Asp Thr Val Cys Gly Val Pro Tyr Thr Ala Leu Pro
65                  70                  75                  80

Leu Ala Thr Val Ile Cys Ser Thr Asn Gln Ile Pro Met Leu Ile Arg
                85                  90                  95

Arg Lys Glu Thr Lys Asp Tyr Gly Thr Lys Arg Leu Val Glu Gly Thr
            100                 105                 110

Ile Asn Pro Gly Glu Thr Cys Leu Ile Ile Glu Asp Val Val Thr Ser
        115                 120                 125

Gly Ser Ser Val Leu Glu Thr Val Glu Val Leu Gln Lys Glu Gly Leu
    130                 135                 140

Lys Val Thr Asp Ala Ile Val Leu Leu Asp Arg Glu Gln Gly Gly Lys
145                 150                 155                 160

Asp Lys Leu Gln Ala His Gly Ile Arg Leu His Ser Val Cys Thr Leu
                165                 170                 175

Ser Lys Met Leu Glu Ile Leu Glu Gln Gln Lys Lys Val Asp Ala Glu
            180                 185                 190

Thr Val Gly Arg Val Lys Arg Phe Ile Gln Glu Asn Val Phe Val Ala
        195                 200                 205

Ala Asn His Asn Gly Ser Pro Leu Ser Ile Lys Glu Ala Pro Lys Glu
    210                 215                 220

Leu Ser Phe Gly Ala Arg Ala Glu Leu Pro Arg Ile His Pro Val Ala
225                 230                 235                 240

Ser Lys Leu Leu Arg Leu Met Gln Lys Lys Glu Thr Asn Leu Cys Leu
                245                 250                 255

Ser Ala Asp Val Ser Leu Ala Arg Glu Leu Leu Gln Leu Ala Asp Ala
            260                 265                 270

Leu Gly Pro Ser Ile Cys Met Leu Lys Thr His Val Asp Ile Leu Asn
        275                 280                 285

Asp Phe Thr Leu Asp Val Met Lys Glu Leu Ile Thr Leu Ala Lys Cys
    290                 295                 300

His Glu Phe Leu Ile Phe Glu Asp Arg Lys Phe Ala Asp Ile Gly Asn
305                 310                 315                 320

Thr Val Lys Lys Gln Tyr Glu Gly Gly Ile Phe Lys Ile Ala Ser Trp
                325                 330                 335

Ala Asp Leu Val Asn Ala His Val Val Pro Gly Ser Gly Val Val Lys
            340                 345                 350

Gly Leu Gln Glu Val Gly Leu Pro Leu His Arg Gly Cys Leu Leu Ile
        355                 360                 365

Ala Glu Met Ser Ser Thr Gly Ser Leu Ala Thr Gly Asp Tyr Thr Arg
    370                 375                 380

Ala Ala Val Arg Met Ala Glu Glu His Ser Glu Phe Val Val Gly Phe
385                 390                 395                 400

Ile Ser Gly Ser Arg Val Ser Met Lys Pro Glu Phe Leu His Leu Thr
                405                 410                 415

Pro Gly Val Gln Leu Glu Ala Gly Gly Asp Asn Leu Gly Gln Gln Tyr
            420                 425                 430

Asn Ser Pro Gln Glu Val Ile Gly Lys Arg Gly Ser Asp Ile Ile Ile
        435                 440                 445
```

```
Val Gly Arg Gly Ile Ile Ser Ala Ala Asp Arg Leu Glu Ala Ala Glu
    450                 455                 460

Met Tyr Arg Lys Ala Ala Trp Glu Ala Tyr Leu Ser Arg Leu Gly Val
465                 470                 475                 480


<210> SEQ ID NO 11
<211> LENGTH: 1227
<212> TYPE: DNA
<213> ORGANISM: Artificial Sequence
<220> FEATURE:
<223> OTHER INFORMATION: Fusion construct CDopt-UPRT
<220> FEATURE:
<221> NAME/KEY: CDS
<222> LOCATION: (1)..(1227)

<400> SEQUENCE: 11

atg gtg acc ggc ggc atg gcc tcc aag tgg gat caa aag ggc atg gat       48
Met Val Thr Gly Gly Met Ala Ser Lys Trp Asp Gln Lys Gly Met Asp
1               5                   10                  15

atc gct tac gag gag gcc ctg ctg ggc tac aag gag ggc ggc gtg cct       96
Ile Ala Tyr Glu Glu Ala Leu Leu Gly Tyr Lys Glu Gly Gly Val Pro
            20                  25                  30

atc ggc ggc tgt ctg atc aac aac aag gac ggc agt gtg ctg ggc agg      144
Ile Gly Gly Cys Leu Ile Asn Asn Lys Asp Gly Ser Val Leu Gly Arg
        35                  40                  45

ggc cac aac atg agg ttc cag aag ggc tcc gcc acc ctg cac ggc gag      192
Gly His Asn Met Arg Phe Gln Lys Gly Ser Ala Thr Leu His Gly Glu
    50                  55                  60

atc tcc acc ctg gag aac tgt ggc agg ctg gag ggc aag gtg tac aag      240
Ile Ser Thr Leu Glu Asn Cys Gly Arg Leu Glu Gly Lys Val Tyr Lys
65                  70                  75                  80

gac acc acc ctg tac acc acc ctg tcc cct tgt gac atg tgt acc ggc      288
Asp Thr Thr Leu Tyr Thr Thr Leu Ser Pro Cys Asp Met Cys Thr Gly
                85                  90                  95

gct atc atc atg tac ggc atc cct agg tgt gtg atc ggc gag aac gtg      336
Ala Ile Ile Met Tyr Gly Ile Pro Arg Cys Val Ile Gly Glu Asn Val
            100                 105                 110

aac ttc aag tcc aag ggc gag aag tac ctg caa acc agg ggc cac gag      384
Asn Phe Lys Ser Lys Gly Glu Lys Tyr Leu Gln Thr Arg Gly His Glu
        115                 120                 125

gtg gtg gtt gtt gac gat gag agg tgt aag aag ctg atg aag cag ttc      432
Val Val Val Val Asp Asp Glu Arg Cys Lys Lys Leu Met Lys Gln Phe
    130                 135                 140

atc gac gag agg cct cag gac tgg ttc gag gat atc ggc gag aac ccg      480
Ile Asp Glu Arg Pro Gln Asp Trp Phe Glu Asp Ile Gly Glu Asn Pro
145                 150                 155                 160

tta ttc ttt ttg gct tct cca ttc ttg tac ctt aca tat ctt ata tat      528
Leu Phe Phe Leu Ala Ser Pro Phe Leu Tyr Leu Thr Tyr Leu Ile Tyr
                165                 170                 175

tat cca aac aaa ggg tct ttc gtt agc aaa cct aga aat ctg caa aaa      576
Tyr Pro Asn Lys Gly Ser Phe Val Ser Lys Pro Arg Asn Leu Gln Lys
            180                 185                 190

atg tct tcg gaa cca ttt aag aac gtc tac ttg cta cct caa aca aac      624
Met Ser Ser Glu Pro Phe Lys Asn Val Tyr Leu Leu Pro Gln Thr Asn
        195                 200                 205

caa ttg ctg ggt ttg tac acc atc atc aga aat aag aat aca act aga      672
Gln Leu Leu Gly Leu Tyr Thr Ile Ile Arg Asn Lys Asn Thr Thr Arg
    210                 215                 220

cct gat ttc att ttc tac tcc gat aga atc atc aga ttg ttg gtt gaa      720
Pro Asp Phe Ile Phe Tyr Ser Asp Arg Ile Ile Arg Leu Leu Val Glu
225                 230                 235                 240
```

```
gaa ggt ttg aac cat cta cct gtg caa aag caa att gtg gaa act gac      768
Glu Gly Leu Asn His Leu Pro Val Gln Lys Gln Ile Val Glu Thr Asp
                245                 250                 255

acc aac gaa aac ttc gaa ggt gtc tca ttc atg ggt aaa atc tgt ggt      816
Thr Asn Glu Asn Phe Glu Gly Val Ser Phe Met Gly Lys Ile Cys Gly
            260                 265                 270

gtt tcc att gtc aga gct ggt gaa tcg atg gag caa gga tta aga gac      864
Val Ser Ile Val Arg Ala Gly Glu Ser Met Glu Gln Gly Leu Arg Asp
        275                 280                 285

tgt tgt agg tct gtg cgt atc ggt aaa att tta att caa agg gac gag      912
Cys Cys Arg Ser Val Arg Ile Gly Lys Ile Leu Ile Gln Arg Asp Glu
    290                 295                 300

gag act gct tta cca aag tta ttc tac gaa aaa tta cca gag gat ata      960
Glu Thr Ala Leu Pro Lys Leu Phe Tyr Glu Lys Leu Pro Glu Asp Ile
305                 310                 315                 320

tct gaa agg tat gtc ttc cta tta gac cca atg ctg gcc acc ggt ggt     1008
Ser Glu Arg Tyr Val Phe Leu Leu Asp Pro Met Leu Ala Thr Gly Gly
                325                 330                 335

agt gct atc atg gct aca gaa gtc ttg att aag aga ggt gtt aag cca     1056
Ser Ala Ile Met Ala Thr Glu Val Leu Ile Lys Arg Gly Val Lys Pro
            340                 345                 350

gag aga att tac ttc tta aac cta atc tgt agt aag gaa ggg att gaa     1104
Glu Arg Ile Tyr Phe Leu Asn Leu Ile Cys Ser Lys Glu Gly Ile Glu
        355                 360                 365

aaa tac cat gcc gcc ttc cca gag gtc aga att gtt act ggt gcc ctc     1152
Lys Tyr His Ala Ala Phe Pro Glu Val Arg Ile Val Thr Gly Ala Leu
    370                 375                 380

gac aga ggt cta gat gaa aac aag tat cta gtt cca ggg ttg ggt gac     1200
Asp Arg Gly Leu Asp Glu Asn Lys Tyr Leu Val Pro Gly Leu Gly Asp
385                 390                 395                 400

ttt ggt gac aga tac tac tgt gtt taa                                 1227
Phe Gly Asp Arg Tyr Tyr Cys Val
                405
```

```
<210> SEQ ID NO 12
<211> LENGTH: 408
<212> TYPE: PRT
<213> ORGANISM: Artificial Sequence
<220> FEATURE:
<223> OTHER INFORMATION: Synthetic Construct

<400> SEQUENCE: 12

Met Val Thr Gly Gly Met Ala Ser Lys Trp Asp Gln Lys Gly Met Asp
1               5                   10                  15

Ile Ala Tyr Glu Glu Ala Leu Leu Gly Tyr Lys Glu Gly Gly Val Pro
            20                  25                  30

Ile Gly Gly Cys Leu Ile Asn Asn Lys Asp Gly Ser Val Leu Gly Arg
        35                  40                  45

Gly His Asn Met Arg Phe Gln Lys Gly Ser Ala Thr Leu His Gly Glu
    50                  55                  60

Ile Ser Thr Leu Glu Asn Cys Gly Arg Leu Glu Gly Lys Val Tyr Lys
65                  70                  75                  80

Asp Thr Thr Leu Tyr Thr Thr Leu Ser Pro Cys Asp Met Cys Thr Gly
                85                  90                  95

Ala Ile Ile Met Tyr Gly Ile Pro Arg Cys Val Ile Gly Glu Asn Val
            100                 105                 110

Asn Phe Lys Ser Lys Gly Glu Lys Tyr Leu Gln Thr Arg Gly His Glu
        115                 120                 125
```

-continued

```
Val Val Val Val Asp Asp Glu Arg Cys Lys Lys Leu Met Lys Gln Phe
    130                 135                 140

Ile Asp Glu Arg Pro Gln Asp Trp Phe Glu Asp Ile Gly Glu Asn Pro
145                 150                 155                 160

Leu Phe Phe Leu Ala Ser Pro Phe Leu Tyr Leu Thr Tyr Leu Ile Tyr
                165                 170                 175

Tyr Pro Asn Lys Gly Ser Phe Val Ser Lys Pro Arg Asn Leu Gln Lys
            180                 185                 190

Met Ser Ser Glu Pro Phe Lys Asn Val Tyr Leu Leu Pro Gln Thr Asn
        195                 200                 205

Gln Leu Leu Gly Leu Tyr Thr Ile Ile Arg Asn Lys Asn Thr Thr Arg
    210                 215                 220

Pro Asp Phe Ile Phe Tyr Ser Asp Arg Ile Ile Arg Leu Leu Val Glu
225                 230                 235                 240

Glu Gly Leu Asn His Leu Pro Val Gln Lys Gln Ile Val Glu Thr Asp
                245                 250                 255

Thr Asn Glu Asn Phe Glu Gly Val Ser Phe Met Gly Lys Ile Cys Gly
            260                 265                 270

Val Ser Ile Val Arg Ala Gly Glu Ser Met Glu Gln Gly Leu Arg Asp
        275                 280                 285

Cys Cys Arg Ser Val Arg Ile Gly Lys Ile Leu Ile Gln Arg Asp Glu
    290                 295                 300

Glu Thr Ala Leu Pro Lys Leu Phe Tyr Glu Lys Leu Pro Glu Asp Ile
305                 310                 315                 320

Ser Glu Arg Tyr Val Phe Leu Leu Asp Pro Met Leu Ala Thr Gly Gly
                325                 330                 335

Ser Ala Ile Met Ala Thr Glu Val Leu Ile Lys Arg Gly Val Lys Pro
            340                 345                 350

Glu Arg Ile Tyr Phe Leu Asn Leu Ile Cys Ser Lys Glu Gly Ile Glu
        355                 360                 365

Lys Tyr His Ala Ala Phe Pro Glu Val Arg Ile Val Thr Gly Ala Leu
    370                 375                 380

Asp Arg Gly Leu Asp Glu Asn Lys Tyr Leu Val Pro Gly Leu Gly Asp
385                 390                 395                 400

Phe Gly Asp Arg Tyr Tyr Cys Val
                405


<210> SEQ ID NO 13
<211> LENGTH: 1287
<212> TYPE: DNA
<213> ORGANISM: Artificial Sequence
<220> FEATURE:
<223> OTHER INFORMATION: Fusion construction - CDopt - linker - UPRT
<220> FEATURE:
<221> NAME/KEY: CDS
<222> LOCATION: (1)..(1287)

<400> SEQUENCE: 13

atg gtg acc ggc ggc atg gcc tcc aag tgg gat caa aag ggc atg gat       48
Met Val Thr Gly Gly Met Ala Ser Lys Trp Asp Gln Lys Gly Met Asp
1               5                   10                  15

atc gct tac gag gag gcc ctg ctg ggc tac aag gag ggc ggc gtg cct       96
Ile Ala Tyr Glu Glu Ala Leu Leu Gly Tyr Lys Glu Gly Gly Val Pro
            20                  25                  30

atc ggc ggc tgt ctg atc aac aac aag gac ggc agt gtg ctg ggc agg      144
Ile Gly Gly Cys Leu Ile Asn Asn Lys Asp Gly Ser Val Leu Gly Arg
        35                  40                  45
```

-continued

```
ggc cac aac atg agg ttc cag aag ggc tcc gcc acc ctg cac ggc gag      192
Gly His Asn Met Arg Phe Gln Lys Gly Ser Ala Thr Leu His Gly Glu
    50                  55                  60

atc tcc acc ctg gag aac tgt ggc agg ctg gag ggc aag gtg tac aag      240
Ile Ser Thr Leu Glu Asn Cys Gly Arg Leu Glu Gly Lys Val Tyr Lys
65                  70                  75                  80

gac acc acc ctg tac acc acc ctg tcc cct tgt gac atg tgt acc ggc      288
Asp Thr Thr Leu Tyr Thr Thr Leu Ser Pro Cys Asp Met Cys Thr Gly
                85                  90                  95

gct atc atc atg tac ggc atc cct agg tgt gtg atc ggc gag aac gtg      336
Ala Ile Ile Met Tyr Gly Ile Pro Arg Cys Val Ile Gly Glu Asn Val
            100                 105                 110

aac ttc aag tcc aag ggc gag aag tac ctg caa acc agg ggc cac gag      384
Asn Phe Lys Ser Lys Gly Glu Lys Tyr Leu Gln Thr Arg Gly His Glu
        115                 120                 125

gtg gtg gtt gtt gac gat gag agg tgt aag aag ctg atg aag cag ttc      432
Val Val Val Val Asp Asp Glu Arg Cys Lys Lys Leu Met Lys Gln Phe
    130                 135                 140

atc gac gag agg cct cag gac tgg ttc gag gat atc ggc gag tcc ggc      480
Ile Asp Glu Arg Pro Gln Asp Trp Phe Glu Asp Ile Gly Glu Ser Gly
145                 150                 155                 160

ggc ggc gcc tcc ggc ggc ggc gcc tcc ggc ggc ggc gcc tcc ggc ggc      528
Gly Gly Ala Ser Gly Gly Gly Ala Ser Gly Gly Gly Ala Ser Gly Gly
                165                 170                 175

ggc gcc aac ccg tta ttc ttt ttg gct tct cca ttc ttg tac ctt aca      576
Gly Ala Asn Pro Leu Phe Phe Leu Ala Ser Pro Phe Leu Tyr Leu Thr
            180                 185                 190

tat ctt ata tat tat cca aac aaa ggg tct ttc gtt agc aaa cct aga      624
Tyr Leu Ile Tyr Tyr Pro Asn Lys Gly Ser Phe Val Ser Lys Pro Arg
        195                 200                 205

aat ctg caa aaa atg tct tcg gaa cca ttt aag aac gtc tac ttg cta      672
Asn Leu Gln Lys Met Ser Ser Glu Pro Phe Lys Asn Val Tyr Leu Leu
    210                 215                 220

cct caa aca aac caa ttg ctg ggt ttg tac acc atc atc aga aat aag      720
Pro Gln Thr Asn Gln Leu Leu Gly Leu Tyr Thr Ile Ile Arg Asn Lys
225                 230                 235                 240

aat aca act aga cct gat ttc att ttc tac tcc gat aga atc atc aga      768
Asn Thr Thr Arg Pro Asp Phe Ile Phe Tyr Ser Asp Arg Ile Ile Arg
                245                 250                 255

ttg ttg gtt gaa gaa ggt ttg aac cat cta cct gtg caa aag caa att      816
Leu Leu Val Glu Glu Gly Leu Asn His Leu Pro Val Gln Lys Gln Ile
            260                 265                 270

gtg gaa act gac acc aac gaa aac ttc gaa ggt gtc tca ttc atg ggt      864
Val Glu Thr Asp Thr Asn Glu Asn Phe Glu Gly Val Ser Phe Met Gly
        275                 280                 285

aaa atc tgt ggt gtt tcc att gtc aga gct ggt gaa tcg atg gag caa      912
Lys Ile Cys Gly Val Ser Ile Val Arg Ala Gly Glu Ser Met Glu Gln
    290                 295                 300

gga tta aga gac tgt tgt agg tct gtg cgt atc ggt aaa att tta att      960
Gly Leu Arg Asp Cys Cys Arg Ser Val Arg Ile Gly Lys Ile Leu Ile
305                 310                 315                 320

caa agg gac gag gag act gct tta cca aag tta ttc tac gaa aaa tta     1008
Gln Arg Asp Glu Glu Thr Ala Leu Pro Lys Leu Phe Tyr Glu Lys Leu
                325                 330                 335

cca gag gat ata tct gaa agg tat gtc ttc cta tta gac cca atg ctg     1056
Pro Glu Asp Ile Ser Glu Arg Tyr Val Phe Leu Leu Asp Pro Met Leu
            340                 345                 350

gcc acc ggt ggt agt gct atc atg gct aca gaa gtc ttg att aag aga     1104
Ala Thr Gly Gly Ser Ala Ile Met Ala Thr Glu Val Leu Ile Lys Arg
        355                 360                 365
```

```
ggt gtt aag cca gag aga att tac ttc tta aac cta atc tgt agt aag      1152
Gly Val Lys Pro Glu Arg Ile Tyr Phe Leu Asn Leu Ile Cys Ser Lys
    370                 375                 380

gaa ggg att gaa aaa tac cat gcc gcc ttc cca gag gtc aga att gtt      1200
Glu Gly Ile Glu Lys Tyr His Ala Ala Phe Pro Glu Val Arg Ile Val
385                 390                 395                 400

act ggt gcc ctc gac aga ggt cta gat gaa aac aag tat cta gtt cca      1248
Thr Gly Ala Leu Asp Arg Gly Leu Asp Glu Asn Lys Tyr Leu Val Pro
                405                 410                 415

ggg ttg ggt gac ttt ggt gac aga tac tac tgt gtt taa                  1287
Gly Leu Gly Asp Phe Gly Asp Arg Tyr Tyr Cys Val
            420                 425


<210> SEQ ID NO 14
<211> LENGTH: 428
<212> TYPE: PRT
<213> ORGANISM: Artificial Sequence
<220> FEATURE:
<223> OTHER INFORMATION: Synthetic Construct

<400> SEQUENCE: 14

Met Val Thr Gly Gly Met Ala Ser Lys Trp Asp Gln Lys Gly Met Asp
1               5                   10                  15

Ile Ala Tyr Glu Glu Ala Leu Leu Gly Tyr Lys Glu Gly Gly Val Pro
            20                  25                  30

Ile Gly Gly Cys Leu Ile Asn Asn Lys Asp Gly Ser Val Leu Gly Arg
        35                  40                  45

Gly His Asn Met Arg Phe Gln Lys Gly Ser Ala Thr Leu His Gly Glu
    50                  55                  60

Ile Ser Thr Leu Glu Asn Cys Gly Arg Leu Glu Gly Lys Val Tyr Lys
65                  70                  75                  80

Asp Thr Thr Leu Tyr Thr Thr Leu Ser Pro Cys Asp Met Cys Thr Gly
                85                  90                  95

Ala Ile Ile Met Tyr Gly Ile Pro Arg Cys Val Ile Gly Glu Asn Val
            100                 105                 110

Asn Phe Lys Ser Lys Gly Glu Lys Tyr Leu Gln Thr Arg Gly His Glu
        115                 120                 125

Val Val Val Val Asp Asp Glu Arg Cys Lys Lys Leu Met Lys Gln Phe
    130                 135                 140

Ile Asp Glu Arg Pro Gln Asp Trp Phe Glu Asp Ile Gly Glu Ser Gly
145                 150                 155                 160

Gly Gly Ala Ser Gly Gly Gly Ala Ser Gly Gly Gly Ala Ser Gly Gly
                165                 170                 175

Gly Ala Asn Pro Leu Phe Phe Leu Ala Ser Pro Phe Leu Tyr Leu Thr
            180                 185                 190

Tyr Leu Ile Tyr Tyr Pro Asn Lys Gly Ser Phe Val Ser Lys Pro Arg
        195                 200                 205

Asn Leu Gln Lys Met Ser Ser Glu Pro Phe Lys Asn Val Tyr Leu Leu
    210                 215                 220

Pro Gln Thr Asn Gln Leu Leu Gly Leu Tyr Thr Ile Ile Arg Asn Lys
225                 230                 235                 240

Asn Thr Thr Arg Pro Asp Phe Ile Phe Tyr Ser Asp Arg Ile Ile Arg
                245                 250                 255

Leu Leu Val Glu Glu Gly Leu Asn His Leu Pro Val Gln Lys Gln Ile
            260                 265                 270

Val Glu Thr Asp Thr Asn Glu Asn Phe Glu Gly Val Ser Phe Met Gly
```

```
        275                 280                 285

Lys Ile Cys Gly Val Ser Ile Val Arg Ala Gly Glu Ser Met Glu Gln
    290                 295                 300

Gly Leu Arg Asp Cys Cys Arg Ser Val Arg Ile Gly Lys Ile Leu Ile
305                 310                 315                 320

Gln Arg Asp Glu Glu Thr Ala Leu Pro Lys Leu Phe Tyr Glu Lys Leu
                325                 330                 335

Pro Glu Asp Ile Ser Glu Arg Tyr Val Phe Leu Leu Asp Pro Met Leu
            340                 345                 350

Ala Thr Gly Gly Ser Ala Ile Met Ala Thr Glu Val Leu Ile Lys Arg
        355                 360                 365

Gly Val Lys Pro Glu Arg Ile Tyr Phe Leu Asn Leu Ile Cys Ser Lys
    370                 375                 380

Glu Gly Ile Glu Lys Tyr His Ala Ala Phe Pro Glu Val Arg Ile Val
385                 390                 395                 400

Thr Gly Ala Leu Asp Arg Gly Leu Asp Glu Asn Lys Tyr Leu Val Pro
                405                 410                 415

Gly Leu Gly Asp Phe Gly Asp Arg Tyr Tyr Cys Val
            420                 425


<210> SEQ ID NO 15
<211> LENGTH: 1200
<212> TYPE: DNA
<213> ORGANISM: Artificial Sequence
<220> FEATURE:
<223> OTHER INFORMATION: Fusion Construct - CDopt3 - OPRT
<220> FEATURE:
<221> NAME/KEY: CDS
<222> LOCATION: (1)..(1200)

<400> SEQUENCE: 15

atg gtg acc ggc ggc atg gcc tcc aag tgg gat caa aag ggc atg gat       48
Met Val Thr Gly Gly Met Ala Ser Lys Trp Asp Gln Lys Gly Met Asp
1               5                   10                  15

atc gct tac gag gag gcc ctg ctg ggc tac aag gag ggc ggc gtg cct       96
Ile Ala Tyr Glu Glu Ala Leu Leu Gly Tyr Lys Glu Gly Gly Val Pro
            20                  25                  30

atc ggc ggc tgt ctg atc aac aac aag gac ggc agt gtg ctg ggc agg      144
Ile Gly Gly Cys Leu Ile Asn Asn Lys Asp Gly Ser Val Leu Gly Arg
        35                  40                  45

ggc cac aac atg agg ttc cag aag ggc tcc gcc acc ctg cac ggc gag      192
Gly His Asn Met Arg Phe Gln Lys Gly Ser Ala Thr Leu His Gly Glu
    50                  55                  60

atc tcc acc ctg gag aac tgt ggc agg ctg gag ggc aag gtg tac aag      240
Ile Ser Thr Leu Glu Asn Cys Gly Arg Leu Glu Gly Lys Val Tyr Lys
65                  70                  75                  80

gac acc acc ctg tac acc acc ctg tcc cct tgt gac atg tgt acc ggc      288
Asp Thr Thr Leu Tyr Thr Thr Leu Ser Pro Cys Asp Met Cys Thr Gly
                85                  90                  95

gct atc atc atg tac ggc atc cct agg tgt gtg atc ggc gag aac gtg      336
Ala Ile Ile Met Tyr Gly Ile Pro Arg Cys Val Ile Gly Glu Asn Val
            100                 105                 110

aac ttc aag tcc aag ggc gag aag tac ctg caa acc agg ggc cac gag      384
Asn Phe Lys Ser Lys Gly Glu Lys Tyr Leu Gln Thr Arg Gly His Glu
        115                 120                 125

gtg gtg gtt gtt gac gat gag agg tgt aag aag ctg atg aag cag ttc      432
Val Val Val Val Asp Asp Glu Arg Cys Lys Lys Leu Met Lys Gln Phe
    130                 135                 140

atc gac gag agg cct cag gac tgg ttc gag gat atc ggc gag gcg gtc      480
```

```
Ile Asp Glu Arg Pro Gln Asp Trp Phe Glu Asp Ile Gly Glu Ala Val
145                 150                 155                 160

gct cgt gca gct ttg ggg cca ttg gtg acg ggt ctg tac gac gtg cag      528
Ala Arg Ala Ala Leu Gly Pro Leu Val Thr Gly Leu Tyr Asp Val Gln
                165                 170                 175

gct ttc aag ttt ggg gac ttc gtg ctg aag agc ggg ctt tcc tcc ccc      576
Ala Phe Lys Phe Gly Asp Phe Val Leu Lys Ser Gly Leu Ser Ser Pro
            180                 185                 190

atc tac atc gat ctg cgg ggc atc gtg tct cga ccg cgt ctt ctg agt      624
Ile Tyr Ile Asp Leu Arg Gly Ile Val Ser Arg Pro Arg Leu Leu Ser
        195                 200                 205

cag gtt gca gat att tta ttc caa act gcc caa aat gca ggc atc agt      672
Gln Val Ala Asp Ile Leu Phe Gln Thr Ala Gln Asn Ala Gly Ile Ser
    210                 215                 220

ttt gac acc gtg tgt gga gtg cct tat aca gct ttg cca ttg gct aca      720
Phe Asp Thr Val Cys Gly Val Pro Tyr Thr Ala Leu Pro Leu Ala Thr
225                 230                 235                 240

gtt atc tgt tca acc aat caa att cca atg ctt att aga agg aaa gaa      768
Val Ile Cys Ser Thr Asn Gln Ile Pro Met Leu Ile Arg Arg Lys Glu
                245                 250                 255

aca aag gat tat gga act aag cgt ctt gta gaa gga act att aat cca      816
Thr Lys Asp Tyr Gly Thr Lys Arg Leu Val Glu Gly Thr Ile Asn Pro
            260                 265                 270

gga gaa acc tgt tta atc att gaa gat gtt gtc acc agt gga tct agt      864
Gly Glu Thr Cys Leu Ile Ile Glu Asp Val Val Thr Ser Gly Ser Ser
        275                 280                 285

gtt ttg gaa act gtt gag gtt ctt cag aag gag ggc ttg aag gtc act      912
Val Leu Glu Thr Val Glu Val Leu Gln Lys Glu Gly Leu Lys Val Thr
    290                 295                 300

gat gcc ata gtg ctg ttg gac aga gag cag gga ggc aag gac aag ttg      960
Asp Ala Ile Val Leu Leu Asp Arg Glu Gln Gly Gly Lys Asp Lys Leu
305                 310                 315                 320

cag gcg cac ggg atc cgc ctc cac tca gtg tgt aca ttg tcc aaa atg     1008
Gln Ala His Gly Ile Arg Leu His Ser Val Cys Thr Leu Ser Lys Met
                325                 330                 335

ctg gag att ctc gag cag cag aaa aaa gtt gat gct gag aca gtt ggg     1056
Leu Glu Ile Leu Glu Gln Gln Lys Lys Val Asp Ala Glu Thr Val Gly
            340                 345                 350

aga gtg aag agg ttt att cag gag aat gtc ttt gtg gca gcg aat cat     1104
Arg Val Lys Arg Phe Ile Gln Glu Asn Val Phe Val Ala Ala Asn His
        355                 360                 365

aat ggt tct ccc ctt tct ata aag gaa gca ccc aaa gaa ctc agc ttc     1152
Asn Gly Ser Pro Leu Ser Ile Lys Glu Ala Pro Lys Glu Leu Ser Phe
    370                 375                 380

ggt gca cgt gca gag ctg ccc agg atc cac cca gtt gca tcg aag taa     1200
Gly Ala Arg Ala Glu Leu Pro Arg Ile His Pro Val Ala Ser Lys
385                 390                 395


<210> SEQ ID NO 16
<211> LENGTH: 399
<212> TYPE: PRT
<213> ORGANISM: Artificial Sequence
<220> FEATURE:
<223> OTHER INFORMATION: Synthetic Construct

<400> SEQUENCE: 16

Met Val Thr Gly Gly Met Ala Ser Lys Trp Asp Gln Lys Gly Met Asp
1               5                   10                  15

Ile Ala Tyr Glu Glu Ala Leu Leu Gly Tyr Lys Glu Gly Gly Val Pro
            20                  25                  30
```

```
Ile Gly Gly Cys Leu Ile Asn Asn Lys Asp Gly Ser Val Leu Gly Arg
        35                  40                  45

Gly His Asn Met Arg Phe Gln Lys Gly Ser Ala Thr Leu His Gly Glu
    50                  55                  60

Ile Ser Thr Leu Glu Asn Cys Gly Arg Leu Glu Gly Lys Val Tyr Lys
65                  70                  75                  80

Asp Thr Thr Leu Tyr Thr Thr Leu Ser Pro Cys Asp Met Cys Thr Gly
                85                  90                  95

Ala Ile Ile Met Tyr Gly Ile Pro Arg Cys Val Ile Gly Glu Asn Val
            100                 105                 110

Asn Phe Lys Ser Lys Gly Glu Lys Tyr Leu Gln Thr Arg Gly His Glu
        115                 120                 125

Val Val Val Val Asp Asp Glu Arg Cys Lys Lys Leu Met Lys Gln Phe
    130                 135                 140

Ile Asp Glu Arg Pro Gln Asp Trp Phe Glu Asp Ile Gly Glu Ala Val
145                 150                 155                 160

Ala Arg Ala Ala Leu Gly Pro Leu Val Thr Gly Leu Tyr Asp Val Gln
                165                 170                 175

Ala Phe Lys Phe Gly Asp Phe Val Leu Lys Ser Gly Leu Ser Ser Pro
            180                 185                 190

Ile Tyr Ile Asp Leu Arg Gly Ile Val Ser Arg Pro Arg Leu Leu Ser
        195                 200                 205

Gln Val Ala Asp Ile Leu Phe Gln Thr Ala Gln Asn Ala Gly Ile Ser
    210                 215                 220

Phe Asp Thr Val Cys Gly Val Pro Tyr Thr Ala Leu Pro Leu Ala Thr
225                 230                 235                 240

Val Ile Cys Ser Thr Asn Gln Ile Pro Met Leu Ile Arg Arg Lys Glu
                245                 250                 255

Thr Lys Asp Tyr Gly Thr Lys Arg Leu Val Glu Gly Thr Ile Asn Pro
            260                 265                 270

Gly Glu Thr Cys Leu Ile Ile Glu Asp Val Val Thr Ser Gly Ser Ser
        275                 280                 285

Val Leu Glu Thr Val Glu Val Leu Gln Lys Glu Gly Leu Lys Val Thr
    290                 295                 300

Asp Ala Ile Val Leu Leu Asp Arg Glu Gln Gly Gly Lys Asp Lys Leu
305                 310                 315                 320

Gln Ala His Gly Ile Arg Leu His Ser Val Cys Thr Leu Ser Lys Met
                325                 330                 335

Leu Glu Ile Leu Glu Gln Gln Lys Lys Val Asp Ala Glu Thr Val Gly
            340                 345                 350

Arg Val Lys Arg Phe Ile Gln Glu Asn Val Phe Val Ala Ala Asn His
        355                 360                 365

Asn Gly Ser Pro Leu Ser Ile Lys Glu Ala Pro Lys Glu Leu Ser Phe
    370                 375                 380

Gly Ala Arg Ala Glu Leu Pro Arg Ile His Pro Val Ala Ser Lys
385                 390                 395
```

<210> SEQ ID NO 17
<211> LENGTH: 1260
<212> TYPE: DNA
<213> ORGANISM: Artificial Sequence
<220> FEATURE:
<223> OTHER INFORMATION: Fusion Construct - CDopt3 - linker - OPRT
<220> FEATURE:
<221> NAME/KEY: CDS
<222> LOCATION: (1)..(1260)

-continued

<400> SEQUENCE: 17

```
atg gtg acc ggc ggc atg gcc tcc aag tgg gat caa aag ggc atg gat       48
Met Val Thr Gly Gly Met Ala Ser Lys Trp Asp Gln Lys Gly Met Asp
1               5                   10                  15

atc gct tac gag gag gcc ctg ctg ggc tac aag gag ggc ggc gtg cct       96
Ile Ala Tyr Glu Glu Ala Leu Leu Gly Tyr Lys Glu Gly Gly Val Pro
            20                  25                  30

atc ggc ggc tgt ctg atc aac aac aag gac ggc agt gtg ctg ggc agg      144
Ile Gly Gly Cys Leu Ile Asn Asn Lys Asp Gly Ser Val Leu Gly Arg
        35                  40                  45

ggc cac aac atg agg ttc cag aag ggc tcc gcc acc ctg cac ggc gag      192
Gly His Asn Met Arg Phe Gln Lys Gly Ser Ala Thr Leu His Gly Glu
    50                  55                  60

atc tcc acc ctg gag aac tgt ggc agg ctg gag ggc aag gtg tac aag      240
Ile Ser Thr Leu Glu Asn Cys Gly Arg Leu Glu Gly Lys Val Tyr Lys
65                  70                  75                  80

gac acc acc ctg tac acc acc ctg tcc cct tgt gac atg tgt acc ggc      288
Asp Thr Thr Leu Tyr Thr Thr Leu Ser Pro Cys Asp Met Cys Thr Gly
                85                  90                  95

gct atc atc atg tac ggc atc cct agg tgt gtg atc ggc gag aac gtg      336
Ala Ile Ile Met Tyr Gly Ile Pro Arg Cys Val Ile Gly Glu Asn Val
            100                 105                 110

aac ttc aag tcc aag ggc gag aag tac ctg caa acc agg ggc cac gag      384
Asn Phe Lys Ser Lys Gly Glu Lys Tyr Leu Gln Thr Arg Gly His Glu
        115                 120                 125

gtg gtg gtt gtt gac gat gag agg tgt aag aag ctg atg aag cag ttc      432
Val Val Val Val Asp Asp Glu Arg Cys Lys Lys Leu Met Lys Gln Phe
    130                 135                 140

atc gac gag agg cct cag gac tgg ttc gag gat atc ggc gag tcc ggc      480
Ile Asp Glu Arg Pro Gln Asp Trp Phe Glu Asp Ile Gly Glu Ser Gly
145                 150                 155                 160

ggc ggc gcc tcc ggc ggc ggc gcc tcc ggc ggc ggc gcc tcc ggc ggc      528
Gly Gly Ala Ser Gly Gly Gly Ala Ser Gly Gly Gly Ala Ser Gly Gly
                165                 170                 175

ggc gcc gcg gtc gct cgt gca gct ttg ggg cca ttg gtg acg ggt ctg      576
Gly Ala Ala Val Ala Arg Ala Ala Leu Gly Pro Leu Val Thr Gly Leu
            180                 185                 190

tac gac gtg cag gct ttc aag ttt ggg gac ttc gtg ctg aag agc ggg      624
Tyr Asp Val Gln Ala Phe Lys Phe Gly Asp Phe Val Leu Lys Ser Gly
        195                 200                 205

ctt tcc tcc ccc atc tac atc gat ctg cgg ggc atc gtg tct cga ccg      672
Leu Ser Ser Pro Ile Tyr Ile Asp Leu Arg Gly Ile Val Ser Arg Pro
    210                 215                 220

cgt ctt ctg agt cag gtt gca gat att tta ttc caa act gcc caa aat      720
Arg Leu Leu Ser Gln Val Ala Asp Ile Leu Phe Gln Thr Ala Gln Asn
225                 230                 235                 240

gca ggc atc agt ttt gac acc gtg tgt gga gtg cct tat aca gct ttg      768
Ala Gly Ile Ser Phe Asp Thr Val Cys Gly Val Pro Tyr Thr Ala Leu
                245                 250                 255

cca ttg gct aca gtt atc tgt tca acc aat caa att cca atg ctt att      816
Pro Leu Ala Thr Val Ile Cys Ser Thr Asn Gln Ile Pro Met Leu Ile
            260                 265                 270

aga agg aaa gaa aca aag gat tat gga act aag cgt ctt gta gaa gga      864
Arg Arg Lys Glu Thr Lys Asp Tyr Gly Thr Lys Arg Leu Val Glu Gly
        275                 280                 285

act att aat cca gga gaa acc tgt tta atc att gaa gat gtt gtc acc      912
Thr Ile Asn Pro Gly Glu Thr Cys Leu Ile Ile Glu Asp Val Val Thr
    290                 295                 300
```

```
agt gga tct agt gtt ttg gaa act gtt gag gtt ctt cag aag gag ggc      960
Ser Gly Ser Ser Val Leu Glu Thr Val Glu Val Leu Gln Lys Glu Gly
305                 310                 315                 320

ttg aag gtc act gat gcc ata gtg ctg ttg gac aga gag cag gga ggc     1008
Leu Lys Val Thr Asp Ala Ile Val Leu Leu Asp Arg Glu Gln Gly Gly
                325                 330                 335

aag gac aag ttg cag gcg cac ggg atc cgc ctc cac tca gtg tgt aca     1056
Lys Asp Lys Leu Gln Ala His Gly Ile Arg Leu His Ser Val Cys Thr
            340                 345                 350

ttg tcc aaa atg ctg gag att ctc gag cag cag aaa aaa gtt gat gct     1104
Leu Ser Lys Met Leu Glu Ile Leu Glu Gln Gln Lys Lys Val Asp Ala
        355                 360                 365

gag aca gtt ggg aga gtg aag agg ttt att cag gag aat gtc ttt gtg     1152
Glu Thr Val Gly Arg Val Lys Arg Phe Ile Gln Glu Asn Val Phe Val
    370                 375                 380

gca gcg aat cat aat ggt tct ccc ctt tct ata aag gaa gca ccc aaa     1200
Ala Ala Asn His Asn Gly Ser Pro Leu Ser Ile Lys Glu Ala Pro Lys
385                 390                 395                 400

gaa ctc agc ttc ggt gca cgt gca gag ctg ccc agg atc cac cca gtt     1248
Glu Leu Ser Phe Gly Ala Arg Ala Glu Leu Pro Arg Ile His Pro Val
                405                 410                 415

gca tcg aag taa                                                     1260
Ala Ser Lys


<210> SEQ ID NO 18
<211> LENGTH: 419
<212> TYPE: PRT
<213> ORGANISM: Artificial Sequence
<220> FEATURE:
<223> OTHER INFORMATION: Synthetic Construct

<400> SEQUENCE: 18

Met Val Thr Gly Gly Met Ala Ser Lys Trp Asp Gln Lys Gly Met Asp
1               5                   10                  15

Ile Ala Tyr Glu Glu Ala Leu Leu Gly Tyr Lys Glu Gly Gly Val Pro
            20                  25                  30

Ile Gly Gly Cys Leu Ile Asn Asn Lys Asp Gly Ser Val Leu Gly Arg
        35                  40                  45

Gly His Asn Met Arg Phe Gln Lys Gly Ser Ala Thr Leu His Gly Glu
    50                  55                  60

Ile Ser Thr Leu Glu Asn Cys Gly Arg Leu Glu Gly Lys Val Tyr Lys
65                  70                  75                  80

Asp Thr Thr Leu Tyr Thr Thr Leu Ser Pro Cys Asp Met Cys Thr Gly
                85                  90                  95

Ala Ile Ile Met Tyr Gly Ile Pro Arg Cys Val Ile Gly Glu Asn Val
            100                 105                 110

Asn Phe Lys Ser Lys Gly Glu Lys Tyr Leu Gln Thr Arg Gly His Glu
        115                 120                 125

Val Val Val Val Asp Asp Glu Arg Cys Lys Lys Leu Met Lys Gln Phe
    130                 135                 140

Ile Asp Glu Arg Pro Gln Asp Trp Phe Glu Asp Ile Gly Glu Ser Gly
145                 150                 155                 160

Gly Gly Ala Ser Gly Gly Gly Ala Ser Gly Gly Gly Ala Ser Gly Gly
                165                 170                 175

Gly Ala Ala Val Ala Arg Ala Ala Leu Gly Pro Leu Val Thr Gly Leu
            180                 185                 190

Tyr Asp Val Gln Ala Phe Lys Phe Gly Asp Phe Val Leu Lys Ser Gly
        195                 200                 205
```

```
Leu Ser Ser Pro Ile Tyr Ile Asp Leu Arg Gly Ile Val Ser Arg Pro
    210                 215                 220

Arg Leu Leu Ser Gln Val Ala Asp Ile Leu Phe Gln Thr Ala Gln Asn
225                 230                 235                 240

Ala Gly Ile Ser Phe Asp Thr Val Cys Gly Val Pro Tyr Thr Ala Leu
                245                 250                 255

Pro Leu Ala Thr Val Ile Cys Ser Thr Asn Gln Ile Pro Met Leu Ile
            260                 265                 270

Arg Arg Lys Glu Thr Lys Asp Tyr Gly Thr Lys Arg Leu Val Glu Gly
        275                 280                 285

Thr Ile Asn Pro Gly Glu Thr Cys Leu Ile Ile Glu Asp Val Val Thr
    290                 295                 300

Ser Gly Ser Ser Val Leu Glu Thr Val Glu Val Leu Gln Lys Glu Gly
305                 310                 315                 320

Leu Lys Val Thr Asp Ala Ile Val Leu Leu Asp Arg Glu Gln Gly Gly
                325                 330                 335

Lys Asp Lys Leu Gln Ala His Gly Ile Arg Leu His Ser Val Cys Thr
            340                 345                 350

Leu Ser Lys Met Leu Glu Ile Leu Glu Gln Gln Lys Lys Val Asp Ala
        355                 360                 365

Glu Thr Val Gly Arg Val Lys Arg Phe Ile Gln Glu Asn Val Phe Val
    370                 375                 380

Ala Ala Asn His Asn Gly Ser Pro Leu Ser Ile Lys Glu Ala Pro Lys
385                 390                 395                 400

Glu Leu Ser Phe Gly Ala Arg Ala Glu Leu Pro Arg Ile His Pro Val
                405                 410                 415

Ala Ser Lys
```

<210> SEQ ID NO 19
<211> LENGTH: 11892
<212> TYPE: DNA
<213> ORGANISM: Artificial Sequence
<220> FEATURE:
<223> OTHER INFORMATION: RCR Vector - pAC3-yCD2

<400> SEQUENCE: 19

```
tagttattaa tagtaatcaa ttacggggtc attagttcat agcccatata tggagttccg      60

cgttacataa cttacggtaa atggcccgcc tggctgaccg cccaacgacc cccgcccatt     120

gacgtcaata atgacgtatg ttcccatagt aacgccaata gggactttcc attgacgtca     180

atgggtggag tatttacggt aaactgccca cttggcagta catcaagtgt atcatatgcc     240

aagtacgccc cctattgacg tcaatgacgg taaatggccc gcctggcatt atgcccagta     300

catgacctta tgggactttc ctacttggca gtacatctac gtattagtca tcgctattac     360

catggtgatg cggttttggc agtacatcaa tgggcgtgga tagcggtttg actcacgggg     420

atttccaagt ctccacccca ttgacgtcaa tgggagtttg ttttggcacc aaaatcaacg     480

ggactttcca aaatgtcgta acaactccgc cccattgacg caaatgggcg gtaggcgtgt     540

acggtgggag gtctatataa gcagagctgg tttagtgaac cggcgccagt cctccgattg     600

actgagtcgc ccgggtaccc gtgtatccaa taaaccctct tgcagttgca tccgacttgt     660

ggtctcgctg ttccttggga gggtctcctc tgagtgattg actacccgtc agcgggggtc     720

tttcatttgg gggctcgtcc gggatcggga gacccctgcc cagggaccac cgacccacca     780

ccgggaggta agctggccag caacttatct gtgtctgtcc gattgtctag tgtctatgac     840
```

```
tgattttatg cgcctgcgtc ggtactagtt agctaactag ctctgtatct ggcggacccg    900
tggtggaact gacgagttcg gaacacccgg ccgcaaccct gggagacgtc ccagggactt    960
cgggggccgt tttgtggcc cgacctgagt ccaaaaatcc cgatcgtttt ggactctttg   1020
gtgcaccccc cttagaggag ggatatgtgg ttctggtagg agacgagaac ctaaaacagt   1080
tcccgcctcc gtctgaattt ttgctttcgg tttgggaccg aagccgcgcc gcgcgtcttg   1140
tctgctgcag catcgttctg tgttgtctct gtctgactgt gtttctgtat ttgtctgaga   1200
atatgggcca gactgttacc actcccttaa gtttgacctt aggtcactgg aaagatgtcg   1260
agcggatcgc tcacaaccag tcggtagatg tcaagaagag acgttgggtt accttctgct   1320
ctgcagaatg gccaaccttt aacgtcggat ggccgcgaga cggcaccttt aaccgagacc   1380
tcatcaccca ggttaagatc aaggtctttt cacctggccc gcatggacac ccagaccagg   1440
tcccctacat cgtgacctgg gaagccttgg cttttgaccc ccctccctgg gtcaagccct   1500
ttgtacaccc taagcctccg cctcctcttc ctccatccgc cccgtctctc cccccttgaac  1560
ctcctcgttc gaccccgcct cgatcctccc tttatccagc cctcactcct tctctaggcg   1620
ccaaacctaa acctcaagtt ctttctgaca gtggggggcc gctcatcgac ctacttacag   1680
aagacccccc gccttatagg gacccaagac cacccccttc cgacagggac ggaaatggtg   1740
gagaagcgac ccctgcggga gaggcaccgg acccctcccc aatggcatct cgcctacgtg   1800
ggagacggga gccccctgtg gccgactcca ctacctcgca ggcattcccc ctccgcgcag   1860
gaggaaacgg acagcttcaa tactggccgt tctcctcttc tgacctttac aactggaaaa   1920
ataataaccc ttctttttct gaagatccag gtaaactgac agctctgatc gagtctgttc   1980
tcatcaccca tcagcccacc tgggacgact gtcagcagct gttggggact ctgctgaccg   2040
gagaagaaaa acaacgggtg ctcttagagg ctagaaaggc ggtgcggggc gatgatgggc   2100
gccccactca actgcccaat gaagtcgatg ccgcttttcc cctcgagcgc ccagactggg   2160
attacaccac ccaggcaggt aggaaccacc tagtccacta tcgccagttg ctcctagcgg   2220
gtctccaaaa cgcgggcaga agccccacca atttggccaa ggtaaaagga ataacacaag   2280
ggcccaatga gtctccctcg gccttcctag agagacttaa ggaagcctat cgcaggtaca   2340
ctccttatga ccctgaggac ccagggcaag aaactaatgt gtctatgtct ttcatttggc   2400
agtctgcccc agacattggg agaaagttag agaggttaga agatttaaaa aacaagacgc   2460
ttggagattt ggttagagag gcagaaaaga tctttaataa acgagaaacc ccggaagaaa   2520
gagaggaacg tatcaggaga gaaacagagg aaaaagaaga acgccgtagg acagaggatg   2580
agcagaaaga gaaagaaaga gatcgtagga gacatagaga gatgagcaag ctattggcca   2640
ctgtcgttag tggacagaaa caggatagac agggaggaga acgaaggagg tcccaactcg   2700
atcgcgacca gtgtgcctac tgcaaagaaa aggggcactg ggctaaagat tgtcccaaga   2760
aaccacgagg acctcgggga ccaagacccc agacctccct cctgacccta gatgactagg   2820
gaggtcaggg tcaggagccc ccccctgaac ccaggataac cctcaaagtc ggggggcaac   2880
ccgtcacctt cctggtagat actggggccc aacactccgt gctgacccaa aatcctggac   2940
ccctaagtga taagtctgcc tgggtccaag ggctactgg aggaaagcgg tatcgctgga    3000
ccacggatcg caaagtacat ctagctaccg gtaaggtcac ccactctttc ctccatgtac   3060
cagactgtcc ctatcctctg ttaggaagag atttgctgac taaactaaaa gcccaaatcc   3120
actttgaggg atcaggagcc caggttatgg gaccaatggg gcagcccctg caagtgttga   3180
```

-continued

```
ccctaaatat agaagatgag catcggctac atgagacctc aaaagagcca gatgtttctc   3240
tagggtccac atggctgtct gattttcctc aggcctgggc ggaaaccggg ggcatgggac   3300
tggcagttcg ccaagctcct ctgatcatac ctctgaaagc aacctctacc cccgtgtcca   3360
taaaacaata ccccatgtca caagaagcca gactggggat caagccccac atacagagac   3420
tgttggacca gggaatactg gtaccctgcc agtccccctg gaacacgccc ctgctacccg   3480
ttaagaaacc agggactaat gattataggc ctgtccagga tctgagagaa gtcaacaagc   3540
gggtggaaga catccacccc accgtgccca acccttacaa cctcttgagc gggctcccac   3600
cgtcccacca gtggtacact gtgcttgatt taaaggatgc ctttttctgc ctgagactcc   3660
accccaccag tcagcctctc ttcgcctttg agtggagaga tccagagatg ggaatctcag   3720
gacaattgac ctggaccaga ctcccacagg gtttcaaaaa cagtcccacc ctgtttgatg   3780
aggcactgca cagagaccta gcagacttcc ggatccagca cccagacttg atcctgctac   3840
agtacgtgga tgacttactg ctggccgcca cttctgagct agactgccaa caaggtactc   3900
gggccctgtt acaaacccta gggaacctcg ggtatcgggc ctcggccaag aaagcccaaa   3960
tttgccagaa acaggtcaag tatctggggt atcttctaaa agagggtcag agatggctga   4020
ctgaggccag aaaagagact gtgatggggc agcctactcc gaagacccct cgacaactaa   4080
gggagttcct agggacggca ggcttctgtc gcctctggat ccctgggttt gcagaaatgg   4140
cagcccccctt gtaccctctc accaaaacgg ggactctgtt taattggggc ccagaccaac   4200
aaaaggccta tcaagaaatc aagcaagctc ttctaactgc cccagccctg ggtttgccag   4260
atttgactaa gccctttgaa ctctttgtcg acgagaagca gggctacgcc aaaggtgtcc   4320
taacgcaaaa actgggacct tggcgtcggc cggtggccta cctgtccaaa aagctagacc   4380
cagtagcagc tgggtggccc ccttgcctac ggatggtagc agccattgcc gtactgacaa   4440
aggatgcagg caagctaacc atgggacagc cactagtcat tctggccccc catgcagtag   4500
aggcactagt caaacaaccc cccgaccgct ggctttccaa cgcccggatg actcactatc   4560
aggccttgct tttggacacg gaccgggtcc agttcggacc ggtggtagcc ctgaacccgg   4620
ctacgctgct cccactgcct gaggaagggc tgcaacacaa ctgccttgat atcctggccg   4680
aagcccacgg aacccgaccc gacctaacgg accagccgct cccagacgcc gaccacacct   4740
ggtacacgga tggaagcagt ctcttacaag agggacagcg taaggcggga gctgcggtga   4800
ccaccgagac cgaggtaatc tgggctaaag ccctgccagc cgggacatcc gctcagcggg   4860
ctgaactgat agcactcacc caggccctaa agatggcaga aggtaagaag ctaaatgttt   4920
atactgatag ccgttatgct tttgctactg cccatatcca tggagaaata tacagaaggc   4980
gtgggttgct cacatcagaa ggcaaagaga tcaaaaataa agacgagatc ttggccctac   5040
taaaagccct ctttctgccc aaaagactta gcataatcca ttgtccagga catcaaaagg   5100
gacacagcgc cgaggctaga ggcaaccgga tggctgacca agcggcccga aaggcagcca   5160
tcacagagac tccagacacc tctaccctcc tcatagaaaa ttcatcaccc tacacctcag   5220
aacattttca ttacacagtg actgatataa aggacctaac caagttgggg gccatttatg   5280
ataaaacaaa gaagtattgg gtctaccaag gaaaacctgt gatgcctgac cagtttactt   5340
ttgaattatt agactttctt catcagctga ctcacctcag cttctcaaaa atgaaggctc   5400
tcctagagag aagccacagt ccctactaca tgctgaaccg ggatcgaaca ctcaaaaata   5460
tcactgagac ctgcaaagct tgtgcacaag tcaacgccag caagtctgcc gttaaacagg   5520
gaactagggt ccgcgggcat cggcccggca ctcattggga gatcgatttc accgagataa   5580
```

```
agcccggatt gtatggctat aaatatcttc tagtttttat agataccttt tctggctgga   5640
tagaagcctt cccaaccaag aaagaaaccg ccaaggtcgt aaccaagaag ctactagagg   5700
agatcttccc caggttcggc atgcctcagg tattgggaac tgacaatggg cctgccttcg   5760
tctccaaggt gagtcagaca gtggccgatc tgttggggat tgattggaaa ttacattgtg   5820
catacagacc ccaaagctca ggccaggtag aaagaatgaa tagaaccatc aaggagactt   5880
taactaaatt aacgcttgca actggctcta gagactgggt gctcctactc cccttagccc   5940
tgtaccgagc ccgcaacacg ccgggccccc atggcctcac cccatatgag atcttatatg   6000
gggcaccccc gccccttgta aacttccctg accctgacat gacaagagtt actaacagcc   6060
cctctctcca agctcactta caggctctct acttagtcca gcacgaagtc tggagacctc   6120
tggcggcagc ctaccaagaa caactggacc gaccggtggt acctcaccct taccgagtcg   6180
gcgacacagt gtgggtccgc cgacaccaga ctaagaacct agaacctcgc tggaaaggac   6240
cttacacagt cctgctgacc acccccaccg ccctcaaagt agacggcatc gcagcttgga   6300
tacacgccgc ccacgtgaag gctgccgacc ccgggggtgg accatcctct agactgacat   6360
ggcgcgttca acgctctcaa aacccccctca agataagatt aacccgtgga agcccttaat   6420
agtcatggga gtcctgttag gagtagggat ggcagagagc cccccatcagg tctttaatgt   6480
aacctggaga gtcaccaacc tgatgactgg gcgtaccgcc aatgccacct ccctcctggg   6540
aactgtacaa gatgccttcc caaaattata ttttgatcta tgtgatctgg tcggagagga   6600
gtgggaccct tcagaccagg aaccgtatgt cgggtatggc tgcaagtacc ccgcagggag   6660
acagcggacc cggacttttg acttttacgt gtgccctggg cataccgtaa agtcggggtg   6720
tgggggacca ggagagggct actgtggtaa atgggggtgt gaaaccaccg gacaggctta   6780
ctggaagccc acatcatcgt gggacctaat ctcccttaag cgcggtaaca ccccctggga   6840
cacgggatgc tctaaagttg cctgtggccc ctgctacgac ctctccaaag tatccaattc   6900
cttccaaggg gctactcgag gggcagatg caaccctcta gtcctagaat tcactgatgc   6960
aggaaaaaag gctaactggg acgggcccaa atcgtgggga ctgagactgt accggacagg   7020
aacagatcct attaccatgt tctccctgac ccggcaggtc cttaatgtgg gaccccgagt   7080
ccccataggg cccaacccag tattacccga ccaaagactc ccttcctcac caatagagat   7140
tgtaccggct ccacagccac ctagcccccct caataccagt taccccccctt ccactaccag   7200
tacaccctca acctccccta caagtccaag tgtcccacag ccacccccag gaactggaga   7260
tagactacta gctctagtca aaggagccta tcaggcgctt aacctcacca atcccgacaa   7320
gacccaagaa tgttggctgt gcttagtgtc gggacctcct tattacgaag gagtagcggt   7380
cgtgggcact tataccaatc attccaccgc tccggccaac tgtacggcca cttcccaaca   7440
taagcttacc ctatctgaag tgacaggaca gggcctatgc atgggggcag tacctaaaac   7500
tcaccaggcc ttatgtaaca ccacccaaag cgccggctca ggatcctact accttgcagc   7560
acccgccgga acaatgtggg cttgcagcac tggattgact ccctgcttgt ccaccacggt   7620
gctcaatcta accacagatt attgtgtatt agttgaactc tggcccagag taatttacca   7680
ctcccccgat tatatgtatg gtcagcttga acagcgtacc aaatataaaa gagagccagt   7740
atcattgacc ctggcccttc tactaggagg attaaccatg ggagggattg cagctggaat   7800
agggacgggg accactgcct taattaaaac ccagcagttt gagcagcttc atgccgctat   7860
ccagacagac ctcaacgaag tcgaaaagtc aattaccaac ctagaaaagt cactgacctc   7920
```

-continued gttgtctgaa gtagtcctac agaaccgcag aggcctagat ttgctattcc taaaggaggg 7980
aggtctctgc gcagccctaa aagaagaatg ttgtttttat gcagaccaca cggggctagt 8040
gagagacagc atggccaaat taagagaaag gcttaatcag agacaaaaac tatttgagac 8100
aggccaagga tggttcgaag ggctgtttaa tagatccccc tggtttacca ccttaatctc 8160
caccatcatg ggacctctaa tagtactctt actgatctta ctctttggac cttgcattct 8220
caatcgattg gtccaatttg ttaaagacag gatctcagtg gtccaggctc tggttttgac 8280
tcagcaatat caccagctaa aacccataga gtacgagcca tgaacgcgtt actggccgaa 8340
gccgcttgga ataaggccgg tgtgcgtttg tctatatgtt attttccacc atattgccgt 8400
cttttggcaa tgtgagggcc cggaaacctg gccctgtctt cttgacgagc attcctaggg 8460
gtctttcccc tctcgccaaa ggaatgcaag gtctgttgaa tgtcgtgaag gaagcagttc 8520
ctctggaagc ttcttgaaga caaacaacgt ctgtagcgac cctttgcagg cagcggaacc 8580
ccccacctgg cgacaggtgc ctctgcggcc aaaagccacg tgtataagat acacctgcaa 8640
aggcggcaca accccagtgc cacgttgtga gttggatagt tgtggaaaga gtcaaatggc 8700
tctcctcaag cgtattcaac aaggggctga aggatgccca gaaggtaccc cattgtatgg 8760
gatctgatct ggggcctcgg tgcacatgct ttacatgtgt ttagtcgagg ttaaaaaaac 8820
gtctaggccc cccgaaccac ggggacgtgg ttttcctttg aaaaacacga ttataaatgg 8880
tgaccggcgg catggcctcc aagtgggatc aaaagggcat ggatatcgct tacgaggagg 8940
ccctgctggg ctacaaggag ggcggcgtgc ctatcggcgg ctgtctgatc aacaacaagg 9000
acggcagtgt gctgggcagg ggccacaaca tgaggttcca gaagggctcc gccaccctgc 9060
acggcgagat ctccaccctg gagaactgtg gcaggctgga gggcaaggtg tacaaggaca 9120
ccaccctgta caccaccctg tccccttgtg acatgtgtac cggcgctatc atcatgtacg 9180
gcatccctag gtgtgtgatc ggcgagaacg tgaacttcaa gtccaagggc gagaagtacc 9240
tgcaaaccag gggccacgag gtggtggttg ttgacgatga gaggtgtaag aagctgatga 9300
agcagttcat cgacgagagg cctcaggact ggttcgagga tatcggcgag taagcggccg 9360
cagataaaat aaaagatttt atttagtctc cagaaaaagg ggggaatgaa agaccccacc 9420
tgtaggtttg gcaagctagc ttaagtaacg ccattttgca aggcatggaa aaatacataa 9480
ctgagaatag agaagttcag atcaaggtca ggaacagatg gaacagctga atatgggcca 9540
aacaggatat ctgtggtaag cagttcctgc cccggctcag ggccaagaac agatggaaca 9600
gctgaatatg ggccaaacag gatatctgtg gtaagcagtt cctgccccgg ctcagggcca 9660
agaacagatg gtccccagat gcggtccagc cctcagcagt ttctagagaa ccatcagatg 9720
tttccagggt gccccaagga cctgaaatga ccctgtgcct tatttgaact aaccaatcag 9780
ttcgcttctc gcttctgttc gcgcgcttct gctccccgag ctcaataaaa gagcccacaa 9840
cccctcactc ggggcgccag tcctccgatt gactgagtcg cccgggtacc cgtgtatcca 9900
ataaaccctc ttgcagttgc atccgacttg tggtctcgct gttccttggg agggtctcct 9960
ctgagtgatt gactacccgt cagcgggggt ctttcattac atgtgagcaa aaggccagca 10020
aaaggccagg aaccgtaaaa aggccgcgtt gctggcgttt ttccataggc tccgcccccc 10080
tgacgagcat cacaaaaatc gacgctcaag tcagaggtgg cgaaacccga caggactata 10140
aagataccag gcgtttcccc ctggaagctc cctcgtgcgc tctcctgttc cgaccctgcc 10200
gcttaccgga tacctgtccg cctttctccc ttcgggaagc gtggcgcttt ctcaatgctc 10260
acgctgtagg tatctcagtt cggtgtaggt cgttcgctcc aagctgggct gtgtgcacga 10320 acccccgtt cagcccgacc gctgcgcctt atccggtaac tatcgtcttg agtccaaccc 10380
ggtaagacac gacttatcgc cactggcagc agccactggt aacaggatta gcagagcgag 10440
gtatgtaggc ggtgctacag agttcttgaa gtggtggcct aactacggct acactagaag 10500
gacagtattt ggtatctgcg ctctgctgaa gccagttacc ttcggaaaaa gagttggtag 10560
ctcttgatcc ggcaaacaaa ccaccgctgg tagcggtggt ttttttgttt gcaagcagca 10620
gattacgcgc agaaaaaaag gatctcaaga agatcctttg atcttttcta cggggtctga 10680
cgctcagtgg aacgaaaact cacgttaagg gattttggtc atgagattat caaaaaggat 10740
cttcacctag atccttttaa attaaaaatg aagttttaaa tcaatctaaa gtatatatga 10800
gtaaacttgg tctgacagtt accaatgctt aatcagtgag gcacctatct cagcgatctg 10860
tctatttcgt tcatccatag ttgcctgact ccccgtcgtg tagataacta cgatacggga 10920
gggcttacca tctggcccca gtgctgcaat gataccgcga gacccacgct caccggctcc 10980
agatttatca gcaataaacc agccagccgg aagggccgag cgcagaagtg gtcctgcaac 11040
tttatccgcc tccatccagt ctattaattg ttgccgggaa gctagagtaa gtagttcgcc 11100
agttaatagt ttgcgcaacg ttgttgccat tgctgcaggc atcgtggtgt cacgctcgtc 11160
gtttggtatg gcttcattca gctccggttc ccaacgatca aggcgagtta catgatcccc 11220
catgttgtgc aaaaaagcgg ttagctcctt cggtcctccg atcgttgtca gaagtaagtt 11280
ggccgcagtg ttatcactca tggttatggc agcactgcat aattctctta ctgtcatgcc 11340
atccgtaaga tgcttttctg tgactggtga gtactcaacc aagtcattct gagaatagtg 11400
tatgcggcga ccgagttgct cttgcccggc gtcaacacgg gataataccg cgccacatag 11460
cagaacttta aaagtgctca tcattggaaa acgttcttcg gggcgaaaac tctcaaggat 11520
cttaccgctg ttgagatcca gttcgatgta acccactcgt gcacccaact gatcttcagc 11580
atcttttact ttcaccagcg tttctgggtg agcaaaaaca ggaaggcaaa atgccgcaaa 11640
aaagggaata agggcgacac ggaaatgttg aatactcata ctcttccttt ttcaatatta 11700
ttgaagcatt tatcagggtt attgtctcat gagcggatac atatttgaat gtatttagaa 11760
aaataaacaa ataggggttc cgcgcacatt tccccgaaaa gtgccacctg acgtctaaga 11820
aaccattatt atcatgacat taacctataa aaataggcgt atcacgaggc cctttcgtct 11880
tcaagaattc at 11892

<210> SEQ ID NO 20
<211> LENGTH: 11892
<212> TYPE: DNA
<213> ORGANISM: Artificial Sequence
<220> FEATURE:
<223> OTHER INFORMATION: RCR Vector - pAC3-yCD

<400> SEQUENCE: 20
tagttattaa tagtaatcaa ttacggggtc attagttcat agcccatata tggagttccg 60
cgttacataa cttacggtaa atggcccgcc tggctgaccg cccaacgacc cccgcccatt 120
gacgtcaata atgacgtatg ttcccatagt aacgccaata gggactttcc attgacgtca 180
atgggtggag tatttacggt aaactgccca cttggcagta catcaagtgt atcatatgcc 240
aagtacgccc cctattgacg tcaatgacgg taaatggccc gcctggcatt atgcccagta 300
catgacctta tgggactttc ctacttggca gtacatctac gtattagtca tcgctattac 360
catggtgatg cggttttggc agtacatcaa tgggcgtgga tagcggtttg actcacgggg 420

-continued

```
atttccaagt ctccacccca ttgacgtcaa tgggagtttg ttttggcacc aaaatcaacg    480
ggactttcca aaatgtcgta acaactccgc cccattgacg caaatgggcg gtaggcgtgt    540
acggtgggag gtctatataa gcagagctgg tttagtgaac cggcgccagt cctccgattg    600
actgagtcgc ccgggtaccc gtgtatccaa taaaccctct tgcagttgca tccgacttgt    660
ggtctcgctg ttccttggga gggtctcctc tgagtgattg actacccgtc agcgggggtc    720
tttcatttgg gggctcgtcc gggatcggga gacccctgcc cagggaccac cgacccacca    780
ccgggaggta agctggccag caacttatct gtgtctgtcc gattgtctag tgtctatgac    840
tgattttatg cgcctgcgtc ggtactagtt agctaactag ctctgtatct ggcggacccg    900
tggtggaact gacgagttcg gaacacccgg ccgcaaccct gggagacgtc ccagggactt    960
cgggggccgt ttttgtggcc cgacctgagt ccaaaaatcc cgatcgtttt ggactctttg   1020
gtgcaccccc cttagaggag ggatatgtgg ttctggtagg agacgagaac ctaaaacagt   1080
tcccgcctcc gtctgaattt ttgctttcgg tttgggaccg aagccgcgcc gcgcgtcttg   1140
tctgctgcag catcgttctg tgttgtctct gtctgactgt gtttctgtat ttgtctgaga   1200
atatgggcca gactgttacc actcccttaa gtttgacctt aggtcactgg aaagatgtcg   1260
agcggatcgc tcacaaccag tcggtagatg tcaagaagag acgttgggtt accttctgct   1320
ctgcagaatg gccaaccttt aacgtcggat ggccgcgaga cggcaccttt aaccgagacc   1380
tcatcaccca ggttaagatc aaggtctttt cacctggccc gcatggacac ccagaccagg   1440
tcccctacat cgtgacctgg gaagccttgg cttttgaccc ccctccctgg gtcaagccct   1500
ttgtacaccc taagcctccg cctcctcttc ctccatccgc cccgtctctc cccctgaac    1560
ctcctcgttc gaccccgcct cgatcctccc tttatccagc cctcactcct tctctaggcg   1620
ccaaacctaa acctcaagtt ctttctgaca gtggggggcc gctcatcgac ctacttacag   1680
aagacccccc gccttatagg gacccaagac caccccccttc cgacagggac ggaaatggtg   1740
gagaagcgac ccctgcggga gaggcaccgg acccctcccc aatggcatct cgcctacgtg   1800
ggagacggga gccccctgtg gccgactcca ctacctcgca ggcattcccc ctccgcgcag   1860
gaggaaacgg acagcttcaa tactggccgt tctcctcttc tgacctttac aactggaaaa   1920
ataataaccc ttctttttct gaagatccag gtaaactgac agctctgatc gagtctgttc   1980
tcatcaccca tcagcccacc tgggacgact gtcagcagct gttggggact ctgctgaccg   2040
gagaagaaaa acaacgggtg ctcttagagg ctagaaaggc ggtgcggggc gatgatgggc   2100
gccccactca actgcccaat gaagtcgatg ccgcttttcc cctcgagcgc ccagactggg   2160
attacaccac ccaggcaggt aggaaccacc tagtccacta tcgccagttg ctcctagcgg   2220
gtctccaaaa cgcgggcaga agccccacca atttggccaa ggtaaaagga ataacacaag   2280
ggcccaatga gtctccctcg gccttcctag agagacttaa ggaagcctat cgcaggtaca   2340
ctccttatga ccctgaggac ccagggcaag aaactaatgt gtctatgtct ttcatttggc   2400
agtctgcccc agacattggg agaaagttag agaggttaga agatttaaaa aacaagacgc   2460
ttggagattt ggttagagag gcagaaaaga tctttaataa acgagaaacc ccggaagaaa   2520
gagaggaacg tatcaggaga gaaacagagg aaaaagaaga acgccgtagg acagaggatg   2580
agcagaaaga gaaagaaaga gatcgtagga gacatagaga gatgagcaag ctattggcca   2640
ctgtcgttag tggacagaaa caggatagac agggaggaga acgaaggagg tcccaactcg   2700
atcgcgacca gtgtgcctac tgcaaagaaa aggggcactg ggctaaagat tgtcccaaga   2760
aaccacgagg acctcgggga ccaagacccc agacctccct cctgacccta gatgactagg   2820
```

```
gaggtcaggg tcaggagccc ccccctgaac ccaggataac cctcaaagtc ggggggcaac   2880
ccgtcacctt cctggtagat actggggccc aacactccgt gctgacccaa aatcctggac   2940
ccctaagtga taagtctgcc tgggtccaag ggcctactgg aggaaagcgg tatcgctgga   3000
ccacggatcg caaagtacat ctagctaccg gtaaggtcac ccactctttc ctccatgtac   3060
cagactgtcc ctatcctctg ttaggaagag atttgctgac taaactaaaa gcccaaatcc   3120
actttgaggg atcaggagcc caggttatgg gaccaatggg gcagcccctg caagtgttga   3180
ccctaaatat agaagatgag catcggctac atgagacctc aaaagagcca gatgtttctc   3240
tagggtccac atggctgtct gattttcctc aggcctgggc ggaaaccggg ggcatgggac   3300
tggcagttcg ccaagctcct ctgatcatac ctctgaaagc aacctctacc cccgtgtcca   3360
taaaacaata ccccatgtca caagaagcca gactggggat caagccccac atacagagac   3420
tgttggacca gggaatactg gtaccctgcc agtccccctg gaacacgccc ctgctacccg   3480
ttaagaaacc agggactaat gattataggc ctgtccagga tctgagagaa gtcaacaagc   3540
gggtggaaga catccacccc accgtgccca acccttacaa cctcttgagc gggctcccac   3600
cgtcccacca gtggtacact gtgcttgatt taaaggatgc ctttttctgc ctgagactcc   3660
accccaccag tcagcctctc ttcgcctttg agtggagaga tccagagatg ggaatctcag   3720
gacaattgac ctggaccaga ctcccacagg gtttcaaaaa cagtcccacc ctgtttgatg   3780
aggcactgca cagagaccta gcagacttcc ggatccagca cccagacttg atcctgctac   3840
agtacgtgga tgacttactg ctggccgcca cttctgagct agactgccaa caaggtactc   3900
gggccctgtt acaaacccta gggaacctcg ggtatcgggc ctcggccaag aaagcccaaa   3960
tttgccagaa acaggtcaag tatctggggt atcttctaaa agagggtcag agatggctga   4020
ctgaggccag aaaagagact gtgatggggc agcctactcc gaagacccct cgacaactaa   4080
gggagttcct agggacggca ggcttctgtc gcctctggat ccctgggttt gcagaaatgg   4140
cagccccctt gtaccctctc accaaaacgg ggactctgtt taattggggc ccagaccaac   4200
aaaaggccta tcaagaaatc aagcaagctc ttctaactgc cccagccctg ggttgccag    4260
atttgactaa gccctttgaa ctctttgtcg acgagaagca gggctacgcc aaaggtgtcc   4320
taacgcaaaa actgggacct tggcgtcggc cggtggccta cctgtccaaa aagctagacc   4380
cagtagcagc tgggtggccc ccttgcctac ggatggtagc agccattgcc gtactgacaa   4440
aggatgcagg caagctaacc atgggacagc cactagtcat tctggccccc catgcagtag   4500
aggcactagt caaacaaccc cccgaccgct ggctttccaa cgcccggatg actcactatc   4560
aggccttgct tttggacacg gaccgggtcc agttcggacc ggtggtagcc ctgaacccgg   4620
ctacgctgct cccactgcct gaggaagggc tgcaacacaa ctgccttgat atcctggccg   4680
aagcccacgg aacccgaccc gacctaacgg accagccgct cccagacgcc gaccacacct   4740
ggtacacgga tggaagcagt ctcttacaag agggacagcg taaggcggga gctgcggtga   4800
ccaccgagac cgaggtaatc tgggctaaag ccctgccagc cgggacatcc gctcagcggg   4860
ctgaactgat agcactcacc caggccctaa agatggcaga aggtaagaag ctaaatgttt   4920
atactgatag ccgttatgct tttgctactg cccatatcca tggagaaata tacagaaggc   4980
gtgggttgct cacatcagaa ggcaaagaga tcaaaaataa agacgagatc ttggccctac   5040
taaaagccct ctttctgccc aaaagactta gcataatcca ttgtccagga catcaaaagg   5100
gacacagcgc cgaggctaga ggcaaccgga tggctgacca agcggcccga aaggcagcca   5160
```

-continued

```
tcacagagac tccagacacc tctaccctcc tcatagaaaa ttcatcaccc tacacctcag   5220
aacattttca ttacacagtg actgatataa aggacctaac caagttgggg gccatttatg   5280
ataaaacaaa gaagtattgg gtctaccaag gaaaacctgt gatgcctgac cagtttactt   5340
ttgaattatt agactttctt catcagctga ctcacctcag cttctcaaaa atgaaggctc   5400
tcctagagag aagccacagt ccctactaca tgctgaaccg ggatcgaaca ctcaaaaata   5460
tcactgagac ctgcaaagct tgtgcacaag tcaacgccag caagtctgcc gttaaacagg   5520
gaactagggt ccgcgggcat cggcccggca ctcattggga gatcgatttc accgagataa   5580
agcccggatt gtatggctat aaatatcttc tagtttttat agataccttt tctggctgga   5640
tagaagcctt cccaaccaag aaagaaaccg ccaaggtcgt aaccaagaag ctactagagg   5700
agatcttccc caggttcggc atgcctcagg tattgggaac tgacaatggg cctgccttcg   5760
tctccaaggt gagtcagaca gtggccgatc tgttggggat tgattggaaa ttacattgtg   5820
catacagacc ccaaagctca ggccaggtag aaagaatgaa tagaaccatc aaggagactt   5880
taactaaatt aacgcttgca actggctcta gagactgggt gctcctactc cccttagccc   5940
tgtaccgagc ccgcaacacg ccgggccccc atggcctcac cccatatgag atcttatatg   6000
gggcaccccc gccccttgta aacttccctg accctgacat gacaagagtt actaacagcc   6060
cctctctcca agctcactta caggctctct acttagtcca gcacgaagtc tggagacctc   6120
tggcggcagc ctaccaagaa caactggacc gaccggtggt acctcaccct taccgagtcg   6180
gcgacacagt gtgggtccgc cgacaccaga ctaagaacct agaacctcgc tggaaaggac   6240
cttacacagt cctgctgacc acccccaccg ccctcaaagt agacggcatc gcagcttgga   6300
tacacgccgc ccacgtgaag gctgccgacc ccgggggtgg accatcctct agactgacat   6360
ggcgcgttca acgctctcaa aacccctca agataagatt aacccgtgga agcccttaat   6420
agtcatggga gtcctgttag gagtagggat ggcagagagc cccccatcagg tctttaatgt   6480
aacctggaga gtcaccaacc tgatgactgg gcgtaccgcc aatgccacct ccctcctggg   6540
aactgtacaa gatgccttcc caaaattata ttttgatcta tgtgatctgg tcggagagga   6600
gtgggaccct tcagaccagg aaccgtatgt cgggtatggc tgcaagtacc ccgcagggag   6660
acagcggacc cggacttttg acttttacgt gtgccctggg cataccgtaa agtcggggtg   6720
tgggggacca ggagagggct actgtggtaa atgggggtgt gaaaccaccg gacaggctta   6780
ctggaagccc acatcatcgt gggacctaat ctcccttaag cgcggtaaca ccccctggga   6840
cacgggatgc tctaaagttg cctgtggccc ctgctacgac ctctccaaag tatccaattc   6900
cttccaaggg gctactcgag gggcagatg caaccctcta gtcctagaat tcactgatgc   6960
aggaaaaaag gctaactggg acgggcccaa atcgtgggga ctgagactgt accggacagg   7020
aacagatcct attaccatgt tctccctgac ccggcaggtc cttaatgtgg gaccccgagt   7080
ccccataggg cccaacccag tattacccga ccaaagactc ccttcctcac caatagagat   7140
tgtaccggct ccacagccac ctagccccct caataccagt taccccctt ccactaccag   7200
tacaccctca acctccccta caagtccaag tgtcccacag ccaccccag gaactggaga   7260
tagactacta gctctagtca aaggagccta tcaggcgctt aacctcacca atcccgacaa   7320
gacccaagaa tgttggctgt gcttagtgtc gggacctcct tattacgaag gagtagcggt   7380
cgtgggcact tataccaatc attccaccgc tccggccaac tgtacggcca cttcccaaca   7440
taagcttacc ctatctgaag tgacaggaca gggcctatgc atgggggcag tacctaaaac   7500
tcaccaggcc ttatgtaaca ccacccaaag cgccggctca ggatcctact accttgcagc   7560
```

-continued

```
acccgccgga acaatgtggg cttgcagcac tggattgact ccctgcttgt ccaccacggt   7620
gctcaatcta accacagatt attgtgtatt agttgaactc tggcccagag taatttacca   7680
ctcccccgat tatatgtatg gtcagcttga acagcgtacc aaatataaaa gagagccagt   7740
atcattgacc ctggcccttc tactaggagg attaaccatg ggagggattg cagctggaat   7800
agggacgggg accactgcct taattaaaac ccagcagttt gagcagcttc atgccgctat   7860
ccagacagac ctcaacgaag tcgaaaagtc aattaccaac ctagaaaagt cactgacctc   7920
gttgtctgaa gtagtcctac agaaccgcag aggcctagat ttgctattcc taaaggaggg   7980
aggtctctgc gcagccctaa aagaagaatg ttgtttttat gcagaccaca cggggctagt   8040
gagagacagc atggccaaat taagagaaag gcttaatcag agacaaaaac tatttgagac   8100
aggccaagga tggttcgaag ggctgtttaa tagatccccc tggtttacca ccttaatctc   8160
caccatcatg ggacctctaa tagtactctt actgatctta ctctttggac cttgcattct   8220
caatcgattg gtccaatttg ttaaagacag gatctcagtg gtccaggctc tggttttgac   8280
tcagcaatat caccagctaa aacccataga gtacgagcca tgaacgcgtt actggccgaa   8340
gccgcttgga ataaggccgg tgtgcgtttg tctatatgtt attttccacc atattgccgt   8400
cttttggcaa tgtgagggcc cggaaacctg gccctgtctt cttgacgagc attcctaggg   8460
gtctttcccc tctcgccaaa ggaatgcaag gtctgttgaa tgtcgtgaag gaagcagttc   8520
ctctggaagc ttcttgaaga caaacaacgt ctgtagcgac cctttgcagg cagcggaacc   8580
ccccacctgg cgacaggtgc ctctgcggcc aaaagccacg tgtataagat acacctgcaa   8640
aggcggcaca accccagtgc cacgttgtga gttggatagt tgtggaaaga gtcaaatggc   8700
tctcctcaag cgtattcaac aaggggctga aggatgccca gaaggtaccc cattgtatgg   8760
gatctgatct ggggcctcgg tgcacatgct ttacatgtgt ttagtcgagg ttaaaaaaac   8820
gtctaggccc cccgaaccac ggggacgtgg ttttcctttg aaaaacacga ttataaatgg   8880
tgacaggggg aatggcaagc aagtgggatc agaagggtat ggacattgcc tatgaggagg   8940
cggccttagg ttacaaagag ggtggtgttc ctattggcgg atgtcttatc aataacaaag   9000
acggaagtgt tctcggtcgt ggtcacaaca tgagatttca aaagggatcc gccacactac   9060
atggtgagat ctccactttg gaaaactgtg ggagattaga gggcaaagtg tacaaagata   9120
ccactttgta tacgacgctg tctccatgcg acatgtgtac aggtgccatc atcatgtatg   9180
gtattccacg ctgtgttgtc ggtgagaacg ttaatttcaa aagtaagggc gagaaatatt   9240
tacaaactag aggtcacgag gttgttgttg ttgacgatga gaggtgtaaa aagatcatga   9300
aacaatttat cgatgaaaga cctcaggatt ggtttgaaga tattggtgag taggcggccg   9360
cagataaaat aaaagatttt atttagtctc cagaaaaagg ggggaatgaa agaccccacc   9420
tgtaggtttg gcaagctagc ttaagtaacg ccattttgca aggcatggaa aaatacataa   9480
ctgagaatag agaagttcag atcaaggtca ggaacagatg gaacagctga atatgggcca   9540
aacaggatat ctgtggtaag cagttcctgc cccggctcag ggccaagaac agatggaaca   9600
gctgaatatg ggccaaacag gatatctgtg gtaagcagtt cctgccccgg ctcagggcca   9660
agaacagatg gtccccagat gcggtccagc cctcagcagt ttctagagaa ccatcagatg   9720
tttccagggt gccccaagga cctgaaatga ccctgtgcct tatttgaact aaccaatcag   9780
ttcgcttctc gcttctgttc gcgcgcttct gctccccgag ctcaataaaa gagcccacaa   9840
cccctcactc ggggcgccag tcctccgatt gactgagtcg cccgggtacc cgtgtatcca   9900
```

```
ataaaccctc ttgcagttgc atccgacttg tggtctcgct gttccttggg agggtctcct   9960
ctgagtgatt gactacccgt cagcgggggt ctttcattac atgtgagcaa aaggccagca  10020
aaaggccagg aaccgtaaaa aggccgcgtt gctggcgttt ttccataggc tccgcccccc  10080
tgacgagcat cacaaaaatc gacgctcaag tcagaggtgg cgaaacccga caggactata  10140
aagataccag gcgtttcccc ctggaagctc cctcgtgcgc tctcctgttc cgaccctgcc  10200
gcttaccgga tacctgtccg cctttctccc ttcgggaagc gtggcgcttt ctcaatgctc  10260
acgctgtagg tatctcagtt cggtgtaggt cgttcgctcc aagctgggct gtgtgcacga  10320
acccccgtt cagcccgacc gctgcgcctt atccggtaac tatcgtcttg agtccaaccc  10380
ggtaagacac gacttatcgc cactggcagc agccactggt aacaggatta gcagagcgag  10440
gtatgtaggc ggtgctacag agttcttgaa gtggtggcct aactacggct acactagaag  10500
gacagtattt ggtatctgcg ctctgctgaa gccagttacc ttcggaaaaa gagttggtag  10560
ctcttgatcc ggcaaacaaa ccaccgctgg tagcggtggt ttttttgttt gcaagcagca  10620
gattacgcgc agaaaaaaag gatctcaaga agatcctttg atcttttcta cggggtctga  10680
cgctcagtgg aacgaaaact cacgttaagg gattttggtc atgagattat caaaaaggat  10740
cttcacctag atccttttaa attaaaaatg aagttttaaa tcaatctaaa gtatatatga  10800
gtaaacttgg tctgacagtt accaatgctt aatcagtgag gcacctatct cagcgatctg  10860
tctatttcgt tcatccatag ttgcctgact ccccgtcgtg tagataacta cgatacggga  10920
gggcttacca tctggcccca gtgctgcaat gataccgcga gacccacgct caccggctcc  10980
agatttatca gcaataaacc agccagccgg aagggccgag cgcagaagtg gtcctgcaac  11040
tttatccgcc tccatccagt ctattaattg ttgccgggaa gctagagtaa gtagttcgcc  11100
agttaatagt ttgcgcaacg ttgttgccat tgctgcaggc atcgtggtgt cacgctcgtc  11160
gtttggtatg gcttcattca gctccggttc ccaacgatca aggcgagtta catgatcccc  11220
catgttgtgc aaaaaagcgg ttagctcctt cggtcctccg atcgttgtca gaagtaagtt  11280
ggccgcagtg ttatcactca tggttatggc agcactgcat aattctctta ctgtcatgcc  11340
atccgtaaga tgcttttctg tgactggtga gtactcaacc aagtcattct gagaatagtg  11400
tatgcggcga ccgagttgct cttgcccggc gtcaacacgg gataataccg cgccacatag  11460
cagaacttta aaagtgctca tcattggaaa acgttcttcg gggcgaaaac tctcaaggat  11520
cttaccgctg ttgagatcca gttcgatgta acccactcgt gcacccaact gatcttcagc  11580
atcttttact ttcaccagcg tttctgggtg agcaaaaaca ggaaggcaaa atgccgcaaa  11640
aaagggaata agggcgacac ggaaatgttg aatactcata ctcttccttt ttcaatatta  11700
ttgaagcatt tatcagggtt attgtctcat gagcggatac atatttgaat gtatttagaa  11760
aaataaacaa ataggggttc cgcgcacatt tccccgaaaa gtgccacctg acgtctaaga  11820
aaccattatt atcatgacat taacctataa aaataggcgt atcacgaggc cctttcgtct  11880
tcaagaattc at                                                      11892
```

```
<210> SEQ ID NO 21
<211> LENGTH: 12007
<212> TYPE: DNA
<213> ORGANISM: Artificial Sequence
<220> FEATURE:
<223> OTHER INFORMATION: RCR Vector - pACE-CD

<400> SEQUENCE: 21

tagttattaa tagtaatcaa ttacggggtc attagttcat agcccatata tggagttccg     60
```

```
cgttacataa cttacggtaa atggcccgcc tggctgaccg cccaacgacc cccgcccatt    120
gacgtcaata atgacgtatg ttcccatagt aacgccaata gggactttcc attgacgtca    180
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta acaactccgc cccattgacg caaatgggcg gtaggcgtgt    540
acggtgggag gtctatataa gcagagctgg tttagtgaac cggcgccagt cctccgattg    600
actgagtcgc ccgggtaccc gtgtatccaa taaaccctct tgcagttgca tccgacttgt    660
ggtctcgctg ttccttggga gggtctcctc tgagtgattg actacccgtc agcgggggtc    720
tttcatttgg gggctcgtcc gggatcggga gacccctgcc cagggaccac cgacccacca    780
ccgggaggta agctggccag caacttatct gtgtctgtcc gattgtctag tgtctatgac    840
tgattttatg cgcctgcgtc ggtactagtt agctaactag ctctgtatct ggcggacccg    900
tggtggaact gacgagttcg gaacacccgg ccgcaaccct gggagacgtc ccagggactt    960
cgggggccgt ttttgtggcc cgacctgagt ccaaaaatcc cgatcgtttt ggactctttg   1020
gtgcaccccc cttagaggag ggatatgtgg ttctggtagg agacgagaac ctaaaacagt   1080
tcccgcctcc gtctgaattt ttgctttcgg tttgggaccg aagccgcgcc gcgcgtcttg   1140
tctgctgcag catcgttctg tgttgtctct gtctgactgt gtttctgtat ttgtctgaga   1200
atatgggcca gactgttacc actcccttaa gtttgacctt aggtcactgg aaagatgtcg   1260
agcggatcgc tcacaaccag tcggtagatg tcaagaagag acgttgggtt accttctgct   1320
ctgcagaatg gccaaccttt aacgtcggat ggccgcgaga cggcaccttt aaccgagacc   1380
tcatcaccca ggttaagatc aaggtctttt cacctggccc gcatggacac ccagaccagg   1440
tcccctacat cgtgacctgg gaagccttgg cttttgaccc ccctccctgg gtcaagccct   1500
ttgtacaccc taagcctccg cctcctcttc ctccatccgc cccgtctctc ccccttgaac   1560
ctcctcgttc gaccccgcct cgatcctccc tttatccagc cctcactcct tctctaggcg   1620
ccaaacctaa acctcaagtt ctttctgaca gtggggggcc gctcatcgac ctacttacag   1680
aagacccccc gccttatagg gacccaagac cacccccttc cgacagggac ggaaatggtg   1740
gagaagcgac ccctgcggga gaggcaccgg accccctccc aatggcatct cgcctacgtg   1800
ggagacggga gcccccctgtg gccgactcca ctacctcgca ggcattcccc ctccgcgcag   1860
gaggaaacgg acagcttcaa tactggccgt tctcctcttc tgacctttac aactggaaaa   1920
ataataaccc ttctttttct gaagatccag gtaaactgac agctctgatc gagtctgttc   1980
tcatcaccca tcagcccacc tggacgact gtcagcagct gttggggact ctgctgaccg    2040
gagaagaaaa acaacgggtg ctcttagagg ctagaaaggc ggtgcggggc gatgatgggc   2100
gccccactca actgcccaat gaagtcgatg ccgcttttcc cctcgagcgc ccagactggg   2160
attacaccac ccaggcaggt aggaaccacc tagtccacta tcgccagttg ctcctagcgg   2220
gtctccaaaa cgcgggcaga agccccacca atttggccaa ggtaaaagga ataacacaag   2280
ggcccaatga gtctccctcg gccttcctag agagacttaa ggaagcctat cgcaggtaca   2340
ctccttatga ccctgaggac ccagggcaag aaactaatgt gtctatgtct ttcatttggc   2400
```

agtctgcccc agacattggg agaaagttag agaggttaga agatttaaaa aacaagacgc 2460
ttggagattt ggttagagag gcagaaaaga tctttaataa acgagaaacc ccggaagaaa 2520
gagaggaacg tatcaggaga gaaacagagg aaaaagaaga acgccgtagg acagaggatg 2580
agcagaaaga gaaagaaaga gatcgtagga gacatagaga gatgagcaag ctattggcca 2640
ctgtcgttag tggacagaaa caggatagac agggaggaga acgaaggagg tcccaactcg 2700
atcgcgacca gtgtgcctac tgcaaagaaa aggggcactg ggctaaagat tgtcccaaga 2760
aaccacgagg acctcgggga ccaagacccc agacctccct cctgacccta gatgactagg 2820
gaggtcaggg tcaggagccc ccccctgaac ccaggataac cctcaaagtc ggggggcaac 2880
ccgtcacctt cctggtagat actggggccc aacactccgt gctgacccaa aatcctggac 2940
ccctaagtga taagtctgcc tgggtccaag ggctactgg aggaaagcgg tatcgctgga 3000
ccacggatcg caaagtacat ctagctaccg gtaaggtcac ccactctttc ctccatgtac 3060
cagactgtcc ctatcctctg ttaggaagag atttgctgac taaactaaaa gcccaaatcc 3120
actttgaggg atcaggagcc caggttatgg gaccaatggg gcagcccctg caagtgttga 3180
ccctaaatat agaagatgag catcggctac atgagacctc aaaagagcca gatgtttctc 3240
tagggtccac atggctgtct gattttcctc aggcctgggc ggaaaccggg ggcatgggac 3300
tggcagttcg ccaagctcct ctgatcatac ctctgaaagc aacctctacc cccgtgtcca 3360
taaaacaata ccccatgtca caagaagcca gactggggat caagccccac atacagagac 3420
tgttggacca gggaatactg gtaccctgcc agtcccccctg gaacacgccc ctgctacccg 3480
ttaagaaacc agggactaat gattataggc ctgtccagga tctgagagaa gtcaacaagc 3540
gggtggaaga catccacccc accgtgccca acccttacaa cctcttgagc gggctcccac 3600
cgtcccacca gtggtacact gtgcttgatt taaaggatgc ctttttctgc ctgagactcc 3660
accccaccag tcagcctctc ttcgcctttg agtggagaga tccagagatg ggaatctcag 3720
gacaattgac ctggaccaga ctcccacagg gtttcaaaaa cagtcccacc ctgtttgatg 3780
aggcactgca cagagaccta gcagacttcc ggatccagca cccagacttg atcctgctac 3840
agtacgtgga tgacttactg ctggccgcca cttctgagct agactgccaa caaggtactc 3900
gggccctgtt acaaacccta gggaacctcg ggtatcgggc ctcggccaag aaagcccaaa 3960
tttgccagaa acaggtcaag tatctggggt atcttctaaa agagggtcag agatggctga 4020
ctgaggccag aaaagagact gtgatggggc agcctactcc gaagacccct cgacaactaa 4080
gggagttcct agggacggca ggcttctgtc gcctctggat ccctgggttt gcagaaatgg 4140 cagcccccctt gtaccctctc accaaaacgg ggactctgtt taattggggc ccagaccaac 4200
aaaaggccta tcaagaaatc aagcaagctc ttctaactgc cccagccctg ggtttgccag 4260
atttgactaa gccctttgaa ctctttgtcg acgagaagca gggctacgcc aaaggtgtcc 4320
taacgcaaaa actgggacct tggcgtcggc cggtggccta cctgtccaaa aagctagacc 4380
cagtagcagc tgggtggccc ccttgcctac ggatggtagc agccattgcc gtactgacaa 4440
aggatgcagg caagctaacc atgggacagc cactagtcat tctggccccc catgcagtag 4500
aggcactagt caaacaaccc cccgaccgct ggctttccaa cgcccggatg actcactatc 4560
aggccttgct tttggacacg gaccgggtcc agttcggacc ggtggtagcc ctgaacccgg 4620
ctacgctgct cccactgcct gaggaagggc tgcaacacaa ctgccttgat atcctggccg 4680
aagcccacgg aacccgaccc gacctaacgg accagccgct cccagacgcc gaccacacct 4740
ggtacacgga tggaagcagt ctcttacaag agggacagcg taaggcggga gctgcggtga 4800

```
ccaccgagac cgaggtaatc tgggctaaag ccctgccagc cgggacatcc gctcagcggg   4860
ctgaactgat agcactcacc caggccctaa agatggcaga aggtaagaag ctaaatgttt   4920
atactgatag ccgttatgct tttgctactg cccatatcca tggagaaata tacagaaggc   4980
gtgggttgct cacatcagaa ggcaaagaga tcaaaaataa agacgagatc ttggccctac   5040
taaaagccct ctttctgccc aaaagactta gcataatcca ttgtccagga catcaaaagg   5100
gacacagcgc cgaggctaga ggcaaccgga tggctgacca agcggcccga aaggcagcca   5160
tcacagagac tccagacacc tctaccctcc tcatagaaaa ttcatcaccc tacacctcag   5220
aacattttca ttacacagtg actgatataa aggacctaac caagttgggg gccatttatg   5280
ataaaacaaa gaagtattgg gtctaccaag gaaaacctgt gatgcctgac cagtttactt   5340
ttgaattatt agactttctt catcagctga ctcacctcag cttctcaaaa atgaaggctc   5400
tcctagagag aagccacagt ccctactaca tgctgaaccg ggatcgaaca ctcaaaaata   5460
tcactgagac ctgcaaagct tgtgcacaag tcaacgccag caagtctgcc gttaaacagg   5520
gaactagggt ccgcgggcat cggcccggca ctcattggga gatcgatttc accgagataa   5580
agcccggatt gtatggctat aaatatcttc tagtttttat agataccttt tctggctgga   5640
tagaagcctt cccaaccaag aaagaaaccg ccaaggtcgt aaccaagaag ctactagagg   5700
agatcttccc caggttcggc atgcctcagg tattgggaac tgacaatggg cctgccttcg   5760
tctccaaggt gagtcagaca gtggccgatc tgttggggat tgattggaaa ttacattgtg   5820
catacagacc ccaaagctca ggccaggtag aaagaatgaa tagaaccatc aaggagactt   5880
taactaaatt aacgcttgca actggctcta gagactgggt gctcctactc cccttagccc   5940
tgtaccgagc ccgcaacacg ccgggccccc atggcctcac cccatatgag atcttatatg   6000
gggcaccccc gccccttgta aacttccctg accctgacat gacaagagtt actaacagcc   6060
cctctctcca agctcactta caggctctct acttagtcca gcacgaagtc tggagacctc   6120
tggcggcagc ctaccaagaa caactggacc gaccggtggt acctcaccct taccgagtcg   6180
gcgacacagt gtgggtccgc cgacaccaga ctaagaacct agaacctcgc tggaaaggac   6240
cttacacagt cctgctgacc acccccaccg ccctcaaagt agacggcatc gcagcttgga   6300
tacacgccgc ccacgtgaag gctgccgacc ccgggggtgg accatcctct agactgacat   6360
ggcgcgttca acgctctcaa aaccccctca agataagatt aacccgtgga agcccttaat   6420
agtcatggga gtcctgttag gagtagggat ggcagagagc cccccatcagg tctttaatgt   6480
aacctggaga gtcaccaacc tgatgactgg gcgtaccgcc aatgccacct ccctcctggg   6540
aactgtacaa gatgccttcc caaaattata ttttgatcta tgtgatctgg tcggagagga   6600
gtgggaccct tcagaccagg aaccgtatgt cgggtatggc tgcaagtacc ccgcagggag   6660
acagcggacc cggacttttg acttttacgt gtgccctggg cataccgtaa agtcggggtg   6720
tgggggacca ggagagggct actgtggtaa atgggggtgt gaaaccaccg gacaggctta   6780
ctggaagccc acatcatcgt gggacctaat ctcccttaag cgcggtaaca ccccctggga   6840
cacgggatgc tctaaagttg cctgtggccc ctgctacgac ctctccaaag tatccaattc   6900
cttccaaggg gctactcgag gggcagatgg caaccctcta gtcctagaat tcactgatgc   6960
aggaaaaaag gctaactggg acgggcccaa atcgtgggga ctgagactgt accggacagg   7020
aacagatcct attaccatgt tctccctgac ccggcaggtc cttaatgtgg gaccccgagt   7080
ccccataggg cccaacccag tattacccga ccaaagactc ccttcctcac caatagagat   7140
```

```
tgtaccggct ccacagccac ctagccccct caataccagt taccccccctt ccactaccag   7200
tacaccctca acctccccta caagtccaag tgtcccacag ccaccccccag gaactggaga   7260
tagactacta gctctagtca aaggagccta tcaggcgctt aacctcacca atcccgacaa   7320
gacccaagaa tgttggctgt gcttagtgtc gggacctcct tattacgaag gagtagcggt   7380
cgtgggcact tataccaatc attccaccgc tccggccaac tgtacggcca cttcccaaca   7440
taagcttacc ctatctgaag tgacaggaca gggcctatgc atgggggcag tacctaaaac   7500
tcaccaggcc ttatgtaaca ccacccaaag cgccggctca ggatcctact accttgcagc   7560
acccgccgga acaatgtggg cttgcagcac tggattgact ccctgcttgt ccaccacggt   7620
gctcaatcta accacagatt attgtgtatt agttgaactc tggcccagag taatttacca   7680
ctcccccgat tatatgtatg gtcagcttga acagcgtacc aaatataaaa gagagccagt   7740
atcattgacc ctggcccttc tactaggagg attaaccatg ggagggattg cagctggaat   7800
agggacgggg accactgcct taattaaaac ccagcagttt gagcagcttc atgccgctat   7860
ccagacagac ctcaacgaag tcgaaaagtc aattaccaac ctagaaaagt cactgacctc   7920
gttgtctgaa gtagtcctac agaaccgcag aggcctagat ttgctattcc taaaggaggg   7980
aggtctctgc gcagccctaa aagaagaatg ttgtttttat gcagaccaca cggggctagt   8040
gagagacagc atggccaaat taagagaaag gcttaatcag agacaaaaac tatttgagac   8100
aggccaagga tggttcgaag ggctgtttaa tagatccccc tggtttacca ccttaatctc   8160
caccatcatg ggacctctaa tagtactctt actgatctta ctctttggac cttgcattct   8220
caatcgatta gtccaatttg ttaaagacag gatatcagtg gtccaggctc tagttttgac   8280
tcaacaatat caccagctga agcctataga gtacgagcca tgacgtacgt tactggccga   8340
agccgcttgg aataaggccg gtgtgcgttt gtctatatgt tattttccac catattgccg   8400
tcttttggca atgtgagggc ccggaaacct ggccctgtct tcttgacgag cattcctagg   8460
ggtctttccc ctctcgccaa aggaatgcaa ggtctgttga atgtcgtgaa ggaagcagtt   8520
cctctggaag cttcttgaag acaaacaacg tctgtagcga ccctttgcag gcagcggaac   8580
cccccacctg gcgacaggtg cctctgcggc caaaagccac gtgtataaga tacacctgca   8640
aaggcggcac aaccccagtg ccacgttgtg agttggatag ttgtggaaag agtcaaatgg   8700
ctctcctcaa gcgtattcaa caaggggctg aaggatgccc agaaggtacc ccattgtatg   8760
ggatctgatc tggggcctcg gtgcacatgc tttacatgtg tttagtcgag gttaaaaaaa   8820
cgtctaggcc ccccgaacca cggggacgtg gttttccttt gaaaaacacg ataataccat   8880
ggtgacaggg ggaatggcaa gcaagtggga tcagaagggt atggacattg cctatgagga   8940
ggcggcctta ggttacaaag agggtggtgt tcctattggc ggatgtctta tcaataacaa   9000
agacggaagt gttctcggtc gtggtcacaa catgagattt caaaagggat ccgccacact   9060
acatggtgag atctccactt tggaaaactg tgggagatta gagggcaaag tgtacaaaga   9120
taccactttg tatacgacgc tgtctccatg cgacatgtgt acaggtgcca tcatcatgta   9180
tggtattcca cgctgtgttg tcggtgagaa cgttaatttc aaaagtaagg gcgagaaata   9240
tttacaaact agaggtcacg aggttgttgt tgttgacgat gagaggtgta aaaagatcat   9300
gaaacaattt atcgatgaaa gacctcagga ttggtttgaa gatattggtg agtaggcggc   9360
cgcgccatag ataaaataaa agattttatt tagtctccag aaaaaggggg gaatgaaaga   9420
ccccacctgt aggtttggca agctagctta agtaacgcca ttttgcaagg catggaaaaa   9480
tacataactg agaatagaga agttcagatc aaggtcagga acagatggaa cagctgaata   9540
```

-continued

```
tgggccaaac aggatatctg tggtaagcag ttcctgcccc ggctcagggc caagaacaga   9600
tggaacagct gaatatgggc caaacaggat atctgtggta agcagttcct gccccggctc   9660
agggccaaga acagatggtc cccagatgcg gtccagccct cagcagtttc tagagaacca   9720
tcagatgttt ccagggtgcc ccaaggacct gaaatgaccc tgtgccttgt ttaaactaac   9780
caatcagttc gcttctcgct tctgttcgcg cgcttctgct ccccgagctc aataaaagag   9840
cccacaaccc ctcactcggg gcgccagtcc tccgattgac tgagtcgccc gggtacccgt   9900
gtatccaata aaccctcttg cagttgcatc cgacttgtgg tctcgctgtt ccttgggagg   9960
gtctcctctg agtgattgac tacccgtcag cgggggtctt tcatttgggg gctcgtccgg  10020
gatcgggaga cccctgccca gggaccaccg acccaccacc gggaggtaag ctggctgcct  10080
cgcgcgtttc ggtgatgacg gtgaaaacct ctgacatgtg agcaaaaggc cagcaaaagg  10140
ccaggaaccg taaaaaggcc gcgttgctgg cgtttttcca taggctccgc ccccctgacg  10200
agcatcacaa aaatcgacgc tcaagtcaga ggtggcgaaa cccgacagga ctataaagat  10260
accaggcgtt tccccctgga agctccctcg tgcgctctcc tgttccgacc ctgccgctta  10320
ccggatacct gtccgccttt ctcccttcgg gaagcgtggc gctttctcaa tgctcacgct  10380
gtaggtatct cagttcggtg taggtcgttc gctccaagct gggctgtgtg cacgaacccc  10440
ccgttcagcc cgaccgctgc gccttatccg gtaactatcg tcttgagtcc aacccggtaa  10500
gacacgactt atcgccactg gcagcagcca ctggtaacag gattagcaga gcgaggtatg  10560
taggcggtgc tacagagttc ttgaagtggt ggcctaacta cggctacact agaaggacag  10620
tatttggtat ctgcgctctg ctgaagccag ttaccttcgg aaaaagagtt ggtagctctt  10680
gatccggcaa acaaaccacc gctggtagcg gtggtttttt tgtttgcaag cagcagatta  10740
cgcgcagaaa aaaaggatct caagaagatc ctttgatctt ttctacgggg tctgacgctc  10800
agtggaacga aaactcacgt taagggattt tggtcatgag attatcaaaa aggatcttca  10860
cctagatcct tttaaattaa aaatgaagtt ttaaatcaat ctaaagtata tatgagtaaa  10920
cttggtctga cagttaccaa tgcttaatca gtgaggcacc tatctcagcg atctgtctat  10980
ttcgttcatc catagttgcc tgactccccg tcgtgtagat aactacgata cgggagggct  11040
taccatctgg ccccagtgct gcaatgatac cgcgagaccc acgctcaccg gctccagatt  11100
tatcagcaat aaaccagcca gccggaaggg ccgagcgcag aagtggtcct gcaactttat  11160
ccgcctccat ccagtctatt aattgttgcc gggaagctag agtaagtagt tcgccagtta  11220
atagtttgcg caacgttgtt gccattgctg caggcatcgt ggtgtcacgc tcgtcgtttg  11280
gtatggcttc attcagctcc ggttcccaac gatcaaggcg agttacatga tcccccatgt  11340
tgtgcaaaaa agcggttagc tccttcggtc ctccgatcgt tgtcagaagt aagttggccg  11400
cagtgttatc actcatggtt atggcagcac tgcataattc tcttactgtc atgccatccg  11460
taagatgctt ttctgtgact ggtgagtact caaccaagtc attctgagaa tagtgtatgc  11520
ggcgaccgag ttgctcttgc ccggcgtcaa cacgggataa taccgcgcca catagcagaa  11580
ctttaaaagt gctcatcatt ggaaaacgtt cttcggggcg aaaactctca aggatcttac  11640
cgctgttgag atccagttcg atgtaaccca ctcgtgcacc caactgatct tcagcatctt  11700
ttactttcac cagcgtttct gggtgagcaa aaacaggaag gcaaaatgcc gcaaaaaagg  11760
gaataagggc gacacggaaa tgttgaatac tcatactctt cctttttcaa tattattgaa  11820
gcatttatca gggttattgt ctcatgagcg gatacatatt tgaatgtatt tagaaaaata  11880
```

aacaaatagg ggttccgcgc acatttcccc gaaaagtgcc acctgacgtc taagaaacca 11940
ttattatcat gacattaacc tataaaaata ggcgtatcac gaggcccttt cgtcttcaag 12000
aattcat 12007

<210> SEQ ID NO 22
<211> LENGTH: 11893
<212> TYPE: DNA
<213> ORGANISM: Artificial Sequence
<220> FEATURE:
<223> OTHER INFORMATION: RCR Vector - pAC3-yCD2

<400> SEQUENCE: 22
tagttattaa tagtaatcaa ttacggggtc attagttcat agcccatata tggagttccg 60
cgttacataa cttacggtaa atggcccgcc tggctgaccg cccaacgacc cccgcccatt 120
gacgtcaata atgacgtatg ttcccatagt aacgccaata gggactttcc attgacgtca 180
atgggtggag tatttacggt aaactgccca cttggcagta catcaagtgt atcatatgcc 240
aagtacgccc cctattgacg tcaatgacgg taaatggccc gcctggcatt atgcccagta 300
catgacctta tgggactttc ctacttggca gtacatctac gtattagtca tcgctattac 360
catggtgatg cggttttggc agtacatcaa tgggcgtgga tagcggtttg actcacgggg 420
atttccaagt ctccacccca ttgacgtcaa tgggagtttg ttttggcacc aaaatcaacg 480
ggactttcca aaatgtcgta acaactccgc cccattgacg caaatgggcg gtaggcgtgt 540
acggtgggag gtctatataa gcagagctgg tttagtgaac cggcgccagt cctccgattg 600
actgagtcgc ccgggtaccc gtgtatccaa taaaccctct tgcagttgca tccgacttgt 660
ggtctcgctg ttccttggga gggtctcctc tgagtgattg actacccgtc agcgggggtc 720
tttcatttgg gggctcgtcc gggatcggga gacccctgcc cagggaccac cgacccacca 780
ccgggaggta agctggccag caacttatct gtgtctgtcc gattgtctag tgtctatgac 840
tgattttatg cgcctgcgtc ggtactagtt agctaactag ctctgtatct ggcggacccg 900
tggtggaact gacgagttcg gaacacccgg ccgcaaccct gggagacgtc ccagggactt 960
cgggggccgt ttttgtggcc cgacctgagt ccaaaaatcc cgatcgtttt ggactctttg 1020
gtgcaccccc cttagaggag ggatatgtgg ttctggtagg agacgagaac ctaaaacagt 1080
tcccgcctcc gtctgaattt ttgctttcgg tttgggaccg aagccgcgcc gcgcgtcttg 1140
tctgctgcag catcgttctg tgttgtctct gtctgactgt gtttctgtat ttgtctgaaa 1200
atatgggcca gactgttacc actcccttaa gtttgacctt aggtcactgg aaagatgtcg 1260
agcggatcgc tcacaaccag tcggtagatg tcaagaagag acgttgggtt accttctgct 1320
ctgcagaatg gccaaccttt aacgtcggat ggccgcgaga cggcaccttt aaccgagacc 1380
tcatcaccca ggttaagatc aaggtctttt cacctggccc gcatggacac ccagaccagg 1440 tccccctacat cgtgacctgg gaagccttgg cttttgaccc ccctccctgg gtcaagccct 1500
ttgtacaccc taagcctccg cctcctcttc ctccatccgc cccgtctctc ccccttgaac 1560
ctcctcgttc gaccccgcct cgatcctccc tttatccagc cctcactcct tctctaggcg 1620
ccaaacctaa acctcaagtt ctttctgaca gtgggggggcc gctcatcgac ctacttacag 1680
aagacccccc gccttatagg gacccaagac caccccccttc cgacagggac ggaaatggtg 1740
gagaagcgac ccctgcggga gaggcaccgg acccctcccc aatggcatct cgcctacgtg 1800
ggagacggga gccccctgtg gccgactcca ctacctcgca ggcattcccc ctccgcgcag 1860
gaggaaacgg acagcttcaa tactggccgt tctcctcttc tgacctttac aactggaaaa 1920

```
ataataaccc ttctttttct gaagatccag gtaaactgac agctctgatc gagtctgtcc   1980
tcatcaccca tcagcccacc tgggacgact gtcagcagct gttggggact ctgctgaccg   2040
gagaagaaaa acaacgggtg ctcttagagg ctagaaaggc ggtgcggggc gatgatgggc   2100
gccccactca actgcccaat gaagtcgatg ccgcttttcc cctcgagcgc ccagactggg   2160
attacaccac ccaggcaggt aggaaccacc tagtccacta tcgccagttg ctcctagcgg   2220
gtctccaaaa cgcgggcaga agccccacca atttggccaa ggtaaaagga ataacacaag   2280
ggcccaatga gtctccctcg gccttcctag agagacttaa ggaagcctat cgcaggtaca   2340
ctccttatga ccctgaggac ccagggcaag aaactaatgt gtctatgtct ttcatttggc   2400
agtctgcccc agacattggg agaaagttag agaggttaga agatttaaaa aacaagacgc   2460
ttggagattt ggttagagag gcagaaaaga tctttaataa acgagaaacc ccggaagaaa   2520
gagaggaacg tatcaggaga gaaacagagg aaaaagaaga acgccgtagg acagaggatg   2580
agcagaaaga gaaagaaaga gatcgtagga gacatagaga gatgagcaag ctattggcca   2640
ctgtcgttag tggacagaaa caggatagac agggaggaga acgaaggagg tcccaactcg   2700
atcgcgacca gtgtgcctac tgcaaagaaa aggggcactg ggctaaagat tgtcccaaga   2760
aaccacgagg acctcgggga ccaagacccc agacctccct cctgacccta gatgactagg   2820
gaggtcaggg tcaggagccc ccccctgaac ccaggataac cctcaaagtc ggggggcaac   2880
ccgtcacctt cctggtagat actggggccc aacactccgt gctgacccaa aatcctggac   2940
ccctaagtga taagtctgcc tgggtccaag ggctactgg aggaaagcgg tatcgctgga    3000
ccacggatcg caaagtacat ctagctaccg gtaaggtcac ccactctttc ctccatgtac   3060
cagactgtcc ctatcctctg ttaggaagag atttgctgac taaactaaaa gcccaaatcc   3120
actttgaggg atcaggagcc caggttatgg gaccaatggg gcagcccctg caagtgttga   3180
ccctaaatat agaagatgag tatcggctac atgagacctc aaaagagcca gatgtttctc   3240
tagggtccac atggctgtct gattttcctc aggcctgggc ggaaaccggg ggcatgggac   3300
tggcagttcg ccaagctcct ctgatcatac ctctgaaagc aacctctacc cccgtgtcca   3360
taaaacaata ccccatgtca caagaagcca gactggggat caagccccac atacagagac   3420
tgttggacca gggaatactg gtaccctgcc agtccccctg gaacacgccc ctgctacccg   3480
ttaagaaacc agggactaat gattataggc ctgtccagga tctgagagaa gtcaacaagc   3540
gggtggaaga catccacccc accgtgccca acccttacaa cctcttgagc gggctcccac   3600
cgtcccacca gtggtacact gtgcttgatt taaaggatgc ctttttctgc ctgagactcc   3660
accccaccag tcagcctctc ttcgcctttg agtggagaga tccagagatg ggaatctcag   3720
gacaattgac ctggaccaga ctcccacagg gtttcaaaaa cagtcccacc ctgtttgatg   3780
aggcactgca cagagaccta gcagacttcc ggatccagca cccagacttg atcctgctac   3840
agtacgtgga tgacttactg ctggccgcca cttctgagct agactgccaa caaggtactc   3900
gggccctgtt acaaacccta gggaacctcg ggtatcgggc ctcggccaag aaagcccaaa   3960
tttgccagaa acaggtcaag tatctggggt atcttctaaa agagggtcag agatggctga   4020
ctgaggccag aaaagagact gtgatggggc agcctactcc gaagacccct cgacaactaa   4080
gggagttcct agggacggca ggcttctgtc gcctctggat ccctgggttt gcagaaatgg   4140
cagccccctt gtaccctctc accaaaacgg ggactctgtt taattggggc ccagaccaac   4200
aaaaggccta tcaagaaatc aagcaagctc ttctaactgc cccagccctg gggttgccag   4260
```

-continued

```
atttgactaa gccctttgaa ctctttgtcg acgagaagca gggctacgcc aaaggtgtcc   4320
taacgcaaaa actgggacct tggcgtcggc cggtggccta cctgtccaaa aagctagacc   4380
cagtagcagc tgggtggccc ccttgcctac ggatggtagc agccattgcc gtactgacaa   4440
aggatgcagg caagctaacc atgggacagc cactagtcat tctggccccc catgcagtag   4500
aggcactagt caaacaaccc cccgaccgct ggctttccaa cgcccggatg actcactatc   4560
aggccttgct tttggacacg gaccgggtcc agttcggacc ggtggtagcc ctgaacccgg   4620
ctacgctgct cccactgcct gaggaagggc tgcaacacaa ctgccttgat atcctggccg   4680
aagcccacgg aacccgaccc gacctaacgg accagccgct cccagacgcc gaccacacct   4740
ggtacacgga tggaagcagt ctcttacaag agggacagcg taaggcggga gctgcggtga   4800
ccaccgagac cgaggtaatc tggggctaaag ccctgccagc cgggacatcc gctcagcggg   4860
ctgaactgat agcactcacc caggccctaa agatggcaga aggtaagaag ctaaatgttt   4920
atactgatag ccgttatgct tttgctactg cccatatcca tggagaaata tacagaaggc   4980
gtgggttgct cacatcagaa ggcaaagaga tcaaaaataa agacgagatc ttggccctac   5040
taaaagccct ctttctgccc aaaagactta gcataatcca ttgtccagga catcaaaagg   5100
gacacagcgc cgaggctaga ggcaaccgga tggctgacca agcggcccga aaggcagcca   5160
tcacagagac tccagacacc tctaccctcc tcatagaaaa ttcatcaccc tacacctcag   5220
aacattttca ttacacagtg actgatataa aggacctaac caagttgggg gccatttatg   5280
ataaaacaaa gaagtattgg gtctaccaag gaaaacctgt gatgcctgac cagtttactt   5340
ttgaattatt agactttctt catcagctga ctcacctcag cttctcaaaa atgaaggctc   5400
tcctagagag aagccacagt ccctactaca tgctgaaccg gatcgaaca ctcaaaaata   5460
tcactgagac ctgcaaagct tgtgcacaag tcaacgccag caagtctgcc gttaaacagg   5520
gaactagggt ccgcgggcat cggcccggca ctcattggga gatcgatttc accgagataa   5580
agcccggatt gtatggctat aaatatcttc tagtttttat agataccttt tctggctgga   5640
tagaagcctt cccaaccaag aaagaaaccg ccaaggtcgt aaccaagaag ctactagagg   5700
agatcttccc caggttcggc atgcctcagg tattgggaac tgacaatggg cctgccttcg   5760
tctccaaggt gagtcagaca gtggccgatc tgttggggat tgattggaaa ttacattgtg   5820
catacagacc ccaaagctca ggccaggtag aaagaatgaa tagaaccatc aaggagactt   5880
taactaaatt aacgcttgca actggctcta gagactgggt gctcctactc cccttagccc   5940
tgtaccgagc ccgcaacacg ccgggccccc atggcctcac ccatatgag atcttatatg   6000
gggcaccccc gccccttgta aacttccctg accctgacat gacaagagtt actaacagcc   6060
cctctctcca agctcactta caggctctct acttagtcca gcacgaagtc tggagacctc   6120
tggcggcagc ctaccaagaa caactggacc gaccggtggt acctcaccct taccgagtcg   6180
gcgacacagt gtgggtccgc cgacaccaga ctaagaacct agaacctcgc tggaaaggac   6240
cttacacagt cctgctgacc acccccaccg ccctcaaagt agacggcatc gcagcttgga   6300
tacacgccgc ccacgtgaag gctgccgacc ccgggggtgg accatcctct agactgacat   6360
ggcgcgttca acgctctcaa aaccccctca agataagatt aacccgtgga agcccttaat   6420
agtcatggga gtcctgttag gagtagggat ggcagagagc cccccatcagg tctttaatgt   6480
aacctggaga gtcaccaacc tgatgactgg gcgtaccgcc aatgccacct ccctcctggg   6540
aactgtacaa gatgccttcc caaaattata ttttgatcta tgtgatctgg tcggagagga   6600
gtgggaccct tcagaccagg aaccgtatgt cgggtatggc tgcaagtacc ccgcagggag   6660
```

-continued

```
acagcggacc cggacttttg acttttacgt gtgccctggg cataccgtaa agtcggggtg   6720
tgggggacca ggagagggct actgtggtaa atgggggtgt gaaaccaccg gacaggctta   6780
ctggaagccc acatcatcgt gggacctaat ctcccttaag cgcggtaaca ccccctggga   6840
cacgggatgc tctaaagttg cctgtggccc ctgctacgac ctctccaaag tatccaattc   6900
cttccaaggg gctactcgag gggcagatg caaccctcta gtcctagaat tcactgatgc   6960
aggaaaaaag gctaactggg acgggcccaa atcgtgggga ctgagactgt accggacagg   7020
aacagatcct attaccatgt tctccctgac ccggcaggtc cttaatgtgg gaccccgagt   7080
ccccataggg cccaacccag tattacccga ccaaagactc ccttcctcac caatagagat   7140
tgtaccggct ccacagccac ctagccccct caataccagt taccccccctt ccactaccag   7200
tacaccctca acctccccta caagtccaag tgtcccacag ccaccccccag gaactggaga   7260
tagactacta gctctagtca aaggagccta tcaggcgctt aacctcacca atcccgacaa   7320
gacccaagaa tgttggctgt gcttagtgtc gggacctcct tattacgaag gagtagcggt   7380
cgtgggcact tataccaatc attccaccgc tccggccaac tgtacggcca cttcccaaca   7440
taagcttacc ctatctgaag tgacaggaca gggcctatgc atgggggcag tacctaaaac   7500
tcaccaggcc ttatgtaaca ccacccaaag cgccggctca ggatcctact accttgcagc   7560
acccgccgga acaatgtggg cttgcagcac tggattgact ccctgcttgt ccaccacggt   7620
gctcaatcta accacagatt attgtgtatt agttgaactc tggcccagag taatttacca   7680
ctcccccgat tatatgtatg gtcagcttga acagcgtacc aaatataaaa gagagccagt   7740
atcattgacc ctggcccttc tactaggagg attaaccatg ggagggattg cagctggaat   7800
agggacgggg accactgcct taattaaaac ccagcagttt gagcagcttc atgccgctat   7860
ccagacagac ctcaacgaag tcgaaaagtc aattaccaac ctagaaaagt cactgacctc   7920
gttgtctgaa gtagtcctac agaaccgcag aggcctagat ttgctattcc taaaggaggg   7980
aggtctctgc gcagccctaa aagaagaatg ttgtttttat gcagaccaca cggggctagt   8040
gagagacagc atggccaaat taagagaaag gcttaatcag agacaaaaac tatttgagac   8100
aggccaagga tggttcgaag ggctgtttaa tagatccccc tggtttacca ccttaatctc   8160
caccatcatg ggacctctaa tagtactctt actgatctta ctctttggac cttgcattct   8220
caatcgattg gtccaatttg ttaaagacag gatctcagtg gtccaggctc tggttttgac   8280
tcagcaatat caccagctaa aacccataga gtacgagcca tgaacgcgtt actggccgaa   8340
gccgcttgga ataaggccgg tgtgcgtttg tctatatgtt attttccacc atattgccgt   8400
cttttggcaa tgtgagggcc cggaaacctg gccctgtctt cttgacgagc attcctaggg   8460
gtctttcccc tctcgccaaa ggaatgcaag gtctgttgaa tgtcgtgaag gaagcagttc   8520
ctctggaagc ttcttgaaga caaacaacgt ctgtagcgac cctttgcagg cagcggaacc   8580
ccccacctgg cgacaggtgc ctctgcggcc aaaagccacg tgtataagat acacctgcaa   8640
aggcggcaca accccagtgc cacgttgtga gttggatagt tgtggaaaga gtcaaatggc   8700
tctcctcaag cgtattcaac aaggggctga aggatgccca gaaggtaccc cattgtatgg   8760
gatctgatct ggggcctcgg tgcacatgct ttacatgtgt ttagtcgagg ttaaaaaaac   8820
gtctaggccc cccgaaccac ggggacgtgg ttttcctttg aaaaacacga ttataaatgg   8880
tgaccggcgg catggcctcc aagtgggatc aaaagggcat ggatatcgct tacgaggagg   8940
ccctgctggg ctacaaggag ggcggcgtgc ctatcggcgg ctgtctgatc aacaacaagg   9000
```

-continued

```
acggcagtgt gctgggcagg ggccacaaca tgaggttcca gaagggctcc gccaccctgc   9060
acggcgagat ctccaccctg gagaactgtg gcaggctgga gggcaaggtg tacaaggaca   9120
ccaccctgta caccaccctg tcccttgtg acatgtgtac cggcgctatc atcatgtacg   9180
gcatccctag gtgtgtgatc ggcgagaacg tgaacttcaa gtccaagggc gagaagtacc   9240
tgcaaaccag gggccacgag gtggtggttg ttgacgatga gaggtgtaag aagctgatga   9300
agcagttcat cgacgagagg cctcaggact ggttcgagga tatcggcgag taagcggccg   9360
cagataaaat aaaagatttt atttagtctc cagaaaaagg ggggaatgaa agaccccacc   9420
tgtaggtttg gcaagctagc ttaagtaacg ccattttgca aggcatggaa aaatacataa   9480
ctgagaatag agaagttcag atcaaggtca ggaacagatg gaacagctga atatgggcca   9540
aacaggatat ctgtggtaag cagttcctgc cccggctcag ggccaagaac agatggaaca   9600
gctgaatatg ggccaaacag gatatctgtg gtaagcagtt cctgccccgg ctcagggcca   9660
agaacagatg gtccccagat gcggtccagc cctcagcagt ttctagagaa ccatcagatg   9720
tttccagggt gccccaagga cctgaaatga ccctgtgcct tatttgaact aaccaatcag   9780
ttcgcttctc gcttctgttc gcgcgcttct gctccccgag ctcaataaaa gagcccacaa   9840
cccctcactc ggggcgccag tcctccgatt gactgagtcg cccgggtacc cgtgtatcca   9900
ataaaccctc ttgcagttgc atccgacttg tggtctcgct gttccttggg agggtctcct   9960
ctgagtgatt gactacccgt cagcgggggt ctttcattac atgtgagcaa aaggccagca  10020
aaaggccagg aaccgtaaaa aggccgcgtt gctggcgttt ttccataggc tccgcccccc  10080
tgacgagcat cacaaaaatc gacgctcaag tcagaggtgg cgaaacccga caggactata  10140
aagataccag gcgtttcccc ctggaagctc cctcgtgcgc tctcctgttc cgaccctgcc  10200
gcttaccgga tacctgtccg cctttctccc ttcgggaagc gtggcgcttt ctcatagctc  10260
acgctgtagg tatctcagtt cggtgtaggt cgttcgctcc aagctgggct gtgtgcacga  10320
accccccgtt cagcccgacc gctgcgcctt atccggtaac tatcgtcttg agtccaaccc  10380
ggtaagacac gacttatcgc cactggcagc agccactggt aacaggatta gcagagcgag  10440
gtatgtaggc ggtgctacag agttcttgaa gtggtggcct aactacggct acactagaag  10500
gacagtattt ggtatctgcg ctctgctgaa gccagttacc ttcggaaaaa gagttggtag  10560
ctcttgatcc ggcaaacaaa ccaccgctgg tagcggtggt ttttttgttt gcaagcagca  10620
gattacgcgc agaaaaaaag gatctcaaga agatcctttg atcttttcta cggggtctga  10680
cgctcagtgg aacgaaaact cacgttaagg gattttggtc atgagattat caaaaaggat  10740
cttcacctag atccttttaa attaaaaatg aagttttaaa tcaatctaaa gtatatatga  10800
gtaaacttgg tctgacagtt accaatgctt aatcagtgag gcacctatct cagcgatctg  10860
tctatttcgt tcatccatag ttgcctgact ccccgtcgtg tagataacta cgatacggga  10920
gggcttacca tctggcccca gtgctgcaat gataccgcga gacccacgct caccggctcc  10980
agatttatca gcaataaacc agccagccgg aagggccgag cgcagaagtg gtcctgcaac  11040
tttatccgcc tccatccagt ctattaattg ttgccgggaa gctagagtaa gtagttcgcc  11100
agttaatagt ttgcgcaacg ttgttgccat tgctgcaggc atcgtggtgt cacgctcgtc  11160
gtttggtatg gcttcattca gctccggttc ccaacgatca aggcgagtta catgatcccc  11220
catgttgtgc aaaaaagcgg ttagctcctt cggtcctccg atcgttgtca gaagtaagtt  11280
ggccgcagtg ttatcactca tggttatggc agcactgcat aattctctta ctgtcatgcc  11340
atccgtaaga tgcttttctg tgactggtga gtactcaacc aagtcattct gagaatagtg  11400
```

-continued

```
tatgcggcga ccgagttgct cttgcccggc gtcaacacgg gataataccg cgccacatag  11460

cagaacttta aaagtgctca tcattggaaa acgttcttcg gggcgaaaac tctcaaggat  11520

cttaccgctg ttgagatcca gttcgatgta acccactcgt gcacccaact gatcttcagc  11580

atcttttact ttcaccagcg tttctgggtg agcaaaaaca ggaaggcaaa atgccgcaaa  11640

aaagggaata agggcgacac ggaaatgttg aatactcata ctcttccttt ttcaatatta  11700

ttgaagcatt tatcagggtt attgtctcat gagcggatac atatttgaat gtatttagaa  11760

aaataaacaa ataggggttc cgcgcacatt tccccgaaaa gtgccacctg acgtctaaga  11820

aaccattatt atcatgacat taacctataa aaataggcgt atcacgaggc cctttcgtct  11880

tcaagaattc cat                                                      11893
```

<210> SEQ ID NO 23
<211> LENGTH: 5
<212> TYPE: PRT
<213> ORGANISM: Artificial Sequence
<220> FEATURE:
<223> OTHER INFORMATION: Peptide linker

<400> SEQUENCE: 23

```
Gly Gly Gly Gly Ser
1               5
```

<210> SEQ ID NO 24
<211> LENGTH: 5
<212> TYPE: PRT
<213> ORGANISM: Artificial Sequence
<220> FEATURE:
<223> OTHER INFORMATION: Peptide linker

<400> SEQUENCE: 24

```
Ser Gly Gly Gly Gly
1               5
```

<210> SEQ ID NO 25
<211> LENGTH: 12
<212> TYPE: PRT
<213> ORGANISM: Artificial Sequence
<220> FEATURE:
<223> OTHER INFORMATION: Peptide linker

<400> SEQUENCE: 25

```
Gly Lys Ser Ser Gly Ser Gly Ser Glu Ser Lys Ser
1               5                   10
```

<210> SEQ ID NO 26
<211> LENGTH: 14
<212> TYPE: PRT
<213> ORGANISM: Artificial Sequence
<220> FEATURE:
<223> OTHER INFORMATION: Peptide linker

<400> SEQUENCE: 26

```
Gly Ser Thr Ser Gly Ser Gly Lys Ser Ser Glu Gly Lys Gly
1               5                   10
```

<210> SEQ ID NO 27
<211> LENGTH: 18
<212> TYPE: PRT
<213> ORGANISM: Artificial Sequence
<220> FEATURE:
<223> OTHER INFORMATION: Peptide linker

<400> SEQUENCE: 27

Gly Ser Thr Ser Gly Ser Gly Lys Ser Ser Glu Gly Ser Gly Ser Thr
1 5 10 15

Lys Gly

<210> SEQ ID NO 28
<211> LENGTH: 18
<212> TYPE: PRT
<213> ORGANISM: Artificial Sequence
<220> FEATURE:
<223> OTHER INFORMATION: Peptide linker

<400> SEQUENCE: 28

Gly Ser Thr Ser Gly Ser Gly Lys Pro Gly Ser Gly Glu Gly Ser Thr
1 5 10 15

Lys Gly

<210> SEQ ID NO 29
<211> LENGTH: 14
<212> TYPE: PRT
<213> ORGANISM: Artificial Sequence
<220> FEATURE:
<223> OTHER INFORMATION: Peptide linker

<400> SEQUENCE: 29

Glu Gly Lys Ser Ser Gly Ser Gly Ser Glu Ser Lys Glu Phe
1 5 10

<210> SEQ ID NO 30
<211> LENGTH: 546
<212> TYPE: DNA
<213> ORGANISM: Artificial Sequence
<220> FEATURE:
<223> OTHER INFORMATION: Cytosine deaminase coding sequence with cloning sites

<400> SEQUENCE: 30
aacacgatta taaatggtga cagggggaat ggcaagcaag tgggatcaga agggtatgga 60
cattgcctat gaggaggcgg ccttaggtta caaagagggt ggtgttccta ttggcggatg 120
tcttatcaat aacaaagacg gaagtgttct cggtcgtggt cacaacatga gatttcaaaa 180
gggatccgcc acactacatg gtgagatctc cactttggaa aactgtggga gattagaggg 240
caaagtgtac aaagatacca ctttgtatac gacgctgtct ccatgcgaca tgtgtacagg 300
tgccatcatc atgtatggta ttccacgctg tgttgtcggt gagaacgtta atttcaaaag 360
taagggcgag aaatatttac aaactagagg tcacgaggtt gttgttgttg acgatgagag 420
gtgtaaaaag atcatgaaac aatttatcga tgaaagacct caggattggt ttgaagatat 480
tggtgagtag gcggccgcgc catagataaa ataaaagatt ttatttagtc tccagaaaaa 540
gggggg 546

<210> SEQ ID NO 31
<211> LENGTH: 537
<212> TYPE: DNA
<213> ORGANISM: Artificial Sequence
<220> FEATURE:
<223> OTHER INFORMATION: Cytosine deaminase codon optimized with cloning site

<400> SEQUENCE: 31
ttataaatgg tgaccggcgg catggcctcc aagtgggatc aaaagggcat ggatatcgct 60

-continued

```
tacgaggagg ccgccctggg ctacaaggag ggcggcgtgc ctatcggcgg ctgtctgatc    120

aacaacaagg acggcagtgt gctgggcagg ggccacaaca tgaggttcca gaagggctcc    180

gccaccctgc acggcgagat ctccaccctg gagaactgtg gcaggctgga gggcaaggtg    240

tacaaggaca ccaccctgta caccaccctg tccccttgtg acatgtgtac cggcgctatc    300

atcatgtacg gcatccctag gtgtgtggtg ggcgagaacg tgaacttcaa gtccaagggc    360

gagaagtacc tgcaaaccag gggccacgag gtggtggttg ttgacgatga gaggtgtaag    420

aagatcatga agcagttcat cgacgagagg cctcaggact ggttcgagga tatcggcgag    480

tgataagcgg ccgcagataa aataaaagat tttatttagt ctccagaaaa agggggg       537


<210> SEQ ID NO 32
<211> LENGTH: 40
<212> TYPE: DNA
<213> ORGANISM: Artificial Sequence
<220> FEATURE:
<223> OTHER INFORMATION: Oligonucleotide Primer

<400> SEQUENCE: 32

tcgaggatat cggcgagtga aacccgttat tctttttggc                           40


<210> SEQ ID NO 33
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 33

gccaaaaaga ataacgggtt tcactcgccg atatcctcga                           40


<210> SEQ ID NO 34
<211> LENGTH: 82
<212> TYPE: DNA
<213> ORGANISM: Artificial Sequence
<220> FEATURE:
<223> OTHER INFORMATION: Oligonucleotide Primer

<400> SEQUENCE: 34

tcggcgagtg atccggcggc ggcgcctccg gcggcggcgc ctccggcggc ggcgcctccg     60

gcggcggcgc caacccgtta tt                                              82


<210> SEQ ID NO 35
<211> LENGTH: 82
<212> TYPE: DNA
<213> ORGANISM: Artificial Sequence
<220> FEATURE:
<223> OTHER INFORMATION: Oligonucleotide Primer

<400> SEQUENCE: 35

aataacgggt tggcgccgcc gccggaggcg ccgccgccgg aggcgccgcc gccggaggcg     60

ccgccgccgg atcactcgcc ga                                              82


<210> SEQ ID NO 36
<211> LENGTH: 533
<212> TYPE: DNA
<213> ORGANISM: Artificial Sequence
<220> FEATURE:
<223> OTHER INFORMATION: Cytosine deaminase heat stabilized

<400> SEQUENCE: 36

atggtgacag ggggaatggc aagcaagtgg gatcagaagg gtatggacat tgcctatgag     60
```

gaggcgttat taggttacaa agagggtggt gttcctattg gcggatgtct tatcaataac 120
aaagacggaa gtgttctcgg tcgtggtcac aacatgagat ttcaaaaggg atccgccaca 180
ctacatggtg agatctccac tttggaaaac tgtgggagat tagagggcaa agtgtacaaa 240
gataccactt tgtatacgac gctgtctcca tgcgacatgt gtacaggtgc catcatcatg 300
tatggtattc cacgctgtgt catcggtgag aacgttaatt tcaaaagtaa gggcgagaaa 360
tatttacaaa ctagaggtca cgaggttgtt gttgttgacg atgagaggtg taaaaagtta 420
atgaaacaat ttatcgatga aagacctcag gattggtttg aagatattgg tgagtaggcg 480
gccgcgccat agataaaata aaagatttta tttagtctcc agaaaaaggg ggg 533

<210> SEQ ID NO 37
<211> LENGTH: 480
<212> TYPE: DNA
<213> ORGANISM: Artificial Sequence
<220> FEATURE:
<223> OTHER INFORMATION: CD human codon optimized heat stabilized

<400> SEQUENCE: 37
atggtgaccg gcggcatggc ctccaagtgg gatcaaaagg gcatggatat cgcttacgag 60
gaggccctgc tgggctacaa ggagggcggc gtgcctatcg gcggctgtct gatcaacaac 120
aaggacggca gtgtgctggg caggggccac aacatgaggt tccagaaggg ctccgccacc 180
ctgcacggcg agatctccac cctggagaac tgtggcaggc tggagggcaa ggtgtacaag 240
gacaccaccc tgtacaccac cctgtcccct tgtgacatgt gtaccggcgc tatcatcatg 300
tacggcatcc ctaggtgtgt gatcggcgag aacgtgaact tcaagtccaa gggcgagaag 360
tacctgcaaa ccaggggcca cgaggtggtg gttgttgacg atgagaggtg taagaagctg 420
atgaagcagt tcatcgacga gaggcctcag gactggttcg aggatatcgg cgagtgataa 480

<210> SEQ ID NO 38
<211> LENGTH: 546
<212> TYPE: DNA
<213> ORGANISM: Artificial Sequence
<220> FEATURE:
<223> OTHER INFORMATION: CD human codon optimized heat stabilitized
cloning sites

<400> SEQUENCE: 38
aacacgatta taaatggtga ccggcggcat ggcctccaag tgggatcaaa agggcatgga 60
tatcgcttac gaggaggccc tgctgggcta caaggagggc ggcgtgccta tcggcggctg 120
tctgatcaac aacaaggacg gcagtgtgct gggcaggggc cacaacatga ggttccagaa 180
gggctccgcc accctgcacg gcgagatctc caccctggag aactgtggca ggctggaggg 240
caaggtgtac aaggacacca ccctgtacac caccctgtcc ccttgtgaca tgtgtaccgg 300
cgctatcatc atgtacggca tccctaggtg tgtgatcggc gagaacgtga acttcaagtc 360
caagggcgag aagtacctgc aaaccagggg ccacgaggtg gtggttgttg acgatgagag 420
gtgtaagaag ctgatgaagc agttcatcga cgagaggcct caggactggt tcgaggatat 480
cggcgagtaa gcggccgcgc catagataaa ataaaagatt ttatttagtc tccagaaaaa 540
gggggg 546

<210> SEQ ID NO 39
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 39
tcgaggatat cggcgagtga aacccgttat tctttttggc 40

<210> SEQ ID NO 40
<211> LENGTH: 40
<212> TYPE: DNA
<213> ORGANISM: Artificial Sequence
<220> FEATURE:
<223> OTHER INFORMATION: Oligonucleotide primer

<400> SEQUENCE: 40
gccaaaaaga ataacgggtt tcactcgccg atatcctcga 40

<210> SEQ ID NO 41
<211> LENGTH: 52
<212> TYPE: DNA
<213> ORGANISM: Artificial Sequence
<220> FEATURE:
<223> OTHER INFORMATION: Oligonucleotide primer

<400> SEQUENCE: 41
ccaagctcct atagccgctc actatctact tgggcaataa gaaaaaccga ag 52

<210> SEQ ID NO 42
<211> LENGTH: 52
<212> TYPE: DNA
<213> ORGANISM: Artificial Sequence
<220> FEATURE:
<223> OTHER INFORMATION: Oligonucleotide Primer

<400> SEQUENCE: 42
ggttcgagga tatcggcgag tgatagatga acccgttatt ctttttggct tc 52

<210> SEQ ID NO 43
<211> LENGTH: 1296
<212> TYPE: DNA
<213> ORGANISM: Artificial Sequence
<220> FEATURE:
<223> OTHER INFORMATION: CD codon optimized-UPRT

<400> SEQUENCE: 43
aacacgatta taaatggtga ccggcggcat ggcctccaag tgggatcaaa agggcatgga 60
tatcgcttac gaggaggccc tgctgggcta caaggagggc ggcgtgccta tcggcggctg 120
tctgatcaac aacaaggacg gcagtgtgct gggcaggggc cacaacatga ggttccagaa 180
gggctccgcc accctgcacg gcgagatctc caccctggag aactgtggca ggctggaggg 240
caaggtgtac aaggacacca ccctgtacac caccctgtcc ccttgtgaca tgtgtaccgg 300
cgctatcatc atgtacggca tccctaggtg tgtgatcggc gagaacgtga acttcaagtc 360
caagggcgag aagtacctgc aaaccagggg ccacgaggtg gtggttgttg acgatgagag 420
gtgtaagaag ctgatgaagc agttcatcga cgagaggcct caggactggt tcgaggatat 480
cggcgagaac ccgttattct ttttggcttc tccattcttg taccttacat atcttatata 540
ttatccaaac aaagggtctt tcgttagcaa acctagaaat ctgcaaaaaa tgtcttcgga 600
accatttaag aacgtctact tgctacctca aacaaaccaa ttgctgggtt tgtacaccat 660
catcagaaat aagaatacaa ctagacctga tttcattttc tactccgata gaatcatcag 720
attgttggtt gaagaaggtt tgaaccatct acctgtgcaa aagcaaattg tggaaactga 780
caccaacgaa aacttcgaag gtgtctcatt catgggtaaa atctgtggtg tttccattgt 840
cagagctggt gaatcgatgg agcaaggatt aagagactgt tgtaggtctg tgcgtatcgg 900
taaaatttta attcaaaggg acgaggagac tgctttacca aagttattct acgaaaaatt 960
accagaggat atatctgaaa ggtatgtctt cctattagac ccaatgctgg ccaccggtgg 1020
tagtgctatc atggctacag aagtcttgat taagagaggt gttaagccag agagaattta 1080
cttcttaaac ctaatctgta gtaaggaagg gattgaaaaa taccatgccg ccttcccaga 1140
ggtcagaatt gttactggtg ccctcgacag aggtctagat gaaaacaagt atctagttcc 1200
agggttgggt gactttggtg acagatacta ctgtgtttaa gcggccgcgc catagataaa 1260
ataaaagatt ttatttagtc tccagaaaaa gggggg 1296

<210> SEQ ID NO 44
<211> LENGTH: 82
<212> TYPE: DNA
<213> ORGANISM: Artificial Sequence
<220> FEATURE:
<223> OTHER INFORMATION: Oligonucleotide primer

<400> SEQUENCE: 44
tcggcgagtg atccggcggc ggcgcctccg gcggcggcgc ctccggcggc ggcgcctccg 60
gcggcggcgc caacccgtta tt 82

<210> SEQ ID NO 45
<211> LENGTH: 82
<212> TYPE: DNA
<213> ORGANISM: Artificial Sequence
<220> FEATURE:
<223> OTHER INFORMATION: Oligonucleotide primer

<400> SEQUENCE: 45
aataacgggt tggcgccgcc gccggaggcg ccgccgccgg aggcgccgcc gccggaggcg 60
ccgccgccgg atcactcgcc ga 82

<210> SEQ ID NO 46
<211> LENGTH: 1356
<212> TYPE: DNA
<213> ORGANISM: Artificial Sequence
<220> FEATURE:
<223> OTHER INFORMATION: CD human codon optimized-linker-UPRT

<400> SEQUENCE: 46
aacacgatta taaatggtga ccggcggcat ggcctccaag tgggatcaaa agggcatgga 60
tatcgcttac gaggaggccc tgctgggcta caaggagggc ggcgtgccta tcggcggctg 120
tctgatcaac aacaaggacg gcagtgtgct gggcaggggc cacaacatga ggttccagaa 180
gggctccgcc accctgcacg gcgagatctc caccctggag aactgtggca ggctggaggg 240
caaggtgtac aaggacacca ccctgtacac caccctgtcc ccttgtgaca tgtgtaccgg 300
cgctatcatc atgtacggca tccctaggtg tgtgatcggc gagaacgtga acttcaagtc 360
caagggcgag aagtacctgc aaaccagggg ccacgaggtg gtggttgttg acgatgagag 420
gtgtaagaag ctgatgaagc agttcatcga cgagaggcct caggactggt tcgaggatat 480
cggcgagtcc ggcggcggcg cctccggcgg cggcgcctcc ggcggcggcg cctccggcgg 540
cggcgccaac ccgttattct ttttggcttc tccattcttg taccttacat atcttatata 600
ttatccaaac aaagggtctt tcgttagcaa acctagaaat ctgcaaaaaa tgtcttcgga 660
accatttaag aacgtctact tgctacctca aacaaaccaa ttgctgggtt tgtacaccat 720
catcagaaat aagaatacaa ctagacctga tttcattttc tactccgata gaatcatcag 780
attgttggtt gaagaaggtt tgaaccatct acctgtgcaa aagcaaattg tggaaactga 840
caccaacgaa aacttcgaag gtgtctcatt catgggtaaa atctgtggtg tttccattgt 900
cagagctggt gaatcgatgg agcaaggatt aagagactgt tgtaggtctg tgcgtatcgg 960
taaaatttta attcaaaggg acgaggagac tgctttacca aagttattct acgaaaaatt 1020
accagaggat atatctgaaa ggtatgtctt cctattagac ccaatgctgg ccaccggtgg 1080
tagtgctatc atggctacag aagtcttgat taagagaggt gttaagccag agagaattta 1140
cttcttaaac ctaatctgta gtaaggaagg gattgaaaaa taccatgccg ccttcccaga 1200
ggtcagaatt gttactggtg ccctcgacag aggtctagat gaaaacaagt atctagttcc 1260
agggttgggt gactttggtg acagatacta ctgtgtttaa gcggccgcgc catagataaa 1320
ataaaagatt ttatttagtc tccagaaaaa gggggg 1356

<210> SEQ ID NO 47
<211> LENGTH: 1269
<212> TYPE: DNA
<213> ORGANISM: Artificial Sequence
<220> FEATURE:
<223> OTHER INFORMATION: CD human codon optimized-OPRT

<400> SEQUENCE: 47
aacacgatta taaatggtga ccggcggcat ggcctccaag tgggatcaaa agggcatgga 60
tatcgcttac gaggaggccc tgctgggcta caaggagggc ggcgtgccta tcggcggctg 120
tctgatcaac aacaaggacg gcagtgtgct gggcaggggc cacaacatga ggttccagaa 180
gggctccgcc accctgcacg gcgagatctc caccctggag aactgtggca ggctggaggg 240
caaggtgtac aaggacacca ccctgtacac caccctgtcc ccttgtgaca tgtgtaccgg 300
cgctatcatc atgtacggca tccctaggtg tgtgatcggc gagaacgtga acttcaagtc 360
caagggcgag aagtacctgc aaaccagggg ccacgaggtg gtggttgttg acgatgagag 420
gtgtaagaag ctgatgaagc agttcatcga cgagaggcct caggactggt tcgaggatat 480
cggcgaggcg gtcgctcgtg cagctttggg gccattggtg acgggtctgt acgacgtgca 540
ggctttcaag tttggggact tcgtgctgaa gagcgggctt tcctccccca tctacatcga 600
tctgcggggc atcgtgtctc gaccgcgtct tctgagtcag gttgcagata ttttattcca 660
aactgcccaa aatgcaggca tcagttttga caccgtgtgt ggagtgcctt atacagcttt 720
gccattggct acagttatct gttcaaccaa tcaaattcca atgcttatta gaaggaaaga 780
aacaaaggat tatggaacta agcgtcttgt agaaggaact attaatccag gagaaacctg 840
tttaatcatt gaagatgttg tcaccagtgg atctagtgtt ttggaaactg ttgaggttct 900
tcagaaggag ggcttgaagg tcactgatgc catagtgctg ttggacagag agcagggagg 960
caaggacaag ttgcaggcgc acgggatccg cctccactca gtgtgtacat tgtccaaaat 1020
gctggagatt ctcgagcagc agaaaaaagt tgatgctgag acagttggga gagtgaagag 1080
gtttattcag gagaatgtct ttgtggcagc gaatcataat ggttctcccc tttctataaa 1140
ggaagcaccc aaagaactca gcttcggtgc acgtgcagag ctgcccagga tccacccagt 1200
tgcatcgaag taagcggccg cgccatagat aaaataaaag attttattta gtctccagaa 1260
aaaggggggg 1269

<210> SEQ ID NO 48

<211> LENGTH: 1329
<212> TYPE: DNA
<213> ORGANISM: Artificial Sequence
<220> FEATURE:
<223> OTHER INFORMATION: CD codon optimized-linker-OPRT

<400> SEQUENCE: 48
aacacgatta taaatggtga ccggcggcat ggcctccaag tgggatcaaa agggcatgga 60
tatcgcttac gaggaggccc tgctgggcta caaggagggc ggcgtgccta tcggcggctg 120
tctgatcaac aacaaggacg gcagtgtgct gggcaggggc cacaacatga ggttccagaa 180
gggctccgcc accctgcacg gcgagatctc caccctggag aactgtggca ggctggaggg 240
caaggtgtac aaggacacca ccctgtacac caccctgtcc ccttgtgaca tgtgtaccgg 300
cgctatcatc atgtacggca tccctaggtg tgtgatcggc gagaacgtga acttcaagtc 360
caagggcgag aagtacctgc aaaccagggg ccacgaggtg gtggttgttg acgatgagag 420
gtgtaagaag ctgatgaagc agttcatcga cgagaggcct caggactggt tcgaggatat 480
cggcgagtcc ggcggcggcg cctccggcgg cggcgcctcc ggcggcggcg cctccggcgg 540
cggcgccgcg gtcgctcgtg cagctttggg gccattggtg acgggtctgt acgacgtgca 600
ggctttcaag tttggggact tcgtgctgaa gagcgggctt tcctccccca tctacatcga 660
tctgcggggc atcgtgtctc gaccgcgtct tctgagtcag gttgcagata ttttattcca 720
aactgcccaa aatgcaggca tcagttttga caccgtgtgt ggagtgcctt atacagcttt 780
gccattggct acagttatct gttcaaccaa tcaaattcca atgcttatta gaaggaaaga 840
aacaaaggat tatggaacta agcgtcttgt agaaggaact attaatccag gagaaacctg 900
tttaatcatt gaagatgttg tcaccagtgg atctagtgtt ttggaaactg ttgaggttct 960
tcagaaggag ggcttgaagg tcactgatgc catagtgctg ttggacagag agcagggagg 1020
caaggacaag ttgcaggcgc acgggatccg cctccactca gtgtgtacat tgtccaaaat 1080
gctggagatt ctcgagcagc agaaaaaagt tgatgctgag acagttggga gagtgaagag 1140
gtttattcag gagaatgtct ttgtggcagc gaatcataat ggttctcccc tttctataaa 1200
ggaagcaccc aaagaactca gcttcggtgc acgtgcagag ctgcccagga tccacccagt 1260
tgcatcgaag taagcggccg cgccatagat aaaataaaag attttattta gtctccagaa 1320
aaaggggggg 1329

<210> SEQ ID NO 49
<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 49
atcatcatgt acggcatccc tag 23

<210> SEQ ID NO 50
<211> LENGTH: 24
<212> TYPE: DNA
<213> ORGANISM: Artificial Sequence
<220> FEATURE:
<223> OTHER INFORMATION: Oligonucleotide Primer

<400> SEQUENCE: 50
tgaactgctt catcagcttc ttac 24

-continued

<210> SEQ ID NO 51
<211> LENGTH: 25
<212> TYPE: DNA
<213> ORGANISM: Artificial Sequence
<220> FEATURE:
<223> OTHER INFORMATION: Oligonucleotide Primer

<400> SEQUENCE: 51
tcatcgtcaa caaccaccac ctcgt 25

<210> SEQ ID NO 52
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 52
aacctcaacc tcccctacaa gt 22

<210> SEQ ID NO 53
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 53
gttaagcgcc tgataggctc 20

<210> SEQ ID NO 54
<211> LENGTH: 26
<212> TYPE: DNA
<213> ORGANISM: Artificial Sequence
<220> FEATURE:
<223> OTHER INFORMATION: Oligonucleotide Primer

<400> SEQUENCE: 54
agccaccccc aggaactgga gataga 26

GENE THERAPY VECTORS AND CYTOSINE DEAMINASES

CROSS REFERENCE TO RELATED APPLICATIONS

This application is a continuation of U.S. patent application Ser. No. 13/072,705, filed Mar. 26, 2011 (now U.S. Pat. No. 8,722,867), which is a continuation-in-part of International Application No. PCT/US09/58510, filed Sep. 26, 2009, which claims priority to U.S. Provisional Application Ser. No. 61/100,666, filed Sep. 26, 2008, U.S. Provisional Application Ser. No. 61/120,618, filed Dec. 8, 2008, U.S. Provisional Application Ser. No. 61/186,823, filed Jun. 13, 2009, and U.S. Provisional Application Ser. No. 61/318,728, filed Mar. 29, 2010, the disclosures of which are incorporated herein by reference.

TECHNICAL FIELD

This disclosure relates to modified cytosine deaminases (CDs). The disclosure further relates to cells expressing such modified CDs and methods of using such modified CDs in the treatment of disease and disorders.

BACKGROUND

The yeast, or bacterial, cytosine deaminase converts the innocuous antibiotic pro-drug 5-FC into the cytotoxic chemotherapeutic agent 5-fluorouracil (5-FU). Humans (and mammals in general) are not known to possess a naturally occurring gene encoding an enzyme with significant cytosine deaminase activity. Yeast and bacterial cytosine deaminase have gained recognition in the treatment of cancers using gene delivery and viral vectors for the delivery of the enzyme followed by treatment with 5-FC, which is then converted by the enzyme to a cytotoxic drug (Miller et al., Can Res 62:773-780 2002; Kievit et al., Can Res 59:1417-1421 1999).

SUMMARY

Provided herein are polypeptides that convert 5-FC to 5-FU. Also provided are nucleic acid molecules that encode such polypeptides, cells expressing such polypeptides, vectors containing such polynucleotide and polypeptides and methods of synthesizing 5-FU or derivatives thereof from a suitable using such polypeptides. Accordingly, in various embodiments, isolated or recombinant polypeptides comprising a cytosine deaminase having a sequence as set forth in SEQ ID NO: 2 is provided. In other embodiments, the polypeptide comprises SEQ ID NO: 2 with a mutation selected from the group consisting of A23L, V108I, I140L and any combination thereof. In yet another embodiment, the polypeptide comprises the sequence as set forth in SEQ ID NO: 4 and includes up to 50, 25, 10, or 5 conservative amino acid substitutions excluding residues: (a) 23, 108 and 140. In general, polypeptides provided herein display cytosine deaminase activity useful for converting 5-FC to 5-FU.

The disclosure also provides polypeptide that comprises a sequence that is at least 80%, 90%, 95%, 98% or 99% identical to SEQ ID NO: 4, wherein the polypeptide has a leucine at position 23, an isoleucine at position 108 and a leucine at position 140, and wherein the polypeptide has cytosine deaminase activity. In yet another embodiment, the polypeptide comprises the sequence as set forth in SEQ ID NO: 4.

The disclosure further provides fusion constructs comprising any one of the foregoing polypeptides operably linked to a uracil phosphoribosyltransferase (UPRT) or an orotate phosphoribosyltransferase (OPRT). In one embodiment, the fusion construct comprises a first polypeptide comprising SEQ ID NO: 2 with a mutation selected from the group consisting of A23L, V108I, I140L and any combination thereof linked to a second polypeptide having UPRT or OPRT activity. In yet another embodiment, the fusion construct comprises a first polypeptide having the sequence as set forth in SEQ ID NO:4 and includes up to 50, 25, 10, or 5 conservative amino acid substitutions excluding residues: 23, 108 and 140 wherein the first polypeptide is linked to a second polypeptide having UPRT or OPRT activity. The disclosure also provides a fusion construct comprising a first polypeptide having cytosine deaminase activity and that comprise a sequence that is at least 80%, 90%, 95%, 98% or 99% identical to SEQ ID NO: 4, wherein the polypeptide has a leucine at position 23, an isoleucine at position 108 and a leucine at position 140, and wherein the first polypeptide is linked to a second polypeptide comprising UPRT or OPRT activity. In one embodiment, the polypeptides having UPRT or OPRT activity comprises a sequence as set forth in SEQ ID NO: 8 and 10, respectively, or variants thereof. In yet another embodiment, a first polypeptide comprising cytosine deaminase activity is linked to a polypeptide having UPRT or OPRT activity, wherein the polypeptides are separated by a peptide linker. In another embodiment, the fusion construct comprises a sequence selected from the group consisting of SEQ ID NO: 12, 14, 16 or 18.

The disclosure further provides polynucleotides encoding any of the foregoing polypeptides. For example, the disclosure provides a polynucleotide encoding a polypeptide comprising SEQ ID NO: 2 with a mutation selected from the group consisting of A23L, V108I, I140L and any combination thereof. In yet another embodiment, the polynucleotide encodes a polypeptide comprising a sequence as set forth in SEQ ID NO:4 and includes up to 50, 25, 10, or 5 conservative amino acid substitutions excluding residues: (a) 23, 108 and 140. In a further embodiment, the disclosure provides a polynucleotide encoding a polypeptide comprising a sequence that is at least 80%, 90%, 95%, 98% or 99% identical to SEQ ID NO: 4, wherein the polypeptide has a leucine at position 23, an isoleucine at position 108 and a leucine at position 140, and wherein the polypeptide has cytosine deaminase activity. In yet another embodiment, the polynucleotide encodes a polypeptide comprising SEQ ID NO: 4. In a further embodiment, the polynucleotide encodes a polypeptide comprising a sequence as set forth in SEQ ID NO: 4, 6, 8, 10, 11, 12, or 13.

The disclosure provides a human codon optimized polynucleotide encoding a cytosine deaminase. In one embodiment, the human codon optimized polynucleotide comprises a sequence as set forth in SEQ ID NO: 3. In yet another embodiment, the polynucleotide comprises a sequence as set forth in SEQ ID NO:5, 7, or 9.

In other embodiments, a cytosine deaminase or fusion construct of the disclosure is delivered using a gene delivery system (GDS). In another aspect, the polynucleotide encoding a cytosine deaminase is delivered with a GDS that is a viral or viral derived vector. The viral vector can be replicating or non-replicating, and can be an adenoviral vector, a measles vector, a herpes vector, a retroviral vector (including a lentiviral vector), a rhabdoviral vector such as a Vesicular Stomatitis viral vector, a reovirus vector, a Seneca Valley Virus vector, a poxvirus vector (including animal pox or vaccinia derived vectors), a parvovirus vector (including an AAV vector), an alphavirus vector or other viral vector known to one skilled in the art. In one embodiment, the viral vector can be a replication competent retroviral vector capable of infecting replicating mammalian cells. The replication competent retroviral vector can comprise an Orthoretrovirus or more typically a gamma retrovirus vector. In one aspect, a replication competent retroviral vector comprises an internal ribosomal entry site (IRES) 5' to the polynucleotide encoding a cytosine deaminase of the disclosure. In one embodiment, the polynucleotide encoding a cytosine deaminase is 3' to a ENV polynucleotide of a retroviral vector.

In other embodiments, host cells transfected with a cytosine deaminase or fusion construct of the disclosure, or a vector that includes a polynucleotide or fusion construct of the disclosure, are provided. Host cells include eukaryotic cells such as yeast cells, insect cells, or animal cells. Host cells also include procaryotic cells such as bacterial cells.

The disclosure also provides methods of treating a cell proliferative disorder including a cancer comprising administering a polynucleotide or polypeptide of the disclosure to a subject and contacting the subject with a cytotoxic drug comprising 5-fluorocytosine (5-FC).

The disclosure provides a recombinant replication competent retrovirus (RCR) comprising: a retroviral GAG protein; a retroviral POL protein; a retroviral envelope; a retroviral polynucleotide comprising Long-Terminal Repeat (LTR) sequences at the 3' end of the retroviral polynucleotide sequence, a promoter sequence at the 5' end of the retroviral polynucleotide, said promoter being suitable for expression in a mammalian cell, a gag nucleic acid domain, a pol nucleic acid domain and an env nucleic acid domain; a cassette comprising an internal ribosome entry site (IRES) operably linked to a heterologous polynucleotide, wherein the cassette is positioned 5' to the 3' LTR and 3' to the env nucleic acid domain encoding the retroviral envelope; and cis-acting sequences necessary for reverse transcription, packaging and integration in a target cell, wherein the RCR maintains higher replication competency after 6 passages compared to a pACE vector (SEQ ID NO:21). In one embodiment, the retroviral polynucleotide sequence is derived from murine leukemia virus (MLV), Moloney murine leukemia virus (MoMLV), Feline leukemia virus or Gibbon ape leukemia virus (GALV). In another embodiment, the MLV is an amphotropic MLV. In yet another embodiment, the retrovirus is an oncoretrovirus. In yet another embodiment, the target cell is a cell having a cell proliferative disorder. The cell proliferative disorder can be selected from the group consisting of, but is not limited to, lung cancer, colon-rectum cancer, breast cancer, prostate cancer, urinary tract cancer, uterine cancer, brain cancer, head and neck cancer, pancreatic cancer, melanoma, stomach cancer and ovarian cancer, rheumatoid arthritis and other auto-immune diseases. In one embodiment, the promoter comprises a CMV promoter having a sequence as set forth in SEQ ID NO:19, 20, or 22 from nucleotide 1 to about nucleotide 582 and may include modification to one or more nucleic acid bases and which is capable of directing and initiating transcription. In yet a further embodiment, the promoter comprises a sequence as set forth in SEQ ID NO:19, 20, or 22 from nucleotide 1 to about nucleotide 582. In a further embodiment, the promoter comprises a CMV-R-U5 domain polynucleotide. In one embodiment, the CMV-R-U5 domain comprises the immediately early promoter from human cytomegalovirus linked to an MLV R-U5 region. In yet another embodiment, the CMV-R-U5 domain polynucleotide comprises a sequence as set forth in SEQ ID NO:19, 20, or 22 from about nucleotide 1 to about nucleotide 1202 or sequences that are at least 95% identical to a sequence as set forth in SEQ ID NO:19, 20, or 22, wherein the polynucleotide promotes transcription of a nucleic acid molecule operably linked thereto. In another embodiment, the gag and pol of the polynucleotide are derived from an oncoretrovirus. The gag nucleic acid domain can comprise a sequence from about nucleotide number 1203 to about nucleotide 2819 of SEQ ID NO: 19 or a sequence having at least 95%, 98%, 99% or 99.8% identity thereto. The pol domain can comprise a sequence from about nucleotide number 2820 to about nucleotide 6358 of SEQ ID NO:19 or a sequence having at least 95%, 98%, 99% or 99.9% identity thereto. In one embodiment, the env domain encodes an amphoteric env protein. The env domain can comprise a sequence from about nucleotide number 6359 to about nucleotide 8323 of SEQ ID NO:19 or a sequence having at least 95%, 98%, 99% or 99.8% identity thereto. The IRES domain of the vector can be any IRES, however, in one embodiment the IRES is derived from an encephalomyocarditis virus. In a further embodiment, the IRES comprises a sequence from about nucleotide number 8327 to about nucleotide 8876 of SEQ ID NO:19 or a sequence having at least 95%, 98%, or 99% identity thereto. In yet a further embodiment, the heterologous polynucleotide comprises a polynucleotide having a sequence as set forth in SEQ ID NO:3, 5, 11, 13, 15 or 17. In a further embodiment, the heterologous sequence encodes a polypeptide comprising a sequence as set forth in SEQ ID NO:4. The heterologous nucleic acid is human codon optimized and encodes a polypeptide as set forth in SEQ ID NO:4. In a further embodiment, the heterologous nucleic acid comprises a sequence as set forth in SEQ ID NO: 19 from about nucleotide number 8877 to about 9353. In one embodiment, the 3' LTR is derived from an oncoretrovirus. In a further embodiment, the 3' LTR comprises a U3-R-U5 domain. In yet a further embodiment, the 3' LTR comprises a sequence as set forth in SEQ ID NO:19 from about nucleotide 9405 to about 9998 or a sequence that is at least 95%, 98% or 99.5% identical thereto.

The disclosure provides a polynucleotide comprising a sequence as set forth in SEQ ID NO:19, 20, or 22.

The disclosure provides an isolated polynucleotide comprising from 5' to 3': a CMV-R-U5 fusion of the immediate early promoter from human cytomegalovirus to an MLV R-U5 region; a PBS, primer binding site for reverse transcriptase; a 5' splice site; Ψ packaging signal; a gag coding sequence for MLV group specific antigen; a pol coding sequence for MLV polymerase polyprotein; a 3' splice site; a 4070A env coding sequence for envelope protein of MLV strain 4070A; an internal ribosome entry site (IRES) from encephalomyocarditis virus; a modified cytosine deaminase coding sequence; a polypurine tract; and a U3-R-U5 MLV long terminal repeat.

The disclosure provides a method of treating a subject with a cell proliferative disorder comprising contacting the subject with a polynucleotide a polypeptide of the disclosure having cytosine deaminase activity under conditions such that the polynucleotide is expressed and contacting the subject with 5-fluorocytosine.

The disclosure also provides a method of treating a cell proliferative disorder in a subject comprising contacting the subject with a retrovirus of the disclosure, wherein the heterologous nucleic acid sequence encodes a therapeutic protein that inhibits proliferation of a neoplastic cell. In one embodiment, the retrovirus comprises a polynucleotide encoding a polypeptide having a sequence as set forth in SEQ ID NO:4, 12, 14, 16, or 18.

The disclosure provides a recombinant replication competent retrovirus (RCR) comprising recombinant replication competent retrovirus, wherein the vector infects the target multiple times leading to a mean of 5 or more copies of the retrovirus genome. The multiple copies provide a "super" infection useful for gene delivery and protein production in vivo and in vitro. In one embodiment, the recombinant replication competent retrovirus (RCR) comprises: a retroviral GAG protein; a retroviral POL protein; a retroviral envelope; a retroviral polynucleotide comprising Long-Terminal Repeat (LTR) sequences at the 3' end of the retroviral polynucleotide sequence, a promoter sequence at the 5' end of the retroviral polynucleotide, said promoter being suitable for expression in a mammalian cell, a gag nucleic acid domain, a pol nucleic acid domain and an env nucleic acid domain; a cassette comprising an internal ribosome entry site (IRES) operably linked to a cytosine deaminase polynucleotide of the disclosure, wherein the cassette is positioned 5' to the 3' LTR and 3' to the env nucleic acid domain encoding the retroviral envelope; and cis-acting sequences necessary for reverse transcription, packaging and integration in a target cell, wherein the RCR maintains higher replication competency after 6 passages compared to a pACE vector (SEQ ID NO:21). In one embodiment, the retroviral polynucleotide sequence is derived from murine leukemia virus (MLV), Moloney murine leukemia virus (MoMLV), Feline leukemia virus (FeLV), Baboon endogenous retrovirus (BEV), porcine endogenous virus (PERV), the cat derived retrovirus RD114, squirrel monkey retrovirus, Xenotropic murine leukemia virus-related virus (XMRV), avian reticuloendotheliosis virus (REV), or Gibbon ape leukemia virus (GALV). In another embodiment, the MLV is an amphotropic MLV. In yet another embodiment, the retrovirus is an oncoretrovirus or gamma retrovirus. In yet another embodiment, the target cell is a cell having a cell proliferative disorder. The cell proliferative disorder can be selected from the group consisting of, but is not limited to, lung cancer, colon-rectum cancer, breast cancer, prostate cancer, urinary tract cancer, uterine cancer, brain cancer, head and neck cancer, pancreatic cancer, melanoma, stomach cancer and ovarian cancer, rheumatoid arthritis and other autoimmune diseases. In one embodiment, the promoter comprises a CMV promoter having a sequence as set forth in SEQ ID NO:19, 20 or 22 from nucleotide 1 to about nucleotide 582 and may include modification to one or more nucleic acid bases and which is capable of directing and initiating transcription. In yet a further embodiment, the promoter comprises a sequence as set forth in SEQ ID NO:19, 20 or 22 from nucleotide 1 to about nucleotide 582. In a further embodiment, the promoter comprises a CMV-R-U5 domain polynucleotide. In one embodiment, the CMV-R-U5 domain comprises the immediately early promoter from human cytomegalovirus linked to an MLV R-U5 region. In yet another embodiment, the CMV-R-U5 domain polynucleotide comprises a sequence as set forth in SEQ ID NO:19, 20 or 22 from about nucleotide 1 to about nucleotide 1202 or sequences that are at least 95% identical to a sequence as set forth in SEQ ID NO:19, 20 or 22, wherein the polynucleotide promotes transcription of a nucleic acid molecule operably linked thereto. In another embodiment, the gag and pol of the polynucleotide are derived from an oncoretrovirus or gamma retrovirus. The gag nucleic acid domain can comprise a sequence from about nucleotide number 1203 to about nucleotide 2819 of SEQ ID NO: 19 or 22 or a sequence having at least 95%, 98%, 99% or 99.8% identity thereto. The pol domain can comprise a sequence from about nucleotide number 2820 to about nucleotide 6358 of SEQ ID NO:19 or 22 or a sequence having at least 95%, 98%, 99% or 99.9% identity thereto. In one embodiment, the env domain encodes an amphotropic env protein. The env domain can comprise a sequence from about nucleotide number 6359 to about nucleotide 8323 of SEQ ID NO:19 or 22 or a sequence having at least 95%, 98%, 99% or 99.8% identity thereto. The IRES domain of the vector can be any IRES, however, in one embodiment the IRES is derived from an encephalomyocarditis virus. In a further embodiment, the IRES comprises a sequence from about nucleotide number 8327 to about nucleotide 8876 of SEQ ID NO:19 or 22 or a sequence having at least 95%, 98%, or 99% identity thereto.

The disclosure provides a method of treating a cell proliferative disorder in a subject comprising contacting the subject with a retrovirus of the disclosure wherein the vector infects the target multiple times leading to a mean of 5 or more copies of the retrovirus genome.

The details of one or more embodiments of the disclosure are set forth in the accompanying drawings and the description below. Other features, objects, and advantages will be apparent from the description and drawings, and from the claims.

BRIEF DESCRIPTION OF DRAWINGS

FIG. 1A-D shows (A) a schematic of a recombinant retroviral vector of the disclosure; (B and C) a plasmid map of a polynucleotide of the disclosure; (D) a sequence of a polynucleotide of the disclosure (SEQ ID NO:19) in various formats.

FIG. 2A-D shows schemes for the generation of various embodiments of the disclosure comprising polypeptides with CD, OPRT and UPRT activity.

Like reference symbols in the various drawings indicate like elements.

DETAILED DESCRIPTION

Figure 1A:
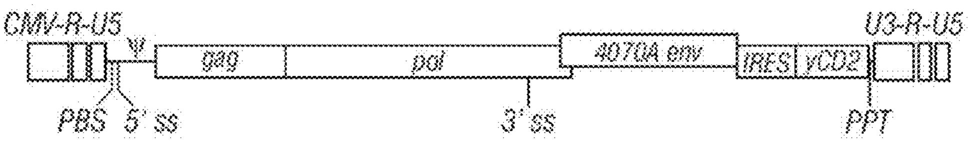

As used herein and in the appended claims, the singular forms "a," "and," and "the" include plural referents unless the context clearly dictates otherwise. Thus, for example, reference to "a cell" includes a plurality of such cells and reference to "the agent" includes reference to one or more agents known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The publications discussed above and throughout the text are provided solely for their disclosure prior to the filing date of the present application. Nothing herein is to be construed as an admission that the inventors are not entitled to antedate such disclosure by virtue of prior disclosure.

A cytosine deaminase (EC 3.5.4.1) is an enzyme that catalyzes the chemical reaction $$cytosine+H_2O \rightarrow uracil+NH_3$$

Thus, the two substrates of this enzyme are cytosine and $H_2O$, whereas its two products are uracil and $NH_3$. This enzyme belongs to the family of hydrolases, those acting on carbon-nitrogen bonds other than peptide bonds, specifically in cyclic amidines. The systematic name of this enzyme class is cytosine aminohydrolase. This enzyme is also called isocytosine deaminase. This enzyme participates in pyrimidine metabolism.

More particularly, cytosine deaminase is an enzyme involved in the metabolic pathway for pyrimidines, through which exogenous cytosine is transformed, via hydrolytic deamination, into uracil. Cytosine deaminase (CDase or CD) activities have been demonstrated in prokaryotes and lower eukaryotes, but they are absent in mammals (Koechlin et al., 1966, Biochem. Pharmacol. 15, 435-446; Polak et al., 1976, Chemotherapy 22, 137-153). The FCY1 gene of *Saccharomyces cerevisiae* (*S. cerevisiae*) and the coda gene of *E. coli*, which encode, respectively, the CDase of these two organisms, are known and their sequences are published (EP 402 108; Erbs et al., 1997, Curr. Genet. 31, 1-6; WO 93/01281). CDase also deaminates a cytosine analogue, 5-fluorocytosine (5-FC) to 5-fluorouracil (5-FU), which is a highly cytotoxic compound, in particular when it is converted to 5-fluoro-UMP (5-FUMP). Cells which lack CDase activity, due either to an inactivating mutation of the gene encoding the enzyme or to their natural deficiency for this enzyme (for example mammalian cells) are resistant to 5-FC (Jund and Lacroute, 1970, J. Bacteriol. 102, 607-615; Kilstrup et al., 1989, J. Bacteriol., 171, 2124-2127). On the other hand, it has been demonstrated that it is possible to transmit 5-FC sensitivity to mammalian cells into which the sequence encoding a CDase activity has been transferred (Huber et al., 1993, Cancer Res. 53, 4619-4626; Mullen et al., 1992, Proc. Natl. Acad. Sci. USA 89, 33-37; WO 93/01281). Accordingly, the use of CD is advantageous in the context of gene therapy, in particular anticancer gene therapy.

However, 5-FC sensitivity varies a great deal depending on the cell lines. Low sensitivity is observed, for example, in PANC-1 (carcinoma of the pancreas) and SK-BR-3 (breast adenocarcinoma) human tumor lines transduced with a retrovirus expressing the coda gene of *E. coli* (Harris et al., 1994, Gene Therapy 1, 170-175). This phenomenon is explained by the absence or poor endogenous conversion of the 5-FU formed by the enzymatic action of the CDase, to cytotoxic 5-FUMP. This step, which is normally carried out in mammalian cells by orotate phosphorybosyltransferase (OPRTase), may be absent in certain tumors and thus make gene therapy based on CDase ineffective. In prokaryotes and lower eukaryotes, uracil is transformed into UMP through the action of uracil phosphoribosyltransferase (UPRTase activity). This enzyme also converts 5-FU to 5-FUMP. Importantly, bacterial uracil phosphoribosyltransferase (UPRT) is functionally equivalent to orotate phosphoribosyltransferase (OPRT) or uridine-5'-monophosphate synthase of mammalian cells. These enzymes mediate the conversion of 5-fluorouracil (5-FU) (a fluorinated analog of uracil) to 5-fluorouridine 5' monophosphate (5-FUMP). 5-fluorouridine 5' monophosphate is subsequently converted to 5-FdUDP and FdUTP via the mammalian de novo pyrimidine pathway. Each 5-FdUTP is an irreversible inhibitor of thymidylate synthase (Thy-A) and results in dTTP starvation. It is widely accepted that this conversion is one of the requisite pathways to achieve cytotoxic effects of 5-fluorouracil and that bacterially uracil phosphoribosyltransferase of bacterial origin is able to convert 5-fluorouracil to the same active metabolite as does mammalian orotate phosphoribosyltransferase. In the absence of UPRTase activity or OPRTase activity, the 5-FU, originating from the deamination of the 5-FC by the CDase, is not transformed into cytotoxic 5-FUMP (Jund and Lacroute, 1970, J. Bacteriol. 102, 607-615).

As described herein, the disclosure provides polynucleotides encoding polypeptides and polypeptides comprising a fusion of a first polypeptide having cytosine deaminase activity and a second polypeptide comprising UPRT or OPRT activity. Such fusion constructs are useful for converting uracil, or a derivative thereof, into a monophosphate analogue, and in particular 5-FU into 5-FUMP.

As will be described in more detail below, the disclosure is based, at least in part, on the generation and expression of novel polypeptides that catalyze the conversion 5-FC to 5-FU. In one embodiment, novel polypeptides that have been engineered to have improved catalytic properties for the conversion of 5-FC to 5-FU are provided. Such polypeptides include variants that have been altered to include amino acid substitutions at specified residues. While these variants will be described in more detail below, it is understood that polypeptides of the disclosure may contain one or more modified amino acids. The presence of modified amino acids may be advantageous in, for example, (a) increasing polypeptide in vivo half-life, (b) reducing or increasing polypeptide antigenicity, and (c) increasing polypeptide storage stability. Amino acid(s) are modified, for example, co-translationally or post-translationally during recombinant production (e.g., N-linked glycosylation at N—X—S/T motifs during expression in mammalian cells) or modified by synthetic means. Accordingly, A "mutant", "variant" or "modified" protein, enzyme, polynucleotide, gene, or cell, means a protein, enzyme, polynucleotide, gene, or cell, that has been altered or derived, or is in some way different or changed, from a parent protein, enzyme, polynucleotide, gene, or cell. A mutant or modified protein or enzyme is usually, although not necessarily, expressed from a mutant polynucleotide or gene.

A "mutation" means any process or mechanism resulting in a mutant protein, enzyme, polynucleotide, gene, or cell. This includes any mutation in which a protein, enzyme, polynucleotide, or gene sequence is altered, and any detectable change in a cell arising from such a mutation. Typically, a mutation occurs in a polynucleotide or gene sequence, by point mutations, deletions, or insertions of single or multiple nucleotide residues. A mutation includes polynucleotide alterations arising within a protein-encoding region of a gene as well as alterations in regions outside of a protein-encoding sequence, such as, but not limited to, regulatory or promoter sequences. A mutation in a gene can be "silent", i.e., not reflected in an amino acid alteration upon expression, leading to a "sequence-conservative" variant of the gene. This generally arises when one amino acid corresponds to more than one codon.

Non-limiting examples of a modified amino acid include a glycosylated amino acid, a sulfated amino acid, a prenlyated (e.g., farnesylated, geranylgeranylated) amino acid, an acetylated amino acid, an acylated amino acid, a pegylated amino acid, a biotinylated amino acid, a carboxylated amino acid, a phosphorylated amino acid, and the like. References adequate to guide one of skill in the modification of amino acids are replete throughout the literature. Example protocols are found in Walker (1998) Protein Protocols on CD-ROM (Humana Press, Towata, N.J.).

Recombinant methods for producing, isolating, and using the modified CD polypeptides and polynucleotides of the disclosure are described herein. In addition to recombinant production, the polypeptides may be produced by direct peptide synthesis using solid-phase techniques (e.g., Stewart et al. (1969) Solid-Phase Peptide Synthesis (WH Freeman Co, San Francisco); and Merrifield (1963) J. Am. Chem. Soc. 85: 2149-2154). Peptide synthesis may be performed using manual techniques or by automation. Automated synthesis may be achieved, for example, using Applied Biosystems 431A Peptide Synthesizer (Perkin Elmer, Foster City, Calif.) in accordance with the instructions provided by the manufacturer.

By way of illustration, the nucleic acid sequences encoding the UPRTases of *E. coli* (Anderson et al., 1992, Eur. J. Biochem 204, 51-56), of *Lactococcus lactis* (Martinussen and Hammer, 1994, J. Bacteriol. 176, 6457-6463), of *Mycobacterium bovis* (Kim et al., 1997, Biochem Mol. Biol. Int 41, 1117-1124) and of *Bacillus subtilis* (Martinussen et al., 1995, J. Bacteriol. 177, 271-274) can be used in the context of the disclosure. However, use of a yeast UPRTase, and in particular that encoded by the FUR1 gene of *S. cerevisiae*, the sequence of which disclosed in Kern et al. (1990, Gene 88, 149-157) is incorporated herein of reference. By way of indication, the sequences of the genes and those of the corresponding UPRTases can be found in the literature and the specialized data banks (SWISSPROT, EMBL, Genbank Medline, etc.).

A "protein" or "polypeptide", which terms are used interchangeably herein, comprises one or more chains of chemical building blocks called amino acids that are linked together by chemical bonds called peptide bonds. An "enzyme" means any substance, preferably composed wholly or largely of protein, that catalyzes or promotes, more or less specifically, one or more chemical or biochemical reactions. The term "enzyme" can also refer to a catalytic polynucleotide (e.g., RNA or DNA). A "native" or "wild-type" protein, enzyme, polynucleotide, gene, or cell, means a protein, enzyme, polynucleotide, gene, or cell that occurs in nature.

Accordingly, in various embodiments, isolated or recombinant polypeptides comprising SEQ ID NO:2 with a mutation selected from the group consisting of A23L, V108I, I140L and any combination thereof are provided. In yet another embodiment, the polypeptide comprises the sequence as set forth in SEQ ID NO:4 and includes up to 50, 25, 10, or 5 conservative amino acid substitutions excluding residues: (a) 23, 108 and 140. In general, polypeptides provided herein display cytosine deaminase activity useful for converting 5-FC to 5-FU.

The disclosure also provides polypeptides that comprise a sequence that is at least 80%, 90%, 95%, 98% or 99% identical to SEQ ID NO:4, wherein the polypeptide has a leucine at position 23, an isoleucine at position 108 and a leucine at position 140, and wherein the polypeptide has cytosine deaminase activity. In yet another embodiment, the polypeptide comprises the sequence as set forth in SEQ ID NO:4.

The disclosure further provides fusion constructs comprising any one of the foregoing polypeptides operably linked to a uracil phosphoribosyltransferase (UPRT) or an oratate phosphoribosyltransferase (OPRT). In one embodiment, the fusion construct comprises a first polypeptide comprising SEQ ID NO:2 with a mutation selected from the group consisting of A23L, V108I, I140L and any combination thereof linked to a second polypeptide having UPRT or OPRT activity. In yet another embodiment, the fusion construct comprises a first polypeptide having the sequence as set forth in SEQ ID NO:4 and includes up to 50, 25, 10, or 5 conservative amino acid substitutions excluding residues: 23, 108 and 140 wherein the first polypeptide is linked to a second polypeptide having UPRT or OPRT activity. The disclosure also provides a fusion construct comprising a first polypeptide having cytosine deaminase activity and that comprise a sequence that is at least 80%, 90%, 95%, 98% or 99% identical to SEQ ID NO:4, wherein the polypeptide has a leucine at position 23, an isoleucine at position 108 and a leucine at position 140, and wherein the first polypeptide is linked to a second polypeptide comprising UPRT or OPRT activity. In one embodiment, the polypeptides having UPRT or OPRT activity comprises a sequence as set forth in SEQ ID NO:8 and 10, respectively, or variants thereof. In yet another embodiment, a first polypeptide comprising cytosine deaminase activity is linked to a polypeptide having UPRT or OPRT activity, wherein the polypeptides are separated by a peptide linker. In another embodiment, the fusion construct comprises a sequence selected from the group consisting of SEQ ID NO:11, 12 or 13.

The term "operably linked" or "operably associated" refers to a functional linkage or association between a regulatory sequence and the polynucleotide regulated by the regulatory sequence or between two distinct polypeptides or polynucleotides encoding such polypeptides.

A fusion construct comprising a polypeptide having CD activity and a polypeptide comprising UPRT or OPRT activity can be engineered to contain a cleavage site to aid in protein recovery or other linker moiety. Typically a linker will be a peptide linker moiety. The length of the linker moiety is chosen to optimize the biological activity of the CD polypeptide and the UPRT or OPRT polypeptide and can be determined empirically without undue experimentation. The linker moiety should be long enough and flexible enough to allow a substrate to interact with the CD polypeptide and a substrate with the UPRT or OPRT polypeptide. A linker moiety is a peptide between about one and 30 amino acid residues in length, typically between about two and 15 amino acid residues. Examples of linker moieties are -Gly-Gly-, GGGGS (SEQ ID NO:23), $(GGGGS)_N$ (SEQ ID NO:23), $(SGGGG)_N$ (SEQ ID NO: 24), GKSSGSGSESKS (SEQ ID NO:25), GSTSGSGKSSEGKG (SEQ ID NO:26), GSTSGSGKSSEGSGSTKG (SEQ ID NO:27), GSTSGSGKPGSGEGSTKG (SEQ ID NO:28), or EGKSSGSGSESKEF (SEQ ID NO:29). Linking moieties are described, for example, in Huston et al., Proc. Nat'l Acad. Sci. 85:5879, 1988; Whitlow et al., Protein Engineering 6:989, 1993; and Newton et al., Biochemistry 35:545, 1996. Other suitable peptide linkers are those described in U.S. Pat. Nos. 4,751,180 and 4,935,233, which are hereby incorporated by reference. A DNA sequence encoding a desired peptide linker can be inserted between, and in the same reading frame as, a polynucleotide encoding a CD polypeptide followed by a UPRT or OPRT polypeptide, using any suitable conventional technique. For example, a chemically synthesized oligonucleotide encoding the linker can be ligated between two coding polynucleotides. In particular embodiments, a fusion polypeptide comprises from two to four separate domains (e.g., a CD domain and a UPRT or OPRT) are separated by peptide linkers.

"Conservative amino acid substitution" or, simply, "conservative variations" of a particular sequence refers to the replacement of one amino acid, or series of amino acids, with essentially identical amino acid sequences. One of skill will recognize that individual substitutions, deletions or additions which alter, add or delete a single amino acid or a percentage of amino acids in an encoded sequence result in "conservative variations" where the alterations result in the deletion of an amino acid, addition of an amino acid, or substitution of an amino acid with a chemically similar amino acid.

Conservative substitution tables providing functionally similar amino acids are well known in the art. For example, one conservative substitution group includes Alanine (A), Serine (S), and Threonine (T). Another conservative substitution group includes Aspartic acid (D) and Glutamic acid (E). Another conservative substitution group includes Asparagine (N) and Glutamine (Q). Yet another conservative substitution group includes Arginine (R) and Lysine (K). Another conservative substitution group includes Isoleucine, (I) Leucine (L), Methionine (M), and Valine (V). Another conservative substitution group includes Phenylalanine (F), Tyrosine (Y), and Tryptophan (W).

Thus, "conservative amino acid substitutions" of a listed polypeptide sequence (e.g., SEQ ID NOs: 2, 4, 6, 8, 10, 11, 12, 13 etc.) include substitutions of a percentage, typically less than 10%, of the amino acids of the polypeptide sequence, with a conservatively selected amino acid of the same conservative substitution group. Accordingly, a conservatively substituted variation of a polypeptide of the disclosure can contain 100, 75, 50, 25, or 10 substitutions with a conservatively substituted variation of the same conservative substitution group.

The "activity" of an enzyme is a measure of its ability to catalyze a reaction, i.e., to "function", and may be expressed as the rate at which the product of the reaction is produced. For example, enzyme activity can be represented as the amount of product produced per unit of time or per unit of enzyme (e.g., concentration or weight), or in terms of affinity or dissociation constants. As used interchangeably herein a "cytosine deaminase activity", "biological activity of cytosine deaminse" or "functional activity of a cytosine deaminse", refers to an activity exerted by a cytosine deaminase protein, or polypeptide of the disclosure, on a cytosine deaminase substrate, as determined in vivo, or in vitro, according to standard techniques. Assays for measuring cytosine deaminase activity are known in the art. For example, an cytosine deaminase activity can measure by determining the rate of conversion of 5-FC to 5-FU or cytosine to uracil. The detection of 5-FC, 5-FU, cytosine and uracil can be performed by chromatography and other methods known in the art.

One of skill in the art will appreciate that many conservative variations of the nucleic acid constructs which are disclosed yield a functionally identical construct. For example, as discussed above, owing to the degeneracy of the genetic code, "silent substitutions" (i.e., substitutions in a nucleic acid sequence which do not result in an alteration in an encoded polypeptide) are an implied feature of every nucleic acid sequence which encodes an amino acid. It will be appreciated by those skilled in the art that due to the degeneracy of the genetic code, a multitude of nucleotide sequences encoding modified cytosine deaminase polypeptides of the disclosure may be produced, some of which bear substantial identity to the nucleic acid sequences explicitly disclosed herein. For instance, codons AGA, AGG, CGA, CGC, CGG, and CGU all encode the amino acid arginine. Thus, at every position in the nucleic acids of the disclosure where an arginine is specified by a codon, the codon can be altered to any of the corresponding codons described above without altering the encoded polypeptide. It is understood that U in an RNA sequence corresponds to T in a DNA sequence.

Similarly, "conservative amino acid substitutions," in one or a few amino acids in an amino acid sequence are substituted with different amino acids with highly similar properties, are also readily identified as being highly similar to a disclosed construct. Such conservative variations of each disclosed sequence are a feature of the polypeptides provided herein.

"Conservative variants" are proteins or enzymes in which a given amino acid residue has been changed without altering overall conformation and function of the protein or enzyme including, but not limited to, replacement of an amino acid with one having similar properties, including polar or non-polar character, size, shape and charge. Amino acids other than those indicated as conserved may differ in a protein or enzyme so that the percent protein or amino acid sequence similarity between any two proteins of similar function may vary and can be, for example, at least 30%, at least 50%, at least 70%, at least 80%, or at least 90%, as determined according to an alignment scheme. As referred to herein, "sequence similarity" means the extent to which nucleotide or protein sequences are related. The extent of similarity between two sequences can be based on percent sequence identity and/or conservation. "Sequence identity" herein means the extent to which two nucleotide or amino acid sequences are invariant. "Sequence alignment" means the process of lining up two or more sequences to achieve maximal levels of identity (and, in the case of amino acid sequences, conservation) for the purpose of assessing the degree of similarity. Numerous methods for aligning sequences and assessing similarity/identity are known in the art such as, for example, the Cluster Method, wherein similarity is based on the MEGALIGN algorithm, as well as BLASTN, BLASTP, and FASTA (Lipman and Pearson, 1985; Pearson and Lipman, 1988). When using all of these programs, the preferred settings are those that results in the highest sequence similarity. For example, the "identity" or "percent identity" with respect to a particular pair of aligned amino acid sequences can refer to the percent amino acid sequence identity that is obtained by ClustalW analysis (version W 1.8 available from European Bioinformatics Institute, Cambridge, UK), counting the number of identical matches in the alignment and dividing such number of identical matches by the greater of (i) the length of the aligned sequences, and (ii) 96, and using the following default ClustalW parameters to achieve slow/accurate pairwise alignments—Gap Open Penalty: 10; Gap Extension Penalty: 0.10; Protein weight matrix: Gonnet series; DNA weight matrix: IUB; Toggle Slow/Fast pairwise alignments=SLOW or FULL Alignment.

Two sequences are "optimally aligned" when they are aligned for similarity scoring using a defined amino acid substitution matrix (e.g., BLOSUM62), gap existence penalty and gap extension penalty so as to arrive at the highest score possible for that pair of sequences. Amino acid substitution matrices and their use in quantifying the similarity between two sequences are well-known in the art and described, e.g., in Dayhoff et al. (1978) "A model of evolutionary change in proteins" in "Atlas of Protein Sequence and Structure," Vol. 5, Suppl. 3 (ed. M. O. Dayhoff), pp. 345-352. Natl. Biomed. Res. Found., Washington, D.C. and Henikoff et al. (1992) Proc. Nat'l. Acad. Sci. USA 89: 10915-10919. The BLOSUM62 matrix (FIG. 10) is often used as a default scoring substitution matrix in sequence alignment protocols such as Gapped BLAST 2.0. The gap existence penalty is imposed for the introduction of a single amino acid gap in one of the aligned sequences, and the gap extension penalty is imposed for each additional empty amino acid position inserted into an already opened gap. The alignment is defined by the amino acids positions of each sequence at which the alignment begins and ends, and optionally by the insertion of a gap or multiple gaps in one or both sequences so as to arrive at the highest possible score. While optimal alignment and scoring can be accomplished manually, the process is facilitated by the use of a computer-implemented alignment algorithm, e.g., gapped BLAST 2.0, described in Altschul et al. (1997) Nucl. Acids Res. 25: 3389-3402, and made available to the public at the National Center for Biotechnology Information (NCBI) Website (www.ncbi.nlm.nih.gov). Optimal alignments, including multiple alignments, can be prepared using, e.g., PSI-BLAST, available through the NCB1 website and described by Altschul et al. (1997) Nucl. Acids Res. 25:3389-3402.

With respect to an amino acid sequence that is optimally aligned with a reference sequence, an amino acid residue "corresponds to" the position in the reference sequence with which the residue is paired in the alignment. The "position" is denoted by a number that sequentially identifies each amino acid in the reference sequence based on its position relative to the N-terminus. Owing to deletions, insertion, truncations, fusions, etc., that must be taken into account when determining an optimal alignment, in general the amino acid residue number in a test sequence as determined by simply counting from the N-terminal will not necessarily be the same as the number of its corresponding position in the reference sequence. For example, in a case where there is a deletion in an aligned test sequence, there will be no amino acid that corresponds to a position in the reference sequence at the site of deletion. Where there is an insertion in an aligned reference sequence, that insertion will not correspond to any amino acid position in the reference sequence. In the case of truncations or fusions there can be stretches of amino acids in either the reference or aligned sequence that do not correspond to any amino acid in the corresponding sequence.

Non-conservative modifications of a particular polypeptide are those which substitute any amino acid not characterized as a conservative substitution. For example, any substitution which crosses the bounds of the six groups set forth above. These include substitutions of basic or acidic amino acids for neutral amino acids (e.g., Asp, Glu, Asn, or Gln for Val, Ile, Leu or Met), aromatic amino acid for basic or acidic amino acids (e.g., Phe, Tyr or Trp for Asp, Asn, Glu or Gln) or any other substitution not replacing an amino acid with a like amino acid. Basic side chains include lysine (K), arginine (R), histidine (H); acidic side chains include aspartic acid (D), glutamic acid (E); uncharged polar side chains include glycine (G), asparagine (N), glutamine (Q), serine (S), threonine (T), tyrosine (Y), cysteine (C); nonpolar side chains include alanine (A), valine (V), leucine (L), isoleucine (I), proline (P), phenylalanine (F), methionine (M), tryptophan (W); beta-branched side chains include threonine (T), valine (V), isoleucine (I); aromatic side chains include tyrosine (Y), phenylalanine (F), tryptophan (W), histidine (H).

Accordingly, some amino acid residues at specific positions in a polypeptide are "excluded" from conservative amino acid substitutions. For example, the disclosure provides a polypeptide comprising a sequence as set forth in SEQ ID NO:4. In some embodiments, the polypeptide may be altered with conservative amino acid substitutions as described above, however, certain residues are desirably left unsubstituted such as residues at positions 23, 108, and 140.

A "parent" protein, enzyme, polynucleotide, gene, or cell, is any protein, enzyme, polynucleotide, gene, or cell, from which any other protein, enzyme, polynucleotide, gene, or cell, is derived or made, using any methods, tools or techniques, and whether or not the parent is itself native or mutant. A parent polynucleotide or gene encodes for a parent protein or enzyme.

A polynucleotide, polypeptide, or other component is "isolated" when it is partially or completely separated from components with which it is normally associated (other proteins, nucleic acids, cells, synthetic reagents, etc.). A nucleic acid or polypeptide is "recombinant" when it is artificial or engineered, or derived from an artificial or engineered protein or nucleic acid. For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

In other embodiments, isolated polynucleotides are provided that encode a cytosine deaminase polypeptide or fusion construct of the disclosure. In one aspect, the disclosure provides an isolated or recombinant polynucleotides referred to herein as "CD optimized polynucleotides", "CD polynucleotides" or "CD-fusion polynucleotides." The terms "polynucleotide," "nucleotide sequence," and "nucleic acid molecule" are used to refer to a polymer of nucleotides (A, C, T, U, G, etc. or naturally occurring or artificial nucleotide analogues), e.g., DNA or RNA, or a representation thereof, e.g., a character string, etc., depending on the relevant context. A given polynucleotide or complementary polynucleotide can be determined from any specified nucleotide sequence.

One embodiment of the disclosure pertains to isolated polynucleotides that encode a cytosine deaminase or a mutant cytosine deaminase polypeptide or biologically active portions thereof. As used herein, the term "nucleic acid molecule" or "polynucleotide" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded.

In one embodiment, a CD optimized polynucleotide or CD polynucleotide comprises recombinant, engineered or isolated forms of naturally occurring nucleic acids isolated from an organism, e.g., a bacterial or yeast strain. Exemplary CD polynucleotides include those that encode the wild-type polypeptides set forth in SEQ ID NO: 2. In another embodiment of the disclosure, CD polynucleotides are produced by diversifying, e.g., recombining and/or mutating one or more naturally occurring, isolated, or recombinant CD polynucleotides. As described in more detail elsewhere herein, it is possible to generate diversified CD polynucleotides encoding CD polypeptides with superior functional attributes, e.g., increased catalytic function, increased stability, or higher expression level, than a CD polynucleotide used as a substrate or parent in the diversification process. Exemplary polynucleotides include SEQ ID NO:3 and 5 and those that encode the CD variant polypeptides of the disclosure.

The polynucleotides of the disclosure have a variety of uses in, for example, recombinant production (i.e., expression) of the CD polypeptides of the disclosure and as substrates for further diversity generation, e.g., recombination reactions or mutation reactions to produce new and/or improved CD homologues, and the like.

It is important to note that certain specific, substantial and credible utilities of CD polynucleotides do not require that the polynucleotide encode a polypeptide with substantial CD activity or even variant CD activity. For example, CD polynucleotides that do not encode active enzymes can be valuable sources of parental polynucleotides for use in diversification procedures to arrive at CD polynucleotide variants, or non-CD polynucleotides, with desirable functional properties (e.g., high $k_{cat}$ or $k_{cat}/K_m$, low $K_m$, high stability towards heat or other environmental factors, high transcription or translation rates, resistance to proteolytic cleavage, etc.).

CD polynucleotides, including nucleotide sequences that encode CD polypeptides and variants thereof, fragments of CD polypeptides, related fusion proteins, or functional equivalents thereof, are used in recombinant DNA molecules that direct the expression of the CD polypeptides in appropriate host cells, such as bacterial cells. Due to the inherent degeneracy of the genetic code, other nucleic acid sequences which encode substantially the same or a functionally equivalent amino acid sequence can also be used to clone and express the CD polynucleotides. The term "host cell", as used herein, includes any cell type which is susceptible to transformation with a nucleic acid construct. The term "transformation" means the introduction of a foreign (i.e., extrinsic or extracellular) gene, DNA or RNA sequence to a host cell, so that the host cell will express the introduced gene or sequence to produce a desired substance, typically a protein or enzyme coded by the introduced gene or sequence. The introduced gene or sequence may include regulatory or control sequences, such as start, stop, promoter, signal, secretion, or other sequences used by the genetic machinery of the cell. A host cell that receives and expresses introduced DNA or RNA has been "transformed" and is a "transformant" or a "clone." The DNA or RNA introduced to a host cell can come from any source, including cells of the same genus or species as the host cell, or cells of a different genus or species.

As will be understood by those of skill in the art, it can be advantageous to modify a coding sequence to enhance its expression in a particular host. The genetic code is redundant with 64 possible codons, but most organisms preferentially use a subset of these codons. The codons that are utilized most often in a species are called optimal codons, and those not utilized very often are classified as rare or low-usage codons (see, e.g., Zhang et al. (1991) Gene 105:61-72). Codons can be substituted to reflect the preferred codon usage of the host, a process sometimes called "codon optimization" or "controlling for species codon bias."

Optimized coding sequences containing codons preferred by a particular prokaryotic or eukaryotic host (see also, Murray et al. (1989) Nucl. Acids Res. 17:477-508) can be prepared, for example, to increase the rate of translation or to produce recombinant RNA transcripts having desirable properties, such as a longer half-life, as compared with transcripts produced from a non-optimized sequence. Translation stop codons can also be modified to reflect host preference. For example, preferred stop codons for *S. cerevisiae* and mammals are UAA and UGA, respectively. The preferred stop codon for monocotyledonous plants is UGA, whereas insects and *E. coli* prefer to use UAA as the stop codon (Dalphin et al. (1996) Nucl. Acids Res. 24: 216-218).

Codon usage bias refers to differences among organisms in the frequency of occurrence of codons in protein-coding DNA sequences (genes). A codon is a series of three nucleotides (triplets) that encodes a specific amino acid residue in a polypeptide chain. Because there are four nucleotides in DNA, adenine (A), guanine (G), cytosine (C) and thymine (T), there are 64 possible triplets encoding 20 amino acids, and three translation termination (nonsense) codons. Because of this redundancy, all but two amino acids are encoded by more than one triplet. Different organisms often show particular preferences for one of the several codons that encode the same amino acid. How these preferences arise is a much debated area of molecular evolution.

It is generally acknowledged that codon preferences reflect a balance between mutational biases and natural selection for translational optimization. Optimal codons in fast-growing microorganisms, like *Escherichia coli* or *Saccharomyces cerevisiae* (baker's yeast), reflect the composition of their respective genomic tRNA pool. It is thought that optimal codons help to achieve faster translation rates and high accuracy. As a result of these factors, translational selection is expected to be stronger in highly expressed genes, as is indeed the case for the above-mentioned organisms. In other organisms that do not show high growing rates or that present small genomes, codon usage optimization is normally absent, and codon preferences are determined by the characteristic mutational biases seen in that particular genome. Examples of this are *Homo sapiens* (human) and *Helicobacter pylori*. Organisms that show an intermediate level of codon usage optimization include *Drosophila melanogaster* (fruit fly), *Caenorhabditis elegans* (nematode worm) or *Arabidopsis thaliana* (wall cress).

The term "codon optimized sequences" generally refers to nucleotide sequences that have been optimized for a particular host species by replacing any codons having a usage frequency of less than about 20%. Nucleotide sequences that have been optimized for expression in a given host species by elimination of spurious polyadenylation sequences, elimination of exon/intron splicing signals, elimination of transposon-like repeats and/or optimization of GC content in addition to codon optimization are referred to herein as an "expression enhanced sequences."

TABLE 1

The human codon usage and codon preference. For each codon, the table displays the frequency of usage of each codon (per thousand) in human coding regions (first column) and the relative frequency of each codon among synonymous codons (second column).
The Human Codon Usage Table

| | | | | | | | | | | | | | | | |
|---|---|---|---|---|---|---|---|---|---|---|---|---|---|---|---|
| Gly | GGG | 17.08 | 0.23 | Arg | AGG | 12.09 | 0.22 | Trp | TGG | 14.74 | 1.00 | Arg | CGG | 10.40 | 0.19 |
| Gly | GGA | 19.31 | 0.26 | Arg | AGA | 11.73 | 0.21 | End | TGA | 2.64 | 0.61 | Arg | CGA | 5.63 | 0.10 |
| Gly | GGT | 13.66 | 0.18 | Ser | AGT | 10.18 | 0.14 | Cys | TGT | 9.99 | 0.42 | Arg | CGT | 5.16 | 0.09 |
| Gly | GGC | 24.94 | 0.33 | Ser | AGC | 18.54 | 0.25 | Cys | TGC | 13.86 | 0.58 | Arg | CGC | 10.82 | 0.19 |
| Glu | GAG | 38.82 | 0.59 | Lys | AAG | 33.79 | 0.60 | End | TAG | 0.73 | 0.17 | Gln | CAG | 32.95 | 0.73 |
| Glu | GAA | 27.51 | 0.41 | Lys | AAA | 22.32 | 0.40 | End | TAA | 0.95 | 0.22 | Gln | CAA | 11.94 | 0.27 |
| Asp | GAT | 21.45 | 0.44 | Asn | AAT | 16.43 | 0.44 | Tyr | TAT | 11.80 | 0.42 | His | CAT | 9.56 | 0.41 |
| Asp | GAC | 27.06 | 0.56 | Asn | AAC | 21.30 | 0.56 | Tyr | TAC | 16.48 | 0.58 | His | CAC | 14.00 | 0.59 |
| Val | GTG | 28.60 | 0.48 | Met | ATG | 21.86 | 1.00 | Leu | TTG | 11.43 | 0.12 | Leu | CTG | 39.93 | 0.43 |
| Val | GTA | 6.09 | 0.10 | Ile | ATA | 6.05 | 0.14 | Leu | TTA | 5.55 | 0.06 | Leu | CTA | 6.42 | 0.07 |
| Val | GTT | 10.30 | 0.17 | Ile | ATT | 15.03 | 0.35 | Phe | TTT | 15.36 | 0.43 | Leu | CTT | 11.24 | 0.12 |
| Val | GTC | 15.01 | 0.25 | Ile | ATC | 22.47 | 0.52 | Phe | TTC | 20.72 | 0.57 | Leu | CTC | 19.14 | 0.20 |
| Ala | GCG | 7.27 | 0.10 | Thr | ACG | 6.80 | 0.12 | Ser | TCG | 4.38 | 0.06 | Pro | CCG | 7.02 | 0.11 |
| Ala | GCA | 15.50 | 0.22 | Thr | ACA | 15.04 | 0.27 | Ser | TCA | 10.96 | 0.15 | Pro | CCA | 17.11 | 0.27 |
| Ala | GCT | 20.23 | 0.28 | Thr | ACT | 13.24 | 0.23 | Ser | TCT | 13.51 | 0.18 | Pro | CCT | 18.03 | 0.29 |
| Ala | GCC | 28.43 | 0.40 | Thr | ACC | 21.52 | 0.38 | Ser | TCC | 17.37 | 0.23 | Pro | CCC | 20.51 | 0.33 |

Accordingly, in some embodiments of the disclosure a polynucleotide comprises a molecule codon optimized for translation in a human cell. For example, SEQ ID NO:3 and 5 comprise sequences that have been optimized for producing cytosine deaminase in a human host cell.

The disclosure thus provides a human codon optimized polynucleotide encoding a polypeptide having cytosine deaminase activity. A human codon optimized polynucleotide of the disclosure (e.g., SEQ ID NO:5) may further include additional mutations resulting in conservative amino acid substitution and or improved activity or stability of the encoded polypeptide. For example, mutations at positions 23, 108 and 140 of the polypeptide comprising SEQ ID NO:6 provide increased thermostability. Accordingly, the disclosure provides a human codon optimized polynucleotide encoding a polypeptide having cytosine deaminase activity and increased thermostability. In one embodiment, the human codon optimized polynucleotide comprises a sequence encoding a polypeptide of SEQ ID NO:4, wherein the codons encoding the amino acids of the polypeptide have been optimized for expression in a human cell. In another embodiment, a polynucleotide of the disclosure comprises SEQ ID NO:3 or 5.

In one embodiment, the disclosure provides a polynucleotide comprising a cytosine deaminase polynucleotide or a codon optimized polynucleotide or mutant linked to a heterologous polynucleotide encoding a polypeptide having UPRT or OPRT activity.

A polynucleotide of the disclosure comprising, e.g., a sequence encoding the polypeptide of SEQ ID NO:4, 8, 10, 12, 14, 16, or 18; or having the nucleotide sequence of set forth in any of SEQ ID NOs:3, 5, 7, 9, 11, 13, 15, or 17, or a portion thereof, can be isolated and generated using standard molecular biology techniques and the sequence information provided herein.

A polynucleotide of the disclosure can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to nucleotide sequences can be prepared by standard synthetic techniques, e.g., using an automated DNA synthesizer. In some embodiments, an isolated nucleic acid molecule of the disclosure comprises a nucleic acid molecule which is a complement of a nucleotide sequence encoding a polypeptide set forth in any of SEQ NOs:2, 4, 6, 8, 10, 12, 14, 16, or 18, or having the nucleotide sequence of set forth in any of SEQ ID NOs:1, 3, 5, 7, 9, 11, 13, 15, or 17.

In another embodiment, an isolated polynucleotide of the disclosure comprises a nucleic acid molecule that hybridizes under stringent conditions to a nucleic acid molecule consisting of the nucleotide sequence encoding a polypeptide set forth in any of SEQ NOs:4, 12, 14, 16 or 18, or consisting of the nucleotide sequence set forth in any of SEQ ID NOs:3, 5, 11, 13, 15, or 17. In other embodiments, the nucleic acid is at least 30, 50, 100, 150, 200, 250, 300, 350, 400, 450, 500, 550, or 600 nucleotides in length. Nucleic acid molecules are "hybridizable" to each other when at least one strand of one polynucleotide can anneal to another polynucleotide under defined stringency conditions. Stringency of hybridization is determined, e.g., by (a) the temperature at which hybridization and/or washing is performed, and (b) the ionic strength and polarity (e.g., formamide) of the hybridization and washing solutions, as well as other parameters. Hybridization requires that the two polynucleotides contain substantially complementary sequences; depending on the stringency of hybridization, however, mismatches may be tolerated. Typically, hybridization of two sequences at high stringency (such as, for example, in an aqueous solution of 0.5×SSC at 65° C.) requires that the sequences exhibit some high degree of complementarity over their entire sequence. Conditions of intermediate stringency (such as, for example, an aqueous solution of 2×SSC at 65° C.) and low stringency (such as, for example, an aqueous solution of 2×SSC at 55° C.), require correspondingly less overall complementarity between the hybridizing sequences (1×SSC is 0.15 M NaCl, 0.015 M Na citrate). Nucleic acid molecules that hybridize include those which anneal under suitable stringency conditions and which encode polypeptides or enzymes having the same function, such as the ability to catalyze the conversion of 5-Fluorocytosine (5-FC) to 5-fluorouracil (5-FU), of the disclosure. Further, the term "hybridizes under stringent conditions" is intended to describe conditions for hybridization and washing under which nucleotide sequences at least 30%, 40%, 50%, or 60% homologous to each other typically remain hybridized to each other. Preferably, the conditions are such that sequences at least about 70%, more preferably at least about 80%, even more preferably at least about 85% or 90% homologous to each other typically remain hybridized to each other. In some cases, an isolated nucleic acid molecule of the disclosure hybridizes under stringent conditions to a nucleic acid sequence encoding a polypeptide set forth in any of SEQ ID NOs: 4, 12, 14, 16, or 18, or having the nucleotide sequence set forth in any of SEQ ID NOs: 3, 5, 11, 13, 15, or 17. As used herein, a "naturally-occurring" nucleic acid molecule refers to an RNA or DNA molecule having a nucleotide sequence that occurs in nature (e.g., encodes a natural protein).

The skilled artisan will appreciate that changes can be introduced by mutation into the nucleotide sequences of any polynucleotides encoding a polypeptide set forth in any of SEQ ID NOs: 2, 4, 6, 8, 10, 12, 14, 16, or 18, or having the nucleotide sequence set forth in any of SEQ ID NOs: 1, 3, 5, 7, 9, 11, 13, 15, or 17, thereby leading to changes in the amino acid sequence of the encoded proteins. In some cases the alteration will lead to altered function of the polypeptide. In other cases the change will not alter the functional ability of the encoded polypeptide. In general, substitutions that do not alter the function of a polypeptide include nucleotide substitutions leading to amino acid substitutions at "non-essential" amino acid residues. A "non-essential" amino acid residue is a residue that can be altered from the parent sequence without altering the biological activity of the resulting polypeptide, e.g., catalyzing the conversion of 5-FC to 5-FU.

Also contemplated are those situations where it is desirable to alter the activity of a parent polypeptide such that the polypeptide has new or increased activity on a particular substrate or increased stability or reduced degradation. It is understood that these amino acid substitutions will generally not constitute "conservative" substitutions. Instead, these substitutions constitute non-conservative substitutions introduced in to a sequence in order to obtain a new or improved activity. For example, SEQ ID NO:1 provides the parent nucleic acid sequence for *S. cervisae* cytosine deaminase (SEQ ID NO:2 provides the corresponding polypeptide). SEQ ID NO:3 provides the nucleic acid sequence of a mutant sequence that includes amino acid substitutions that impart increased stability to the polypeptide. Accordingly, the nucleic acid molecule encoding the amino acid sequence of SEQ ID NO:2 provides a "parent" nucleic acid molecule from which mutations can be made to obtain a nucleic acid molecule that encodes a modified polypeptide that includes amino acid substitutions.

It is also understood that a modified polypeptide can constitute a "parent" polypeptide from which additional substitutions can be made. Accordingly, a parent polypeptide, and a nucleic acid molecule that encodes a parent polypeptide, includes modified polypeptides and not just "wild-type" sequences. For example, the polynucleotide of SEQ ID NO:5 is a modified polynucleotide with respect to SEQ ID NO:1 (i.e., the "parent" polynucleotide). Similarly, the polynucleotide of SEQ ID NO:3 is a modified polynucleotide with respect to SEQ ID NO:5. Accordingly, SEQ ID NO:5 is the parent sequence of SEQ ID NO:3.

Mutational methods of generating diversity include, for example, site-directed mutagenesis (Ling et al. (1997) "Approaches to DNA mutagenesis: an overview" Anal Biochem. 254(2): 157-178; Dale et al. (1996) "Oligonucleotide-directed random mutagenesis using the phosphorothioate method" Methods Mol. Biol. 57:369-374; Smith (1985) "In vitro mutagenesis" Ann. Rev. Genet. 19:423-462; Botstein & Shortle (1985) "Strategies and applications of in vitro mutagenesis" Science 229:1193-1201; Carter (1986) "Site-directed mutagenesis" Biochem. J. 237:1-7; and Kunkel (1987) "The efficiency of oligonucleotide directed mutagenesis" in Nucleic Acids & Molecular Biology (Eckstein, F. and Lilley, D. M. J. eds., Springer Verlag, Berlin)); mutagenesis using uracil containing templates (Kunkel (1985) "Rapid and efficient site-specific mutagenesis without phenotypic selection" Proc. Natl. Acad. Sci. USA 82:488-492; Kunkel et al. (1987) "Rapid and efficient site-specific mutagenesis without phenotypic selection" Methods in Enzymol. 154, 367-382; and Bass et al. (1988) "Mutant Trp repressors with new DNA-binding specificities" Science 242:240-245); oligonucleotide-directed mutagenesis (Methods in Enzymol. 100: 468-500 (1983); Methods in Enzymol. 154: 329-350 (1987); Zoller & Smith (1982) "Oligonucleotide-directed mutagenesis using M13-derived vectors: an efficient and general procedure for the production of point mutations in any DNA fragment" Nucleic Acids Res. 10:6487-6500; Zoller & Smith (1983) "Oligonucleotide-directed mutagenesis of DNA fragments cloned into M13 vectors" Methods in Enzymol. 100:468-500; and Zoller & Smith (1987) "Oligonucleotide-directed mutagenesis: a simple method using two oligonucleotide primers and a single-stranded DNA template" Methods in Enzymol. 154:329-350); phosphorothioate-modified DNA mutagenesis (Taylor et al. (1985) "The use of phosphorothioate-modified DNA in restriction enzyme reactions to prepare nicked DNA" Nucl. Acids Res. 13: 8749-8764; Taylor et al. (1985) "The rapid generation of oligonucleotide-directed mutations at high frequency using phosphorothioate-modified DNA" Nucl. Acids Res. 13: 8765-8787; Nakamaye & Eckstein (1986) "Inhibition of restriction endonuclease Nci I cleavage by phosphorothioate groups and its application to oligonucleotide-directed mutagenesis" Nucl. Acids Res. 14: 9679-9698; Sayers et al. (1988) "Y-T Exonucleases in phosphorothioate-based oligonucleotide-directed mutagenesis" Nucl. Acids Res. 16:791-802; and Sayers et al. (1988) "Strand specific cleavage of phosphorothioate-containing DNA by reaction with restriction endonucleases in the presence of ethidium bromide" Nucl. Acids Res. 16: 803-814); mutagenesis using gapped duplex DNA (Kramer et al. (1984) "The gapped duplex DNA approach to oligonucleotide-directed mutation construction" Nucl. Acids Res. 12: 9441-9456; Kramer & Fritz (1987) Methods in Enzymol. "Oligonucleotide-directed construction of mutations via gapped duplex DNA" 154: 350-367; Kramer et al. (1988) "Improved enzymatic in vitro reactions in the gapped duplex DNA approach to oligonucleotide-directed construction of mutations" Nucl. Acids Res. 16: 7207; and Fritz et al. (1988) "Oligonucleotide-directed construction of mutations: a gapped duplex DNA procedure without enzymatic reactions in vitro" Nucl. Acids Res. 16: 6987-6999).

Additional suitable methods include point mismatch repair (Kramer et al. (1984) "Point Mismatch Repair" Cell 38:879-887), mutagenesis using repair-deficient host strains (Carter et al. (1985) "Improved oligonucleotide site-directed mutagenesis using M13 vectors" Nucl. Acids Res. 13: 4431-4443; and Carter (1987) "Improved oligonucleotide-directed mutagenesis using M13 vectors" Methods in Enzymol. 154: 382-403), deletion mutagenesis (Eghtedarzadeh & Henikoff (1986) "Use of oligonucleotides to generate large deletions" Nucl. Acids Res. 14: 5115), restriction-selection and restriction-purification (Wells et al. (1986) "Importance of hydrogen-bond formation in stabilizing the transition state of subtilisin" Phil. Trans. R. Soc. Lond. A 317: 415-423), mutagenesis by total gene synthesis (Nambiar et al. (1984) "Total synthesis and cloning of a gene coding for the ribonuclease S protein" Science 223: 1299-1301; Sakamar and Khorana (1988) "Total synthesis and expression of a gene for the a-subunit of bovine rod outer segment guanine nucleotide-binding protein (transducin)" Nucl. Acids Res. 14: 6361-6372; Wells et al. (1985) "Cassette mutagenesis: an efficient method for generation of multiple mutations at defined sites" Gene 34:315-323; and Grundstrom et al. (1985) "Oligonucleotide-directed mutagenesis by microscale 'shot-gun' gene synthesis" Nucl. Acids Res. 13: 3305-3316); double-strand break repair (Mandecki (1986); Arnold (1993) "Protein engineering for unusual environments" Current Opinion in Biotechnology 4:450-455; and "Oligonucleotide-directed double-strand break repair in plasmids of *Escherichia coli*: a method for site-specific mutagenesis" Proc. Natl. Acad. Sci. USA, 83:7177-7181). Additional details on many of the above methods can be found in Methods in Enzymology Volume 154, which also describes useful controls for trouble-shooting problems with various mutagenesis methods.

Additional details regarding various diversity generating methods can be found in the following U.S. patents, PCT publications, and EPO publications: U.S. Pat. No. 5,605,793 to Stemmer (Feb. 25, 1997), "Methods for In vitro Recombination;" U.S. Pat. No. 5,811,238 to Stemmer et al. (Sep. 22, 1998) "Methods for Generating Polynucleotides having Desired Characteristics by Iterative Selection and Recombination;" U.S. Pat. No. 5,830,721 to Stemmer et al. (Nov. 3, 1998), "DNA Mutagenesis by Random Fragmentation and Reassembly;" U.S. Pat. No. 5,834,252 to Stemmer, et al. (Nov. 10, 1998) "End-Complementary Polymerase Reaction;" U.S. Pat. No. 5,837,458 to Minshull, et al. (Nov. 17, 1998), "Methods and Compositions for Cellular and Metabolic Engineering;" WO 95/22625, Stemmer and Crameri, "Mutagenesis by Random Fragmentation and Reassembly;" WO 96/33207 by Stemmer and Lipschutz "End Complementary Polymerase Chain Reaction;" WO 97/20078 by Stemmer and Crameri "Methods for Generating Polynucleotides having Desired Characteristics by Iterative Selection and Recombination;" WO 97/35966 by Minshull and Stemmer, "Methods and Compositions for Cellular and Metabolic Engineering;" WO 99/41402 by Punnonen et al. "Targeting of Genetic Vaccine Vectors;" WO 99/41383 by Punnonen et al. "Antigen Library Immunization;" WO 99/41369 by Punnonen et al. "Genetic Vaccine Vector Engineering;" WO 99/41368 by Punnonen et al. "Optimization of Immunomodulatory Properties of Genetic Vaccines;" EP 752008 by Stemmer and Crameri, "DNA Mutagenesis by Random Fragmentation and Reassembly;" EP 0932670 by Stemmer "Evolving Cellular DNA Uptake by Recursive Sequence Recombination;" WO 99/23107 by Stemmer et al., "Modification of Virus Tropism and Host Range by Viral Genome Shuffling;" WO 99/21979 by Apt et al., "Human Papillomavirus Vectors;" WO 98/31837 by del Cardayre et al. "Evolution of Whole Cells and Organisms by Recursive Sequence Recombination;" WO 98/27230 by Patten and Stemmer, "Methods and Compositions for Polypeptide Engineering;" WO 98/13487 by Stemmer et al., "Methods for Optimization of Gene Therapy by Recursive Sequence Shuffling and Selection;" WO 00/00632, "Methods for Generating Highly Diverse Libraries;" WO 00/09679, "Methods for Obtaining in vitro Recombined Polynucleotide Sequence Banks and Resulting Sequences;" WO 98/42832 by Arnold et al., "Recombination of Polynucleotide Sequences Using Random or Defined Primers;" WO 99/29902 by Arnold et al., "Method for Creating Polynucleotide and Polypeptide Sequences;" WO 98/41653 by Vind, "An in vitro Method for Construction of a DNA Library;" WO 98/41622 by Borchert et al., "Method for Constructing a Library Using DNA Shuffling;" WO 98/42727 by Pati and Zarling, "Sequence Alterations using Homologous Recombination;" WO 00/18906 by Patten et al., "Shuffling of Codon-Altered Genes;" WO 00/04190 by del Cardayre et al. "Evolution of Whole Cells and Organisms by Recursive Recombination;" WO 00/42561 by Crameri et al., "Oligonucleotide Mediated Nucleic Acid Recombination;" WO 00/42559 by Selifonov and Stemmer "Methods of Populating Data Structures for Use in Evolutionary Simulations;" WO 00/42560 by Selifonov et al., "Methods for Making Character Strings, Polynucleotides & Polypeptides Having Desired Characteristics;" WO 01/23401 by Welch et al., "Use of Codon-Varied Oligonucleotide Synthesis for Synthetic Shuffling;" and WO 01/64864 "Single-Stranded Nucleic Acid Template-Mediated Recombination and Nucleic Acid Fragment Isolation" by Affholter.

Also provided are recombinant constructs comprising one or more of the nucleic acid sequences as broadly described above. The constructs comprise a vector, such as, a plasmid, a cosmid, a phage, a virus, a bacterial artificial chromosome (BAC), a yeast artificial chromosome (YAC), a viral vector or the like, into which a polynucleotide of the disclosure has been inserted, in a forward or reverse orientation. Large numbers of suitable vectors and promoters are known to those of skill in the art, and are commercially available. In one embodiment, the viral vector is a retroviral vector.

The terms "vector", "vector construct" and "expression vector" mean the vehicle by which a DNA or RNA sequence (e.g. a foreign gene) can be introduced into a host cell, so as to transform the host and promote expression (e.g. transcription and translation) of the introduced sequence. Vectors typically comprise the DNA of a transmissible agent, into which foreign DNA encoding a protein is inserted by restriction enzyme technology. A common type of vector is a "plasmid", which generally is a self-contained molecule of double-stranded DNA that can readily accept additional (foreign) DNA and which can readily introduced into a suitable host cell. A large number of vectors, including plasmid and fungal vectors, have been described for replication and/or expression in a variety of eukaryotic and prokaryotic hosts. Non-limiting examples include pKK plasmids (Clonetech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. Recombinant cloning vectors will often include one or more replication systems for cloning or expression, one or more markers for selection in the host, e.g., antibiotic resistance, and one or more expression cassettes.

The terms "express" and "expression" mean allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. A polynucleotide or polypeptide is expressed recombinantly, for example, when it is expressed or produced in a foreign host cell under the control of a foreign or native promoter, or in a native host cell under the control of a foreign promoter.

Polynucleotides provided herein can be incorporated into any one of a variety of expression vectors suitable for expressing a polypeptide. Suitable vectors include chromosomal, non-chromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated viruses, retroviruses and many others. Any vector that transduces genetic material into a cell, and, if replication is desired, which is replicable and viable in the relevant host can be used. These nucleic acid vectors can be delivered using a non-viral delivery system such as described in P. Midoux et al. Brit J Pharm 157: 166-178 2009 or Kamimura & Liu J AAPS 10:589-595 (2008) or a viral system as described below.

In another aspect, the polynucleotide encoding a cytosine deaminase or mutant thereof is delivered with a gene delivery system that is a viral or viral derived vector. The viral vector can be replicating or non-replicating, and can be an adenoviral vector, a measles vector, a herpes vector, a retroviral vector (including a lentiviral vector), a rhabdoviral vector such as a Vesicular Stomatitis viral vector, a reovirus vector, a Seneca Valley Virus vector, a poxvirus vector (including animal pox or vaccinia derived vectors), a parvovirus vector (including an AAV vector), an alphavirus vector or other viral vector known to one skilled in the art (see also, e.g., Concepts in Genetic Medicine, ed. Boro Dropulic and Barrie Carter, Wiley, 2008, Hoboken, N.J.; *The Development of Human Gene Therapy*, ed. Theodore Friedmann, Cold Springs Harbor Laboratory Press, Cold springs Harbor, N.Y., 1999; *Gene and Cell Therapy*, ed. Nancy Smyth Templeton, Marcel Dekker Inc., New York, N.Y., 2000 and *Gene Therapy: Therapeutic Mechanism and Strategies*, ed. Nancy Smyth Templetone and Danilo D Lasic, Marcel Dekker, Inc., New York, N.Y., 2000; the disclosures of which are incorporated herein by reference).

In one embodiment, the viral vector can be a replication competent retroviral vector capable of infecting only replicating mammalian cells. Retroviruses have been classified in various ways but the nomenclature has been standardized in the last decade (see ICTVdB—The Universal Virus Database, v 4 on the World Wide Web (www) at ncbi.nlm.nih.gov/ICTVdb/ICTVdB/and the text book "Retroviruses" Eds Coffin, Hughs and Varmus, Cold Spring Harbor Press 1997; the disclosure of which are incorporated herein by reference). The replication competent retroviral vector can comprise an Orthoretrovirus or more typically a gamma retrovirus vector. In one aspect, a replication competent retroviral vector comprises an internal ribosomal entry site (IRES) 5' to the polynucleotide encoding a cytosine deaminase. In one embodiment, the polynucleotide encoding a cytosine deaminase is 3' to an ENV polynucleotide of a retroviral vector. In one embodiment the viral vector is a retroviral vector capable of infecting target cells multiple times (5 or more per diploid cell).

Accordingly, in other embodiments, vectors that include a polynucleotide of the disclosure are provided. In other embodiments, host cells transfected with a nucleic acid molecule of the disclosure, or a vector that includes a polynucleotide of the disclosure, are provided. Host cells include eucaryotic cells such as yeast cells, insect cells, or animal cells. Host cells also include prokaryotic cells such as bacterial cells.

As previously discussed, general texts which describe molecular biological techniques useful herein, including the use of vectors, promoters and many other relevant topics, include Berger and Kimmel, Guide to Molecular Cloning Techniques, Methods in Enzymology Volume 152, (Academic Press, Inc., San Diego, Calif.) ("Berger"); Sambrook et al., Molecular Cloning—A Laboratory Manual, 2d ed., Vol. 1-3, Cold Spring Harbor Laboratory, Cold Spring Harbor, N.Y., 1989 ("Sambrook") and Current Protocols in Molecular Biology, F. M. Ausubel et al., eds., Current Protocols, a joint venture between Greene Publishing Associates, Inc. and John Wiley & Sons, Inc., (supplemented through 1999) ("Ausubel"). Examples of protocols sufficient to direct persons of skill through in vitro amplification methods, including the polymerase chain reaction (PCR), the ligase chain reaction (LCR), QP-replicase amplification and other RNA polymerase mediated techniques (e.g., NASBA), e.g., for the production of the homologous nucleic acids of the disclosure are found in Berger, Sambrook, and Ausubel, as well as in Mullis et al. (1987) U.S. Pat. No. 4,683,202; Innis et al., eds. (1990) PCR Protocols: A Guide to Methods and Applications (Academic Press Inc. San Diego, Calif.) ("Innis"); Arnheim & Levinson (Oct. 1, 1990) C&EN 36-47; The Journal Of NIH Research (1991) 3: 81-94; Kwoh et al. (1989) Proc. Natl. Acad. Sci. USA 86: 1173; Guatelli et al. (1990) Proc. Nat'l. Acad. Sci. USA 87: 1874; Lomell et al. (1989) J. Clin. Chem. 35: 1826; Landegren et al. (1988) Science 241: 1077-1080; Van Brunt (1990) Biotechnology 8: 291-294; Wu and Wallace (1989) Gene 4:560; Barringer et al. (1990) Gene 89:117; and Sooknanan and Malek (1995) Biotechnology 13: 563-564. Improved methods for cloning in vitro amplified nucleic acids are described in Wallace et al., U.S. Pat. No. 5,426,039. Improved methods for amplifying large nucleic acids by PCR are summarized in Cheng et al. (1994) Nature 369: 684-685 and the references cited therein, in which PCR amplicons of up to 40 kb are generated. One of skill will appreciate that essentially any RNA can be converted into a double stranded DNA suitable for restriction digestion, PCR expansion and sequencing using reverse transcriptase and a polymerase. See, e.g., Ausubel, Sambrook and Berger, all supra.

Also provided are engineered host cells that are transduced (transformed or transfected) with a vector provided herein (e.g., a cloning vector or an expression vector), as well as the production of polypeptides of the disclosure by recombinant techniques. The vector may be, for example, a plasmid, a viral particle, a phage, etc. The engineered host cells can be cultured in conventional nutrient media modified as appropriate for activating promoters, selecting transformants, or amplifying a coding polynucleotide. Culture conditions, such as temperature, pH and the like, are those previously used with the host cell selected for expression, and will be apparent to those skilled in the art and in the references cited herein, including, e.g., Sambrook, Ausubel and Berger, as well as e.g., Freshney (1994) Culture of Animal Cells: A Manual of Basic Technique, 3rd ed. (Wiley-Liss, New York) and the references cited therein.

Vectors can be employed to transform an appropriate host to permit the host to express a protein or polypeptide. Examples of appropriate expression hosts include: bacterial cells, such as *E. coli, B. subtilis, Streptomyces*, and *Salmonella typhimurium*; fungal cells, such as *Saccharomyces cerevisiae, Pichia pastoris*, and *Neurospora crassa*; insect cells such as *Drosophila* and *Spodoptera frugiperda*; mammalian cells such as CHO, COS, BHK, HEK 293 or Bowes melanoma; or plant cells or explants, etc.

In bacterial systems, a number of expression vectors may be selected depending upon the use intended cytosine deaminase polypeptide. For example, when large quantities of CD polypeptide or fragments thereof are needed for commercial production or for induction of antibodies, vectors which direct high level expression of fusion proteins that are readily purified can be desirable. Such vectors include, but are not limited to, multifunctional *E. coli* cloning and expression vectors such as BLUESCRIPT (Stratagene), in which the CD polypeptide coding sequence may be ligated into the vector in-frame with sequences for the amino-terminal Met and the subsequent 7 residues of beta-galactosidase so that a hybrid protein is produced; pIN vectors (Van Heeke & Schuster (1989) J. Biol. Chem. 264: 5503-5509); pET vectors (Novagen, Madison Wis.); and the like.

Similarly, in the yeast *Saccharomyces cerevisiae* a number of vectors containing constitutive or inducible promoters such as alpha factor, alcohol oxidase and PGH may be used for production of the CD polypeptides of the disclosure. For reviews, see Ausubel (supra) and Grant et al. (1987) Methods in Enzymology 153:516-544.

The disclosure also provides replication competent retroviral vectors having increased stability relative to prior retroviral vectors. Such increased stability during infection and replication is important for the treatment of cell proliferative disorders. The combination of transduction efficiency, transgene stability and target selectivity is provided by the replication competent retrovirus. The compositions and methods provide insert stability and maintain transcription activity of the transgene and the translational viability of the encoded polypeptide.

Retroviruses can be transmitted horizontally and vertically. Efficient infectious transmission of retroviruses requires the expression on the target cell of receptors which specifically recognize the viral envelope proteins, although viruses may use receptor-independent, nonspecific routes of entry at low efficiency. Normally a viral infection leads to a single or few copies of viral genome per cell because of receptor masking or down-regulation, that in turn leads to resistance to superinfection (Ch3 p 104 in "Retroviruses" J M Coffin, S H Hughes, & H E Varmus 1997 Cold Spring Harbor Laboratory Press, Cold Spring Harbor N.Y.; Fan et al. J. Virol 28:802, 1978). By manipulating the situation in tissue culture it is possible to get some level of multiple infection but this is less than 5 copies/diploid genome. In addition, the target cell type must be able to support all stages of the replication cycle after virus has bound and penetrated. Vertical transmission occurs when the viral genome becomes integrated in the germ line of the host. The provirus will then be passed from generation to generation as though it were a cellular gene. Hence endogenous proviruses become established which frequently lie latent, but which can become activated when the host is exposed to appropriate agents.

In many situations for using a recombinant replication competent retrovirus therapeutically, it is advantageous to have high levels of expression of the transgene that is encoded by the recombinant replication competent retrovirus. For example, with a prodrug activating gene such as the cytosine deaminase gene it is advantageous to have higher levels of expression of the CD protein in a cell so that the conversion of the prodrug 5-FC to 5-FU is more efficient. Similarly high levels of expression of siRNA or shRNA lead to more efficient suppression of target gene expression. Also for cytokines or single chain antibodies (scAbs) it is usually advantageous to express high levels of the cytokine or scAb. In addition, in the case that there are mutations in some copies of the vector that inactivate or impair the activity of the vector or transgene, it is advantageous to have multiple copies of the vector in the target cell as this provides a high probability of efficient expression of the intact transgene. The disclosure provides recombinant replication competent retroviruses capable of infecting a target cell or target cell population multiple times resulting in an average number of copies/diploid genome of 5 or greater. The disclosure also provides methods of testing for this property. Also provided are methods of treating a cell proliferative disorder, using a recombinant replication competent retrovirus capable of infecting a target cell or target cell population multiple times resulting in an average number of copies/diploid genome of 5 or greater.

As mentioned above, the integrated DNA intermediate is referred to as a provirus. Prior gene therapy or gene delivery systems use methods and retroviruses that require transcription of the provirus and assembly into infectious virus while in the presence of an appropriate helper virus or in a cell line containing appropriate sequences enabling encapsidation without coincident production of a contaminating helper virus. As described below, a helper virus is not required for the production of the recombinant retrovirus of the disclosure, since the sequences for encapsidation are provided in the genome thus providing a replication competent retroviral vector for gene delivery or therapy.

A retroviral genome useful in the methods and compositions of the disclosure comprises a proviral DNA having at least three genes: the gag, the pol, and the env, these genes may be flanked by one or two long terminal (LTR) repeat, or in the provirus are flanked by two long terminal repeat (LTR) and sequences containing cis-acting sequences such as psi. The gag gene encodes the internal structural (matrix, capsid, and nucleocapsid) proteins; the pol gene encodes the RNA-directed DNA polymerase (reverse transcriptase), protease and integrase; and the env gene encodes viral envelope glycoproteins. The 5' and/or 3' LTRs serve to promote transcription and polyadenylation of the virion RNAs. The LTR contains all other cis-acting sequences necessary for viral replication. Lentiviruses have additional genes including vif, vpr, tat, rev, vpu, nef, and vpx (in HIV-1, HIV-2 and/or SIV).

Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virion) are missing from the viral genome, the result is a cis defect which prevents encapsidation of genomic viral RNA. This type of modified vector is what has typically been used in prior gene delivery systems (i.e., systems lacking elements which are required for encapsidation of the virion).

In one embodiment, the disclosure provides a recombinant retrovirus capable of infecting a non-dividing cell, a dividing cell, or a cell having a cell proliferative disorder. The recombinant replication competent retrovirus of the disclosure comprises a polynucleotide sequence encoding a viral GAG, a viral POL, a viral ENV, a heterologous polynucleotide preceded by an internal ribosome entry site (IRES) encapsulated within a virion.

The heterologous nucleic acid sequence is operably linked to an IRES. As used herein, the term "heterologous" nucleic acid sequence or transgene refers to (i) a sequence that does not normally exist in a wild-type retrovirus, (ii) a sequence that originates from a foreign species, or (iii) if from the same species, it may be substantially modified from its original form. Alternatively, an unchanged nucleic acid sequence that is not normally expressed in a cell is a heterologous nucleic acid sequence. In a specific embodiment, the heterologous polynucleotide is a polypeptide of the disclosure having cytosine deaminase activity.

The phrase "non-dividing" cell refers to a cell that does not go through mitosis. Non-dividing cells may be blocked at any point in the cell cycle, (e.g., $G_0/G_1$, $G_{1/S}$, $G_{2/M}$), as long as the cell is not actively dividing. For ex vivo infection, a dividing cell can be treated to block cell division by standard techniques used by those of skill in the art, including, irradiation, aphidocolin treatment, serum starvation, and contact inhibition. However, it should be understood that ex vivo infection is often performed without blocking the cells since many cells are already arrested (e.g., stem cells). For example, a recombinant lentivirus vector is capable of infecting non-dividing cell. Examples of pre-existing non-dividing cells in the body include neuronal, muscle, liver, skin, heart, lung, and bone marrow cells, and their derivatives. For dividing cells onco-retroviral vectors can be used.

By "dividing" cell is meant a cell that undergoes active mitosis, or meiosis. Such dividing cells include stem cells, skin cells (e.g., fibroblasts and keratinocytes), gametes, and other dividing cells known in the art. Of particular interest and encompassed by the term dividing cell are cells having cell proliferative disorders, such as neoplastic cells. The term "cell proliferative disorder" refers to a condition characterized by an abnormal number of cells. The condition can include both hypertrophic (the continual multiplication of cells resulting in an overgrowth of a cell population within a tissue) and hypotrophic (a lack or deficiency of cells within a tissue) cell growth or an excessive influx or migration of cells into an area of a body. The cell populations are not necessarily transformed, tumorigenic or malignant cells, but can include normal cells as well. Cell proliferative disorders include disorders associated with an overgrowth of connective tissues, such as various fibrotic conditions, including scleroderma, arthritis and liver cirrhosis. Cell proliferative disorders include neoplastic disorders such as head and neck carcinomas. Head and neck carcinomas would include, for example, carcinoma of the mouth, esophagus, throat, larynx, thyroid gland, tongue, lips, salivary glands, nose, paranasal sinuses, nasopharynx, superior nasal vault and sinus tumors, esthesioneuroblastoma, squamous cell cancer, malignant melanoma, sinonasal undifferentiated carcinoma (SNUC), brain (including glioblastomas) or blood neoplasia. Also included are carcinoma's of the regional lymph nodes including cervical lymph nodes, prelaryngeal lymph nodes, pulmonary juxtaesophageal lymph nodes and submandibular lymph nodes (Harrison's Principles of Internal Medicine (eds., Isselbacher, et al., McGraw-Hill, Inc., 13th Edition, pp 1850-1853, 1994). Other cancer types, include, but are not limited to, lung cancer, colon-rectum cancer, breast cancer, prostate cancer, urinary tract cancer, uterine cancer lymphoma, oral cancer, pancreatic cancer, leukemia, melanoma, stomach cancer, skin cancer and ovarian cancer.

In one embodiment, the heterologous polynucleotide within the vector comprises a cytosine deaminase that has been optimized for expression in a human cell. In a further embodiment, the cytosine deaminase comprises a sequence that has been human codon optimized and comprises mutations that increase the cytosine deaminase's stability (e.g., reduced degradation or increased thermo-stability) compared to a wild-type cytosine deaminase. In yet another embodiment, the heterologous polynucleotide encodes a fusion construct comprising a cytosine deaminase (either human codon optimized or non-optimized, either mutated or non-mutated) operably linked to a polynucleotide encoding a polypeptide having UPRT or OPRT activity. In another embodiment, the heterologous polynucleotide comprises a CD polynucleotide or fusion construct of the disclosure (e.g., SEQ ID NO:3, 5, 11, 13, 15, or 17).

In another embodiment, replication competent retroviral vector can comprise a heterologous polynucleotide encoding a polypeptide comprising a cytosine deaminase (as described herein) and may further comprise a polynucleotide comprising a miRNA or siRNA molecule linked to a cell-type or tissue specific promoter.

The term "regulatory nucleic acid sequence" refers collectively to promoter sequences, polyadenylation signals, transcription termination sequences, upstream regulatory domains, origins of replication, enhancers and the like, which collectively provide for the replication, transcription and translation of a coding sequence in a recipient cell. Not all of these control sequences need always be present so long as the selected coding sequence is capable of being replicated, transcribed and translated in an appropriate host cell. One skilled in the art can readily identify regulatory nucleic acid sequence from public databases and materials. Furthermore, one skilled in the art can identify a regulatory sequence that is applicable for the intended use, for example, in vivo, ex vivo, or in vitro.

The term "promoter region" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence. The regulatory sequence may be homologous or heterologous to the desired gene sequence. For example, a wide range of promoters may be utilized, including viral or mammalian promoter as described above.

An internal ribosome entry sites ("IRES") refers to a segment of nucleic acid that promotes the entry or retention of a ribosome during translation of a coding sequence usually 3' to the IRES. In some embodiments the IRES may comprise a splice acceptor/donor site, however, preferred IRESs lack a splice acceptor/donor site. Normally, the entry of ribosomes into messenger RNA takes place via the cap located at the 5' end of all eukaryotic mRNAs. However, there are exceptions to this universal rule. The absence of a cap in some viral mRNAs suggests the existence of alternative structures permitting the entry of ribosomes at an internal site of these RNAs. To date, a number of these structures, designated IRES on account of their function, have been identified in the 5' noncoding region of uncapped viral mRNAs, such as that, in particular, of picornaviruses such as the poliomyelitis virus (Pelletier et al., 1988, Mol. Cell. Biol., 8, 1103-1112) and the EMCV virus (encephalomyocarditis virus (Jang et al., J. Virol., 1988, 62, 2636-2643). The disclosure provides the use of an IRES in the context of a replication-competent retroviral vector.

The heterologous nucleic acid sequence is typically under control of either the viral LTR promoter-enhancer signals or an internal promoter, and retained signals within the retroviral LTR can still bring about efficient integration of the vector into the host cell genome. Accordingly, the recombinant retroviral vectors of the disclosure, the desired sequences, genes and/or gene fragments can be inserted at several sites and under different regulatory sequences. For example, a site for insertion can be the viral enhancer/promoter proximal site (i.e., 5' LTR-driven gene locus). Alternatively, the desired sequences can be inserted into a distal site (e.g., the IRES sequence 3' to the env gene) or where two or more heterologous sequences are present one heterologous sequence may be under the control of a first regulatory region and a second heterologous sequence under the control of a second regulatory region. Other distal sites include viral promoter sequences, where the expression of the desired sequence or sequences is through splicing of the promoter proximal cistron, an internal heterologous promoter as SV40 or CMV, or an internal ribosome entry site (IRES) can be used.

In one embodiment, the retroviral genome of the disclosure contains an IRES comprising a cloning site for insertion of a desired polynucleotide sequence. In one embodiment, the IRES is located 3' to the env gene in the retroviral vector, but 5' to the desired heterologous nucleic acid. Accordingly, a heterologous polynucleotide sequence encoding a desired polypeptide may be operably linked to the IRES.

In another embodiment a targeting polynucleotide sequence is included as part of the recombinant retroviral vector of the disclosure. The targeting polynucleotide sequence is a targeting ligand (e.g., peptide hormones such as heregulin, a single-chain antibodies, a receptor or a ligand for a receptor), a tissue-specific or cell-type specific regulatory element (e.g., a tissue-specific or cell-type specific promoter or enhancer), or a combination of a targeting ligand and a tissue-specific/cell-type specific regulatory element. Preferably, the targeting ligand is operably linked to the env protein of the retrovirus, creating a chimeric retroviral env protein. The viral GAG, viral POL and viral ENV proteins can be derived from any suitable retrovirus (e.g., MLV or lentivirus-derived). In another embodiment, the viral ENV protein is non-retrovirus-derived (e.g., CMV or VSV).

The recombinant retrovirus of the disclosure is therefore genetically modified in such a way that the virus is targeted to a particular cell type (e.g., smooth muscle cells, hepatic cells, renal cells, fibroblasts, keratinocytes, mesenchymal stem cells, bone marrow cells, chondrocyte, epithelial cells, intestinal cells, neoplastic cells, glioma cells, neuronal cells and others known in the art) such that the nucleic acid genome is delivered to a target non-dividing, a target dividing cell, or a target cell having a cell proliferative disorder. Targeting can be achieved in two ways. The first way directs the retrovirus to a target cell by binding to cells having a molecule on the external surface of the cell. This method of targeting the retrovirus utilizes expression of a targeting ligand on the coat of the retrovirus to assist in targeting the virus to cells or tissues that have a receptor or binding molecule which interacts with the targeting ligand on the surface of the retrovirus. After infection of a cell by the virus, the virus injects its nucleic acid into the cell and the retrovirus genetic material can integrate into the host cell genome. The second method for targeting uses cell- or tissue-specific regulatory elements to promote expression and transcription of the viral genome in a targeted cell which actively utilizes the regulatory elements, as described more fully below. The transferred retrovirus genetic material is then transcribed and translated into proteins within the host cell. The targeting regulatory element is typically linked to the 5' and/or 3' LTR, creating a chimeric LTR.

By inserting a heterologous nucleic acid sequence of interest into the viral vector of the disclosure, along with another gene which encodes, for example, the ligand for a receptor on a specific target cell, the vector is now target specific. Viral vectors can be made target specific by attaching, for example, a sugar, a glycolipid, or a protein. Targeting can be accomplished by using an antibody to target the viral vector. Those of skill in the art will know of, or can readily ascertain, specific polynucleotide sequences which can be inserted into the viral genome or proteins which can be attached to a viral envelope to allow target specific delivery of the viral vector containing the nucleic acid sequence of interest.

Thus, the disclosure includes in one embodiment, a chimeric env protein comprising a retroviral env protein operably linked to a targeting polypeptide. The targeting polypeptide can be a cell specific receptor molecule, a ligand for a cell specific receptor, an antibody or antibody fragment to a cell specific antigenic epitope or any other ligand easily identified in the art which is capable of binding or interacting with a target cell. Examples of targeting polypeptides or molecules include bivalent antibodies using biotin-streptavidin as linkers (Etienne-Julan et al., J. Of General Virol., 73, 3251-3255 (1992); Roux et al., Proc. Natl. Acad. Sci. USA 86, 9079-9083 (1989)), recombinant virus containing in its envelope a sequence encoding a single-chain antibody variable region against a hapten (Russell et al., Nucleic Acids Research, 21, 108I-1085 (1993)), cloning of peptide hormone ligands into the retrovirus envelope (Kasahara et al., Science, 266, 1373-1376 (1994)), chimeric EPO/env constructs (Kasahara et al., 1994), single-chain antibody against the low density lipoprotein (LDL) receptor in the ecotropic MLV envelope, resulting in specific infection of HeLa cells expressing LDL receptor (Somia et al., Proc. Natl. Acad. Sci. USA, 92, 7570-7574 (1995)), similarly the host range of ALV can be altered by incorporation of an integrin ligand, enabling the virus to now cross species to specifically infect rat glioblastoma cells (Valsesia-Wittmann et al., J. Virol. 68, 4609-4619 (1994)), and Dornberg and co-workers (Chu and Dornburg, J. Virol 69, 2659-2663 (1995)) have reported tissue-specific targeting of spleen necrosis virus (SNV), an avian retrovirus, using envelopes containing single-chain antibodies directed against tumor markers.

The disclosure provides a method of producing a recombinant retrovirus capable of infecting a target cell comprising transfecting a suitable host cell with the following: a vector comprising a polynucleotide sequence encoding a viral gag, a viral pol and a viral env, wherein the vector contains a cloning site for introduction of a heterologous gene, operably linked to a regulatory nucleic acid sequence, and recovering the recombinant virus.

The retrovirus and methods of the disclosure provide a replication competent retrovirus that does not require helper virus or additional nucleic acid sequence or proteins in order to propagate and produce virion. For example, the nucleic acid sequences of the retrovirus of the disclosure encode, for example, a group specific antigen and reverse transcriptase, (and integrase and protease-enzymes necessary for maturation and reverse transcription), respectively, as discussed above. The viral gag and pol can be derived from a lentivirus, such as HIV or an oncovirus such as MoMLV. In addition, the nucleic acid genome of the retrovirus of the disclosure includes a sequence encoding a viral envelope (ENV) protein. The env gene can be derived from any retroviruses. The env may be an amphotropic envelope protein which allows transduction of cells of human and other species, or may be an ecotropic envelope protein, which is able to transduce only mouse and rat cells. Further, it may be desirable to target the recombinant virus by linkage of the envelope protein with an antibody or a particular ligand for targeting to a receptor of a particular cell-type. As mentioned above, retroviral vectors can be made target specific by inserting, for example, a glycolipid, or a protein. Targeting is often accomplished by using an antibody to target the retroviral vector to an antigen on a particular cell-type (e.g., a cell type found in a certain tissue, or a cancer cell type). Those of skill in the art will know of, or can readily ascertain without undue experimentation, specific methods to achieve delivery of a retroviral vector to a specific target. In one embodiment, the env gene is derived from a non-retrovirus (e.g., CMV or VSV). Examples of retroviral-derived env genes include, but are not limited to: Moloney murine leukemia virus (MoMuLV), Harvey murine sarcoma virus (HaMuSV), murine mammary tumor virus (MuMTV), gibbon ape leukemia virus (GaLV), human immunodeficiency virus (HIV) and Rous Sarcoma Virus (RSV). Other env genes such as Vesicular stomatitis virus (VSV) (Protein G), cytomegalovirus envelope (CMV), or influenza virus hemagglutinin (HA) can also be used.

In one embodiment, the retroviral genome is derived from an onco-retrovirus or gammaretrovirus, and more particularly a mammalian onco-retrovirus or gamma retrovirus. By "derived" is meant that the parent polynucleotide sequence is an wild-type oncovirus which has been modified by insertion or removal of naturally occurring sequences (e.g., insertion of an IRES, insertion of a heterologous polynucleotide encoding, for example, a polypeptide having cytosine deaminase activity of the disclosure and the like).

In another embodiment, the disclosure provides retroviral vectors that are targeted using regulatory sequences. Cell- or tissue-specific regulatory sequences (e.g., promoters) can be utilized to target expression of gene sequences in specific cell populations. Suitable mammalian and viral promoters for the disclosure are described elsewhere herein. Accordingly, in one embodiment, the disclosure provides a retrovirus having tissue-specific promoter elements at the 5' end of the retroviral genome. Preferably, the tissue-specific regulatory elements/sequences are in the U3 region of the LTR of the retroviral genome, including for example cell- or tissue-specific promoters and enhancers to neoplastic cells (e.g., tumor cell-specific enhancers and promoters), and inducible promoters (e.g., tetracycline).

In some circumstances, it may be desirable to regulate expression. For example, different viral promoters with varying strengths of activity may be utilized depending on the level of expression desired. In mammalian cells, the CMV immediate early promoter if often used to provide strong transcriptional activation. Modified versions of the CMV promoter that are less potent have also been used when reduced levels of expression of the transgene are desired. When expression of a transgene in hematopoietic cells is desired, retroviral promoters such as the LTRs from MLV or MMTV can be used. Other viral promoters that can be used include SV40, RSV LTR, HIV-1 and HIV-2 LTR, adenovirus promoters such as from the E1A, E2A, or MLP region, AAV LTR, cauliflower mosaic virus, HSV-TK, and avian sarcoma virus.

Similarly tissue specific or selective promoters may be used to effect transcription in specific tissues or cells so as to reduce potential toxicity or undesirable effects to non-targeted tissues. For example, promoters such as the PSA, probasin, prostatic acid phosphatase or prostate-specific glandular kallikrein (hK2) may be used to target gene expression in the prostate. Other promoters/regulatory domains that can be used are set forth in Table 1.

In certain indications, it may be desirable to activate transcription at specific times after administration of the gene therapy vector. This may be done with such promoters as those that are hormone or cytokine regulatable. For example in therapeutic applications where the indication is a gonadal tissue where specific steroids are produced or routed to, use of androgen or estrogen regulated promoters may be advantageous. Such promoters that are hormone regulatable include MMTV, MT-1, ecdysone and RuBisco. Other hormone regulated promoters such as those responsive to thyroid, pituitary and adrenal hormones may be used. Cytokine and inflammatory protein responsive promoters that could be used include K and T Kininogen (Kageyama et al., 1987), c-fos, TNF-alpha, C-reactive protein (Arcone et al., 1988), haptoglobin (Oliviero et al., 1987), serum amyloid A2, C/EBP alpha, IL-1, IL-6 (Poli and Cortese, 1989), Complement C3 (Wilson et al., 1990), IL-8, alpha-1 acid glycoprotein (Prowse and Baumann, 1988), alpha-1 antitrypsin, lipoprotein lipase (Zechner et al., 1988), angiotensinogen (Ron et al., 1990), fibrinogen, c-jun (inducible by phorbol esters, TNF-alpha, UV radiation, retinoic acid, and hydrogen peroxide), collagenase (induced by phorbol esters and retinoic acid), metallothionein (heavy metal and glucocorticoid inducible), Stromelysin (inducible by phorbol ester, interleukin-1 and EGF), alpha-2 macroglobulin and alpha-1 antichymotrypsin. Tumor specific promoters such as osteocalcin, hypoxia-responsive element (HRE), MAGE-4, CEA, alpha-fetoprotein, GRP78/BiP and tyrosinase may also be used to regulate gene expression in tumor cells.

In addition, this list of promoters should not be construed to be exhaustive or limiting, those of skill in the art will know of other promoters that may be used in conjunction with the promoters and methods disclosed herein.

TABLE 1

TISSUE SPECIFIC PROMOTERS

| Tissue | Promoter |
|---|---|
| Pancreas | Insulin Elastin Amylase pdr-1 pdx-1 glucokinase |
| Liver | Albumin PEPCK HBV enhancer α fetoprotein apolipoprotein C α-1 antitrypsin vitellogenin, NF-AB Transthyretin |
| Skeletal muscle | Myosin H chain Muscle creatine kinase Dystrophin Calpain p94 Skeletal alpha-actin fast troponin 1 |
| Skin | Keratin K6 Keratin K1 |
| Lung | CFTR Human cytokeratin 18 (K18) Pulmonary surfactant proteins A, B and C CC-10 P1 |
| Smooth muscle | sm22 α SM-alpha-actin |
| Endothelium | Endothelin-1 E-selectin von Willebrand factor TIE, KDR/flk-1 Melanocytes Tyrosinase |
| Adipose tissue | Lipoprotein lipase (Zechner et al., 1988) Adipsin (Spiegelman et al., 1989) acetyl-CoA carboxylase (Pape and Kim, 1989) glycerophosphate dehydrogenase (Dani et al., 1989) adipocyte P2 (Hunt et al., 1986) |
| Breast | Whey Acidic Protein (WAP) (Andres et al. PNAS 84:1299-1303 1987 |
| Blood | β-globin |

"Tissue-specific regulatory elements" are regulatory elements (e.g., promoters) that are capable of driving transcription of a gene in one tissue while remaining largely "silent" in other tissue types. It will be understood, however, that tissue-specific promoters may have a detectable amount of "background" or "base" activity in those tissues where they are silent. The degree to which a promoter is selectively activated in a target tissue can be expressed as a selectivity ratio (activity in a target tissue/activity in a control tissue). In this regard, a tissue specific promoter useful in the practice of the disclosure typically has a selectivity ratio of greater than about 5. Preferably, the selectivity ratio is greater than about 15.

It will be further understood that certain promoters, while not restricted in activity to a single tissue type, may nevertheless show selectivity in that they may be active in one group of tissues, and less active or silent in another group. Such promoters are also termed "tissue specific", and are contemplated for use with the disclosure. Accordingly, the tissue-specific regulatory elements used in the disclosure, have applicability to regulation of the heterologous proteins such as the polypeptides having cytosine deaminase activity of the disclosure as well as a applicability as a targeting polynucleotide sequence in retroviral vectors.

The retroviral vectors and CD polynucleotides and polypeptides of the disclosure can be used to treat a wide range of disease and disorders including a number of cell proliferative diseases and disorders (see, e.g., U.S. Pat. Nos. 4,405,712 and 4,650,764; Friedmann, 1989, Science, 244: 1275-1281; Mulligan, 1993, Science, 260:926-932, R. Crystal, 1995, Science 270:404-410, each of which are incorporated herein by reference in their entirety, see also, The Development of Human Gene Therapy, Theodore Friedmann, Ed., Cold Spring Harbor Laboratory Press, Cold Spring Harbor, N.Y., 1999. ISBN 0-87969-528-5, which is incorporated herein by reference in its entirety).

The disclosure also provides gene therapy for the treatment of cell proliferative disorders. Such therapy would achieve its therapeutic effect by introduction of an appropriate therapeutic polynucleotide sequence (e.g., a polypeptide of the disclosure having cytosine deaminase activity), into cells of subject having the proliferative disorder. Delivery of polynucleotide constructs can be achieved using the recombinant retroviral vector of the disclosure.

In addition, the therapeutic methods (e.g., the gene therapy or gene delivery methods) as described herein can be performed in vivo or ex vivo. For example, in the methods for treatment of cell proliferative diseases or disorders it may be useful to remove the majority of a tumor prior to gene therapy, for example surgically or by radiation. In some embodiments, the retroviral therapy may be preceded or followed by chemotherapy.

Thus, the disclosure provides a recombinant retrovirus capable of infecting a non-dividing cell, a dividing cell or a neoplastic cell, wherein the recombinant retrovirus comprises a viral GAG; a viral POL; a viral ENV; a heterologous nucleic acid (e.g., comprising a polypeptide of the disclosure having cytosine deaminase activity) operably linked to an IRES; and cis-acting nucleic acid sequences necessary for packaging, reverse transcription and integration. The recombinant retrovirus can be a lentivirus, such as HIV, or can be an oncovirus. As described above for the method of producing a recombinant retrovirus, the recombinant retrovirus of the disclosure may further include at least one of VPR, VIF, NEF, VPX, TAT, REV, and VPU protein. While not wanting to be bound by a particular theory, it is believed that one or more of these genes/protein products are important for increasing the viral titer of the recombinant retrovirus produced (e.g., NEF) or may be necessary for infection and packaging of virion.

The disclosure also provides a method of nucleic acid transfer to a target cell to provide expression of a particular nucleic acid (e.g., a heterologous sequence such as a polynucleotide encoding a polypeptide having cytosine deaminase activity). Therefore, in another embodiment, the disclosure provides a method for introduction and expression of a heterologous nucleic acid in a target cell comprising infecting the target cell with the recombinant virus of the disclosure and expressing the heterologous nucleic acid in the target cell. As mentioned above, the target cell can be any cell type including dividing, non-dividing, neoplastic, immortalized, modified and other cell types recognized by those of skill in the art, so long as they are capable of infection by a retrovirus.

The disclosure also provides gene therapy for the treatment of cell proliferative or immunologic disorders. In one embodiment, a cell proliferative disorder is treated by introducing a CD polynucleotide of the disclosure, expressing the polynucleotide to produce a polypeptide comprising cytosine deaminase activity and contacting the cell with 5-fluorocytosine in an amount and for a period of time to produce a cytotoxic amount of 5-FU.

In addition, the disclosure provides polynucleotide sequence encoding a recombinant retroviral vector of the disclosure. The polynucleotide sequence can be incorporated into various viral particles. For example, various viral vectors which can be utilized for gene therapy include adenovirus, herpes virus, vaccinia, or, preferably, an RNA virus such as a retrovirus and more particularly a mammalian oncovirus. The retroviral vector can be a derivative of a murine, simian or human retrovirus. Examples of retroviral vectors in which a foreign gene (e.g., a heterologous polynucleotide sequence) can be inserted include, but are not limited to: derivatives of Moloney murine leukemia virus (MoMuLV), Harvey murine sarcoma virus (HaMuSV), murine mammary tumor virus (MuMTV), and Rous Sarcoma Virus (RSV). All of these vectors can transfer or incorporate a gene for a selectable marker so that transduced cells can be identified and generated. In yet another embodiment, the disclosure provides plasmids comprising a recombinant retroviral derived construct. The plasmid can be directly introduced into a target cell or a cell culture such as NIH 3T3, HT1080 (human), CF2 (dog) or other tissue culture cells. The resulting cells release the retroviral vector into the culture medium.

The disclosure provides a polynucleotide construct comprising from 5' to 3': a promoter or regulatory region useful for initiating transcription; a psi packaging signal; a gag encoding nucleic acid sequence, a pol encoding nucleic acid sequence; an env encoding nucleic acid sequence; an internal ribosome entry site nucleic acid sequence; a heterologous polynucleotide encoding a marker, therapeutic (e.g., a polypeptide having cytosine deaminase activity) or diagnostic polypeptide; and a LTR nucleic acid sequence. In specific embodiments, a heterologous polynucleotide encoding a polypeptide having cytosine deaminase activity may further comprise a domain encoding a polypeptide comprising UPRT or OPRT activity.

As described elsewhere herein and as follows the various segment of the polynucleotide construct of the disclosure (e.g., a recombinant replication competent retroviral polynucleotide) are engineered depending in part upon the desired host cell, expression timing or amount, and the heterologous polynucleotide. A replication competent retroviral construct of the disclosure can be divided up into a number of domains that may be individually modified by those of skill in the art.

For example, the promoter can comprise a CMV promoter having a sequence as set forth in SEQ ID NO:19, 20, or 22 from nucleotide 1 to about nucleotide 582 and may include modification to one or more (e.g., 2-5, 5-10, 10-20, 20-30, 30-50, 50-100 or more nucleic acid bases) so long as the modified promoter is capable of directing and initiating transcription. In one embodiment, the promoter or regulatory region comprises a CMV-R-U5 domain polynucleotide. The CMV-R-U5 domain comprise the immediately early promoter from human cytomegalovirus to the MLV R-U5 region. In one embodiment, the CMV-R-U5 domain polynucleotide comprises a sequence as set forth in SEQ ID NO:19, 20, or 22 from about nucleotide 1 to about nucleotide 1202 or sequences that are at least 95% identical to a sequence as set forth in SEQ ID NO:19, 20, or 22, wherein the polynucleotide promotes transcription of a nucleic acid molecule operably linked thereto. The gag domain of the polynucleotide may be derived from any number of retroviruses, but will typically be derived from an oncoretrovirus and more particularly from a mammalian oncoretrovirus. In one embodiment the gag domain comprises a sequence from about nucleotide number 1203 to about nucleotide 2819 or a sequence having at least 95%, 98%, 99% or 99.8% (rounded to the nearest $10^{th}$) identity thereto. The pol domain of the polynucleotide may be derived from any number of retroviruses, but will typically be derived from an oncoretrovirus and more particularly from a mammalian oncoretrovirus. In one embodiment the pol domain comprises a sequence from about nucleotide number 2820 to about nucleotide 6358 or a sequence having at least 95%, 98%, 99% or 99.9% (roundest to the nearest $10^{th}$) identity thereto. The env domain of the polynucleotide may be derived from any number of retroviruses, but will typically be derived from an oncoretrovirus and more particularly from a mammalian oncoretrovirus. In some embodiments the env coding domain comprises an amphotropic env domain. In one embodiment the env domain comprises a sequence from about nucleotide number 6359 to about nucleotide 8323 or a sequence having at least 95%, 98%, 99% or 99.8% (roundest to the nearest $10^{th}$) identity thereto. The IRES domain of the polynucleotide may be obtained from any number of internal ribosome entry sites. In one embodiment, IRES is derived from an encephalomyocarditis virus. In one embodiment the IRES domain comprises a sequence from about nucleotide number 8327 to about nucleotide 8876 or a sequence having at least 95%, 98%, or 99% (roundest to the nearest $10^{th}$) identity thereto so long as the domain allows for entry of a ribosome. The heterologous domain can comprise a cytosine deaminase of the disclosure. In one embodiment, the CD polynucleotide comprises a human codon optimized sequence. In yet another embodiment, the CD polynucleotide encodes a mutant polypeptide having cytosine deaminase, wherein the mutations confer increased thermal stabilization that increase the melting temperature (Tm) by 10° C. allowing sustained kinetic activity over a broader temperature range and increased accumulated levels of protein. In one embodiment, the cytosine deaminase comprises a sequence as set forth in SEQ ID NO:19 from about nucleotide number 8877 to about 9353. The heterologous domain may be followed by a polypurine rich domain. The 3' LTR can be derived from any number of retroviruses, typically an oncoretrovirus and preferably a mammalian oncoretrovirus. In one embodiment, the 3' LTR comprises a U3-R-U5 domain. In yet another embodiment the LTR comprises a sequence as set forth in SEQ ID NO:19 from about nucleotide 9405 to about 9998 or a sequence that is at least 95%, 98% or 99.5% (rounded to the nearest $10^{th}$) identical thereto.

The disclosure also provides a recombinant retroviral vector comprising from 5' to 3' a CMV-R-U5, fusion of the immediate early promoter from human cytomegalovirus to the MLV R-U5 region; a PBS, primer binding site for reverse transcriptase; a 5' splice site; a Ψ packaging signal; a gag, ORF for MLV group specific antigen; a pol, ORF for MLV polymerase polyprotein; a 3' splice site; a 4070A env, ORF for envelope protein of MLV strain 4070A; an IRES, internal ribosome entry site of encephalomyocarditis virus; a modified cytosine deaminase (thermostabilized and codon optimized); a PPT, polypurine tract; and a U3-R-U5, MLV long terminal repeat. This structure is further depicted in FIG. 1.

The disclosure also provides a retroviral vector comprising a sequence as set forth in SEQ ID NO:19, 20, or 22.

In another embodiment, the disclosure provides a method of treating a subject having a cell proliferative disorder. The subject can be any mammal, and is preferably a human. The subject is contacted with a recombinant replication competent retroviral vector of the disclosure. The contacting can be in vivo or ex vivo. Methods of administering the retroviral vector of the disclosure are known in the art and include, for example, systemic administration, topical administration, intraperitoneal administration, intra-muscular administration, intracranial, cerebrospinal, as well as administration directly at the site of a tumor or cell-proliferative disorder. Other routes of administration known in the art.

Thus, the disclosure includes various pharmaceutical compositions useful for treating a cell proliferative disorder. The pharmaceutical compositions according to the disclosure are prepared by bringing a retroviral vector containing a heterologous polynucleotide sequence useful in treating or modulating a cell proliferative disorder according to the disclosure into a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in Remington's Pharmaceutical Sciences, 15th ed. Easton: Mack Publishing Co., 1405-1412, 1461-1487 (1975) and The National Formulary XIV., 14th ed. Washington: American Pharmaceutical Association (1975), the contents of which are hereby incorporated by reference. The pH and exact concentration of the various components of the pharmaceutical composition are adjusted according to routine skills in the art. See Goodman and Gilman's The Pharmacological Basis for Therapeutics (7th ed.).

For example, and not by way of limitation, a retroviral vector useful in treating a cell proliferative disorder will include an amphotropic ENV protein, GAG, and POL proteins, a promoter sequence in the U3 region retroviral genome, and all cis-acting sequence necessary for replication, packaging and integration of the retroviral genome into the target cell.

The following Examples are intended to illustrate, but not to limit the disclosure. While such Examples are typical of those that might be used, other procedures known to those skilled in the art may alternatively be utilized.

EXAMPLES

Example 1 Construction of Modified CD Genes and Insertion into Plasmid Vectors Genetic enhancements to the wild type yeast cytosine deaminase gene have been made to include: (1) three positional mutations which change three amino acids (A23L, I140L and V108I) to increase thermal stability of the yeast cytosine deaminase protein and (2) additional gene sequence modifications to enhance human codon usage sequences to improve protein translation efficiency in human cells without further changes to the amino acid sequence.

Sequence design for CD included CD-optimized, CD-UPRT (+/−linker) and CD-OPRTase (+/−linker). The final cytosine deaminase coding sequence can comprise at the 5' end a PSI1 site (full length) and 3' end Not1 site plus poly A tail for PSI1/Not1 cassette based strategy.

Figure 1B:
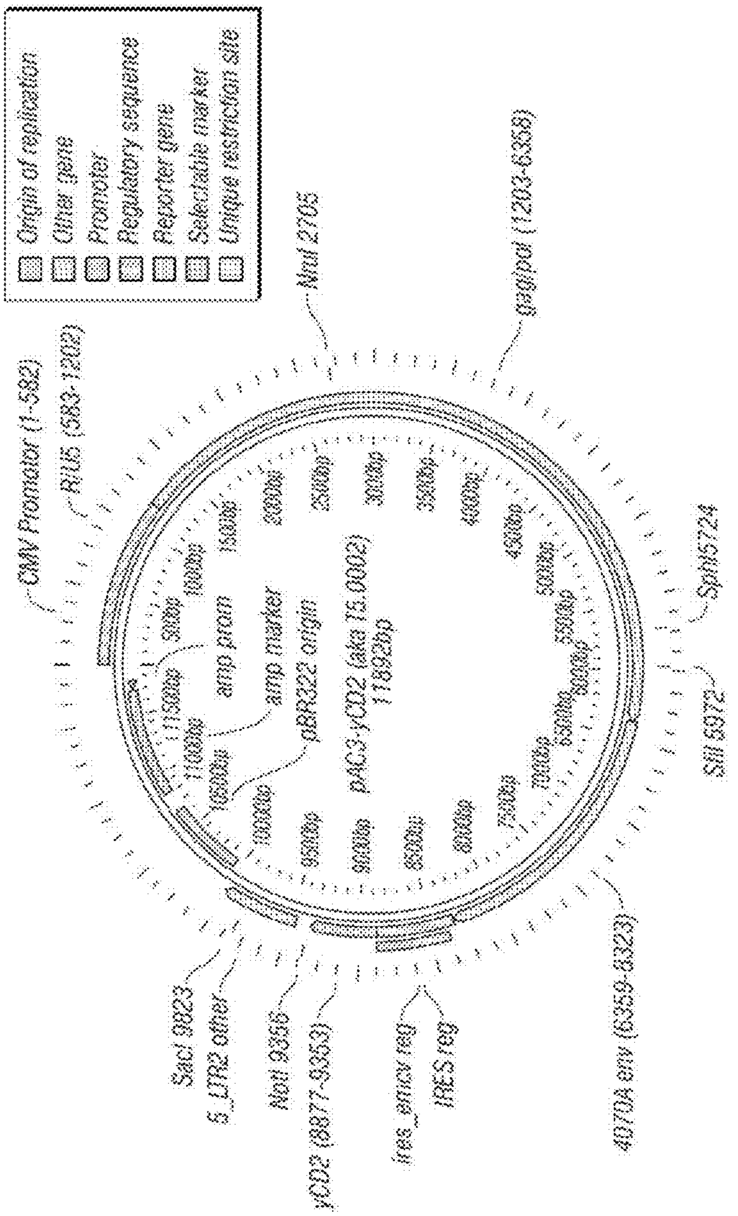
Figure 1C:
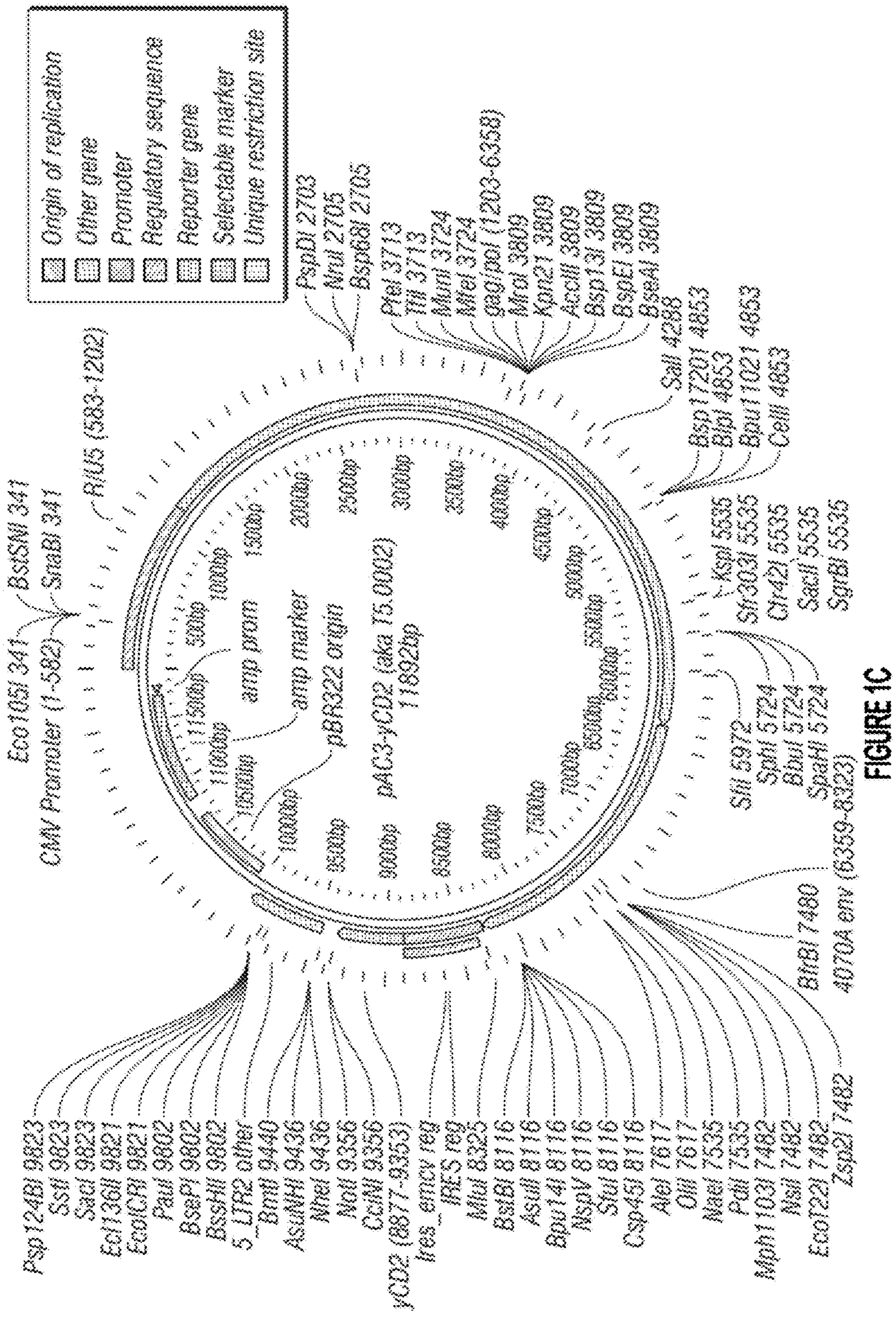

The following sequence comprising a yeast cytosine deaminase was used for cloning, optimizing and mutation (the boxed nucleic acids comprise the restriction sites used in subsequent methods for cloning:

regions. 1B and 1D shows the plasmid structure and a sequence of the disclosure. After the genes were synthesized at a contractor (Bio Basic Inc., Markham, Ontario, Canada) they were inserted into the Psi1-Not1 site of the pAC3 vector backbone (FIG. 1). The plasmid backbone was normally generated by cutting the plasmid pAC3-eGFP with Psi1 and Not1 and purifying the large (about 11 kb) fragment encoding the plasmid and retroviral backbone)

A. Humanized Codon Optimized CD Gene (CD-Opt, aka CD1, T5.0001).

A comparison of a human codon optimized cytosine deaminase of Conrad et al. and PCT WO 99/60008 indicates (SEQ ID NO: 30)

AACACGATTATAAATGGTGACAGGGGGAATGGCAAGCAAGTGGGATCAGAAGGGTATGGACATTGCCT

ATGAGGAGGCGGCCTTAGGTTACAAAGAGGGTGGTGTTCCTATTGGCGGATGTCTTATCAATAACAAA

GACGGAAGTGTTCTCGGTCGTGGTCACAACATGAGATTTCAAAAGGGATCCGCCACACTACATGGTGA

GATCTCCACTTTGGAAAACTGTGGGAGATTAGAGGGCAAAGTGTACAAAGATACCACTTTGTATACGA

CGCTGTCTCCATGCGACATGTGTACAGGTGCCATCATCATGTATGGTATTCCACGCTGTGTTGTCGGT

GAGAACGTTAATTTCAAAAGTAAGGGCGAGAAATATTTACAAACTAGAGGTCACGAGGTTGTTGTTGT

TGACGATGAGAGGTGTAAAAAGATCATGAAACAATTTATCGATGAAAGACCTCAGGATTGGTTTGAAG

ATATTGGTGAGTAGGCGGCCGCGCCATAGATAAAATAAAAGATTTTATTTAGTCTCCAGAAAAAGGGG

GG

The following Table summarizes the genes and resulting plasmid vectors that were made and their names.

91 total codons optimized in both, 36 codons identical, 47 codons had third base pair changes (all encode same amino

TABLE

Vector constructs and names

| Identity Code | Reference name | Original Name | 5'LTR Prom | Envelope | Vector | IRES | Trans-gene | 3'LTR |
|---|---|---|---|---|---|---|---|---|
| T5.0000 | pACE-yCD | pACE-CD (Tai et al. 2005) | CMV | Ampho (4070A) | pACE | EMCV | Wt yeast CD | MLV U3 |
| T5.0001 | pAC3-yCD1 | CD-opt sequence | CMV | Ampho (4070A) | pAC3 | EMCV | modified CD | MLV U3 |
| T5.0002 | pAC3-yCD2 | CDopt + 3pt | CMV | Ampho (4070A) | pAC3 | EMCV | Modified CD | MLV U3 |
| T5.0003 | pAC3-yCD2-U | Cdopt + 3pt-UPRT | CMV | Ampho (4070A) | pAC3 | EMCV | CD2-UPRT | MLV U3 |
| T5.0004 | pAC3-yCD2-O | CDopt + 3pt-OPRT | CMV | Ampho (4070A) | pAC3 | EMCV | CD2-OPRT | MLV U3 |
| T5.0005 | pAC3-yCD2-LO | CDopt + 3pt-LINK-OPRT | CMV | Ampho (4070A) | pAC3 | EMCV | CD2-L-OPRT | MLV U3 |
| T5.0006 | pAC3-eGFP | pAC3-emd, pAC3GFP | CMV | Ampho (4070A) | pAC3 | EMCV | Emerald GFP | MLV U3 |
| T5.0007 | pAC3-yCD | pAC3-yCD | CMV | Ampho (4070A) | pAC3 | EMCV | Wt yeast CD | MLV U3 |

The replication competent retroviral vector described by Kasahara et al. pACE-CD (U.S. Pat. No. 6,899,871, the disclosure of which is incorporated herein) was used as a basis for additional modifications. A vector (pAC3-yCD) was modified to express a modified yeast cytosine deaminase gene as described herein and was used in the constructs. See 1A below for a diagram of the vector construct for the initial transfected replication-competent retrovirus. CMV is the human CMV immediate early promoter, U3, R and U5 are the corresponding regions of the viral long terminal repeat (LTR). Gag, pol and env are the viral protein coding acid) and 9 codons were different (however they encoded same amino acid). Of the 9 codons that differed:

AGC (Ser) to TCC (Ser)

CGT (Arg) to AGG (Arg)

CCA (Pro) to CCT (Pro)

All have equivalent GC content and encode the same amino acid. The native yeast gene sequence above was separately codon optimized to give the following CD gene (CD1) and was called T5.0001 when inserted into the plasmid vector pAC3 which encodes the replication competent retrovirus (RCR) with IRES.

(SEQ ID NO: 31)

TTATAAATGGTGACCGGCGGCATGGCCTCCAAGTGGGATCAAAAGGGCATGGATATCGCTTA
CGAGGAGGCCGCCCTGGGCTACAAGGAGGGCGGCGTGCCTATCGGCGGCTGTCTGATCAACA
ACAAGGACGGCAGTGTGCTGGGCAGGGGCCACAACATGAGGTTCCAGAAGGGCTCCGCCACC
CTGCACGGCGAGATCTCCACCCTGGAGAACTGTGGCAGGCTGGAGGGCAAGGTGTACAAGGA
CACCACCCTGTACACCACCCTGTCCCCTTGTGACATGTGTACCGGCGCTATCATCATGTACG
GCATCCCTAGGTGTGTGGTGGGCGAGAACGTGAACTTCAAGTCCAAGGGCGAGAAGTACCTG
CAAACCAGGGGCCACGAGGTGGTGGTTGTTGACGATGAGAGGTGTAAGAAGATCATGAAGCA
GTTCATCGACGAGAGGCCTCAGGACTGGTTCGAGGATATCGGCGAGTGATAAGCGGCCGCAG
ATAAAATAAAAGATTTTATTTAGTCTCCAGAAAAAGGGGGG.

B. Heat Stabilized CD Gene.

Additional modifications were made to enhance the stability of the cytosine deaminase. Genetic enhancements to the wild type yeast cytosine deaminase gene were made to include three positional mutations which change three amino acids (A23L, I140L and V108I) to increase thermal stability of the yeast cytosine deaminase protein.

The following primer pairs were used in the generation of the gene for the cytosine deaminase polypeptide of the disclosure:

(SEQ ID NO: 32)
sense: 5'-tcgaggatatcggcgagtgaaacccgttattcttttggc-3'

(SEQ ID NO: 33)
antisense: 5'-gccaaaaagaataacgggtttcactcgccgatatcctcga-3'

-continued (SEQ ID NO: 34)
sense: 5'tcggcgagtgatccggcggcggcgcctccggcggcggcgcctccggcggcggcgcctccggcggcggcgccaacccgttatt-3'

(SEQ ID NO: 35)
antisense: 5'-aataacgggttggcgccgccgccggaggcgccgccgccggaggcgccgccgccggaggcgccgccgccggatcactcgccga-3'

To increase the stability of the native yeast CD, three amino acid substitutions were engineered into the protein. These substitutions were alone or in combination with human codon optimization.

The three amino acid substitutions are: A23L, V108I, I140L. A sequence encoding these substitutions is shown below.

(SEQ ID NO: 36)

ATGGTGACAGGGGGAATGGCAAGCAAGTGGGATCAGAAGGGTATGGACATTGCCTATGAGGA
GGCT<u>TTA</u>TTAGGTTACAAAGAGGGTGGTGTTCCTATTGGCGGATGTCTTATCAATAACAAAG
ACGGAAGTGTTCTCGGTCGTGGTCACAACATGAGATTTCAAAAGGGATCCGCCACACTACAT
GGTGAGATCTCCACTTTGGAAAACTGTGGGAGATTAGAGGGCAAAGTGTACAAAGATACCAC
TTTGTATACGACGCTGTCTCCATGCGACATGTGTACAGGTGCCATCATCATGTATGGTATTC
CACGCTGTGTC<u>ATC</u>GGTGAGAACGTTAATTTCAAAAGTAAGGGCGAGAAATATTTACAAACT
AGAGGTCACGAGGTTGTTGTTGTTGACGATGAGAGGTGTAAAAAG<u>TTA</u>ATGAAACAATTTAT
CGATGAAAGACCTCAGGATTGGTTTGAAGATATTGGTGAGTAGGCGGCCGCGCCATAGATAA
AATAAAAGATTTTATTTAGTCTCCAGAAAAAGGGGGG

The encoded polypeptide comprises the following sequence (substituted amino acids bold-underlined):

1 MVTGGMASKWDQKGMDIAYEEA<u>L</u>LGYKEGGVPIGGCLINNKDGSVLGRGHNMRFQKGSAT
61 LHGEISTLENCGRLEGKVYKDTTLYTTLSPCDMCTGAIIMYGIPRCV<u>I</u>GENVNFKSKGEK
121 YLQTRGHEVVVVDDERCKK<u>L</u>MKQFIDERPQDWFEDIGE- (SEQ ID NO: 4)

Final construct design that integrates 3 amino acid substitutions A23L/V108I/I140L utilizing preferred codons and uses preferred human codon usage for entire sequence (this gene is called CDopt+3pt [aka CD2] and T5.0002 when inserted into the plasmid vector pAC3 which encodes the RCR with IRES) (SEQ ID NO:37):

```
  1 ATGGTGACCGGCGGCATGGCCTCCAAGTGGGATCAAAAGGGCATGGATATCGCTTACGAG
 61 GAGGCCCTGCTGGGCTACAAGGAGGGCGGCGTGCCTATCGGCGGCTGTCTGATCAACAAC
121 AAGGACGGCAGTGTGCTGGGCAGGGGCCACAACATGAGGTTCCAGAAGGGCTCCGCCACC
181 CTGCACGGCGAGATCTCCACCCTGGAGAACTGTGGCAGGCTGGAGGGCAAGGTGTACAAG
241 GACACCACCCTGTACACCACCCTGTCCCCTTGTGACATGTGTACCGGCGCTATCATCATG
301 TACGGCATCCCTAGGTGTGTGATCGGCGAGAACGTGAACTTCAAGTCCAAGGGCGAGAAG
361 TACCTGCAAACCAGGGGCCACGAGGTGGTGGTTGTTGACGATGAGAGGTGTAAGAAGCTG
421 ATGAAGCAGTTCATCGACGAGAGGCCTCAGGACTGGTTCGAGGATATCGGCGAGTGATAA
```

Underlined codons denotes preferred codons for amino acid substitutions.

```
CD-optimized sequence design (human codon preference + 3
amino acid substitutions)

                                                  (SEQ ID NO: 38)
AACACGATTATAAATGGTGACCGGCGGCATGGCCTCCAAGTGGGATCAAAAGGGCATGGATA
TCGCTTACGAGGAGGCCCTGCTGGGCTACAAGGAGGGCGGCGTGCCTATCGGCGGCTGTCTG
ATCAACAACAAGGACGGCAGTGTGCTGGGCAGGGGCCACAACATGAGGTTCCAGAAGGGCTC
CGCCACCCTGCACGGCGAGATCTCCACCCTGGAGAACTGTGGCAGGCTGGAGGGCAAGGTGT
ACAAGGACACCACCCTGTACACCACCCTGTCCCCTTGTGACATGTGTACCGGCGCTATCATC
ATGTACGGCATCCCTAGGTGTGTGATCGGCGAGAACGTGAACTTCAAGTCCAAGGGCGAGAA
GTACCTGCAAACCAGGGGCCACGAGGTGGTGGTTCTTGACGATGAGAGGTGTAAGAAGCTGA
TGAAGCAGTTCATCGACGAGAGGCCTCAGGACTGGTTCGAGGATATCGGCGAGTAAGCGGCC
GCGCCATAGATAAAATAAAAGATTTTATTTAGTCTCCAGAAAAAGGGGGG
```

Construction of CD-UPRT Fusion Gene (CDopt+3Pt-UPRT, [aka CD-Opt-UPRT and CD2-UPRT], T5.0003 in the pAC3 Plasmid RCR Vector).

Figure 2B:
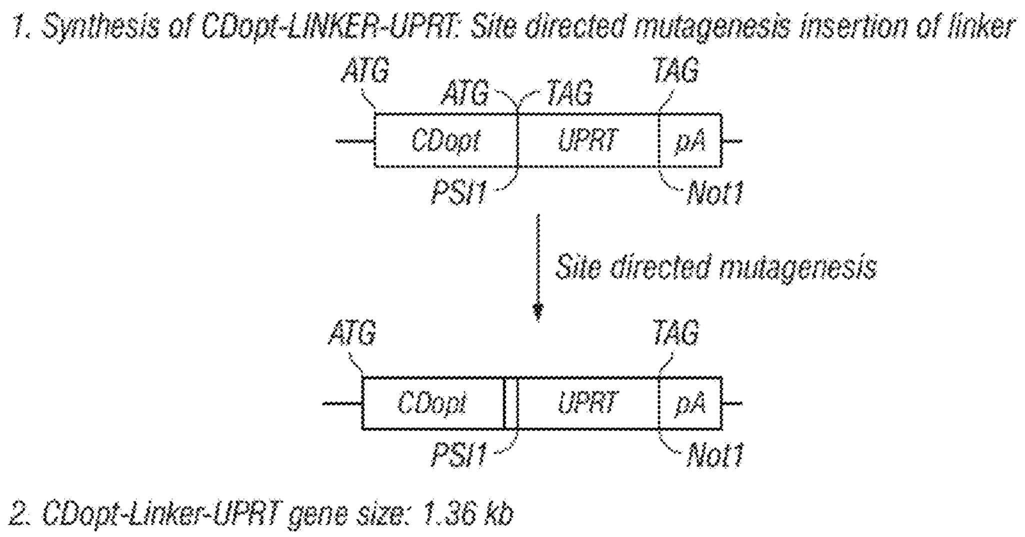

A fusion construct was also developed comprising a CD polypeptide as described above linked to a UPRT polypeptide to generate a CD-optimized-UPRT sequence using Scheme I as set forth in FIG. 2A. The following primers were used to delete the stop-start between the CD and UPRT.

Primer Sequences:

<table>
<tr><td>Primer name</td><td colspan="4">Primer Sequence (5′ to 3′) (SEQ ID NO:)</td></tr>
<tr><td>de1118-123</td><td colspan="4">5′-tcgaggatatcggcgagtgaaacccgttattctttttggc-3′ (39)</td></tr>
<tr><td>de1118-123-anitsense</td><td colspan="4">5′-gccaaaaagaataacgggtttcactcgccgatatcctcga-3′ (40)</td></tr>
<tr><td>Primer name</td><td>Length (nt.)</td><td>Tm</td><td>Duplex Energy at 68° C.</td><td>Energy Cost of Mismatches</td></tr>
<tr><td>de1118-123</td><td>40</td><td>79.06° C.</td><td>-44.37 kcal/mole</td><td>21.1%</td></tr>
<tr><td>de1118-123-anitsense</td><td>40</td><td>79.06° C.</td><td>-47.95 kcal/mole</td><td>20.3%</td></tr>
<tr><td>Primer name</td><td colspan="4">Primer-Template Duplex</td></tr>
<tr><td>de1118-123 (SEQ ID NO: 39 and 41, respectively)</td><td colspan="4">5′-tcgaggatatcggcgagtga------aacccgttattctttttggc-3′<br>||||||||||||||||||||      ||||||||||||||||||||<br>ccaagctcctatagccgctcactatctacttgggcaataagaaaaaccgaag</td></tr>
<tr><td>de1118-123-antisense (SEQ ID NO: 40 and 42 respectively)</td><td colspan="4">ggttcgaggatatcggcgagtgatagatgaacccgttattctttttggcttc<br>||||||||||||||||||||      ||||||||||||||||||||<br>3′-agctcctatagccgctcact------ttgggcaataagaaaaaccg</td></tr>
</table>

The resulting fusion polynucleotide comprises 1296 bp and the sequence set forth immediately below:

(SEQ ID NO: 43)

AACACGATTATAAATGGTGACCGGCGGCATGGCCTCCAAGTGGGATCAAAAGGGCATGGATATCGCTT

ACGAGGAGGCCCTGCTGGGCTACAAGGAGGGCGGCGTGCCTATCGGCGGCTGTCTGATCAACAACAAG

GACGGCAGTGTGCTGGGCAGGGGCCACAACATGAGGTTCCAGAAGGGCTCCGCCACCCTGCACGGCGA

GATCTCCACCCTGGAGAACTGTGGCAGGCTGGAGGGCAAGGTGTACAAGGACACCACCCTGTACACCA

CCCTGTCCCCTTGTGACATGTGTACCGGCGCTATCATCATGTACGGCATCCCTAGGTGTGTGATCGGC

GAGAACGTGAACTTCAAGTCCAAGGGCGAGAAGTACCTGCAAACCAGGGGCCACGAGGTGGTGGTTGT

TGACGATGAGAGGTGTAAGAAGCTGATGAAGCAGTTCATCGACGAGAGGCCTCAGGACTGGTTCGAGG

ATATCGGCGAGAACCCGTTATTCTTTTTGGCTTCTCCATTCTTGTACCTTACATATCTTATATATTAT

CCAAACAAAGGGTCTTTCGTTAGCAAACCTAGAAATCTGCAAAAAATGTCTTCGGAACCATTTAAGAA

CGTCTACTTGCTACCTCAAACAAACCAATTGCTGGGTTTGTACACCATCATCAGAAATAAGAATACAA

CTAGACCTGATTTCATTTTCTACTCCGATAGAATCATCAGATTGTTGGTTGAAGAAGGTTTGAACCAT

CTACCTGTGCAAAAGCAAATTGTGGAAACTGACACCAACGAAAACTTCGAAGGTGTCTCATTCATGGG

TAAAATCTGTGGTGTTTCCATTGTCAGAGCTGGTGAATCGATGGAGCAAGGATTAAGAGACTGTTGTA

GGTCTGTGCGTATCGGTAAAATTTTAATTCAAAGGGACGAGGAGACTGCTTTACCAAAGTTATTCTAC

GAAAAATTACCAGAGGATATATCTGAAAGGTATGTCTTCCTATTAGACCCAATGCTGGCCACCGGTGG

TAGTGCTATCATGGCTACAGAAGTCTTGATTAAGAGAGGTGTTAAGCCAGAGAGAATTTACTTCTTAA

ACCTAATCTGTAGTAAGGAAGGGATTGAAAAATACCATGCCGCCTTCCCAGAGGTCAGAATTGTTACT

GGTGCCCTCGACAGAGGTCTAGATGAAAACAAGTATCTAGTTCCAGGGTTGGGTGACTTTGGTGACAG

ATACTACTGTGTTTAAGCGGCCGCGCCATAGATAAAATAAAAGATTTTATTTAGTCTCCAGAAAAAGG

GGGG

Construction of CD-Linker UPRT Fusion Gene (CDopt+3Pt-LINK-UPRT [aka CD-Opt-LINKER-UPRT and CD2-L-UPRT]).

A fusion construct was also developed by cloning a linker (Ser-Gly-Gly-Gly-Gly)$_4$ domain between and in frame with the CD polypeptide and the UPRT polypeptide to generate a CD-optimized-linker-UPRT sequence using Scheme II as depicted in 2B. The following primers were used to insert the linker.

| Primer Name | Primer Sequence (5' to 3') (SEQ ID NO:) |
|---|---|
| ins_60nt_after_477 | 5'-tcggcgagtgatccggcggcggcgcctccggcggcggcgcctccggcg gcggcgcctccggcggcggcgccaacccgttatt-3' (44) |
| ins_60nt_after_477-antisense | 5'-aataacgggttggcgccgccgccggaggcgccgccgccggaggcgcc gccgccggaggcgccgccgccggatcactcgccga-3' (45) |

| Primer Name | Length (nt.) | Tm | Duplex Energy at 68° C. | Energy Cost of Mismatches |
|---|---|---|---|---|
| ins_60nt_after_477 | 82 | 79.77° C. | −30.19 kcal/mole | 83.3% |
| ins_60nt_after_477-antisense | 82 | 79.77° C. | −32.31 kcal/mole | 82.2% |

The resulting construct has size: 1356 bp and the sequence immediately below:

(SEQ ID NO: 46)

AACACGATTATAAATGGTGACCGGCGGCATGGCCTCCAAGTGGGATCAAAAGGGCATGGATATCGCTT

ACGAGGAGGCCCTGCTGGGCTACAAGGAGGGCGGCGTGCCTATCGGCGGCTGTCTGATCAACAACAAG

GACGGCAGTGTGCTGGGCAGGGGCCACAACATGAGGTTCCAGAAGGGCTCCGCCACCCTGCACGGCGA

GATCTCCACCCTGGAGAACTGTGGCAGGCTGGAGGGCAAGGTGTACAAGGACACCACCCTGTACACCA

CCCTGTCCCCTTGTGACATGTGTACCGGCGCTATCATCATGTACGGCATCCCTAGGTGTGTGATCGGC

GAGAACGTGAACTTCAAGTCCAAGGGCGAGAAGTACCTGCAAACCAGGGGCCACGAGGTGGTGGTTGT

TGACGATGAGAGGTGTAAGAAGCTGATGAAGCAGTTCATCGACGAGAGGCCTCAGGACTGGTTCGAGG

ATATCGGCGAGTCCGGCGGCGGCGCCTCCGGCGGCGGCGCCTCCGGCGGCGGCGCCTCCGGCGGCGGC

GCCAACCCGTTATTCTTTTTGGCTTCTCCATTCTTGTACCTTACATATCTTATATATTATCCAAACAA

AGGGTCTTTCGTTAGCAAACCTAGAAATCTGCAAAAAATGTCTTCGGAACCATTTAAGAACGTCTACT

TGCTACCTCAAACAAACCAATTGCTGGGTTTGTACACCATCATCAGAAATAAGAATACAACTAGACCT

GATTTCATTTTCTACTCCGATAGAATCATCAGATTGTTGGTTGAAGAAGGTTTGAACCATCTACCTGT

GCAAAAGCAAATTGTGGAAACTGACACCAACGAAAACTTCGAAGGTGTCTCATTCATGGGTAAAATCT

GTGGTGTTTCCATTGTCAGAGCTGGTGAATCGATGGAGCAAGGATTAAGAGACTGTTGTAGGTCTGTG

CGTATCGGTAAAATTTTAATTCAAAGGGACGAGGAGACTGCTTTACCAAAGTTATTCTACGAAAAATT

ACCAGAGGATATATCTGAAAGGTATGTCTTCCTATTAGACCCAATGCTGGCCACCGGTGGTAGTGCTA

TCATGGCTACAGAAGTCTTGATTAAGAGAGGTGTTAAGCCAGAGAGAATTTACTTCTTAAACCTAATC

TGTAGTAAGGAAGGGATTGAAAAATACCATGCCGCCTTCCCAGAGGTCAGAATTGTTACTGGTGCCCT

CGACAGAGGTCTAGATGAAAACAAGTATCTAGTTCCAGGGTTGGGTGACTTTGGTGACAGATACTACT

GTGTTTAAGCGGCCGCGCCATAGATAAAATAAAAGATTTTATTTAGTCTCCAGAAAAGGGG

Construction of CD-OPRT Fusion Gene (CDopt+3Pt-OPRT [aka CD-Opt-OPRT and CD2-OPRT], T5.0004 when Inserted into the pAC3 Plasmid RCR Vector).

Figure 2C:
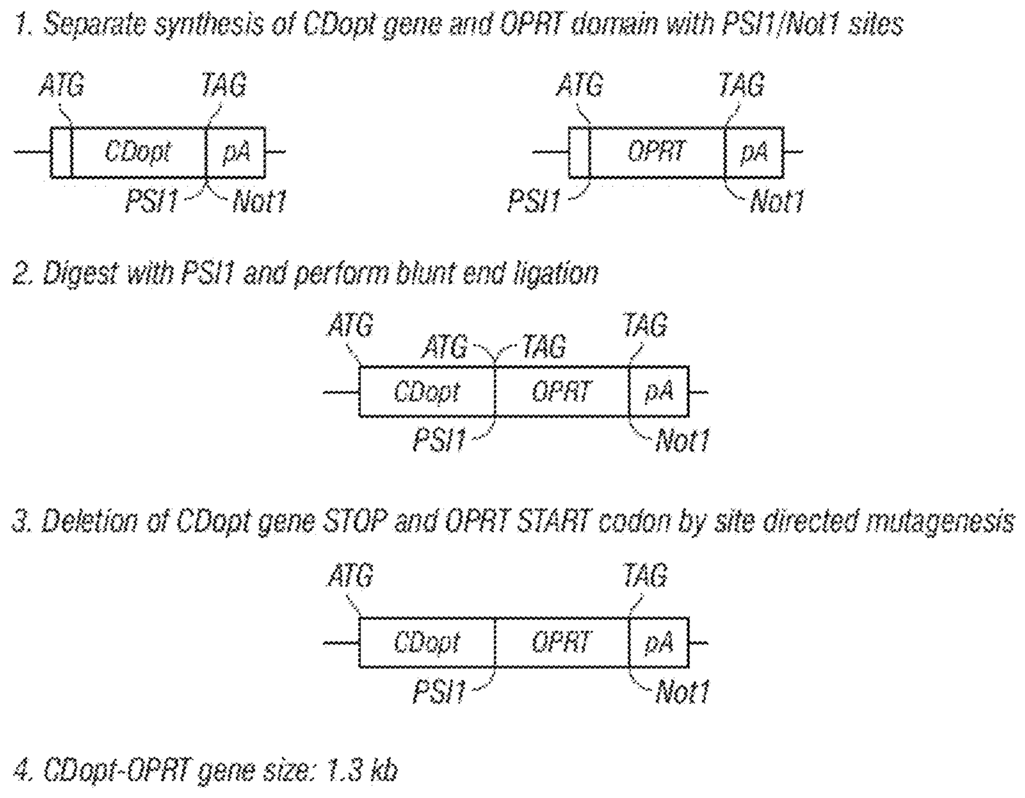

A fusion construct was also developed comprising a CD polypeptide as described above linked to an OPRT polypeptide to generated a CD-optimized-OPRTase (CD humanized+3ptmutation+OPRTase functional domain human) using Scheme III as shown in FIG. 2C.

The resulting construct comprises a size of 1269 bp and the sequence immediately below:

(SEQ ID NO: 47)

AACACGATTATAAATGGTGACCGGCGGCATGGCCTCCAAGTGGGATCAAAAGGGCATGGATATCGCTT

ACGAGGAGGCCCTGCTGGGCTACAAGGAGGGCGGCGTGCCTATCGGCGGCTGTCTGATCAACAACAAG

-continued

```
GACGGCAGTGTGCTGGGCAGGGGCCACAACATGAGGTTCCAGAAGGGCTCCGCCACCCTGCACGGCGA
GATCTCCACCCTGGAGAACTGTGGCAGGCTGGAGGGCAAGGTGTACAAGGACACCACCCTGTACACCA
CCCTGTCCCCTTGTGACATGTGTACCGGCGCTATCATCATGTACGGCATCCCTAGGTGTGTGATCGGC
GAGAACGTGAACTTCAAGTCCAAGGGCGAGAAGTACCTGCAAACCAGGGGCCACGAGGTGGTGGTTGT
TGACGATGAGAGGTGTAAGAAGCTGATGAAGCAGTTCATCGACGAGAGGCCTCAGGACTGGTTCGAGG
ATATCGGCGAGGCGGTCGCTCGTGcagctttggggccattggtgacgggtctgtacgacgtgcaggct
ttcaagtttggggacttcgtgctgaagagcgggctttcctcccccatctacatcgatctgcggggcat
cgtgtctcgaccgcgtcttctgagtcaggttgcagatattttattccaaactgcccaaaatgcaggca
tcagttttgacaccgtgtgtggagtgccttatacagctttgccattggctacagttatctgttcaacc
aatcaaattccaatgcttattagaaggaaagaaacaaaggattatggaactaagcgtcttgtagaagg
aactattaatccaggagaaacctgtttaatcattgaagatgttgtcaccagtggatctagtgttttgg
aaactgttgaggttcttcagaaggagggcttgaaggtcactgatgccatagtgctgttggacagagag
cagggaggcaaggacaagttgcaggcgcacgggatccgcctccactcagtgtgtacattgtccaaaat
gctggagattctcgagcagcagaaaaaagttgatgctgagacagttgggagagtgaagaggtttattc
aggagaatgtctttgtggcagcgaatcataatggttctcccctttctataaaggaagcacccaaagaa
ctcaGCTTCGGTGCACGTGCAGAGCTGCCCAGGATCCACCCAGTTGCATCGAAGTAAGCGGCCGCGCC
ATAGATAAAATAAAAGATTTTATTTAGTCTCCAGAAAAAGGGGGG
```

Construction of CD-Linker-OPRT Fusion Gene (CDopt+3Pt-LINK-OPRT, [Aka CD-Opt-LINKER-OPRT and CD2-L-OPRT], T5.0005 in the pAC3 Plasmid RCR Vector).

Figure 2D:
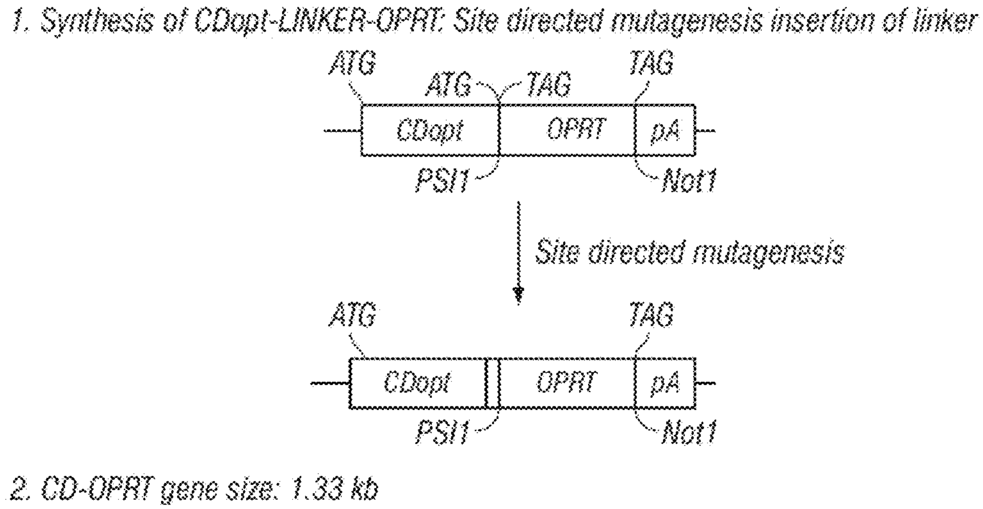

A fusion construct was also developed by cloning a linker (Ser-Gly-Gly-Gly-Gly)$_4$) (SEQ ID NO:24) domain between and in frame with the CD polypeptide and the OPRT polypeptide to generated a CD-optimized-linker-OPRT sequence using Scheme IV as shown in FIG. 2D.

The resulting construct comprises a size of 1329 bp and the sequence immediately below:

(SEQ ID NO: 48)

```
AACACGATTATAAATGGTGACCGGCGGCATGGCCTCCAAGTGGGATCAAAAGGGCATGGATATCGCTT
ACGAGGAGGCCCTGCTGGGCTACAAGGAGGGCGGCGTGCCTATCGGCGGCTGTCTGATCAACAACAAG
GACGGCAGTGTGCTGGGCAGGGGCCACAACATGAGGTTCCAGAAGGGCTCCGCCACCCTGCACGGCGA
GATCTCCACCCTGGAGAACTGTGGCAGGCTGGAGGGCAAGGTGTACAAGGACACCACCCTGTACACCA
CCCTGTCCCCTTGTGACATGTGTACCGGCGCTATCATCATGTACGGCATCCCTAGGTGTGTGATCGGC
GAGAACGTGAACTTCAAGTCCAAGGGCGAGAAGTACCTGCAAACCAGGGGCCACGAGGTGGTGGTTGT
TGACGATGAGAGGTGTAAGAAGCTCATGAAGCAGTTCATCGACGAGAGGCCTCAGGACTGGTTCGAGG
ATATCGGCGAGTCCGGCGGCGGCGCCTCCGGCGGCGGCGCCTCCGGCGGCGGCGCCTCCGGCGGCGGC
GCCGCGGTCGCTCGTGcagctttggggccattggtgacgggtctgtacgacgtgcaggctttcaagtt
tggggacttcgtgctgaagagcgggctttcctcccccatctacatcgatctgcggggcatcgtgtctc
gaccgcgtcttctgagtcaggttgcagatattttattccaaactgcccaaaatgcaggcatcagtttt
gacaccgtgtgtggagtgccttatacagctttgccattggctacagttatctgttcaaccaatcaaat
tccaatgcttattagaaggaaagaaacaaaggattatggaactaagcgtcttgtagaaggaactatta
atccaggagaaacctgtttaatcattgaagatgttgtcaccagtggatctagtgttttggaaactgtt
gaggttcttcagaaggagggcttgaaggtcactgatgccatagtgctgttggacagagagcagggagg
caaggacaagttgcaggcgcacgggatccgcctccactcagtgtgtacattgtccaaaatgctggaga
ttctcgagcagcagaaaaaagttgatgctgagacagttgggagagtgaagaggtttattcaggagaat
```

-continued gtctttgtggcagcgaatcataatggttctcccctttctataaaggaagcacccaaagaactcaGCTT

CGGTGCACGTGCAGAGCTGCCCAGGATCCACCCAGTTGCATCGAAGTAAGCGGCCGCGCCATAGATAA

AATAAAAGATTTTATTTAGTCTCCAGAAAAAGGGGGG.

Example 2 Infectious Vector Production

Vector can be produced in a number of ways, but the first step is to introduce the plasmid DNA vector into cells to allow production of infectious particles, that can then be harvested from the cell supernatant. Once infectious particles have been generated other methods of production can be implemented by those skilled in the art. Vector particles were generated by transient transfection of 293T cells (Pear et al. Proc Natl Acad Sci USA. 90:8392-8396 1993). The 293T cells were thawed and put into culture, then passaged twice in T-75 flasks containing 15 mL of the DMEM medium that was prepared by mixing DMEM High Glucose medium (Hyclone#30081, 500 mL) with FBS (Hyclone#SH30070, 50 mL), L-Glutamine (Cellgro#25-005-CI, 5 mL), NEAA (Hyclone #SH30238, 5 mL), and Penicillin-strep (Cellgro#30-002-CI, 5 mL). The flasks were incubated at 37° C. and 5% CO2. After the $3^{rd}$ passage cells were seeded in 6 T-25's, each containing 5 mL of the medium, at a cell density of $1.8\times10^6$ cells/T-25 (or $7.2\times10^4$ cells/$cm^2$). One day after seeding the T-25's, the cells were transfected with the T5.0002 plasmid that expressed the viral vector using the Calcium Phosphate Transfection Kit from Promega (Cat#E1200). Eighteen hours following transfection, the media in one set of the flasks (3 flasks each set) were replaced with fresh medium containing 10 mM NaB. The media in the $2^{nd}$ set of the flasks were not replaced, which served as a control (zero NaB). Eight hours post NaB treatment, the media in all flasks were replaced with the fresh medium containing no NaB. The expression was allowed to continue for both sets of flasks until the next day (22 hours duration). The supernatants from both sets of flasks were harvested and assayed for their titers by qPCR expressed in Transducing Units (TU)/ml (see example 3).

The titer results are shown in the following table.

| Condition | First titer | Second titer (after storing at −80° C. for 68 days) |
|---|---|---|
| Without NaB | 1.5 (±0.05) × $10^6$ TU/mL | 1.2 (±0.2) × $10^6$ TU/mL |
| 10 mM NaB | 1.4 (±0.3) × $10^6$ TU/mL | 7.0 (±0.14) × $10^5$ TU/mL |

Subsequent vector preparations were produced in this manner, without sodium butyrate. The other vector plasmids have been used in the same way to generate vector preparations with titers between 10e5 TU/ml and 10e7 TU/ml. Such material can be further purified and concentrated, if desired, as described below and see also: U.S. Pat. No. 5,792,643; T. Rodriguez et al. J Gene Med 9:233 2007; see, e.g., International Application No. PCT/US10/38996, the disclosure of which is incorporated herein by reference. In certain embodiments of the disclosure the dosing was calculated by grams of brain weight. In such embodiments, the dosing of a replication competent retroviral vector of the disclosure useful in the methods for treatment can range from $10^3$ to $10^7$ TU per gram brain weight.

Example 3 Quantitative PCR Titering Assay

The functional vector concentration, or titer, is determined using a quantitative PCR-based (qPCR) method. In this method, vector is titered by infecting a transducible host cell line (e.g. PC-3 human prostatic carcinoma cells, ATCC Cat#CRL-1435) with a standard volume of vector and measuring the resulting amount of provirus present within the host cells after transduction. The cells and vector are incubated under standard culturing condition (37° C., 5% CO2) for 24 hr to allow for complete infection prior to the addition of the anti-retroviral AZT to stop vector replication. Next, the cells are harvested from the culture dish and the genomic DNA (gDNA) is purified using an Invitrogen Purelink gDNA purification kit and eluted from the purification column with sterile RNase-/DNase-free water. The A260/A280 absorbance ratio is measured on a spectrophotometer to determine the concentration and relative purity of the sample. The gDNA concentrations are normalized with additional RNase-/DNase-free water to the lowest concentration of any given set of gDNA preparations such that the input DNA for the qPCR is constant for all samples analyzed. Genomic DNA purity is further assessed by electrophoresis of an aliquot of each sample on an ethidium bromide stained 0.8% agarose gel. If the sample passes an A260/A280 absorbance range of 1.8-2.0 and shows a single band of gDNA, then the sample is ready for qPCR analysis of provirus copy number of the vector. Using primers that interrogate the LTR region of the provirus (reverse-transcribed vector DNA and vector DNA that is integrated into the host gDNA), qPCR is performed to estimate the total number of transduction events that occurred when the known volume of vector was used to transduce the known number of cells. The number of transduction events per reaction is calculated from a standard curve that utilizes a target-carrying plasmid of known copy-number that is serial diluted from 1E7 to 1E1 copies and measured under identical qPCR conditions as the samples. Knowing how many genomic equivalents were used for each qPCR reaction (from the concentration previously determined) and how many transduction events that occurred per reaction, we determine the total number of transduction events that occurred based on the total number of cells that were present at the time of transduction. This value is the titer of the vector after dilution into the medium containing the cells during the initial transduction. To calculate the corrected titer value, the dilution is corrected for by multiplying through by the volume of culture and the volume of titer divided by the volume of titer. These experiments are performed in replicate cultures and analyzed by qPCR using triplicate measurements for each condition to determine an average titer and with its associated standard deviation and coefficient of variance.

Example 4 Expression Levels Measured by Western Blot

Figure 3:
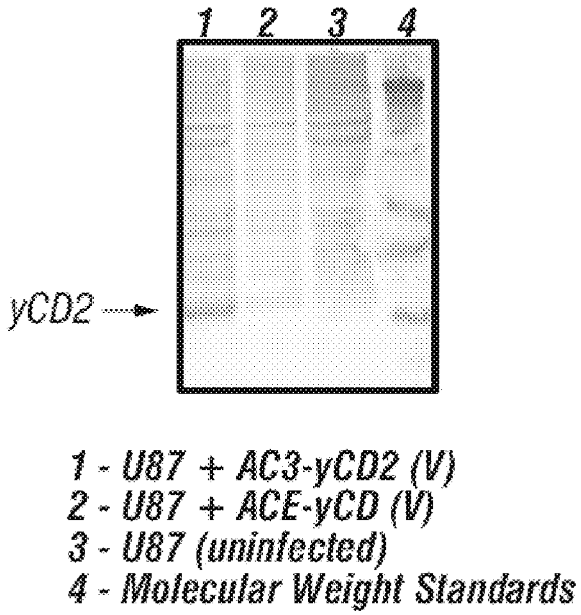
FIG. 3 shows that higher levels of yCD2 protein are observed compared to wild type yCD protein in infected U-87 cells.

FIG. 3 demonstrates that higher levels of the human codon optimized with the three mutations for higher stability are observed compared to wild type yCD protein in a Western blot analysis of U-87 cells infected with virus encoding either the wild type (ACE-yCD) or fully optimized (AC3-yCD2) cytosine deaminase genes.

Example 5 Genetic Stability of Viral Vectors

Figure 4:
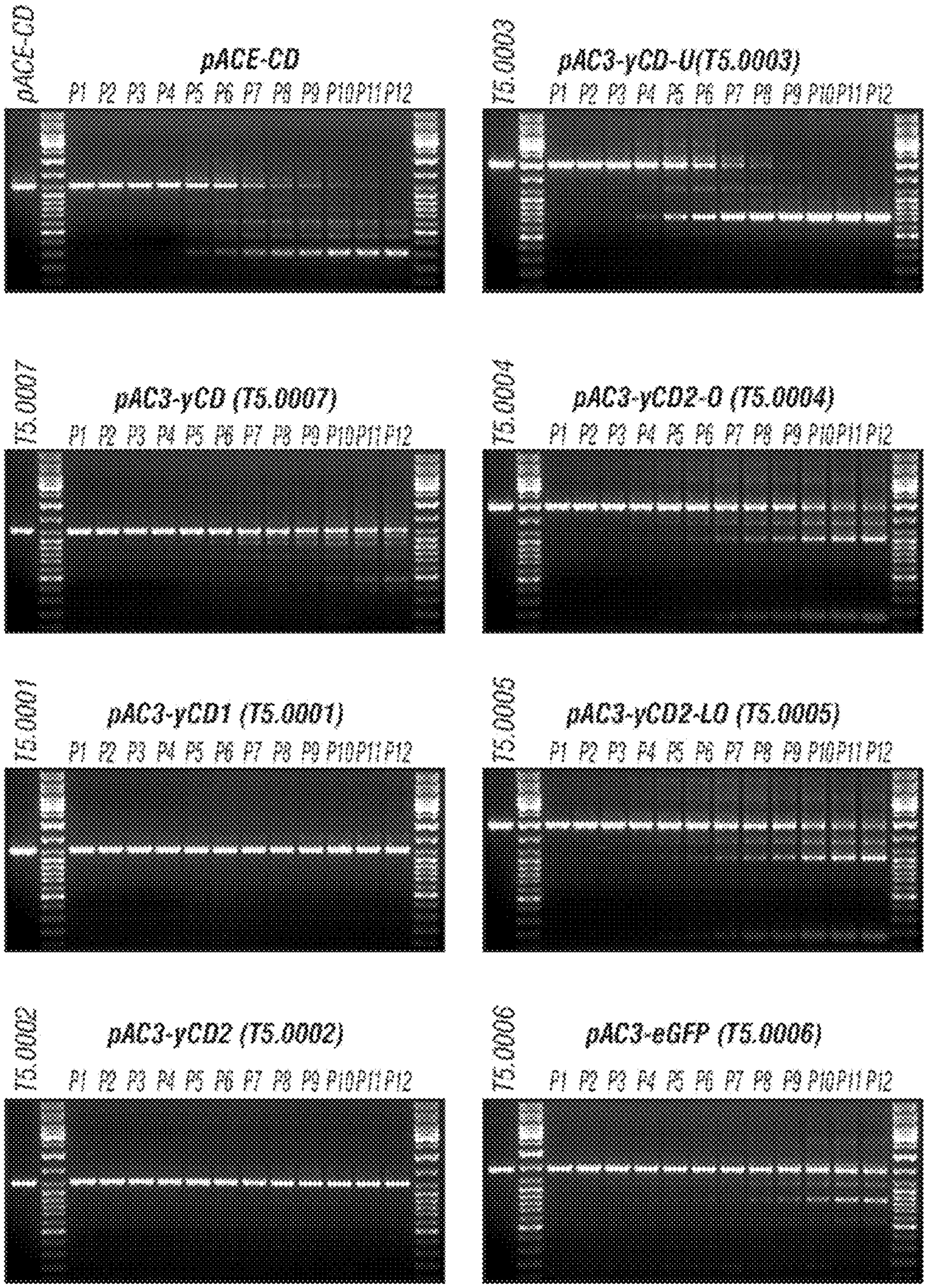
FIG. 4 shows the stability of a vector comprising a CD polypeptide of the disclosure and the comparison to other vectors of the disclosure.

It is recognized that after reverse transcription and the first integration event into treated cells, the DNA provirus and any subsequent progeny retrovirus has a conventional LTR structure from MLV on either end. This configuration has been shown to be stable after multiple cycles of infection (See FIG. 4 below).

Approximately $10^6$ naïve U-87 cells were initially infected with the viral vector at an MOI of 0.01, and grown until fully infected to complete a single cycle of infection. Supernatant is then repassed onto uninfected cells and the cycle repeated. Genomic stability of the yCD2 sequence was assessed by PCR amplification of the integrated provirus from the infected cells using MLV specific primers flanking the transgene insertion site. For each set of infections, amplification of the vector plasmid (pAC3-yCD2 and the Kasahara et al. vector pACE-CD) was also performed to track full-length amplicon sizing on the gel. The appearance of any bands smaller than full-length amplicon would be an indicator of vector instability. Such experiments demonstrated that a vector of the disclosure (T5.0002—comprising the modified vector and CDopt+3pt (CD2) heterologous polynucleotide maintained stability for more passages than pACE-CD or T5.007 both of which carry the wild type yeast.

Example 6 Cell Killing Experiments

Figure 5A:
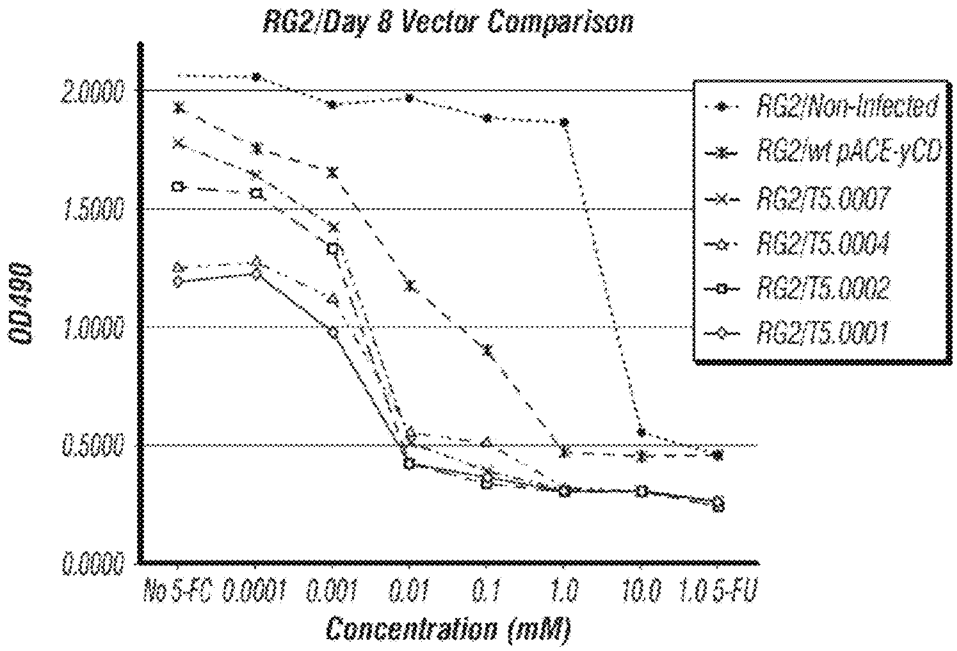
FIG. 5A-B show that a cytosine deaminase activity and vector of the disclosure provide comparable or better expression, and hence killing, of infected rat RG2 (A) or U87 cells (B) compared to wild type yCD activity (T5.0007), when infected cells are exposed to increasing levels of 5-FC.
Figure 5B:
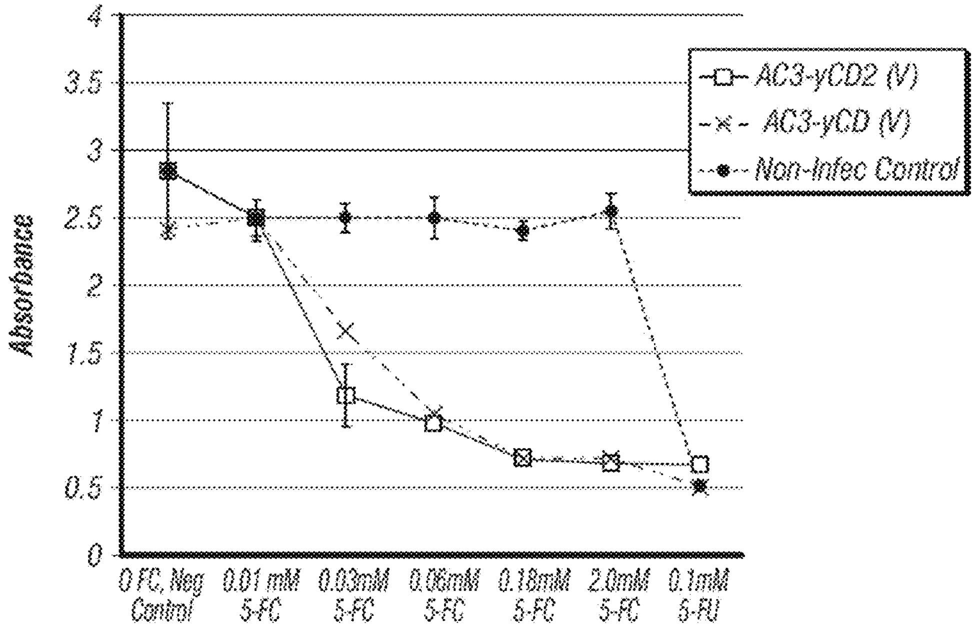

In in-vitro cell culture experiments, the experiments demonstrate that the cytosine deaminase in cells expressing the yCD2 protein is at least as active as that from cells expressing the wild type yCD protein, by performing 5-FC titrations on RG2 rat cells (FIG. 5A) or U-87 cells (FIG. 5B) infected either with virus made from pAC3-yCD2/T5.0002) [AC3-yCD2(V)] from pAC3-yCD/T5.0007 [AC3-yCD(V)] or the other vectors. Briefly, for U-87 cells, 5 days post infection at a multiplicity of infection of 0.1 (i.e. 100% infected) with either AC3-yCD (wild type CD) vector or AC3-yCD2 (thermostabilized & codon optimized) vector were subject to increasing amounts of 5-FC or 0.1 mM of 5-FU as a positive control for 8 days. On day 8 of 5-FC treatment, cell cultures were assessed for viability using an MTS assay (Promega CellTiter 96 AQUEOUS One Solution Proliferation Assay). Data shows comparable killing between the two retroviral vectors at increasing doses of 5-FC treatment. The RG2 cultures were treated similarly and also show if anything a slight shift in the killing curve towards lower concentration of 5-FC for virus from T5.0002CD expression assay. U87 cells were transduced at a multiplicity of infection (MOI) of 0.1, cultivated for 5 days to allow viral spread and cells from day 5 post transduction were harvested. The cells were then collected by centrifugation at 800×g for 5 min. The supernatant was aspirated away from the cell pellet and washed with 5 mL of phosphate buffered saline (PBS) and again centrifuged at 800×g for 5 min. The resulting cell pellet was taken up in 1.5 mL of PBS, resuspended by passage through a pipette tip and placed in a freezer at −20° C. Cells were lysed by a freeze/thaw method. Previously resuspended cells were allowed to thaw at room temperature, passed through a pipette tip, mixed with protease inhibitor cocktail and again refrozen at −20 C. Previous to the enzyme assay, the sample was again thawed at room temperature and passed through a pipette tip. The suspension was then centrifuged at 14,000 rpm in a tabletop centrifuge for 5 min. The supernatant was decanted away from the pellet and placed in a fresh eppendorf tube and placed on ice. yCD enzyme activity was assessed by using an HPLC assay.

Figure 6:
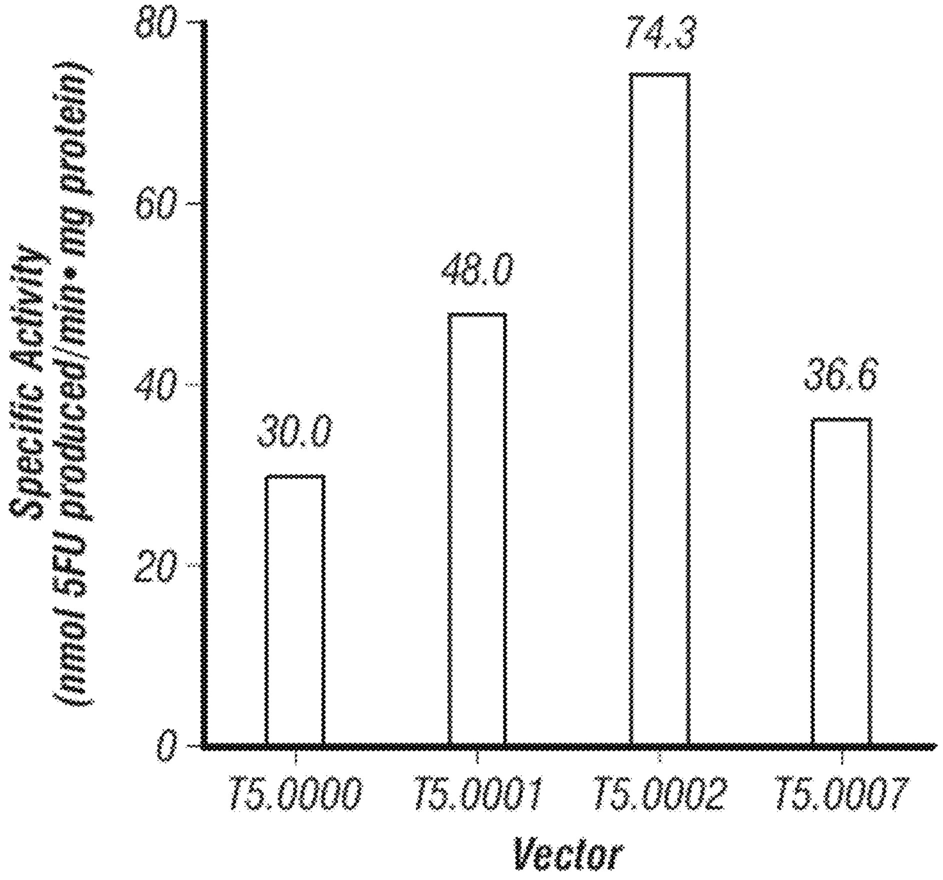
FIG. 6 shows that the specific activity in infected U87 cells of T5.0002 (yCD2) is greater than T5.0001 (partially optimized yCD) which is greater than T5.0007 (wt yCD).

The HPLC assay was performed on a Shimadzu LC20AT unit connected in series with a photoarray detector and autoinjector. The solid phase was a Hypersil BDS C18 HPLC column with a 5 um sphere size and 4.0×250 mm column dimensions. The mobile phase was 50 mM ammonium phosphate, pH 2.1, containing 0.01% tert-butylammonium perchlorate and 5% methanol; the system was equilibrated at 22 C. All reagents were ACS grade and solvents were HPLC grade. A reaction mix was made consisting of 800 μL with a final concentration of 0.125 mg/mL 5FC (1 mM) in PBS and placed in a 1.5 mL autosampler vial. The reaction was then initiated by adding 200 uL of each cell lysate. The reaction/autosampler vials were placed in the auto sampler and 5 uL of the reaction mixture was injected. Time points were taken periodically by retrieving a 5 uL aliquot from each reaction vial and analyzing on the HPLC column. The conversion rates of 5FC to 5FU were calculated by comparing the peak areas with known amounts from a previously generated standard curve of 5FU. The rate of 5FC conversion to 5FU was derived by plotting the amount of 5FU (in nmol) generated against its corresponding time interval. Protein concentration for the cell sample was derived and the Specific Activity of the cell lysate samples were calculated by dividing the conversion rate (nmol/min) by the amount of protein used in the assay in mg. FIG. 6 shows the specific activity of various vectors after 5 days on transduction at an MOI of 0.1. The data demonstrate that pACE-yCD (T5.0000)<pAC3-yCD1(T5.0001)<pAC3-CD2 (T5.0002) in terms of the specific activity of cytosine deaminase in tissue culture cells.

Example 7 Tumors Treated with the Fully Modified CD Gene (yCD2) are Eliminated More Efficiently than Tumor Treated with the Unmodified Yeast CD Gene, and do not Recur (PR-01-08-001)

To determine which vector construct gives rise to the most effective vector in a subcutaneous mouse/human xenograft model. Three different constructs were evaluated: T5.0001 (partially modified CD); T5.0007 (unmodified yeast CD gene); T5.0002 (fully modified yCD2 gene). Tumor growth, survival and tumor regression post 5-FC prodrug administration was evaluated in a subcutaneous model of human glioma (U87) in immunodeficient mice. Two different 5-FC concentrations were evaluated to determine a dose response seen between 5-FC and the tumor-vector constructs.

A total of 12 groups consisting of 9-11 female mice per group were studied. All mice underwent right dorsal flank implantation on Day 0 with either: a 98% mixture of an uninfected U-87 tumor cell line and a 2% mixture of a U-87 cell line that has been infected with one of three TOCA 511 vector constructs, T5.0002, T5.0001, T5.0007; or an uninfected control U-87 cell line (100%). Mice were inoculated with 2×10e6 cells/mouse. Mice in groups 1-3 had uninfected U87 cells, groups 4-6 had U87 cell mixture containing transduced T5.0002 U87, groups 7-9 had U87 cell mixture containing transduced with T5.0001, and groups 10-12 had U87 cell mixture containing transduced with T5.0007. The tumors were allowed to grow for 6 days, until tumor size was approximately 100 $mm^3$. Each vector dose group of mice was randomized to receive one of two doses of 5-FC (200 or 500 mg/kg/day), administered as a single IP injection, beginning on Day 6, or no 5-FC. 5-FC administration continued daily for 28 consecutive days. Surviving mice after day 29 were evaluated for tumor size and then sacrificed on varying days with tumors, if present, extracted for analysis. At day 29, mice from group 4-12 were re-randomized and the mice were subdivided into 2 subgroups (either continued on 5-FC to monitor tumor regression or discontinued 5-FC treatment to monitor tumor regrowth).

Results:

Tumors treated with T5.0002, T5.0000 and T5.0007 all demonstrated tumor regression to undetectable at 200 and 500 mg/kg dose at day 29. All T5.0002 treated animals did not reform tumors when 5FC treatment was discontinued, out to 39 days. In contrast some tumors treated with T5.0001 and T5.0007 did recur by the 39 day time point. The experiment was terminated at day 39.

Conclusion:

T5.0002 plus 5-FC is a more effective antitumor therapy than T5.0001 or T5.0007 plus 5-FC.

Example 8 Tumor Explants have Multiple Copies of the Vector Genome and Show Continued Susceptibility to Super-Infection In order to examine in more detail the mechanism of action of the replicating retrovirus tumors from some animals in the mouse and human tumor models described in example 9 (athymic nude-Foxn1^nu (nude) mice with Human U87 intracranial implants) and example 10 (BALB/c mice with syngeneic CT26 intracranial implants) were explanted and examined for 5-FC sensitivity, vector copy number/diploid genome, and CD protein expression.

Explant Assignments.

The experimental design is summarized below. The study consisted of 5 tumor explants. The history of each tumor removed for implantation is given below.

Explant History:

| Animal # | Study | Treatment | # of 5-FC dosings before explant | Cell Type | Dosing regimen |
|---|---|---|---|---|---|
| 833 | Example 9 FIG. 8 | AC3-yCD2(V) E6 + 5-FC | 4 | Human U87 | QD, 7 days every 21 days |
| 953 | Example 9 FIG. 8 | AC3-yCD2(V) E5 + 5-FC | 4 | Human U87 | QD, 7 days every 21 days |
| 969 | Example 9 FIG. 8 | AC3-yCD2(V) E5 + 5-FC | 4 | Human U87 | QD, 7 days every 21 days |
| 31 | Example 10 FIG. 9 | AC3-yCD2(V) E5 + 5-FC | 3.5 | Mouse CT26 | BID 7 days, every 17 days |
| 61 | Example 10 FIG. 9 | AC3-yCD2(V) E4 + 5-FC | 3 | Mouse CT26 | BID 7 days, every 17 days |

The 5-FC cell killing assays were carried out as described in Example 5 above, measuring viability after 8 days of 5-FC treatment.

Copy number/microgram of DNA was determined by PCR as described for the vector titering assay in Example 5, and converted to copy number/diploid genome by dividing by 150,000, the approximate number of diploid mouse/human genomes in 1 microgram of genomic DNA. Western Blot analysis was performed on 1E6 cells/lysate in RIPA buffer using antibodies from clone 83A25 for GP70 and Abcam anti-CD antibody ab3525 for the CD protein. Cell explants underwent super-infection procedures with a AC3-eGFP(V) and a mock procedure to determine which explants were potentially further infectable. The extent of GFP expression was measured by FACS analyses, with uptake and expression of GFP indicating the relative susceptibility to further infection.

Results. 5-FC Cell Killing Assay and Copy Number of Integrated Vector.

Cultured explants were tested for 5-FC sensitivity by generating a killing profile from treated cell lines at varying 5-FC concentrations (summarized in the Table below). Results from the killing profile measured by MTS viability assay show that U87 human tumors derived from animals #833, 953, 969 on average ($IC_{50}$=0.009 mM) had a similar response compared to an in vitro U87 positive control ($IC_{50}$==0.008 mM) to 5-FC treatment. Analysis of CT26 murine tumors (Example 10) showed that the 5-FC responsive animal #61 had an $IC_{50}$ of 0.003 mM, which is similar to in vitro 100% transduced CT26 results ($IC_{50}$==0.001 mM). Animal #31 was poorly responsive to 5-FC. PCR results for copy number per cell are also shown in the table below.

| Animal # | Study | 5-FC sensitivity IC50 (mM) | Vector copy number per diploid genome |
|---|---|---|---|
| 833 | Example 9 | 0.009 | 22.3 |
| 953 | Example 9 | 0.009 | 9.6 |
| 969 | Example 9 | 0.009 | 18.7 |
| 61 | Example 10 | 0.003 | 6.0 |
| 31 | Example 10 | Not sensitive | 0.9 |

Western Blot Analysis of GP70 and CD Protein Expression.

Further analysis of cells by western blot from the CT26 study showed that both tumor explants derived from mice #31 and #61 had observable GP70 protein expression when using U87+AC3-yCD2(V) infected lysates as a reference positive control.

However, analysis of CD expression showed that only #61 still had observable CD expression. Cells from #31 were run in duplicate wells (#31(A) and #31(B)) to verify negative CD gene expression results.

GFP Expression after AC3-eGFP(V) Transduction.

Attempts to transduce explants with an MLV vector expressing GFP showed that U87 tumors derived from animals #833, 953, 969 were scarcely transducible (<0.5%). CT26 explanted tumor cells derived from animal #61 could be partially transduced (7% GFP positive) while explanted cells from animal #31 could not.

All U87 gliomas isolated from the brains of nude mice after 4 full cycles of 5-FC treatment were still sensitive to 5-FC treatment in vitro with an ICH the same as in vitro transduced U87 and, surprisingly, showed multiple vector superinfections had taken place. Two CT26 tumors were isolated from BALB/c mice after 3 and 3.5 cycles of 5-FC treatment. Of the two, only one tumor showed 5-FC sensitivity while the other did not. Further analysis showed that the 5-FC resistant tumor is refractory to further MLV transduction, expresses GP70 but no longer expresses the CD, and has low copy number compared to the other CT26 and all U87 explants tested. These observations show that whereas a virus that has undergone a deletion of the CD gene behaves as expected for a normal retrovirus and excludes further infection, cells infected with vector carrying the CD transgene behave atypically and allow multiple superinfections (range: 6.0-23.3, mean 14.5 copies per diploid genome). Typical tumors are not diploid but are polyploid with a genome larger than the diploid genome. This would further increase the actual vector copy number per cell. The multiple vector copy numbers contributes to the therapeutic effect as more of the protein derived from the transgene (in this case CD) is produced than from a single vector integration. It also means that in general, even if some members of a viral vector population undergo rearrangements, other members will donate protein activity (in this case sensitivity to 5-FC). The experiments described here also provide a method of testing a recombinant replication competent retrovirus for the property of multiple infections of a target cell population.

Example 9 Direct Measurement from Excised Tumors Treated with AC3-yCD2(V) Shows Unexpectedly High Levels of Viral Vector Copies Per Genome and Susceptibility to Superinfection in the Syngeneic Tu2449 Glioma Model Objective.

This study was conducted to compare the efficacy of two dose levels of AC3(V)-yCD2 (aka Toca511) delivered via IC injection in combination with 5-FC treatment in a TU-2449 glioma tumor bearing, immunocompetent mouse model, and examined survival in the setting of active tumor growth. TU-2449 cells implanted IC in syngeneic B6C3F1 mice have been used as an experimental murine glioma model. This model was also used for survival and short term (15-18 day) experiments where tumors were implanted, treated with vector and dosed short term with 5-FC then excised for further characterization of gene copy number and CD activity.

Mice.

Female B6C3F1 mice (age ~8 weeks) were purchased from Harlan (Indianapolis Ind.). Mice were acclimated for 7 days after arrival.

Mice underwent surgical placement of an indwelling guide cannula with a 3.0 mm projection implanted into the right striatum, and fitted with a cap containing a 3.5 mm projection. The stereotaxic coordinates were AP=+0.5 mm, ML=−1.8 mm (from bregma).

Cells.

TU-2449 cells (Smilowitz et al. J. Neurosurg. 2007 106: 652-659 2007) derived originally from Glial fibrillary acidic protein (GFAP)-v-src transgenic mice, were cultured in Dulbecco's modified Eagles medium with 10% fetal bovine serum, sodium pyruvate, and Glutamax (Hyclone, Logan Utah, and Invitrogen, San Diego Calif.). Cells were resuspended in PBS (Hyclone, Logan Utah) for implantation. TU-2449 cells (1E4 in 1 μL) were infused at 0.2 μL per minute (5 minutes, followed by a hold of 5 minutes) IC through an injection cannula with a 3.5 mm projection inserted through the guide cannula.

The study consisted of 6 groups of female mice (see Table below). On day 0, mice from Groups 1, 3, 4, 6, and 7 underwent intracranial implantation of 1E4 TU-2449 cells. Group 8 mice were not implanted with tumor. On Day 4, mice were injected (IC; 5 μL/mouse) with vehicle (Group 1); IC with AC3-yCD2(V) at 1.7E5 TU/g (Groups 6, 7); IC with AC3-yCD2(V) at 1.7E6 TU/g (Groups 3, 4); Group 8 mice were not treated. Starting on Day 10, mice were treated IP BID for 4 consecutive days with PBS (Groups 1, 3, 7) or 5-FC (500 mg/kg/dose, Groups 4, 6, 8). Cycles of 4 days BID treatment with PBS or 5-FC followed by 10 days of viral spread were repeated. Survival analysis to Day 180 was performed on 10 mice each from Groups 3-7. Group Assignments

| | | N per analysis category | |
|---|---|---|---|
| Group | Treatment | Survival | Scheduled Sacrifice |
| 1 | Control (vehicle injection) + PBS | | 1 at day 10 |
| 3 | AC3-yCD2(V) E6 + PBS | 10 | |
| 4 | AC3-yCD2(V) E6 + 5-FC | 10 | 3 at day 10, 24, 38, and 52 |
| 6 | AC3-yCD2(V) E5 + 5-FC | 10 | 3 at day 10, 24, 38, and 52. |
| 7 | AC3-yCD2(V) E5 + PBS | 10 | |
| 8 (no tumor) | 5-FC | | 1 at day 10, 24, 38, and 52 |
| TOTAL | | 40 | 29 |

AC3-yCD2(V) (5 μL) was infused at 0.33 μL per minute (15 minutes, followed by a hold of 5 minutes) intracranially through an injection cannula with a 3.5 mm projection inserted through the guide cannula. 5-FC (500 mg/kg/dose) or PBS (800 μL) was administered IP BID for 4 consecutive days starting at days 10, 24, 38, and 52.

Example 10 Short Term Experiments to Determine the Level of Viral Genome and Super-Infection in Tu2449 Tumors In Vivo The study consisted of 6 groups of female mice (see Table below). All groups underwent intracranial administration into the right striatum of 1E4 TU-2449 cells administered/mouse on Day 0. At Day 4, all groups received intracranial/intratumoral administration of AC3-YCD2(V) vector at 2.4E6 TU/5ul (Lot#T511019) or PBS buffer control. Two days of BID 5-FC administration began when the mice started losing weight (approximately 15 days post-tumor implantation). Group 5 had 5-FC delivered by oral gavage (OG) and all other groups IP. One more dose of 5-FC was given 1 hour before sacrifice the following day. From each brain, the tumor was isolated and processed directly into RIPA buffer for analysis of 5-FC and 5-FU by HPLC. A small portion of the tumor was retained for western blot analysis.

Group Assignments and Dose Levels

| Group | Treatment | Route | TX | Route | Dosing | N |
|---|---|---|---|---|---|---|
| 1 | AC3-YCD2(V) | IC | NONE | N/A | N/A | 3 |
| 2 | PBS | IC | 5FC | IP | 250 mg/kg | 4 |
| 3 | PBS | IC | 5FC | IP | 500 mg/kg | 2 |
| 4 | AC3-YCD2(V) | IC | 5FC | IP | 250 mg/kg | 3 |
| 5 | AC3-YCD2(V) | IC | 5FC | OG | 250 mg/kg | 2 |
| 6 | AC3-YCD2(V) | IC | 5FC | IP | 500 mg/kg | 2 |
| | | | Total animals | | | 16 |

IC—intracranial;
IP—intraperitoneal;
OG—oral gavage

AC3-yCD2(V) (5 μL) was infused at 0.33 μL per minute (15 minutes, followed by a hold of 5 minutes) intracranially at the same coordinates as TU-2449 cells were injected. 5-FC or PBS was administered IP or OG BID for 2 consecutive days and 1 hour before sacrifice.

Tissue Processing Procedures.

From each brain, tumors were isolated and trimmed if large enough for multiple analyses (more than 0.05 g). Tumors sections for HPLC analysis were crushed in a 1.5 mL centrifuge tube using a plunger from a 1 mL syringe. Crushed samples were mixed with 150 uL RIPA buffer and vortexed vigorously for 10 minutes. Samples were spun at 4° C. at 20000 rcf for 10 minutes. Supernatants were removed and mixed thoroughly with 150 uL of 10% trichloroacetic acid and spun as above. Supernatants were removed for analysis by the Agilent HPLC unit with a Hypersil BDS C18 column run isocratically at 1 mL/min with 95% Buffer A containing 50 mM ammonium phosphate and 0.1% tetra-n-butylammoniumperchlorate with pH adjustment of the buffer to 2.1 with phosphoric acid and 5% Solvent B which is 100% methanol (see WI RD-053). The run time is 5 minutes with each sample run twice. The photodiode detector array scans from 190 to 350 nm with chromatograms selected to display at 285 nm for 5-fluorocytosine and 264 nm for 5-fluorouracil. Data was expressed in relative milli absorbance units (mAU) of peak area from the chromatograms.

Protein Gels and Western Blots.

When sufficient tumor was available, tumor fragments for protein gels and Western blots were mixed with a separate aliquot of RIPA lysis buffer, and 20 ug of total protein from each sample was electrophoresed on polyacrylamide gels, Western blotted and the blot developed with sheep anti-yeast CD antibody as in Example 10. Western blot data was scanned and quantified using BioRad Quantity One software (version 4.6.7).

QPCR on Tumor Fragments.

Remaining pellets, after supernatants were removed for HPLC analysis, were extracted for genomic DNA. Samples were analyzed by qPCR for proviral integration copy number using primers and probe for MLV LTR as in example 10. Samples were also analyzed in parallel using previously characterized primers and probes for the amphotropic env gene (Env2) and the CD gene (yCD2).

yCD2 Primer and Probe Set:

| | | |
|---|---|---|
| 5' AC3-YCD2(V) yCD2 Primer: | ATCATCATGTACGGCATCCCTAG | (SEQ ID NO: 49) |
| 3' AC3-YCD2(V) yCD2 Primer: | TGAACTGCTTCATCAGCTTCTTAC | (SEQ ID NO: 50) |
| yCD2 Probe: | /5FAM/TCATCGTCAACAACCACCACCTCGT/3BHQ_1/ | (SEQ ID NO: 51) |

These primers and probe target and amplify the CD gene exclusively.

Env2 Primer and Probe Set:

| | | |
|---|---|---|
| Env2-Forward: | AACCTCAACCTCCCCTACAAGT | (SEQ ID NO: 52) |
| Env2-Reverse: | GTTAAGCGCCTGATAGGCTC | (SEQ ID NO: 53) |
| Env2-Probe: | /5TEX615/AGCCACCCCCAGGAACTGGAGATAGA/3IAbRQSp/ | (SEQ ID NO: 54) |

These primers and probe target and amplify the envelope (Env) gene exclusively.

Results. Survival Analysis.

The median survival of AC3-yCD2(V) control groups treated with PBS (Group 3 and 7) was approximately 33-38 days. The survival medians of mid and high dose AC3-yCD2(V) in combination with 5-FC (Group 6 and 4) were not reached before sacrifice at 189 days. Log-Rank (Mantel-Cox) pairwise comparison showed no difference in survival between the two control groups; AC3-yCD2(V) E5 dose plus PBS (Group 7) and AC3-yCD2(V) E6 dose plus PBS (Group 3).

AC3-yCD2(V) treatment at both dose levels in combination with 5-FC resulted in prolonged survival. A statistically significant survival advantage was observed for AC3-yCD2(V) E5 plus 5-FC (Group 6) treated mice compared to vector plus PBS control (Group 7) mice ($p<0.0354$, hazard ratio 0.2605, 95% CI 0.07439 to 0.9119). A statistically significant survival advantage was observed for AC3-yCD2(V) E6 plus 5-FC (Group 4) treated mice compared to vector plus PBS control (Group 3) mice ($p<0.0036$, hazard ratio 0.1130, 95% CI 0.02598 to 0.4911).

Example 11 Short Term Experiments to Determine the Level of Viral Genome and Super-Infection in Tu2449 Tumors In Vivo HPLC Analysis.

In vivo conversion of 5-FC to 5-FU was detected by HPLC in all groups dosed with Toca511 and 5-FC. Group 1 that was given AC3-yCD2(V) but no 5-FC had neither 5-FC nor 5-FU detectable signals as expected. The small counts observed (47-84) for 5-FC is attributable to background from nearby peaks on the chromatography trace. Groups 2 and 3 that were not dosed with AC3-yCD2(V) but dosed with varying levels of 5-FC had detectable 5-FC signals but no signal for 5-FU. Group 4 mice dosed with AC3-yCD2(V) and 5-FC IP and Group 5 mice dosed with AC3-yCD2(V) and 5-FC OG had comparable signal levels of 5-FU and very low or background levels of 5-FC. Group 6 mice dosed with Toca-511 and high levels of 5-FC showed readily detectable levels of 5-FU and low signal for 5-FC.

CD Western Blot Analysis.

Tissue samples from isolated TU-2449 tumors were processed for western blot analysis of CD expression. All groups (1, 4, and 5) treated with AC3-yCD2(V) had readily observable CD expression while Group 2 that was not given AC3-yCD2(V) did not have detectable CD expression.

PCR Analysis of Genomic DNA Isolated from Tumors.

The remaining pellets, after supernatants were removed for HPLC analysis, were extracted for genomic DNA. Samples were analyzed by quantitative PCR for proviral integration using the standardized assay and MLV-LTR primers and probe. Parallel assays using the envelope and CD gene primers and probes analyses gave similar C(t) values showing that the viral genome appeared quite stable. An in vitro transduced cell line served as positive control. The negative control was genomic tumor DNA from Group 2 that was not dosed with AC3-yCD2(V) and did not have detectable signal for any of the qPCR protocols.

Table of relative CD protein levels, viral vector copy #, and relative levels of 5-FU production

| Group | Mouse # | Relative CD protein levels | Copies#/ diploid genome | 5-FU (relative peak area units) |
|---|---|---|---|---|
| Group 1 | 194 | 21,746 | 1.4 | 0 |
| | 199 | No Data | 14.6 | 0 |
| Group 2 | 191 | 162 | 0 | 0 |
| | 187 | 75 | 0 | 0 |
| | 188 | −453 | 0 | 0 |
| Group 4 | 185 | 17,349 | 1.8 | 1642 |
| | 200 | 45,446 | 7.3 | 1576 |
| Group 5 | 189 | 25,417 | 3.7 | 942 |
| | 198 | 23,660 | 6.6 | 1371 |

For samples with enough starting material for all three analyses to be done, the relationship between integrated MLV copy number, expression of CD, and the amount of 5-FC to 5-FU conversion is summarized in the above table (199 did not have material for Western analysis). The relative CD protein levels (estimated from Western blots) vary over a three-fold range and the DNA copy number over a 5-fold range. There is some correlation between DNA copy number and relative level of CD expression. All of the tumors have vector copy numbers/genome above 1, showing that even at this early time-point after vector administration (13-14 days) superinfection of tumor cells is a usual occurrence, and may contribute to observed therapeutic effects. The CD values displayed represent the values after average background correction, and the Group 2 numbers represent the variability in that background.

This study supports the proposed mechanism of action and shows that this efficacy can be attributed to the conversion of the 5-FC prodrug into the anticancer drug 5-FU after delivery of the CD gene by AC3-yCD2(V). Using the TU-2449 mouse glioma model, AC3-yCD2(V) treatment in combination with 5-FC resulted in efficient in vivo conversion of 5-FC into 5-FU. 5-FC was converted efficiently into 5-FU at two dose levels (500 and 250 mg/kg) as 5-FC levels were at least ten fold lower than the controls, and 5-FU levels were readily detectable in AC3-yCD2(V) treated but not in the untreated controls. IP or OG delivery of 5-FC did not affect the efficiency of conversion. Tumors isolated from mice given AC3-yCD2(V) had observable expression of CD protein that had some correlation with the numbers of copies of the vector genome. The number of integrated vector genomes ranged from 1.4 to 15 copies/diploid genome (mean: 5.9). The infection here was the result of about 12 days infection and previous experiments with GFP vectors in other models suggest that this corresponds to infection of approximately 50% of the cells in the tumor, giving an adjusted vector copy number/cell of 11.8 copies/diploid genome. Typical tumors are not diploid but are triploid or further polyploid with a genome larger than the diploid genome. This would further increase the actual vector copy number per cell. The experiments described here also provide a method of testing a recombinant replication competent retrovirus for the property of multiple infections of a target cell population. These observations support the conclusion that AC3-yCD2(V) is efficiently delivering a functional CD gene for expression in glioma cells. In the efficacy study with this model, almost no spread of vector from the site of injection (tumor in the right cerebrum) was observed in the first 24 days. The observations in this study show that over the same initial period of time there is extensive viral vector infection of the tumor, showing that infection is quite tumor specific, and that already at this early time-point there is extensive super-infection of the tumor cells by the viral vector.

Example 11 Clonal Analyses of HT1080 Cell Line Infected with AC3-yCD2(V) Shows that the Majority of the Clones have Multiple Copies of the Viral Vector Genome and were Susceptible to Super-Infection The human sarcoma line HT1080 (ATCC: CCL 121) was grown in tissue culture under standard culture conditions. 2E7 cells were infected with AC3-yCD2(V) made by transient transfection on 293 cells, at a multiplicity of 0.1, allowed to grow for 14 days, and frozen down as a pool. About 1 month later cells were thawed and clonal cell lines from this culture were isolated by limiting dilution in 96 well dishes at 0.3 cells/well. The clones that grew out were expanded and analyzed by qPCR with the MLV LTR primers for vector genome copy number per microgram DNA in triplicate. This was converted to copy number/diploid genome by dividing by 150,000, as described in example 10. The Table below lists the clones that were analyzed and the corresponding copy number for the viral vector genome. Only 1 of 10 clones (13-5) has approximately 1 copy of the viral genome per diploid genome. The range was 0.9 to 20.4 copies/cell and the mean copy number was 10.6 copies/cell. Typical tumors are not diploid but are triploid or further polyploid with a genome larger than the diploid genome. This would further increase the actual vector copy number per cell. It is well known that normally a viral infection of this nature leads to a single or few copies of viral genome/cell, due to resistance to superinfection through receptor masking or down regulation (see, for example, Ch3 p 104 of "Retroviruses" J M Coffin, S H Hughes & H E Varmus, 1997 Cold Spring Harbor Laboratory Press, Cold Spring Harbor N.Y.).

Listing of viral vector copy number in infected HT1080 clones infected with AC3-yCD2 and expanded.

| Sample # | Test article | Average copy number/genome |
|---|---|---|
| 1 | Negative control (HT1080) | 0 |
| 2 | Positive control (recently transduced HT1080 pool) | 1.89 |
| 3 | Clone #3-5 | 18.26 |
| 4 | Clone #4-1 | 5.28 |
| 5 | Clone #7-1 | 18.87 |
| 6 | Clone #8-3 | 14.04 |
| 7 | Clone #9-1 | 15.29 |
| 8 | Clone #10-1 | 9.73 |
| 9 | Clone #11-1 | 20.44 |
| 10 | Clone #12-6 | 6.08 |
| 11 | Clone #13-5 | 0.93 |
| 12 | Clone #19-2 | 5.24 |

Therefore this is an unexpected and surprising result that confirms the in vivo tumor model data of Examples 30 and 31. More particularly, the data demonstrate that this virus allows multiple super-infections in the great majority of the cells it infects, unlike normal MLV infection. The experiments described here also provide a method of testing a recombinant replication competent retrovirus for the property of multiple infections of a target cell population.

A number of embodiments of the disclosure been described. Nevertheless, it will be understood that various modifications may be made without departing from the spirit and scope of the disclosure. Accordingly, other embodiments are within the scope of the following claims.

What is claimed is:

1. A recombinant replication competent gamma-retrovirus (RCR) comprising:

a retroviral GAG protein;

a retroviral POL protein;

a retroviral envelope;

a gamma-retroviral polynucleotide encoding a retroviral proviral polynucleotide comprising from 5' to 3': R-U5-gag-pol-env-cassette-U3-R, wherein the "R" is a retroviral Long-Terminal Repeat (LTR) repeat sequence, the "U5" is a 5' untranslated region of the LTR and the "U3" is the 3' untranslated region of the LTR, wherein the R-U5 region comprises a promoter suitable for expression in a mammalian cell; the "gag" encodes the GAG protein wherein the gag is at least 95% identical to nucleotides 1203 to 2819 of SEQ ID NO:19; the "pol" encodes the POL protein wherein the pol is at least 95% identical to nucleotides 2820 to 6358 of SEQ ID NO:19; the "env" encodes the envelope protein wherein the env is at least 95% identical to nucleotides 6359 to 8323 of SEQ ID NO:19; the "cassette" comprises an internal ribosome entry site (IRES) operably linked to a human codon optimized nucleic acid encoding the polypeptide of SEQ ID NO:4, wherein the cassette is linked to the env coding sequence by about 1-5 nucleotides;

and cis-acting sequences necessary for reverse transcription, packaging and integration in a target cell.

2. The RCR of claim 1, wherein the gamma-retroviral polynucleotide is obtained from murine leukemia virus (MLV), Moloney murine leukemia virus (MoMLV), Feline leukemia Virus or Gibbon ape leukemia virus (GALV).

3. The RCR of claim 2, wherein the MLV is an amphotropic MLV.

4. The RCR of claim 1, wherein the IRES is from an encephalomyocarditis virus.

5. The RCR of claim 4, wherein the IRES comprises a sequence that is at least 95% identical to nucleotides 8327 to 8876 of SEQ ID NO:19.

6. The RCR of claim 1, wherein the human codon optimized nucleic acid comprises the nucleotide sequence of SEQ ID NO: 19 from about nucleotide number 8877 to about 9353.

* * * * *